(12) United States Patent
Takahashi et al.

(10) Patent No.: US 9,475,813 B2
(45) Date of Patent: Oct. 25, 2016

(54) TRICYCLIC PYRROLOPYRIDINE COMPOUND, AND JAK INHIBITOR

(71) Applicant: NISSAN CHEMICAL INDUSTRIES, LTD., Chiyoda-ku (JP)

(72) Inventors: Keiji Takahashi, Funabashi (JP); Tsuneo Watanabe, Funabashi (JP); Keishi Hayashi, Funabashi (JP); Kazunori Kurihara, Funabashi (JP); Takanori Nakamura, Shiraoka (JP); Akio Yamamoto, Funabashi (JP); Takuya Nishimura, Funabashi (JP); Toshihiko Kamiyama, Funabashi (JP); Yuuki Hidaka, Shiraoka (JP)

(73) Assignee: Nissan Chemical Industries, Ltd., Chiyoda-ku (JP)

( * ) Notice: Subject to any disclaimer, the term of this patent is extended or adjusted under 35 U.S.C. 154(b) by 0 days.

(21) Appl. No.: 14/764,652

(22) PCT Filed: Feb. 5, 2014

(86) PCT No.: PCT/JP2014/052700
§ 371 (c)(1),
(2) Date: Jul. 30, 2015

(87) PCT Pub. No.: WO2014/123167
PCT Pub. Date: Aug. 14, 2014

(65) Prior Publication Data
US 2015/0368245 A1    Dec. 24, 2015

(30) Foreign Application Priority Data

Feb. 8, 2013 (JP) .................................. 2013-023650
Mar. 27, 2013 (JP) .................................. 2013-066124

(51) Int. Cl.
*A61K 31/00*    (2006.01)
*C07D 471/14*   (2006.01)

(52) U.S. Cl.
CPC .................................. *C07D 471/14* (2013.01)

(58) Field of Classification Search
None
See application file for complete search history.

(56) References Cited

U.S. PATENT DOCUMENTS

| 2010/0048552 A1 | 2/2010  | Ren et al.     |
| 2011/0201593 A1 | 8/2011  | Babu et al.    |
| 2012/0330012 A1 | 12/2012 | Frank et al.   |
| 2013/0216497 A1 | 8/2013  | Wishart et al. |

FOREIGN PATENT DOCUMENTS

| WO | WO 01/42246 A2    | 6/2001  |
| WO | WO 2007/007919 A2 | 1/2007  |
| WO | WO 2007/077949 A1 | 7/2007  |
| WO | WO 2007/134259 A2 | 11/2007 |
| WO | WO 2008/084861 A1 | 7/2008  |
| WO | WO 2009/152133 A1 | 12/2009 |
| WO | WO 2010/119875 A1 | 10/2010 |
| WO | WO 2011/045702 A1 | 4/2011  |
| WO | WO 2011/068881 A1 | 6/2011  |
| WO | WO 2011/068899 A1 | 6/2011  |
| WO | WO 2011/075334 A1 | 6/2011  |
| WO | WO 2011/086053 A1 | 7/2011  |
| WO | WO 2012/085176 A1 | 6/2012  |
| WO | WO 2012/127506 A1 | 9/2012  |
| WO | WO 2012/149280 A2 | 11/2012 |
| WO | WO 2013/024895  * | 2/2013 ........... C07D 487/14 |
| WO | WO 2013/024895 A1 | 2/2013  |

OTHER PUBLICATIONS

International Search Report issued Mar. 4, 2014, in PCT/JP2014/052700, filed Feb. 5, 2014.
John J. O'Shea, et al., "Cytokine Signaling in 2002: New Surprises in the Jak/Stat Pathway", Cell, vol. 109, Apr. 2002, pp. S121-S131.
Katsutoshi Ozaki, et al., "A Critical Role for IL-21 in Regulating Immunoglobulin Production", Science, vol. 298, Nov. 22, 2002, pp. 1630-1634.
Paolo Macchi, et al., "Mutations of Jak-3 gene in patients with autosomal severe combined immune deficiency (SCID)", Letters to Nature, vol. 377, Sep. 7, 1995, pp. 65-68.
Sarah M. Russell, et al., "Mutation of Jak3 in a Patient with SCID: Essential Role of Jak3 in Lymphoid Development", Science, vol. 270, Nov. 3, 1995, pp. 797-800.

(Continued)

*Primary Examiner* — Craig Ricci
(74) *Attorney, Agent, or Firm* — Oblonn, McClelland, Maier & Neustadt, L.L.P.

(57) ABSTRACT

To provide a novel tricyclic pyrrolopyridine compound having a JAK inhibitory activity and useful for prevention, treatment and/or improvement of particularly autoimmune diseases, inflammatory diseases and allergic diseases.
A novel tricyclic pyrrolopyridine compound represented by the formula (I), a tautomer or pharmaceutically acceptable salt of the compound or a solvate thereof:

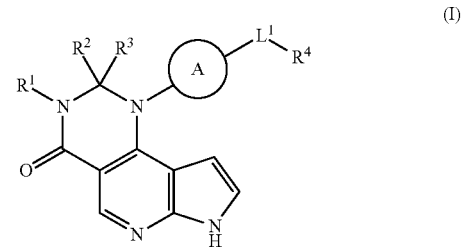

wherein the respective substituents are defined in detail in the specification, and $R^1$ is a $C_{1-6}$ alkyl group or the like, $R^2$ is a hydrogen atom or the like, $R^3$ is a hydrogen atom or the like, the ring A is $C_{3-11}$ cycloalkane or the like, $L^1$ is a $C_{1-6}$ alkylene group or the like, and $R^4$ is $NR^aR^b$ or the like.

7 Claims, No Drawings

(56) References Cited

OTHER PUBLICATIONS

Peter J. Murray, "The JAK-STAT Signaling Pathway: Input and Output Integration", The Journal of Immunology, vol. 178, 2007, pp. 2623-2629.

J. Staerk, et al., "JAK2, the JAK2 V617F mutant and cytokine receptors", Pathologie Biologie, vol. 55, 2007, pp. 88-91.

Jong-Ha Yoo, et al., "JAK2 V617F/C618R mutation in a patient with polycythemia vera: A case study and review of the literature", Cancer Genetics and Cytogenetics, vol. 189, 2009, pp. 43-47.

William Vainchenker, et al., "JAKs in pathology: Role of Janus kinases in hematopoietic malignancies and immunodeficiencies", Seminars in Cell & Developmental Biology, vol. 19, 2008, pp. 385-393.

Joel M. Kremer, et al., "The Safety and Efficacy of a JAK Inhibitor in Patients With Active Rheumatoid Arthritis", Arthritis & Rheumatism, vol. 60, No. 7, Jul. 2009, pp. 1895-1905.

Mg Boy, et al., "Double-Blind, Placebo-Controlled, Dose-Escalation Study to Evaluate the Pharmacologic Effect of CP-690,550 in Patients With Psoriasis", Journal of Investigative Dermatology, vol. 129, 2009, pp. 2299-2302.

Paul S. Changelian, et al., "Prevention of Organ Allograft Rejection by a Specific Janus Kinase 3 Inhibitor", Science, vol. 302, Oct. 31, 2003, pp. 875-878.

Elizabeth Kudlacz, at al., "The JAK-3 inhibitor CP-690550 is a potent anti-inflammatory agent in a murine model of pulmonary eosinophilia", European Journal of Pharmacology, vol. 582, 2008, pp. 154-161.

* cited by examiner

TRICYCLIC PYRROLOPYRIDINE COMPOUND, AND JAK INHIBITOR

TECHNICAL FIELD

The present invention relates to novel tricyclic pyrrolopyridine compounds having a JAK inhibitory effect.

BACKGROUND ART

A JAK (Janus kinase) family is one type of tyrosine kinase and four types of JAK1, JAK2, JAK3 and Tyk2 (tyrosine kinase 2) are known, and they have an important role in cytokine signaling.

While the kinases of this family, except for JAK3, are widely expressed in tissues, the expression of JAK3 is restricted to immune cells. This does not conflict with that JAK3 plays an important role in signaling via various receptors for IL (interleukin)-2, IL-4, IL-7, IL-9, IL-15, IL-21, etc., by being non-covalently associated with the common γ chain (Non-Patent Documents 1 and 2).

Further, in a group of patients with an immune deficiency disease called X-linked severe combined immune deficiency (XSCID), a decrease in the JAK3 protein level or the gene defect of the common γ chain is observed. This indicates that the immunosuppression is caused by blocking of the signaling pathway via JAK3 (Non-Patent Documents 3 and 4). Animal tests indicate that JAK3 not only plays an important role in maturation of B- and T-lymphocytes but also is important to maintain the function of the T-lymphocytes. Accordingly, by controlling the immune response by means of such a mechanism, treatment of diseases relating to abnormal proliferation of T-lymphocytes such as organ transplant rejection or autoimmune diseases is expected.

Analyses of JAK1 knockout mice and JAK1 deficient cells indicate that JAK1 relates to signaling via various receptors for IFN (interferon)α, IFNβ, IFNγ, IL-2, IL-4, IL-6, IL-7, IL-15, etc. (Non-Patent Document 5). Accordingly, by controlling inflammatory responses via such signaling, treatment of diseases relating to activation of macrophages or lymphocytes such as autoimmune diseases and acute and chronic organ transplant rejection is expected.

Analyses of JAK2 knockout mice and JAK deficient cells indicate that JAK2 relates to signaling via various receptors for EPO (erythropoietin), thrombopoietin, IFNγ, IL-3, GM-CSF, etc. (Non-Patent Document 6, 7 and 8). Such signaling is considered to relate to differentiation of precursor cells of erythrocytes, platelets, etc. in bone marrow. Meanwhile, it is suggest that the mutation which is defined by a valine-to-phenylalanine substitution at amino acid position 617 in JAK2, is associated with myeloproliferative neoplasms (Non-Patent Document 6). Thus, by regulating differentiation of bone marrow precursor cells by means of such a mechanism, treatment of myeloproliferative neoplasms is expected.

Further, it has been reported that CP-690,550 which is a JAK inhibitor has an effect to improve the clinical condition of rheumatoid arthritis and psoriasis in clinical trials (Non-Patent Documents 9 and 10) and has an effect to suppress rejection in monkey renal transplantation models and airway inflammation in mouse asthma models (Non-Patent Documents 11 and 12). From these findings, suppression of immune activity by a JAK inhibitor is considered to be advantageous for prevention or treatment of organ transplant rejection, graft versus host reaction after transplantation, autoimmune diseases and allergic diseases. Compounds having a JAK inhibitory effect other than CP-690,550 are known e.g. in the following reports (for example, Patent Documents 1 to 14), and further development of pharmaceutical agents has been desired.

In a patent document published after filing of the application on the basis of which the priority of the present application is claimed, tricyclic pyrrolopyridine compounds having a JAK inhibitory effect are reported, however, the patent document failed to specifically disclose the compounds of the present invention (Patent Document 15).

PRIOR ART DOCUMENTS

Patent Documents

Patent Document 1: WO2001/42246
Patent Document 2: WO2008/084861
Patent Document 3: WO2010/119875
Patent Document 4: WO2011/045702
Patent Document 5: WO2011/068881
Patent Document 6: WO2011/075334
Patent Document 7: WO2007/007919
Patent Document 8: WO2007/077949
Patent Document 9: WO2009/152133
Patent Document 10: WO2011/086053
Patent Document 11: WO2011/068899
Patent Document 12: WO2012/085176
Patent Document 13: WO2012/127506
Patent Document 14: WO2012/149280
Patent Document 15: WO2013/024895

Non-Patent Documents

Non-Patent Document 1: Cell, 2002, 109, pp. S121-131
Non-Patent Document 2: Science, 2002, 298, pp. 1630-1634
Non-Patent Document 3: Nature, 1995, 377, pp. 65-68
Non-Patent Document 4: Science, 1995, 270, pp. 797-800
Non-Patent Document 5: J. Immunol., 2007, 178, pp. 2623-2629
Non-Patent Document 6: Pathol. Biol., 2007, 55, pp. 88-91
Non-Patent Document 7: Cancer Genet. Cytogenet., 2009, 189, pp. 43-47
Non-Patent Document 8: Semin. Cell. Dev. Biol., 2008, 19, pp. 385-393
Non-Patent Document 9: Arthritis Rheum., 2009, 60, pp. 1895-1905
Non-Patent Document 10: J Invest. Dermatol., 2009, 129, pp. 2299-2302
Non-Patent Document 11: Science, 2003, 302, pp. 875-878
Non-Patent Document 12: Eur. J. Pharmacol., 2008, 582, pp. 154-161

DISCLOSURE OF INVENTION

Technical Problem

The object of the present invention is to provide novel pharmaceutical compounds which have an excellent JAK inhibitory activity and are useful for prevention or treatment of autoimmune diseases, inflammatory diseases and allergic diseases.

Solution to Problem

The present inventors have conducted extensive studies to find a novel low molecular weight compounds having a JAK inhibitory activity and as a result, found that the compounds of the present invention have a high inhibitory effect and accomplished the present invention. That is, the present invention provides the following.

(1) A compound represented by the formula (I), a tautomer or pharmaceutically acceptable salt of the compound or a solvate thereof:

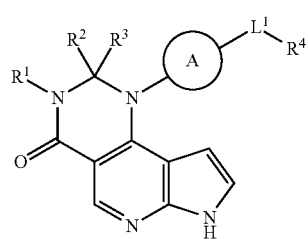

(I)

wherein the ring A is $C_{3-11}$ cycloalkane, or
a 4 to 7-membered non-aromatic heterocyclic ring,
$R^1$ is a hydrogen atom,
a $C_{3-6}$ cycloalkyl group,
a 4 to 7-membered non-aromatic heterocyclic group,
a $C_{1-6}$ haloalkyl group, or
a $C_{1-6}$ alkyl group
(the $C_{1-6}$ alkyl group is not substituted or is substituted with one hydroxy group, cyano group, $C_{1-6}$ alkoxy group, $C_{1-6}$ alkylthio group, $C_{1-6}$ alkylsulfonyl group, carboxy group, carbamoyl group, mono-$C_{1-6}$ alkylaminocarbonyl group, di-$C_{1-6}$ alkylaminocarbonyl group, $C_{3-6}$ cycloalkyl group or 4 to 7-membered non-aromatic heterocyclic group), each of $R^2$ and $R^3$ is independently a hydrogen atom, or
a $C_{1-6}$ alkyl group,
$L^1$ is a single bond,
a $C_{1-6}$ alkylene group, or
a $C_{1-6}$ haloalkylene group,
$R^4$ is a hydrogen atom,
a halogen atom,
$NR^aR^b$,
$NR^cS(=O)_2R^d$,
$OR^e$,
the formula (II)-1, or
the formula (II)-2:

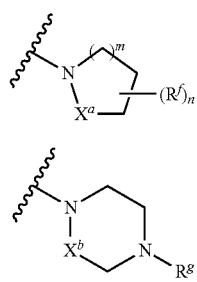

(II)-1

(II)-2 each of $R^a$ and $R^e$ is independently a hydrogen atom,
a $C_{1-6}$ alkyl group,
a cyano-substituted $C_{1-6}$ alkyl group,
a $C_{1-6}$ alkylsulfonyl-substituted $C_{1-6}$ alkyl group,
a $C_{1-6}$ haloalkyl group,
a $C_{3-6}$ cycloalkyl group,
a cyano-substituted $C_{3-6}$ cycloalkyl group, or
a $C_{1-6}$ haloalkyl-substituted $C_{3-6}$ cycloalkyl group,
each of $R^b$ and $R^c$ is independently a hydrogen atom,
a $C_{1-6}$ alkyl group, or
a $C_{1-6}$ haloalkyl group,
$R^d$ is a $C_{1-6}$ alkyl group,
a cyano-substituted $C_{1-6}$ alkyl group,
a $C_{1-6}$ haloalkyl group,
a $C_{3-6}$ cycloalkyl group,
a cyano-substituted $C_{3-6}$ cycloalkyl group, or
a $C_{1-6}$ haloalkyl-substituted $C_{3-6}$ cycloalkyl group,
$R^f$ is a halogen atom,
a hydroxy group,
a cyano group,
a $C_{1-6}$ alkyl group, or
a $C_{1-6}$ haloalkyl group,
$R^g$ is a hydrogen atom,
a $C_{1-6}$ alkyl group,
a cyano-substituted $C_{1-6}$ alkyl group, or
a $C_{1-6}$ haloalkyl group,
each of $X^a$ and $X^b$ is independently
$S(=O)_2$,
$C=O$, or
$CH_2$,
n is 0, 1 or 2 (when n is 2, each $R^f$ may be identical with or different from each other), and
m is 0, 1 or 2.

(2) The compound, a tautomer or pharmaceutically acceptable salt of the compound or a solvate thereof according to (1), wherein the ring A is $C_{4-7}$ cycloalkane.

(3) The compound, a tautomer or pharmaceutically acceptable salt of the compound or a solvate thereof according to (1), which is represented by the formula (III):

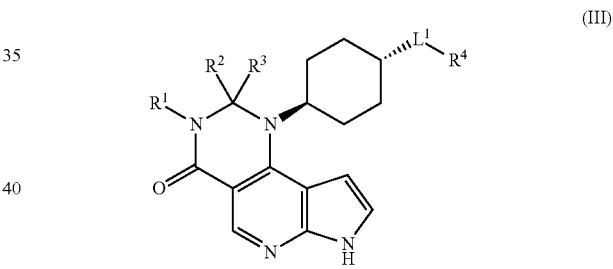

(III)

(4) The compound, a tautomer or pharmaceutically acceptable salt of the compound or a solvate thereof according to any one of (1) to (3), wherein $R^2$ and $R^3$ are a hydrogen atom.

(5) The compound, a tautomer or pharmaceutically acceptable salt of the compound or a solvate thereof according to any one of (1) to (4), wherein $R^1$ is a hydrogen atom,
a $C_{1-3}$ haloalkyl group,
a $C_{3-6}$ cycloalkyl group, or
a $C_{1-3}$ alkyl group
(the $C_{1-3}$ alkyl group is not substituted or is substituted with one cyano group, $C_{1-3}$ alkoxy group, $C_{1-3}$ alkylthio group, di-$C_{1-3}$ alkylaminocarbonyl group, $C_{3-6}$ cycloalkyl group or 4 to 7-membered non-aromatic heterocyclic group).

(6) The compound, a tautomer or pharmaceutically acceptable salt of the compound or a solvate thereof according to (5), wherein $R^1$ is a $C_{1-3}$ haloalkyl group,
a $C_{3-6}$ cycloalkyl group, or
a $C_{1-3}$ alkyl group
(the $C_{1-3}$ alkyl group is not substituted or is substituted with one cyano group, $C_{1-3}$ alkoxy group, $C_{1-3}$ alkylthio group, di-$C_{1-3}$ alkylaminocarbonyl group, $C_{3-6}$ cycloalkyl group or tetrahydrofuranyl group).

(7) The compound, a tautomer or pharmaceutically acceptable salt of the compound or a solvate thereof according to any one of (1) to (6), wherein $L^1$ is a single bond,
a $C_{1-3}$ alkylene group, or
a $C_{1-3}$ haloalkylene group,
$R^4$ is a hydrogen atom,
$NR^aR^b$,
$NR^cS(=O)_2R^d$,
$OR^e$,
the formula (II)-1, or
the formula (II)-2:

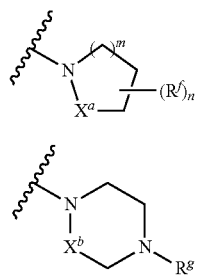

(II)-1

(II)-2

$R^a$ is a $C_{1-3}$ alkyl group,
a cyano-substituted $C_{1-3}$ alkyl group,
a $C_{1-3}$ haloalkyl group,
a $C_{3-6}$ cycloalkyl group,
a cyano-substituted $C_{3-6}$ cycloalkyl group, or
a $C_{1-3}$ haloalkyl-substituted $C_{3-6}$ cycloalkyl group,
each of $R^b$ and $R^c$ is independently a hydrogen atom, or
a $C_{1-3}$ alkyl group,
$R^d$ is a $C_{1-3}$ alkyl group,
a $C_{1-3}$ haloalkyl group, or
a $C_{3-6}$ cycloalkyl group,
$R^e$ is a hydrogen atom, or
a cyano-substituted $C_{1-3}$ alkyl group,
$R^f$ is a halogen atom, or
a hydroxy group,
$R^g$ is a cyano-substituted $C_{1-3}$ alkyl group,
$X^a$ is
$S(=O)_2$, or
$CH_2$,
$X^b$ is $CH_2$,
n is 0 or 1, and
m is 0 or 1.

(8) The compound, a tautomer or pharmaceutically acceptable salt of the compound or a solvate thereof according to (7), wherein $L^1$ is a single bond or a $C_{1-3}$ haloalkylene group, and
$R^4$ is a hydrogen atom.

(9) The compound, a tautomer or pharmaceutically acceptable salt of the compound or a solvate thereof according to (7), wherein $L^1$ is a methylene group,
$R^4$ is
$NR^aR^b$,
$NR^cS(=O)_2R^d$,
$OR^e$, or any one of the formulae (IV)-1 to (IV)-4:

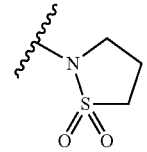

(IV)-1

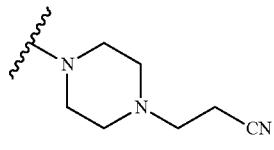

(IV)-2

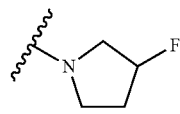

(IV)-3

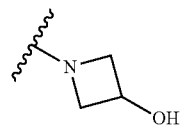

(IV)-4

$R^a$ is a methyl group, a cyanomethyl group, a 2,2,2-trifluoroethyl group, a 2,2-difluoroethyl group, a 2-bromo-2,2-difluoroethyl group, a cyclopropyl group, a 1-cyanocyclopropyl group or a 1-trifluoromethylcyclopropyl group, each of $R^b$ and $R^c$ is independently a hydrogen atom or a methyl group, $R^d$ is a methyl group, a 2,2,2-trifluoroethyl group or a cyclopropyl group, and $R^e$ is a hydrogen atom or a 2-cyanoethyl group.

(10) A compound represented by any one of the following chemical structural formulae, a tautomer or pharmaceutically acceptable salt of the compound or a solvate thereof:

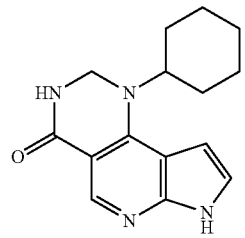

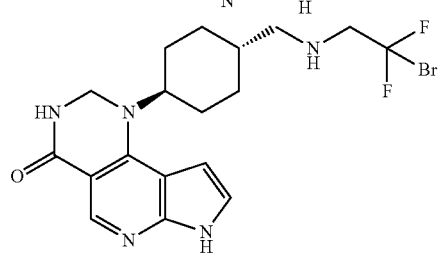

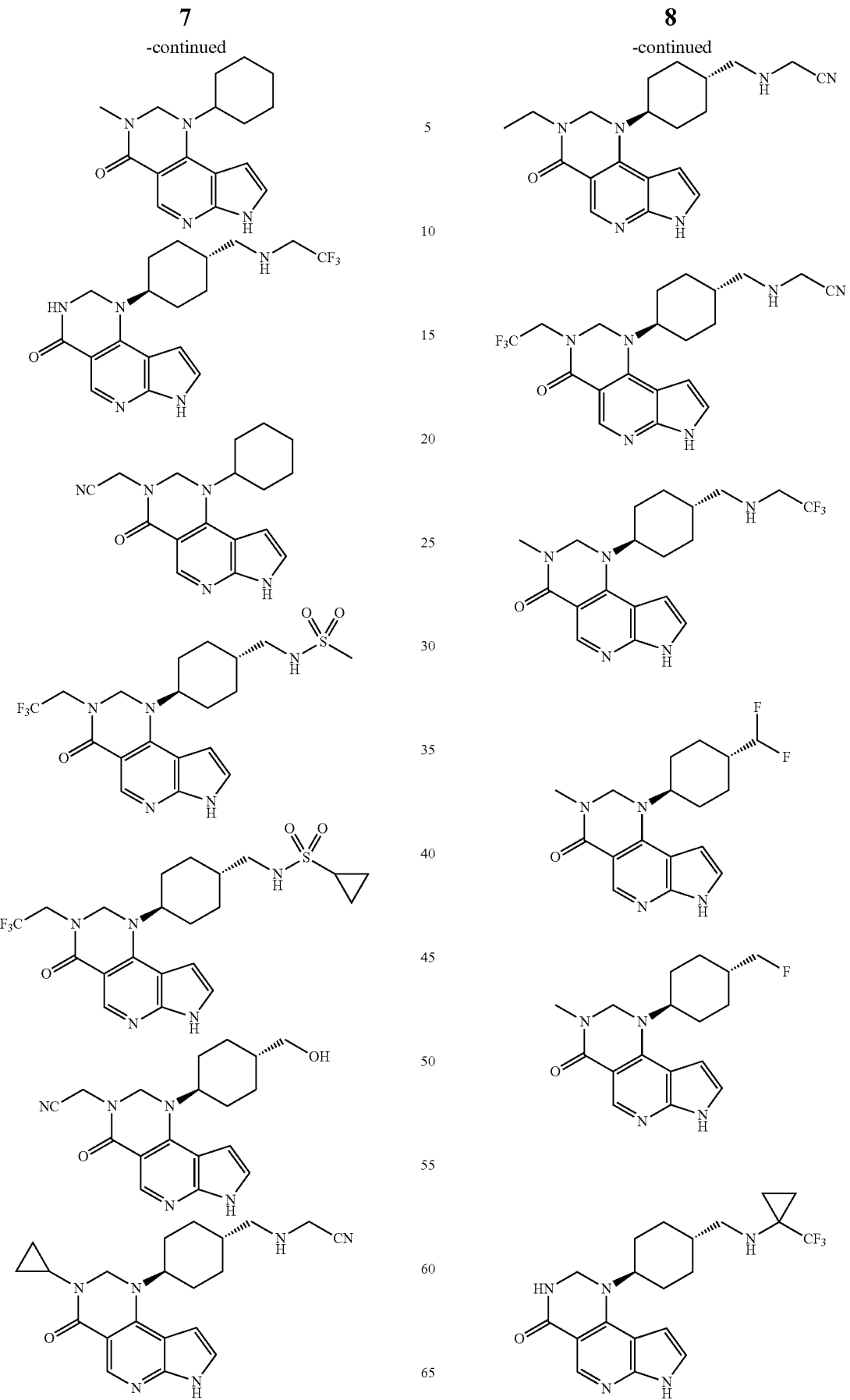

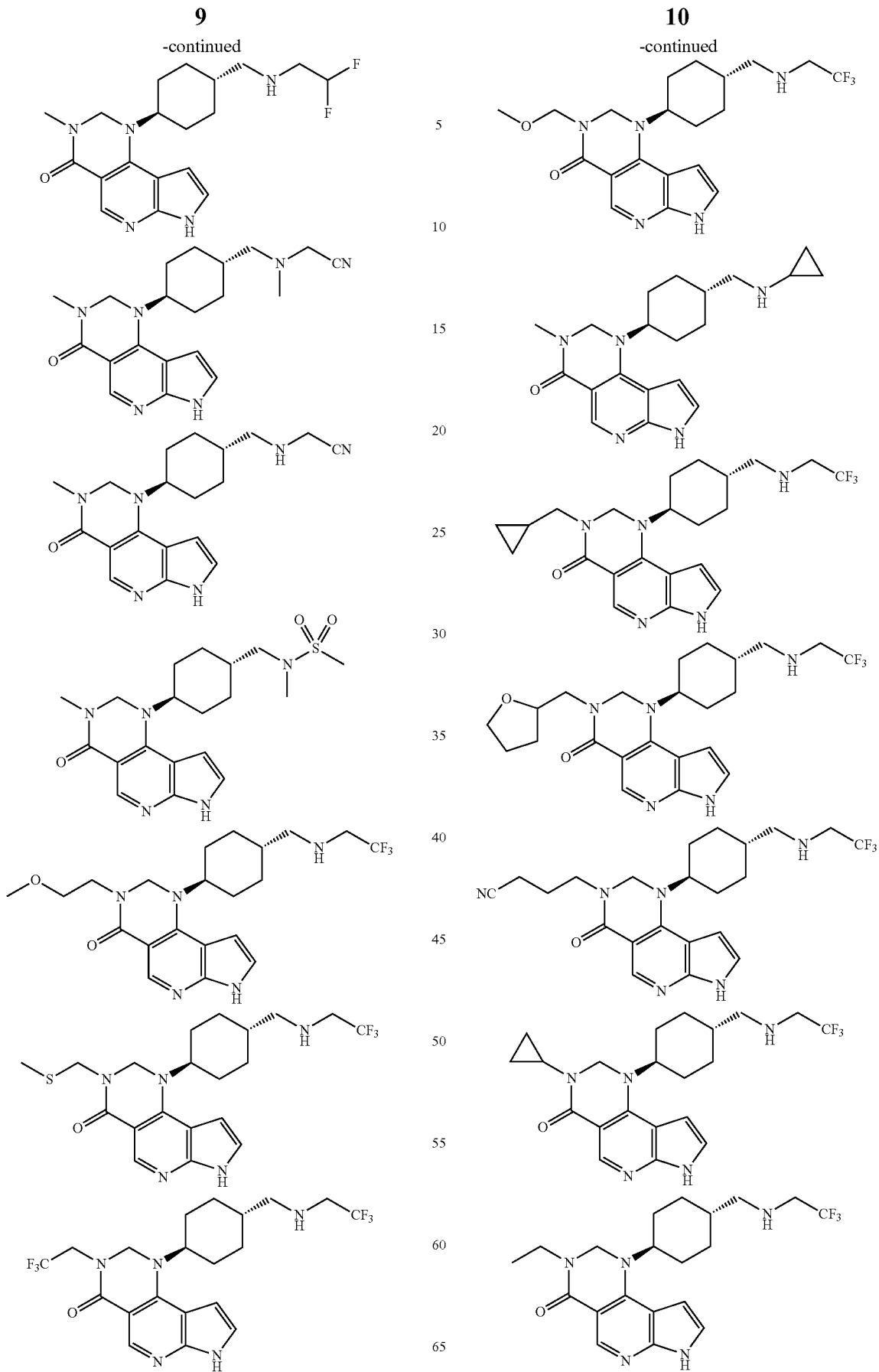

11
-continued
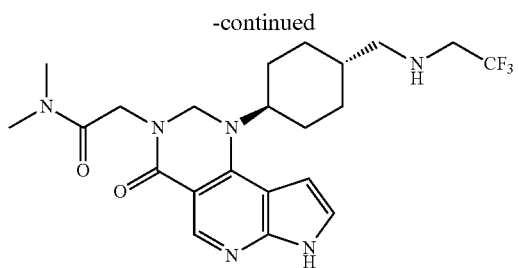
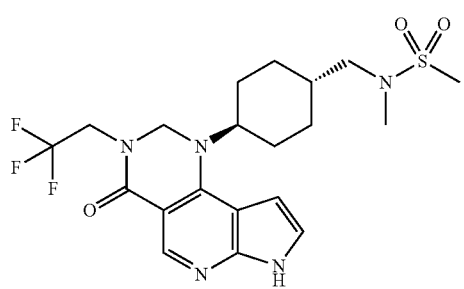
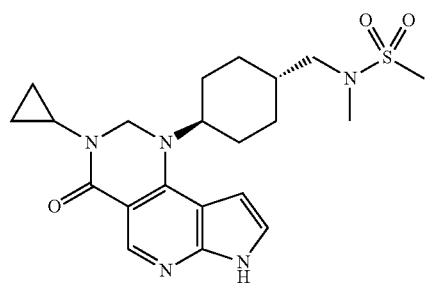
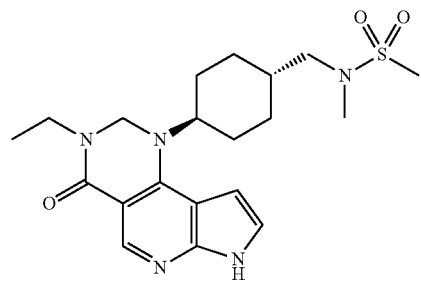
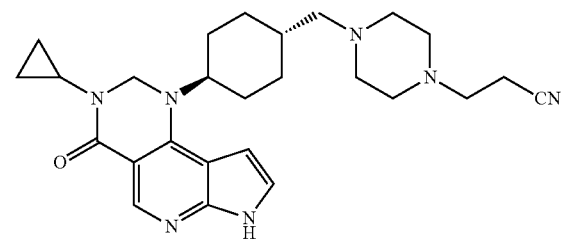
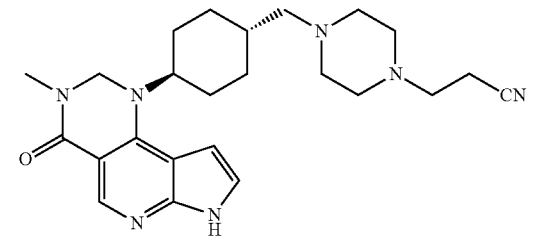
12
-continued
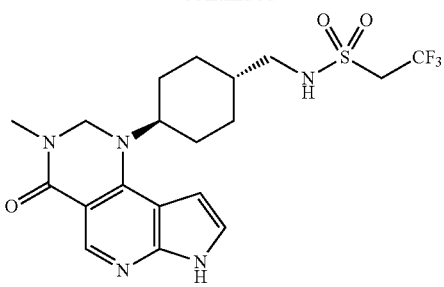
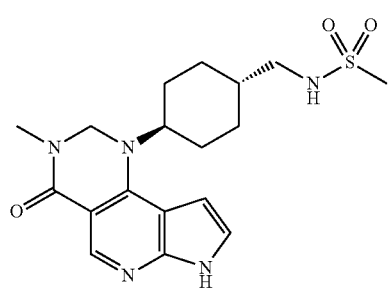
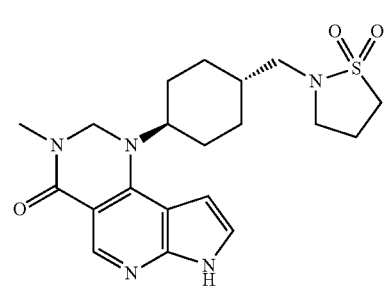
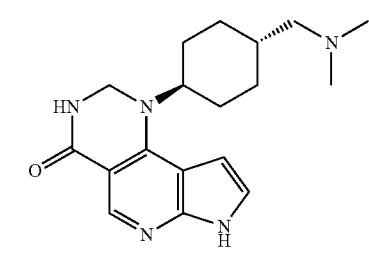
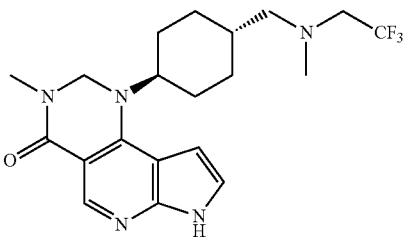
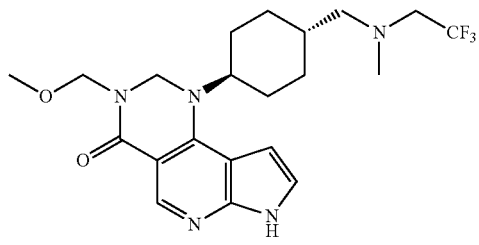

13
-continued
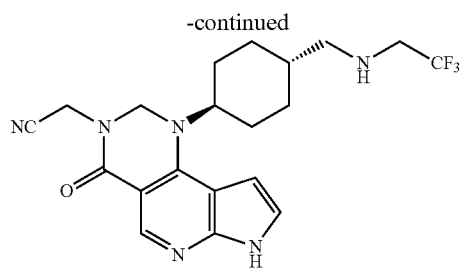
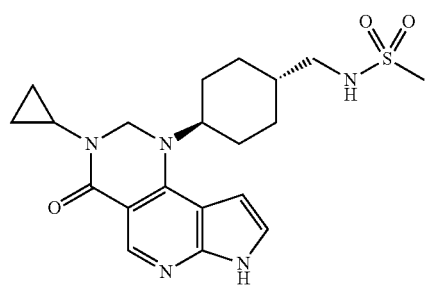
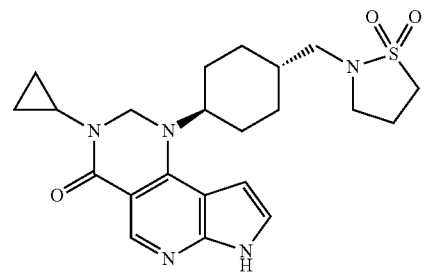
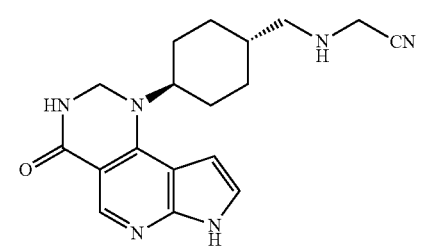
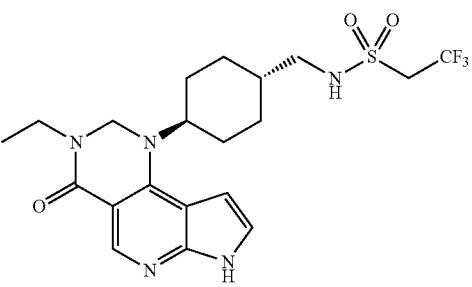
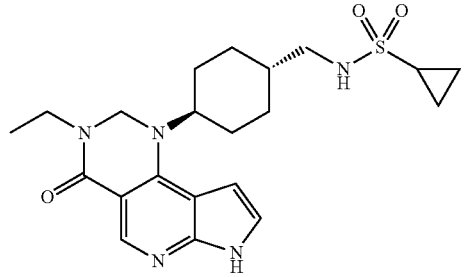
14
-continued
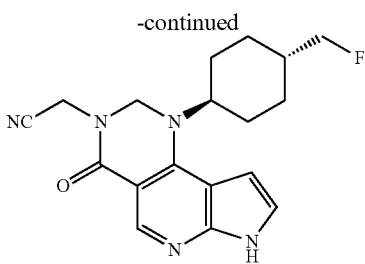
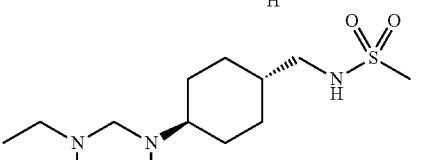
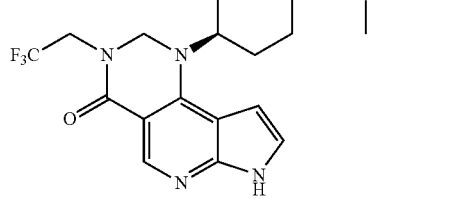
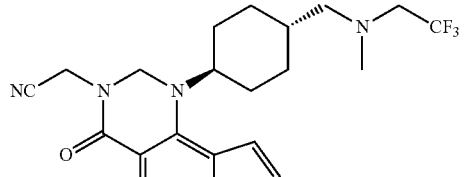
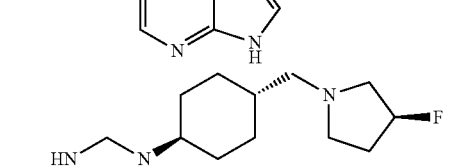
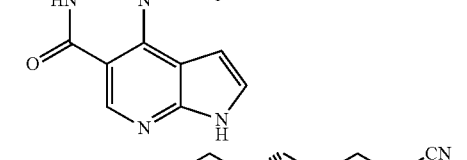
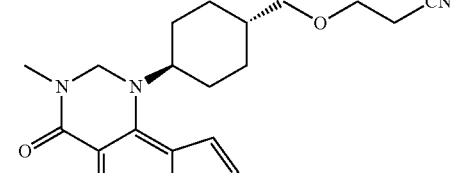
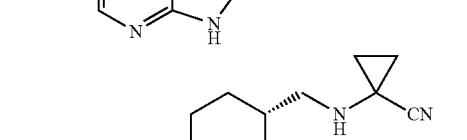
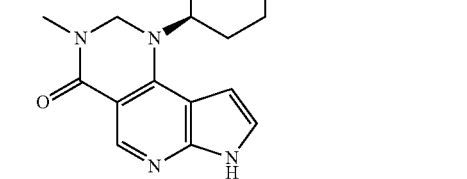

15
-continued
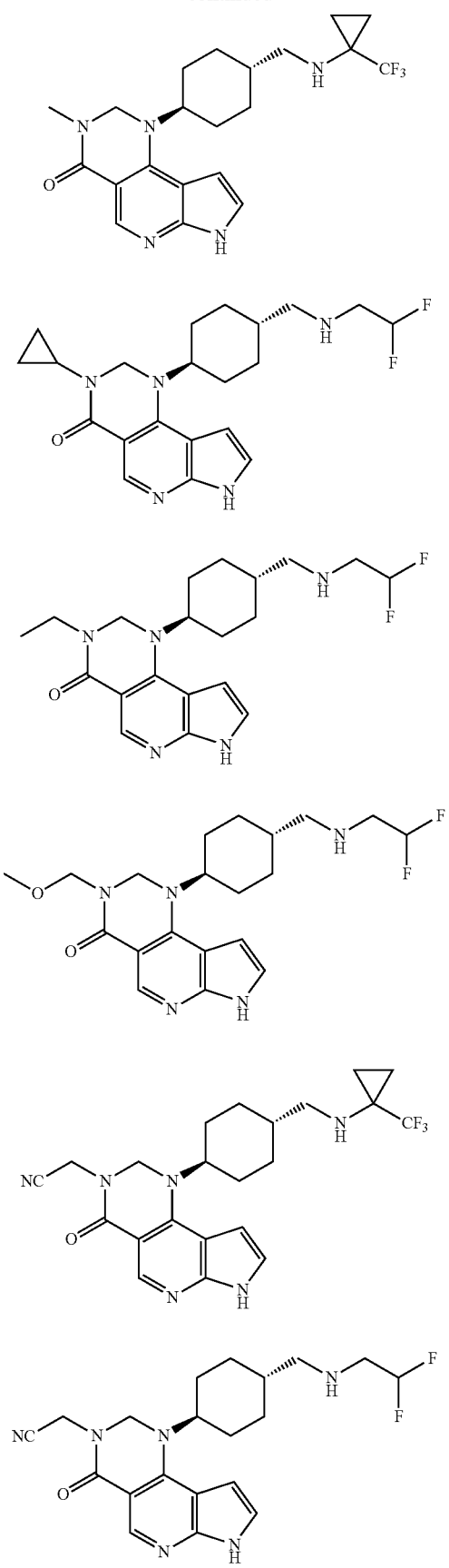
16
-continued
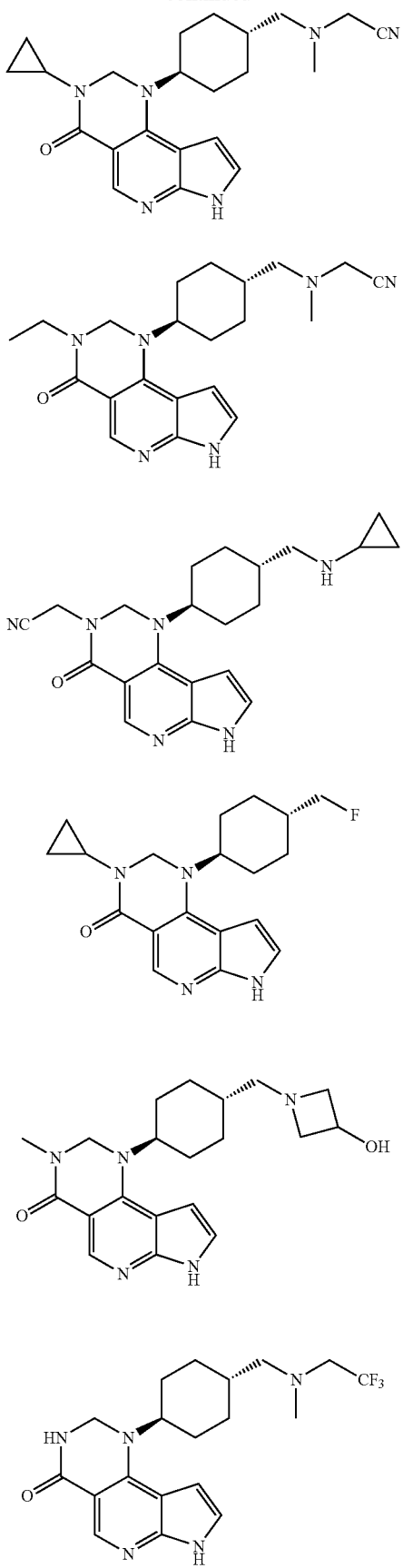

-continued

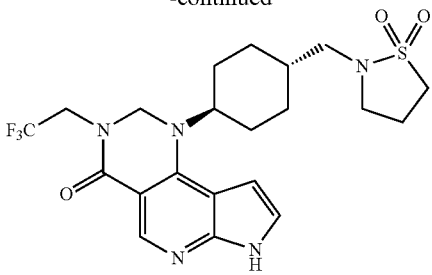

(11) A JAK inhibitor containing the compound, a tautomer or pharmaceutically acceptable salt of the compound or a solvate thereof as defined in any one of (1) to (10) as an active ingredient.
(12) A preventing, therapeutic and/or alleviating agent for diseases against which a JAK inhibitory effect is effective, which contains the JAK inhibitor as defined in (11) as an active ingredient.
(13) A therapeutic agent for rheumatoid arthritis, which contains the JAK inhibitor as defined in (11) as an active ingredient.
(14) A pharmaceutical agent containing the compound, a tautomer or pharmaceutically acceptable salt of the compound or a solvate thereof as defined in any one of (1) to (10) as an active ingredient.

Advantageous Effects of Invention

According to the present invention, it is possible to provide novel tricyclic pyrrolopyridine compounds which have an excellent JAK inhibitory effect and are useful for prevention or treatment of particularly autoimmune diseases, inflammatory diseases and allergic diseases.

DESCRIPTION OF EMBODIMENTS

Now, the present invention will be described in detail.
In the present invention, "n-" denotes normal, "i-" denotes iso, "s-" and "sec-" denote secondary, "t-" and "tert-" denote tertiary, "c-" denotes cyclo, "o-" denotes ortho, "m-" denotes meta, "p-" denotes para, "cis-" denotes a cis-isomer, "trans-" denotes a trans-isomer, "(E)-" denotes an E-isomer, "(Z)-" denotes a Z-isomer, "rac-" and "racemate" denotes racemate, "diastereomixture" denotes a mixture of diastereomers, "Ph" denotes phenyl, "Py" denotes pyridyl, "Me" denotes methyl, "Et" denotes ethyl, "Pr" denotes propyl, "Bu" denotes butyl, "Boc" denotes tertiary butoxycarbonyl, "Cbz" denotes benzyloxycarbonyl, "Ms" denotes methanesulfonyl, "Tf" denotes trifluoromethanesulfonyl, "Ts" denotes p-toluenesulfonyl, "SEM" denotes [2-(trimethylsilyl)ethoxy]methyl, "TIPS" denotes triisopropylsilyl, "TBDPS" denotes tertiary butyldiphenylsilyl, and "TBS" denotes tertiary butyldimethylsilyl.
First, the terms used in the description of the chemical structures in this specification will be described.
"A halogen atom" means a fluorine atom, a chlorine atom, a bromine atom or an iodine atom.
"A $C_{1-3}$ alkyl group" means a methyl group, an ethyl group, a propyl group or an isopropyl group.
"A $C_{1-6}$ alkyl group" means a linear or branched alkyl group containing one to six carbon atoms, such as a methyl group, an ethyl group, a n-propyl group, an isopropyl group, a n-butyl group, an isobutyl group, a t-butyl group, a n-pentyl group or a n-hexyl group.

"A $C_{1-3}$ haloalkyl group" means the above-defined "$C_{1-3}$ alkyl group" which is substituted with one or more halogen atom(s) which may be identical with or different from one another selected from a group of substituents consisting of a fluorine atom, a chlorine atom, a bromine atom and an iodine atom, at optional position(s).
"A $C_{1-6}$ haloalkyl group" means the above-defined "$C_{1-6}$ alkyl group" which is substituted with one or more halogen atom(s) which may be identical with or different from one another selected from a group of substituents consisting of a fluorine atom, a chlorine atom, a bromine atom and an iodine atom, at optional position(s).
"$C_{3-11}$ cycloalkane" means a monocyclic, fused cyclic, bridged cyclic or spirocyclic aliphatic hydrocarbon ring containing 3 to 11 ring-constituting carbon atoms, such as cyclopropane, cyclobutane, cyclopentane, cyclohexane, cycloheptane, cyclooctane, adamantane, bicyclo[3.1.0]octane, bicyclo[2.2.1]heptane or spiro[5.5]undecane.
"A $C_{3-11}$ cycloalkyl group" means a monovalent substituent having one hydrogen atom at an optional position removed from the above-defined "$C_{3-11}$ cycloalkane".
"$C_{3-6}$ cycloalkane" means one having from 3 to 6 ring-constituting carbon atoms among the above-defined "$C_{3-11}$ cycloalkane", such as cyclopropane, cyclobutane, cyclopentane or cyclohexane.
"A $C_{3-6}$ cycloalkyl group" means one having from 3 to 6 ring-constituting carbon atoms among the above-defined "$C_{3-11}$ cycloalkyl group", such as a cyclopropyl group, a cyclobutyl group, a cyclopentyl group or a cyclohexyl group.
"$C_{4-7}$ cycloalkane" means one having from 4 to 7 ring-constituting carbon atoms among the above-defined "$C_{3-11}$ cycloalkane", such as cyclobutane, cyclopentane, cyclohexane or cycloheptane.
"A $C_{1-6}$ alkoxy group" means a linear or branched alkyl group containing one to six carbon atoms, such as a methoxy group, an ethoxy group, a n-propoxy group, an isopropoxy group, a n-butoxy group, an isobutoxy group, a t-butoxy group, a n-pentyloxy group or a n-hexyloxy group.
"A $C_{1-3}$ alkoxy group" means a methoxy group, an ethoxy group, a n-propoxy group or an i-propoxy group.
"A $C_{1-6}$ alkylene group" means a bivalent substituent having one hydrogen atom at an optional position removed from the above-defined "$C_{1-6}$ alkyl group", such as a methylene group, an ethylene group, a propane-1,3-diyl group, a propane-1,2-diyl group, a 2,2-dimethyl-propane-1,3-diyl group, a hexane-1,6-diyl group or a 3-methylbutane-1,2-diyl group.
"A $C_{1-3}$ alkylene group" means a methylene group, an ethylene group, a propane-1,3-diyl group or a propane-1,2-diyl group.
"A $C_{1-6}$ haloalkylene group" means the above-defined "$C_{1-6}$ alkylene group" substituted with one or more halogen atoms which may be identical with or different from one another selected from a group of substituents consisting of a fluorine atom, a chlorine atom, a bromine atom and an iodine atom, at optional position(s).
"A $C_{1-3}$ haloalkylene group" means the above-defined "$C_{1-3}$ alkylene group" substituted with one or more halogen atoms which may be identical with or different from one another selected from a group of substituents consisting of a fluorine atom, a chlorine atom, a bromine atom and an iodine atom, at optional position(s).
"A 4 to 7-membered non-aromatic heterocyclic ring" means a monocyclic non-aromatic heterocyclic ring such that 1) it contains from 4 to 7 ring-constituting atoms,
2) it contains from 1 to 3 hetero atom(s) (the hetero atom means a nitrogen atom, an oxygen atom or a sulfur atom) among the ring-constituting atoms,
3) it may contain a carbonyl group, a double bond or a triple bond in the ring, and
4) in a case where it contains a sulfur atom among the ring-constituting atoms, the sulfur atom may be in a sulfinyl group or a sulfonyl group,
such as azetidine, pyrrolidine, pyrrolidinone, oxazolidine, isoxazolidine, thiazolidine, isothiazolidine, piperazine, piperazinone, piperidine, piperidinone, morpholine, thiomorpholine, azepine, diazepine, oxetane, tetrahydrofuran, 1,3-dioxolane, tetrahydropyran, 1,4-dioxane, oxepane or homomorpholine.

"A 4 to 7-membered non-aromatic heterocyclic group" means a monovalent substituent having one hydrogen atom at an optional position removed from the above-defined "4 to 7-membered non-aromatic heterocyclic ring". The site of bonding is not particularly limited and is optional.

"A $C_{1-6}$ alkylthio group" means a group having one of the above "$C_{1-6}$ alkyl group" bonded to a sulfur atom, such as a methylthio group, an ethylthio group, a n-propylthio group, an isopropylthio group, a n-butylthio group, an isobutylthio group, a t-butylthio group, a n-pentylthio group or a n-hexylthio group.

"A $C_{1-3}$ alkylthio group" means a group having one of the above "$C_{1-3}$ alkyl group" bonded to a sulfur atom, such as a methylthio group, an ethylthio group, a n-propylthio group or an isopropylthio group.

"A $C_{1-6}$ alkylsulfonyl group" means a group having one of the above "$C_{1-6}$ alkyl group" bonded to a sulfonyl group, such as a methylsulfonyl group, an ethylsulfonyl group, a n-propylsulfonyl group, an isopropylsulfonyl group, a n-butylsulfonyl group, an isobutylsulfonyl group, a t-butylsulfonyl group, a n-pentylsulfonyl group or a n-hexylsulfonyl group.

"A $C_{1-3}$ alkylsulfonyl group" means a group having one of the above "$C_{1-3}$ alkyl group" bonded to a sulfonyl group, such as a methylsulfonyl group, an ethylsulfonyl group, a n-propylsulfonyl group or an i-propylsulfonyl group.

"A mono-$C_{1-6}$ alkylamino group" means a group having one of the above "$C_{1-6}$ alkyl group" bonded to an amino group, such as a methylamino group, an ethylamino group, a n-propylamino group, an isopropylamino group, a n-butylamino group, an isobutylamino group, a t-butylamino group, n-pentylamino group or a n-hexylamino group.

"A mono-$C_{1-3}$ alkylamino group" means a methylamino group, an ethylamino group, a n-propylamino group or an isopropylamino group.

"A di-$C_{1-6}$ alkylamino group" means a group having two of the above "$C_{1-6}$ alkyl groups" which may be identical with or different from each other bonded to an amino group, such as a dimethylamino group, a diethylamino group, a di-n-propylamino group, a diisopropylamino group, a di-n-butylamino group, a diisobutylamino group, a di-t-butylamino group, a di-n-pentylamino group, a di-n-hexylamino group, an N-ethyl-N-methylamino group, an N-methyl-N-n-propylamino group, an N-isopropyl-N-methylamino group, an N-n-butyl-N-methylamino group, an N-isobutyl-N-methylamino group, an N-t-butyl-N-methylamino group, an N-methyl-N-n-pentylamino group, an N-n-hexyl-N-methylamino group, an N-ethyl-N-n-propylamino group, an N-ethyl-N-isopropylamino group, an N-n-butyl-N-ethylamino group, an N-ethyl-N-isobutylamino group, an N-t-butyl-N-ethylamino group, an N-ethyl-N-n-pentylamino group or an N-ethyl-N-n-hexylamino group.

"A di-$C_{1-3}$ alkylamino group" means a dimethylamino group, a diethylamino group, a di-n-propylamino group, a diisopropylamino group, an N-ethyl-N-methylamino group, an N-methyl-N-n-propylamino group, an N-isopropyl-N-methylamino group, an N-ethyl-N-n-propylamino group or an N-ethyl-N-isopropylamino group.

"A mono $C_{1-6}$ alkylaminocarbonyl group" means a group having one of the above "mono $C_{1-6}$ alkylamino group" bonded to a carbonyl group, such as a methylaminocarbonyl group, an ethylaminocarbonyl group, a n-propylaminocarbonyl group, an isopropylaminocarbonyl group, a n-butylaminocarbonyl group, an isobutylaminocarbonyl group, a t-butylaminocarbonyl group, a n-pentylaminocarbonyl group or a n-hexylaminocarbonyl group.

"A mono-$C_{1-3}$ alkylaminocarbonyl group" means a methylaminocarbonyl group, an ethylaminocarbonyl group, a n-propylaminocarbonyl group or an isopropylaminocarbonyl group.

"A di-$C_{1-6}$ alkylaminocarbonyl group" means a group having one of the above "di-$C_{1-6}$ alkylamino group" bonded to a carbonyl group, such as a dimethylaminocarbonyl group, a diethylaminocarbonyl group, a di-n-propylaminocarbonyl group, a diisopropylaminocarbonyl group, a di-n-butylaminocarbonyl group, a diisobutylaminocarbonyl group, a di-t-butylaminocarbonyl group, a di-n-pentylaminocarbonyl group, a di-n-hexylaminocarbonyl group, an N-ethyl-N-methylaminocarbonyl group, an N-methyl-N-n-propylaminocarbonyl group, an N-isopropyl-N-methylaminocarbonyl group, an N-n-butyl-N-methylaminocarbonyl group, an N-isobutyl-N-methylaminocarbonyl group, an N-t-butyl-N-methylaminocarbonyl group, an N-methyl-N-n-pentylaminocarbonyl group, an N-n-hexyl-N-methylaminocarbonyl group, an N-ethyl-N-n-propylaminocarbonyl group, an N-ethyl-N-isopropylaminocarbonyl group, an N-n-butyl-N-ethylaminocarbonyl group, an N-ethyl-N-isobutylaminocarbonyl group, an N-t-butyl-N-ethylaminocarbonyl group, an N-ethyl-N-n-pentylaminocarbonyl group or an N-ethyl-N-n-hexylaminocarbonyl group.

"A di-$C_{1-3}$ alkylaminocarbonyl group" means a dimethylaminocarbonyl group, a diethylaminocarbonyl group, a di-n-propylaminocarbonyl group, a diisopropylaminocarbonyl group, an N-ethyl-N-methylaminocarbonyl group, an N-methyl-N-n-propylaminocarbonyl group, an N-isopropyl-N-methylaminocarbonyl group, an N-ethyl-N-n-propylaminocarbonyl group or an N-ethyl-N-isopropylaminocarbonyl group.

"A cyano-substituted $C_{1-6}$ alkyl group" means the above-defined "$C_{1-6}$ alkyl group" substituted with one or more cyano group(s) at optional position(s).

"A cyano-substituted $C_{1-3}$ alkyl group" means the above-defined "$C_{1-3}$ alkyl group" substituted with one or more cyano group(s) at optional position(s).

"A $C_{1-6}$ alkylsulfonyl-substituted $C_{1-6}$ alkyl group" means the above-defined "$C_{1-6}$ alkyl group" substituted with one or more of the above-defined "$C_{1-6}$ alkylsulfonyl group(s)" at optional position(s).

"A $C_{1-3}$ alkylsulfonyl-substituted $C_{1-3}$ alkyl group" means the above-defined "$C_{1-3}$ alkyl group" substituted with one of the above-defined "$C_{1-3}$ alkylsulfonyl group" at an optional position.

"A cyano-substituted $C_{3-6}$ cycloalkyl group" means the above-defined "$C_{3-6}$ cycloalkyl group" substituted with one or more cyano group(s) at optional position(s).

"A $C_{1-6}$ haloalkyl-substituted $C_{3-6}$ cycloalkyl group" means the above-defined "$C_{3-6}$ cycloalkyl group" substituted with one or more of the above-defined "$C_{1-6}$ haloalkyl group(s)" at optional position(s).

"A $C_{1-3}$ haloalkyl-substituted $C_{3-6}$ cycloalkyl group" means the above-defined "$C_{3-6}$ cycloalkyl group" substituted with one or more of the above-defined "$C_{1-3}$ haloalkyl group(s)" at optional position(s).

Now, preferred structures of the respective substituents in the present invention will be described.

The substitute $R^1$ is preferably a hydrogen atom,
a $C_{1-3}$ haloalkyl group,
a $C_{3-6}$ cycloalkyl group, or
a $C_{1-3}$ alkyl group
(the $C_{1-3}$ alkyl group is not substituted or is substituted with one cyano group, methoxy group, methylthio group, dimethylaminocarbonyl group, cyclopropyl group or tetrahydrofuran-2-yl group).

The substituted $R^1$ is more preferably a $C_{1-3}$ haloalkyl group,
a $C_{3-6}$ cycloalkyl group, or
a $C_{1-3}$ alkyl group
(the $C_{1-3}$ alkyl group is not substituted or is substituted with one cyano group, methoxy group, methylthio group, dimethylaminocarbonyl group, cyclopropyl group or tetrahydrofuran-2-yl group).

The substituent $R^1$ is further preferably a methyl group,
a cyanomethyl group,
a methoxymethyl group,
a methylthiomethyl group,
a dimethylaminocarbonylmethyl group,
a cyclopropylmethyl group,
a (tetrahydrofuran-2-yl)methyl group,
an ethyl group,
a 2,2,2-trifluoroethyl group,
a 2-methoxyethyl group,
a 3-cyanopropyl group, or
a cyclopropyl group.

The substituents $R^2$ and $R^3$ are preferably a hydrogen atom.

The ring A is preferably $C_{4-7}$ cycloalkane.
The ring A is more preferably cyclohexane.

As a preferred example of the substituent $L^1$, a single bond may be mentioned.

As another preferred example of the substituent $L^1$, a $C_{1-3}$ alkylene group may be mentioned. The $C_{1-3}$ alkylene group is more preferably a methylene group.

As another preferred example of the substituent $L^1$, a $C_{1-3}$ haloalkylene group may be mentioned. The $C_{1-3}$ haloalkylene group is more preferably a fluoromethylene group or a difluoromethylene group.

As a preferred example of the substituent $R^4$, a hydrogen atom may be mentioned.

As another preferred example of the substituent $R^4$, a halogen atom may be mentioned.

As another preferred example of the substituent $R^4$,
$NR^aR^b$,
$NR^cS(=O)_2R^d$,
$OR^e$
the formula (II)-1 or formula (II)-2 may be mentioned:

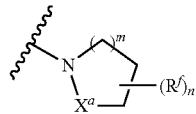
(II)-1

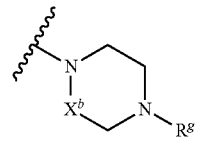
(II)-2 and as a more preferred example,
$NR^aR^b$,
$NR^cS(=O)_2R^d$, or
$OR^e$ may be mentioned.

The substituent $R^a$ is preferably a $C_{1-3}$ alkyl group,
a cyano-substituted $C_{1-3}$ alkyl group,
a $C_{1-3}$ haloalkyl group,
a $C_{3-6}$ cycloalkyl group,
a cyano-substituted $C_{3-6}$ cycloalkyl group, or
a $C_{1-3}$ haloalkyl-substituted $C_{3-6}$ cycloalkyl group.

The substituent $R^a$ is more preferably a methyl group,
a cyanomethyl group,
a 2,2,2-trifluoroethyl group,
a 2,2-difluoroethyl group,
a 2-bromo-2,2-difluoroethyl group,
a cyclopropyl group,
a 1-cyanocyclopropyl group, or
a 1-trifluoromethylcyclopropyl group.

The substituent $R^b$ is preferably a hydrogen atom or a $C_{1-3}$ alkyl group.

The substituent $R^b$ is more preferably a hydrogen atom or a methyl group.

The substituent $R^c$ is preferably a hydrogen atom or a $C_{1-3}$ alkyl group.

The substituent $R^c$ is more preferably a hydrogen atom or a methyl group.

The substituent $R^d$ is preferably a $C_{1-3}$ alkyl group,
a $C_{1-3}$ haloalkyl group, or
a cyclopropyl group.

The substituent $R^d$ is more preferably a methyl group,
a 2,2,2-trifluoroethyl group, or
a cyclopropyl group.

The substituent $R^e$ is preferably a hydrogen atom or a cyano-substituted $C_{1-3}$ alkyl group.

The substituent $R^e$ is more preferably a hydrogen atom or a 2-cyanoethyl group.

The substituent $R^f$ is preferably a halogen atom or a hydroxy group.

The substituent $R^g$ is preferably a cyano-substituted $C_{1-3}$ alkyl group.

The substituent $R^g$ is more preferably a 2-cyanoethyl group.

The substituent $X^a$ is preferably $S(=O)_2$ or $CH_2$.
The substituent $X^b$ is preferably $CH_2$.
n is preferably 0 or 1.
m is preferably 0 or 1.

A preferred example of the structure of the compound of the present invention may be mentioned by combining the above-described preferred substituents in the structure of the formula (I). As a particularly preferred example of the structure of the compound of the present invention, the following may be mentioned.

1)
A compound represented by the formula (I) wherein the substituents are a combination of any of the following, a tautomer or pharmaceutically acceptable salt of the compound or a solvate thereof:

(I)

wherein the ring A is $C_{4-7}$ cycloalkane,
$R^1$ is a hydrogen atom,
a $C_{3-6}$ cycloalkyl group,
a $C_{1-3}$ haloalkyl group, or
a $C_{1-3}$ alkyl group
(the $C_{1-3}$ alkyl group is not substituted or is substituted with one hydroxy group, cyano group, $C_{1-3}$ alkoxy group, $C_{1-3}$ alkylthio group, $C_{1-3}$ alkylsulfonyl group, carboxy group, carbamoyl group, mono-$C_{1-3}$ alkylaminocarbonyl group, di-$C_{1-3}$ alkylaminocarbonyl group, $C_{3-6}$ cycloalkyl group or 4 to 7-membered non-aromatic heterocyclic group), each of $R^2$ and $R^3$ is independently a hydrogen atom, or
a $C_{1-3}$ alkyl group,
$L^1$ is a single bond,
a $C_{1-3}$ alkylene group, or
a $C_{1-3}$ haloalkylene group,
$R^4$ is a hydrogen atom,
a halogen atom,
$NR^aR^b$,
$NR^cS(=O)_2R^d$,
$OR^e$,
the formula (II)-1, or
the formula (II)-2:

(II)-1

(II)-2 each of $R^a$ and $R^e$ is independently a hydrogen atom,
a $C_{1-3}$ alkyl group,
a cyano-substituted $C_{1-3}$ alkyl group,
a $C_{1-3}$ alkylsulfonyl-substituted $C_{1-3}$ alkyl group,
a $C_{1-3}$ haloalkyl group,
a $C_{3-6}$ cycloalkyl group,
a cyano-substituted $C_{3-6}$ cycloalkyl group, or
a $C_{1-3}$ haloalkyl-substituted $C_{3-6}$ cycloalkyl group,
each of $R^b$ and $R^c$ is independently a hydrogen atom,
a $C_{1-3}$ alkyl group, or
a $C_{1-3}$ haloalkyl group,
$R^d$ is a $C_{1-3}$ alkyl group,
a cyano-substituted $C_{1-3}$ alkyl group,
a $C_{1-3}$ haloalkyl group,
a $C_{3-6}$ cycloalkyl group,
a cyano-substituted $C_{3-6}$ cycloalkyl group, or
a $C_{1-3}$ haloalkyl-substituted $C_{3-6}$ cycloalkyl group, $R^f$ is a halogen atom,
a hydroxy group,
a cyano group,
a $C_{1-3}$ alkyl group, or
a $C_{1-3}$ haloalkyl group,
$R^g$ is a hydrogen atom,
a $C_{1-3}$ alkyl group,
a cyano-substituted $C_{1-3}$ alkyl group, or
a $C_{1-3}$ haloalkyl group,
each of $X^a$ and $X^b$ is independently
$S(=O)_2$,
$C=O$, or
$CH_2$,
n is 0, 1 or 2 (when n is 2, each $R^f$ may be identical with or different from each other), and
m is 0, 1 or 2.

2) The compound, a tautomer or pharmaceutically acceptable salt of the compound or a solvate thereof according to the above 1), wherein the ring A is cyclohexane.

3) The compound, a tautomer or pharmaceutically acceptable salt of the compound or a solvate thereof according to the above 1), which is represented by the formula (III):

(III)

4) The compound, a tautomer or pharmaceutically acceptable salt of the compound or a solvate thereof according to any one of the above 1) to 3), wherein the substituent $R^1$ is a hydrogen atom.

5) The compound, a tautomer or pharmaceutically acceptable salt of the compound or a solvate thereof according to any one of the above 1) to 3), wherein the substituent $R^1$ is any one of the formulae (V)-1 to (V)-12:

(V)-1

(V)-2

(V)-3

(V)-4

(V)-5

6) The compound, a tautomer or pharmaceutically acceptable salt of the compound or a solvate thereof according to any one of the above 1) to 5), wherein the substituent $L^1$ is a single bond.

7) The compound, a tautomer or pharmaceutically acceptable salt of the compound or a solvate thereof according to any one of the above 1) to 5), wherein the substituent $L^1$ is a methylene group.

8) The compound, a tautomer or pharmaceutically acceptable salt of the compound or a solvate thereof according to any one of the above 1) to 5), wherein the substituent $L^1$ is a fluoromethylene group or a difluoromethylene group.

9) The compound, a tautomer or pharmaceutically acceptable salt of the compound or a solvate thereof according to any one of the above 1) to 8), wherein the substituent $R^4$ is a hydrogen atom.

10) The compound, a tautomer or pharmaceutically acceptable salt of the compound or a solvate thereof according to any one of the above 1) to 8), wherein the substituent $R^4$ is any one of the formulae (VI)-1 to (VI)-20:

-continued

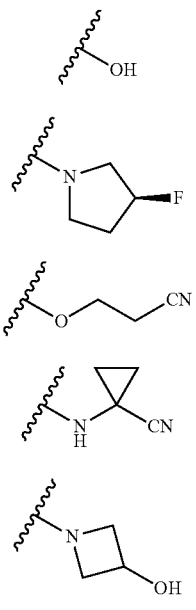

(VI)-16
(VI)-17
(VI)-18
(VI)-19
(VI)-20

11) The compound, a tautomer or pharmaceutically acceptable salt of the compound or a solvate thereof according to any one of the above 1) to 5), wherein the substituent $L^1$ is a single bond, and the substituent $R^4$ is a hydrogen atom.

12) The compound, a tautomer or pharmaceutically acceptable salt of the compound or a solvate thereof according to any one of the above 1) to 5), wherein the substituent $L^1$ is a fluoromethylene group or a difluoromethylene group, and the substituent $R^4$ is a hydrogen atom.

13) The compound, a tautomer or pharmaceutically acceptable salt of the compound or a solvate thereof according to any one of the above 1) to 5), wherein the substituent $L^1$ is a methylene group, and the substituent $R^4$ is any one of the formulae (VI)-1 to (VI)-20:

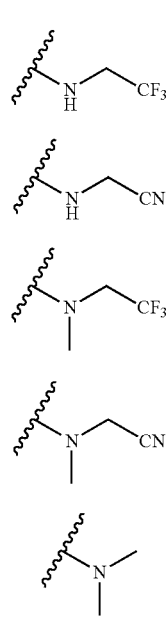

(VI)-1
(VI)-2
(VI)-3
(VI)-4
(VI)-5

-continued

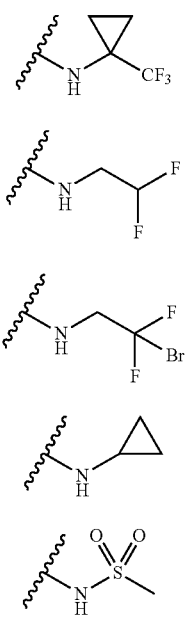

(VI)-6
(VI)-7
(VI)-8
(VI)-9
(VI)-10

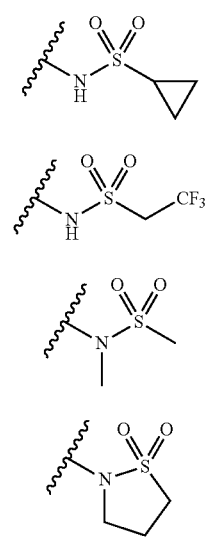

(VI)-11
(VI)-12
(VI)-13
(VI)-14
(VI)-15

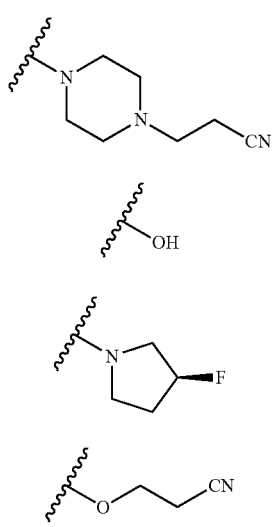

(VI)-16
(VI)-17
(VI)-18

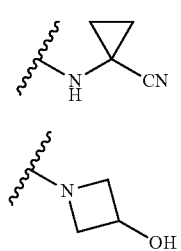

(VI)-19

(VI)-20

14) A JAK inhibitor which contains the compound, a tautomer or pharmaceutically acceptable salt of the compound or a solvate thereof as defined in any one of the above 1) to 13) as an active ingredient.

15) A preventing, therapeutic or alleviating agent for diseases against which a JAK inhibitory effect is effective, which contains the JAK inhibitor as defined in the above 14) as an active ingredient.

16) A therapeutic agent for rheumatoid arthritis, which contains the JAK inhibitor as defined in the above 14) as an active ingredient.

17) A pharmaceutical agent which contains the compound, a tautomer or pharmaceutically acceptable salt of the compound or a solvate thereof as defined in any one of the above 1) to 13) as an active ingredient.

The compounds of the present invention may be prepared by the following process, however, the following production process is an example of a common production process, and the process is not limited to the following production process.

The compounds of the present invention can be usually purified by column chromatography, thin-layer chromatography, high performance liquid chromatography (HPLC), high performance liquid chromatography/mass spectrometry (LC/MS) or the like and as the case requires, compounds with higher purity may be obtained by recrystallization or washing with a solvent.

In the description of the common process for producing the compounds of the present invention, the solvent is not particularly limited so long as it is stable under the reaction conditions and is inert to the reaction, and may, for example, be a sulfoxide type solvent (such as dimethylsulfoxide), an amide type solvent (such as N,N-dimethylformamide or N,N-dimethylacetamide), an ether type solvent (such as ethyl ether, 1,2-dimethoxyethane, tetrahydrofuran, 1,4-dioxane or cyclopentyl methyl ether), a halogen type solvent (such as dichloromethane, chloroform or 1,2-dichlorothene), a nitrile type solvent (such as acetonitrile or propionitrile), an aromatic hydrocarbon type solvent (such as benzene or toluene), an aliphatic hydrocarbon type solvent (such as hexane or heptane), an ester type solvent (such as ethyl acetate), an alcohol type solvent (such as methanol, ethanol, 1-propanol, 2-propanol or ethylene glycol), or water. Further, the reaction may be carried out in an optional mixture of the above solvents or without the solvent.

In a case where a plurality of compounds are to be reacted, their equivalency may be properly determined. That is, the compounds may be used in equivalent amounts, or a specific compound may be used in excess.

In the common process for producing the compounds of the present invention, the reaction temperature may be properly set within a range of from −78° C. to the boiling point of the solvent used for the reaction, and the present production process may be carried out under normal pressure, under elevated pressure, under irradiation with microwaves, etc.

Particularly in production of compounds (1)-6, (1)-7, (1)-11, (2)-2 and (2)-3, reaction under irradiation with microwaves is effective in some cases so as to allow the reaction to proceed smoothly.

An acid to be used in the common process for producing the compounds of the present invention may, for example, be an organic acid (such as acetic acid, trifluoroacetic acid or p-toluenesulfonic acid) or an inorganic acid (such as sulfuric acid or hydrochloric acid).

Particularly in production of compound (1)-11, reaction in the presence of an acid is effective in some cases so as to allow the reaction to proceed smoothly.

Particularly in production of compounds (1)-7 and (2)-3, reaction in the presence of an acid catalyst such as ytterbium (III) trifluoromethanesulfonate or scandium(III) trifluoromethanesulfonate is effective in some cases so as to allow the reaction to proceed smoothly.

A base to be used in the common process for producing the compounds of the present invention may, for example, be an organic metal compound (such as n-butyllithium, s-butyllithium, lithium diisopropylamide or isopropylmagnesium bromide), an organic base (such as triethylamine, N,N-diisopropylethylamine or N,N-dimethylaminopyridine) or an inorganic base (such as sodium carbonate, potassium carbonate, cesium carbonate, sodium hydroxide, potassium hydroxide or sodium hydride).

Particularly in production of compounds (1)-6 and (2)-2, reaction in the presence of a base is preferred in some cases so as to allow the reaction to proceed smoothly.

In the following common process for producing the compounds of the present invention, general formulae of intermediates and final products in the respective steps are shown, and the general formulae of the intermediates and the final products include derivatives protected by a protecting group. Here, a derivative protected by a protecting group means a compound which may be induced to a desired product by hydrolysis, reduction, oxidation, alkylation or the like as the case requires, and includes a compound protected by a protecting group acceptable in terms of synthetic organic chemistry.

Protection and deprotection may be carried out using a known protecting group by a protection/deprotection reaction (for example, Protective Groups in Organic Synthesis, Fourth edition, T. W. Greene, John Wiley & Sons Inc., 2006).

Hydrolysis, reduction and oxidation may be carried out by a known functional group conversion method (for example, Comprehensive Organic Transformations, Second Edition, R. C. Larock, Wiley-VCH, 1999).

A process for producing the tricyclic pyrrolopyridine compound represented by the formula (I) will be described.

Among compounds represented by the formula (I), compounds (1)-8, (1)-9, (1)-11 and (1)-12 may be produced, for example, by the following reaction scheme (in the scheme, PG$^1$ represents a hydrogen atom or a protecting group such as a Ts group, a TIPS group or a SEM group, and the other symbols are as defined above):

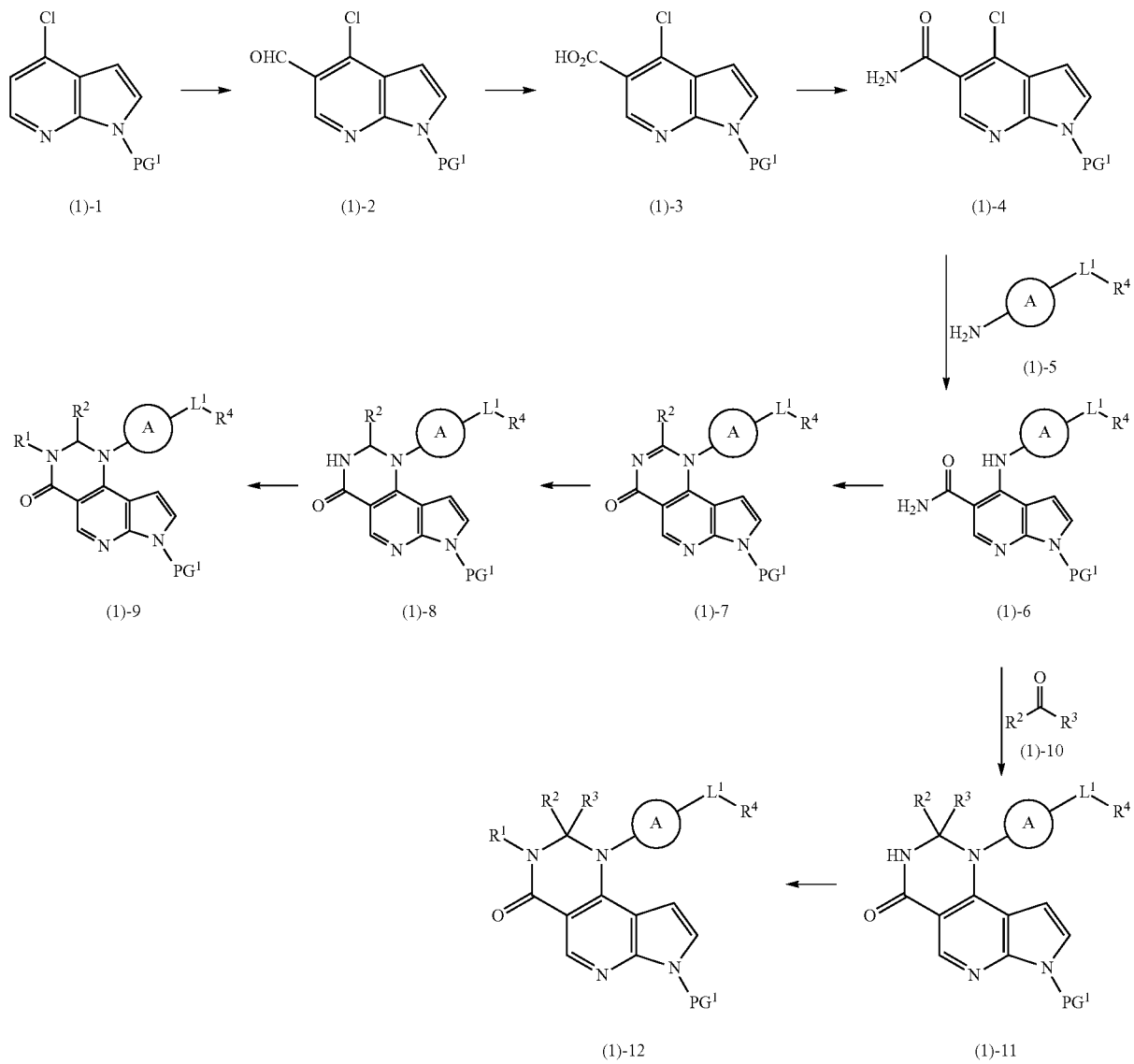

Compound (1)-2 is obtained by carrying out lithiation at −78° C. to room temperature using compound (1)-1 and an organic metal reagent such as n-butyllithium or s-butyllithium, and then reacting N,N-dimethylformamide.

Compound (1)-3 may be synthesized at room temperature to the refluxing temperature using compound (1)-2 and an oxidizing agent such as potassium permanganate or sodium chlorite.

Compound (1)-4 may be synthesized by forming an acid chloride at 0° C. to the refluxing temperature using compound (1)-3 and thionyl chloride or phosphorus oxychloride, followed by reaction at 0° C. to the refluxing temperature using ammonia/methanol or its equivalent.

Compound (1)-6 may be synthesized at room temperature to the refluxing temperature using compound (1)-4 and amine derivative (1)-5. Further, it may be prepared also under reaction conditions used for Buchwald-Hartwig reaction (for example, Advanced Synthesis & Catalysis, 2000, 346, pp. 1599-1626). The metal species and the ligand used in the reaction are not particularly limited, and tris(dibenzylideneacetone)dipalladium(0), tetrakis(triphenylphosphine)palladium(0), palladium(II) acetate or the like and 4,5-bis(diphenylphosphino)-9,9-dimethylxanthene (Xantphos), 2-dicyclohexylphosphino-2',6'-dimethoxybiphenyl (SPhos), 2-dicyclohexylphosphino-2',4',6'-triisopropylbiphenyl (XPhos) or the like may properly be combined.

Compound (1)-7 may be synthesized at room temperature to the refluxing temperature using compound (1)-6 and $R^2CO_2R^Q$, $R^2C(OR^Q)_3$ or the like ($R^Q$ is a hydrogen atom or a $C_{1-6}$ alkyl group).

Compound (1)-8 may be synthesized at 0° C. to the refluxing temperature using compound (1)-7 and a reducing agent such as sodium borohydride.

Compound (1)-11 may be synthesized at room temperature to the refluxing temperature using compound (1)-6 and carbonyl compound (1)-10.

Compounds (1)-9 and (1)-12 may be synthesized at −78° C. to the refluxing temperature using compound (1)-8 or (1)-11, an electrophile represented by $R^1$-$R^L$ ($R^L$ is a leaving group such as a halogen atom, a methanesulfonyloxy group or a p-toluenesulfonyloxy group, and $R^1$-$R^L$ may, for example, be an alkyl halide, a methanesulfonate or an acid halide) and a base such as potassium carbonate or sodium hydroxide.

Compounds (1)-8, (1)-9, (1)-11 and (1)-12 wherein $PG^1$ is a protecting group may further be subjected to deprotection to obtain the corresponding compounds wherein $PG^1$ is a hydrogen atom.

Among compounds represented by the formula (I), compounds (2)-8, (2)-10 and (2)-11 may be produced, for example, by the following reaction scheme (in the scheme, $PG^1$ represents a hydrogen atom or a protecting group such as a Ts group, a TIPS group or a SEM group, $PG^2$ represents a protecting group such as a TIPS group or a TBS group, and the other symbols are as defined above):

Compound (2)-4 may be synthesized at 0° C. to the refluxing temperature using compound (2)-3 and a reducing agent such as sodium borohydride.

Compound (2)-5 may be synthesized by alkylation at −78° C. to the refluxing temperature using compound (2)-4, an electrophile represented by $R^1$-$R^L$ ($R^L$ is a leaving group such as a halogen atom, a methanesulfonyloxy group or a p-toluenesulfonyloxy group, and $R^1$-$R^L$ may, for example, be an alkyl halide, a methanesulfonate or an acid halide) and a base such as potassium carbonate or sodium hydroxide, followed by deprotection of $PG^2$.

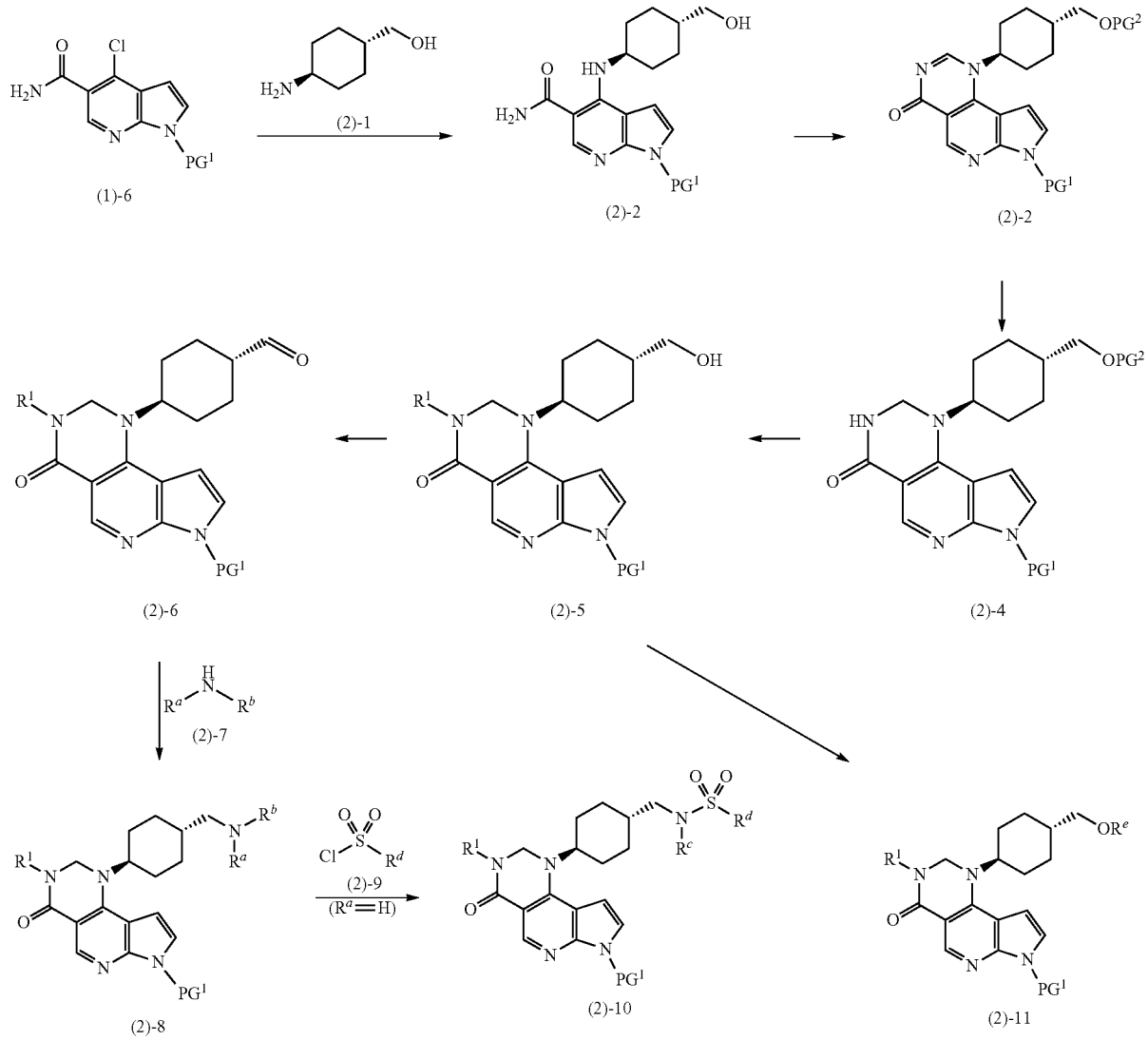

Compound (2)-2 may be synthesized at room temperature to the refluxing temperature using compounds (1)-6 and (2)-1.

Compound (2)-3 may be synthesized by protecting the hydroxy group of compound (2)-2 with $PG^2$, followed by reaction at room temperature to the refluxing temperature using methyl orthoformate or its equivalent.

Compound (2)-6 may be synthesized at −78° C. to the refluxing temperature using compound (2)-5 and an oxidizing agent such as 2-iodoxybenzoic acid or pyridinium chlorochromate.

Compound (2)-8 may be synthesized at room temperature to the refluxing temperature using compound (2)-6, compound (2)-7 and a reducing agent such as 2-picoline borane or sodium triacetoxyborohydride.

Compound (2)-10 may be synthesized at −78° C. to the refluxing temperature using compound (2)-8 wherein $R^a$ is a hydrogen atom and sulfonyl chloride (2)-9 with a base such as potassium carbonate or triethylamine.

Compound (2)-11 may be synthesized at −78° C. to the refluxing temperature using compound (2)-5, an electrophile such as $R^e$—$R^L$ ($R^L$ means a leaving group such as a halogen atom, a methanesulfonyloxy group or a p-toluenesulfonyloxy group, and $R^e$—$R^L$ may, for example, be an alkyl halide, a methanesulfonate or an acid halide), an α, β unsaturated nitrile compound or an α, β unsaturated sulfonyl compound, and a base such as potassium carbonate or sodium carbonate.

Compounds (2)-5, (2)-8 and (2)-10 wherein $PG^1$ is a protecting group may further be subjected to deprotection to obtain the corresponding compounds wherein $PG^1$ is a hydrogen atom.

In the present invention, the tricyclic pyrrolopyridine compounds represented by the formula (I) may be present in the form of endocyclic or exocyclic tautomers or geometric isomers, their mixtures, or mixtures of the isomers. Further, when the compounds of the present invention have an asymmetric center or have an asymmetric center caused by isomerization, they may be in the form of optical isomers or in the form of mixtures containing them in certain ratios. Further, in the case of compounds having two or more asymmetric centers, diastereomers due to each optical isomerism are present. The compounds of the present invention may be in the form of any one of diastereomers or in the form of any of all such isomers in certain ratios. For example, a diastereomer may be isolated from a mixture of the isomers by a method well known to those skilled in the art, such as fractional crystallization method, and an optically active substance may be also obtained by organic chemical methods known for such a purpose.

The tricyclic pyrrolopyridine compounds represented by the formula (I) of the present invention or pharmaceutically acceptable salts thereof may be in the form of arbitrary crystals or arbitrary hydrates, depending on the production conditions. The present invention covers these crystals, hydrates and their mixtures. These compounds may be also in the form of a solvate with an organic solvent such as acetone, ethanol, 1-propanol or 2-propanol, and the present invention covers any of these forms.

The present invention covers pharmaceutically acceptable salts of the compounds of the formula (I) of the present invention.

The compounds represented by the formula (I) of the present invention may be converted to pharmaceutically acceptable salts or may be dissociated from the resulting salts, if necessary. The pharmaceutically acceptable salt of the present invention may, for example, be a salt with an alkali metal (such as lithium, sodium or potassium), an alkaline earth metal (such as magnesium or calcium), ammonium, an organic base, an amino acid, an inorganic acid (such as hydrochloric acid, hydrobromic acid, phosphoric acid or sulfuric acid), or an organic acid (such as acetic acid, citric acid, maleic acid, fumaric acid, tartaric acid, benzenesulfonic acid, methanesulfonic acid or p-toluenesulfonic acid).

The present invention also covers prodrugs of the compounds represented by the formula (I) of the present invention.

A prodrug is a derivative of a pharmaceutical compound having a chemically or metabolically degradable group and is a compound which is induced into a pharmacologically active compound by degradation upon solvolysis or under physiological conditions in vivo. Methods for selecting or producing appropriate prodrugs are disclosed, for example, in Design of Prodrugs (Elsevier, Amsterdam 1985). In the present invention, when the compound has a hydroxy group, an acyloxy derivative obtained by reacting the compound with an appropriate acyl halide, an appropriate acid anhydride or an appropriate haloalkoxycarbonyl compound may, for example, be mentioned as a prodrug. Structures particularly preferred as prodrugs include —O—$COC_2H_5$, —O—CO(t-Bu), —O—$COC_{15}H_{31}$, —O—CO(m-$CO_2$Na-Ph), —O—$COCH_2CH_2CO_2$Na, —OCOCH($NH_2$)$CH_3$, —O—$COCH_2N(CH_3)_2$ and —O—$CH_2OC$(=O)$CH_3$. When the compound of the present invention has a —NH— group, a prodrug obtained by reacting the compound having a —NH— group with an appropriate acid halide, an appropriate mixed acid anhydride or an appropriate haloalkoxycarbonyl compound may, for example, be mentioned. Structures particularly preferred as prodrugs include —N—CO$(CH_2)_{20}OCH_3$, —N—COCH($NH_2$)$CH_3$ and —N—$CH_2O$(C=O)$CH_3$.

The preventing, therapeutic and/or alleviating agent for diseases against which a JAK inhibitory effect is effective, which contains the JAK inhibitor of the present invention as an active ingredient, may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of pharmaceutical compositions. These pharmaceutical preparations can be obtained by adding pharmacologically and pharmaceutically acceptable additives by conventional methods. That is, for oral medicines, ordinary additives such as excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1,000 mg/body/day in the case of oral drugs or rectal administration and about from 0.05 mg to 500 mg/body/day in the case of injections into an adult, though it depends on the age and conditions of the patient. The above-mentioned ranges are mere examples, and the dose should be determined from the conditions of the patient.

The present invention is used when it is expected to improve pathology of diseases associated with JAK1, JAK2 and JAK3 separately or in combination. Among these diseases, JAK3-associated diseases are, in addition to rheumatoid arthritis, inflammatory or proliferative dermatoses such as psoriasis, atopic dermatitis, contact dermatitis, eczematoid dermatitis, seborrheic dermatitis, lichen planus, pemphigus, pemphigoid, epidermolysis bullosa, hives, angioedema, angiitis, erythema, dermal eosinophilia, lupus erythematosus, acne, alopecia areata, immune dermatoses, reversible airway obstruction, mucitis and angitis. Among the diseases, JAK3- and JAK1-associated diseases are, in addition to rheumatoid arthritis, allergic diseases such as asthma and atopic dermatitis, Alzheimer disease, atherosclerosis, cancer, leukemia, rejection of organ or tissue grafts (such as heart, kidney, liver, bone marrow, skin, horn, lung, pancreas, islet, small intestine, extremities, muscles, nerves, intervertebral disks, trachea, myoblasts and cartilage), graft-versus-host reaction after bone marrow transplantation and autoimmune diseases such as rheumatic disease, systemic lupus erythematosus (SLE), Hashimoto's disease, multiple sclerosis, myasthenia gravis, type I diabetes and diabetic complications. Among the diseases, JAK2-associated diseases include, for example, myeloproliferative neoplasms.

As an application of the present invention, treatment and prevention of the above-mentioned diseases may be mentioned, but there is no restriction.

The compounds of the present invention may be used alone or in combination with one or more pharmaceutical agents such as immunosuppressants, anti-inflammatory agents and antirheumatic agents. The agents which may be combined may, for example, be Cyclosporin A, Tacrolimus, Leflunomide, Deoxyspergualin, Mycophenolate, Azathioprine, Etanercept (e.g. Embrel), Infliximab (e.g. REMICADE), Adalimumab (e.g. HUMIRA), Certolizumab pegol (e.g. CIMZIA), Golimumab (e.g. Simponi), Anakinra (e.g. Kineret), Rituximab (e.g. Rituxan), Tocilizumab (e.g. ACTEMRA), Methotrexate, Aspirin, acetaminophen, ibuprofen, naproxen, piroxicam, and anti-inflammatory steroid (such as prednisolone or dexamethasone), but there is no restriction.

In order that the agent is highly effective for diseases against which a JAK inhibitory effect is effective, particularly for rheumatoid arthritis, the compound more preferably has a favorable inhibitory effect in the whole blood. One of the characteristics of the present invention is to provide a compound having a favorable JAK inhibitory effect in the whole blood.

It is preferred for treatment of diseases against which a JAK inhibitory effect is effective that the compound has oral adsorption properties. One of the characteristics of the present invention is to provide a JAK inhibitor having favorable oral adsorption properties.

EXAMPLES

Now, the present invention will be described in further detail with reference to Reference Synthetic Examples, Synthetic Examples, Assay Examples and Formulation Examples. However, it should be understood that the present invention is by no means restricted by these specific Examples.

In Examples, "NMR" denotes nuclear magnetic resonance, "LC/MS" denotes high performance liquid chromatography/mass spectrometry, "v/v" means volume ratio. In the tables, "Rf" denotes Reference Synthetic Example, "Ex" denotes Synthetic Example, "Structure" denotes a chemical structural formula, "diastereomixture" denotes a diastereomer mixture, "racemate" denotes a racemic mixture, "cis/trans mixture" denotes a cis- and trans-isomeric mixture, and "E/Z mixture" denotes a E- and Z-isomeric mixture, and "Data" denotes physical property data, "condition" denotes measurement condition, "retention time" and "R. time" denote retention time in LC/MS, "Compound Name" denotes compound name of the synthesized compound, "Morphology" denotes morphology of a synthesized compound, "Yield" denotes yield of a synthesized compound, "quant" denotes quantitative, "min" denotes minute.

In the Examples herein, "rac-" or "racemate" used in texts or tables for a compound having more than one asymmetric center means that the compound is in the form of a racemic mixture of the compound possessing the specified absolute configuration and its enantiomer.

The $^1$H-NMR data show chemical shifts δ (unit: ppm) (splitting pattern, value of integral) measured at 300 MHz (with JNM-ECP300, manufactured by JEOL Ltd or JNM-ECX300, manufactured by JEOL Ltd) using tetramethylsilane as an internal standard. "s" denotes singlet, "d" denotes doublet, "t" denotes triplet, "q" denotes quartet, "quint" denotes quintet, "sextet" denotes sextet, "septet" denotes septet, "dd" denotes doublet of doublets, "dt" denotes doublet of triplets, "td" denotes triplet of doublets, "dq" denotes doublet of quartets, "qd" denotes quartet of doublets, "tt" denotes triplet of triplets, "ddd" denotes doublet of doublet of doublets, "m" denotes multiplet, "br" denotes broad, "J" denotes coupling constant, "CDCl$_3$" denotes deuterated chloroform, "CD$_3$OD" denotes deuterated methanol, and "DMSO-d$_6$" denotes deuterated dimethyl sulfoxide.

For purification by silica gel column chromatography, Hi Flash column manufactured by Yamazen Corporation, a silica gel 60 manufactured by Merck KGaA or PSQ60B manufactured by FUJI SILYSIA CHEMICAL LTD. was used unless otherwise noted.

For purification by silica gel thin-layer chromatography, PLC plate manufactured by Merck KGaA was used unless otherwise noted.

As a microwave reactor, Initiator sixty manufactured by Biotage was used.

LC/MS spectra were measured by using ESI (electrospray ionization). "ESI$^+$" or "ESI+" denotes ESI-positive mode, and "ESI$^-$" or "ESI−" denotes ESI-negative mode.

LC/MS Measurement Condition 1:
  Instrument: Waters Alliance-ZQ
  Column: Waters SunFire C18 (3.5 μm, 2.1×20 mm)
  Column Temp.: 40° C.
  Eluents: Liquid A: 0.1% aqueous formic acid
  Liquid B: 0.1% formic acid in acetonitrile
  Elution: A mixture of Liquids A and B was flown at 0.4 mL/min while the mixing ratio was linearly changed from 90/10 (v/v) to 15/85 (v/v) over the first 3 minutes, and then the flow rate was linearly changed to 0.5 mL/min for 2 minutes at a constant mixing ratio of 15/85 (v/v). Then, the mixing ratio was linearly changed to 90/10 (v/v) over 0.5 minute and maintained at 90/10 (v/v) for 2.5 minutes.

LC/MS Measurement Condition 2
  Instrument: Thermo LTQ XL
  Column: Waters AQUITY UPLC BEH C18 (1.7 μm, 2.1×50 mm)
  Column Temp.: 40° C.
  Eluents: Liquid A: 0.1% aqueous formic acid
  Liquid B: 0.1% formic acid in acetonitrile
  Elution: A mixture of Liquids A and B was flown at 0.6 mL/min at a mixing ratio of 90/10 (v/v) for the first 0.5 minute, and then the mixing ratio was linearly changed to 10/90 (v/v) over 2.5 minutes and then maintained at 10/90 (v/v) for 0.7 minute. The mixing ratio and the flow rate were linearly changed to 90/10 (v/v) and 0.8 mL/min, respectively, over 0.1 minute, maintained constant for 1 minute and linearly changed to 90/10 (v/v) and 0.6 mL/min, respectively, over 0.1 minute.

LC/MS Measurement Condition 3
Instrument: Thermo LTQ XL
Column: Waters AQUITY UPLC BEH C18 (1.7 µm, 2.1×50 mm)
Column Temp.: 40° C.
Eluents: Liquid A: 0.1% aqueous formic acid
Liquid B: 0.1% formic acid in acetonitrile
Elution: A mixture of Liquids A and B was flown at 0.6 mL/min at a mixing ratio of 95/5 (v/v) for the first 0.5 minute, and then the mixing ratio was linearly changed to 40/60 (v/v) over 2.5 minutes and then maintained at 40/60 (v/v) for 0.6 minute. The mixing ratio and the flow rate were linearly changed to 0/100 (v/v) and 0.8 mL/min, respectively, over 0.1 minute, and maintained constant for 0.1 minute. The mixing ratio was linearly changed to 95/5 (v/v) over 0.1 minute and maintained constant for 0.9 minute at a constant flow rate of 0.8 mL/min. Then, the mixing ratio and the flow rate were linearly changed to 90/10 (v/v) and 0.6 mL/min, respectively, over 0.1 minute.

LC/MS Measurement Condition 4:
Instrument: Waters Alliance-ZQ
Column: Waters SunFire C18 (3.5 µm, 2.1×20 mm)
Column Temp.: 40° C.
Eluents: Liquid A: 0.1% aqueous formic acid
Liquid B: 0.1% formic acid in acetonitrile
Elution: A mixture of Liquids A and B was flown at 0.4 mL/min while the mixing ratio was linearly changed from 60/40 (v/v) to 0/100 (v/v) over the first 3 minutes, and then the flow rate was linearly changed to 0.5 mL/min over 2.5 minutes at a constant mixing ratio of 0/100 (v/v). Then, the mixing ratio was linearly changed to 90/10 (v/v) over 0.5 minute and maintained at 90/10 (v/v) for 2 minutes.

Reference Synthetic Example 1

1H-Pyrrolo[2,3-b]pyridine 7-oxide

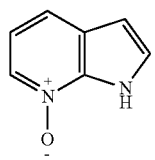

A solution of 1H-pyrrolo[2,3-b]pyridine (5.14 g, 43.5 mmol) in ethyl acetate (45 mL) was cooled to ice bath temperature, and a solution of m-chloroperbenzoic acid (25 wt % hydrate, 12.7 g, 55.2 mmol) in ethyl acetate (30 mL) was slowly added dropwise to it, and then the mixture was stirred at room temperature for 1 day. A solution of m-chloroperbenzoic acid (25 wt % hydrate, 3.93 g, 17.1 mmol) in ethyl acetate (4 mL) was added again, and the mixture was stirred at room temperature for 4 hours. The reaction mixture was cooled to ice bath temperature, and the precipitated solid was collected by filtration and purified with silica gel column chromatography (silica gel NH type manufactured by FUJI SILYSIA CHEMICAL LTD. chloroform/methanol=10/1 (v/v)) to obtain the title compound as a yellow solid (4.95 g, yield: 85%).

Reference Synthetic Example 2

4-Chloro-1H-pyrrolo[2,3-b]pyridine

A solution of 1H-pyrrolo[2,3-b]pyridine 7-oxide (4.95 g, 36.9 mmol) in N,N-dimethylformamide (10 mL) was warmed to 50° C., and methanesulfonyl chloride (8.00 mL, 103 mmol) was added to it, and the mixture was stirred at 73° C. for 3 hours. Water (70 mL) was added to the iced reaction mixture, and the mixture was neutralized with sodium hydroxide, followed by stirring at ice bath temperature for 10 minutes. The precipitated solid was collected by filtration, washed with water and dried under reduced pressure to obtain the title compound as a reddish brown solid (4.65 g, yield: 83%).

Reference Synthetic Example 3

4-Chloro-1-(triisopropylsilyl)-1H-pyrrolo[2,3-b]pyridine

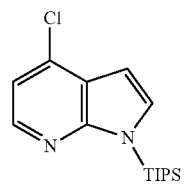

4-Chloro-1H-pyrrolo[2,3-b]pyridine (2.84 g, 18.6 mmol) was dissolved in a mixed solvent of N,N-dimethylformamide (10 mL) and tetrahydrofuran (10 mL), and sodium hydride (55 wt % dispersion in mineral oil, 1.08 g, 27.0 mmol) was added to it at ice bath temperature, and the mixture was stirred for 1 hour. Triisopropylsilyl chloride (6.0 mL, 28 mmol) was added to the reaction mixture, and the mixture was stirred at room temperature for 1 day. The reaction mixture was mixed with water and extracted with hexane twice. The resulting organic layers were combined, washed with saturated aqueous sodium chloride, dried over anhydrous magnesium sulfate and concentrated under reduced pressure. The residue was purified by silica gel column chromatography (only hexane) to obtain the title compound as a reddish brown oil (5.74 g, yield: 99%).

Reference Synthetic Example 4

4-Chloro-1H-pyrrolo[2,3-b]pyridine-5-carbaldehyde

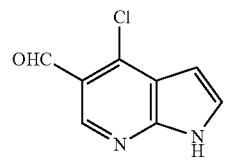 [SMILES: O=Cc1cnc2[nH]ccc2c1Cl]

A solution of 4-chloro-1-(triisopropylsilyl)-1H-pyrrolo[2,3-b]pyridine (5.74 g, 18.6 mmol) in tetrahydrofuran (50 mL) was cooled to −78° C., and a solution of s-butyllithium in hexane/cyclohexane (1.06 M, 27 mL, 29 mmol) was added to it, and then the mixture was stirred for 1 hour. To the reaction mixture, N,N-dimethylformamide (7.0 mL, 90 mmol) was added, and the mixture was stirred for additional 1 hour. The reaction mixture was mixed with 4 M hydrogen chloride in 1,4-dioxane (20 mL), followed by stirring for 30 minutes, and then mixed with water and extracted with ethyl acetate. The organic layer was washed with saturated aqueous sodium chloride, dried over anhydrous magnesium sulfate and concentrated under reduced pressure. The resulting residue was dissolved in dichloromethane (15 mL), and mixed with trifluoroacetic acid (15 mL), and the mixture was stirred for 1 day. The reaction mixture was concentrated under reduced pressure, mixed with water and neutralized with saturated aqueous sodium hydrogencarbonate, and the precipitated solid was collected by filtration and dried under reduced pressure. To the resulting solid, ethyl acetate (20 mL) and hexane (20 mL) were added, and the solid was collected by filtration, washed with hexane and dried under reduced pressure to obtain the title compound as a pale yellow solid (2.72 g, yield: 81%).

Reference Synthetic Example 5

4-Chloro-1-{[2-(trimethylsilyl)ethoxy]methyl}-1H-pyrrolo[2,3-b]pyridine-5-carbaldehyde

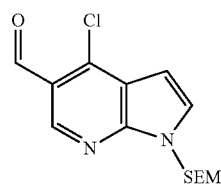 [SMILES: C[Si](C)(C)CCOCn1ccc2c(Cl)c(C=O)cnc21]

To a solution of 4-chloro-1H-pyrrolo[2,3-b]pyridine-5-carbaldehyde (550 mg, 3.05 mmol) in N,N-dimethylformamide (5 mL), sodium hydride (60 wt % suspended in liquid paraffin, 150 mg, 3.75 mmol) was added at ice bath temperature, and the mixture was stirred for 10 minutes Then [2-(chloromethoxy)ethyl]trimethylsilane (650 μL, 3.67 mmol) was added, and the mixture was stirred at room temperature for 30 minutes. The reaction mixture was mixed with saturated aqueous ammonium chloride and extracted with ethyl acetate. The organic layer was washed with saturated aqueous sodium chloride, dried over anhydrous magnesium sulfate and concentrated under reduced pressure. The residue was purified by silica gel column chromatography (hexane/ethyl acetate=5/1 (v/v)) to obtain the title compound as a white solid (815 mg, yield: 86%).

Reference Synthetic Example 6

4-Chloro-1-{[2-(trimethylsilyl)ethoxy]methyl}-1H-pyrrolo[2,3-b]pyridine-5-carboxylic acid

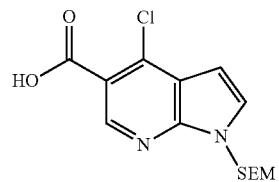 [SMILES: C[Si](C)(C)CCOCn1ccc2c(Cl)c(C(=O)O)cnc21]

To a solution of 4-chloro-1-{[2-(trimethylsilyl)ethoxy]methyl}-1H-pyrrolo[2,3-b]pyridine-5-carbaldehyde (486 mg, 1.56 mmol) in acetic acid (10 mL), sulfamic acid (227 mg, 2.34 mmol) and 2-methyl-2-butene (486 μL, 4.58 mmol) were added, and then 0.5 mL of aqueous sodium chlorite (254 mg, 2.81 mmol) was added dropwise, and the mixture was stirred at room temperature for 2 hours. The reaction mixture was mixed with water, mixed with 1M aqueous sodium hydroxide until pH 7, and extracted with chloroform. The organic layer was dried over anhydrous sodium sulfate and concentrated under reduced pressure. The residue was purified by silica gel column chromatography (ethyl acetate/methanol=10/1→1/1 (v/v)) to obtain the title compound as a white solid (484 mg, yield: 95%).

Reference Synthetic Example 7

4-Chloro-1-{[2-(trimethylsilyl)ethoxy]methyl}-1H-pyrrolo[2,3-b]pyridine-5-carboxamide

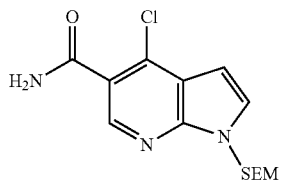 [SMILES: C[Si](C)(C)CCOCn1ccc2c(Cl)c(C(N)=O)cnc21]

A solution of 4-chloro-1-{[2-(trimethylsilyl)ethoxy]methyl}-1H-pyrrolo[2,3-b]pyridine-5-carboxylic acid (480 mg, 1.47 mmol) in thionyl chloride (3 mL) was stirred at room temperature for 2 hours. The reaction mixture was mixed with toluene and concentrated under reduced pressure, and the residue was mixed with toluene and concentrated under reduced pressure again. The residue was dissolved in dichloromethane (5 mL), and a solution of ammonia in methanol (7.0 M, 1.0 mL, 7.0 mmol) was added dropwise at ice bath temperature, followed by stirring for 1 hour. The reaction mixture was mixed with saturated aqueous sodium chloride and extracted with ethyl acetate. The organic layer was dried over anhydrous sodium sulfate and concentrated under reduced pressure to obtain the title compound as a white solid (461 mg, yield: 96%).

Reference Synthetic Example 8

4-(Cyclohexylamino)-1-{[2-(trimethylsilyl)ethoxy]methyl}-1H-pyrrolo[2,3-b]pyridine-5-carboxamide

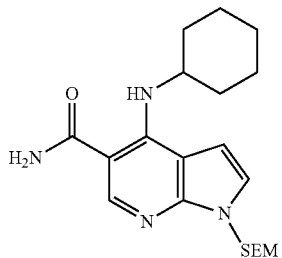 [SMILES: C[Si](C)(C)CCOCn1ccc2c(NC3CCCCC3)c(C(N)=O)cnc21]

To a solution of 4-chloro-1-{[2-(trimethylsilyl)ethoxy]methyl}-1H-pyrrolo[2,3-b]pyridine-5-carboxamide (500 mg, 1.54 mmol) in N,N-dimethylacetamide (2.5 mL), N,N-diisopropylethylamine (0.526 mL, 3.07 mmol) and cyclohexylamine (0.525 mL, 4.61 mmol) were added, and the mixture was stirred at 150° C. for 3 hours. The reaction mixture was mixed with water and extracted with ethyl acetate. The organic layer was washed with water, saturated aqueous ammonium chloride, water and saturated aqueous sodium chloride, dried over anhydrous sodium sulfate and concentrated under reduced pressure to obtain the title compound as a colorless oil (645 mg, quantitative yield). The resulting oil was used for the next step without further purification.

Reference Synthetic Example 9

1-Cyclohexyl-7-{[2-(trimethylsilyl)ethoxy]methyl}-1H-pyrrolo[3',2':5,6]pyrido[4,3-d]pyrimidin-4(7H)-one

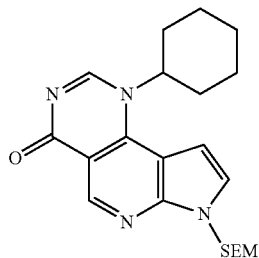 [SMILES: C[Si](C)(C)CCOCn1ccc2c1ncc1c(=O)ncn(C3CCCCC3)c12]

To 4-(cyclohexylamino)-1-{[2-(trimethylsilyl)ethoxy]methyl}-1H-pyrrolo[2,3-b]pyridine-5-carboxamide (645 mg, 1.54 mmol), triethyl orthoformate (13 mL) and scandium(III) trifluoromethanesulfonate (75.8 mg, 0.154 mmol) were added, and the mixture was stirred at 50° C. for 24 hours. The reaction mixture was allowed to cool to room temperature, mixed with saturated aqueous sodium hydrogencarbonate and extracted with ethyl acetate. The organic layer was washed with water and saturated aqueous sodium chloride, dried over anhydrous sodium sulfate and concentrated under reduced pressure. The resulting yellowish-white solid was washed with hexane and dried under reduced pressure at 50° C. to obtain the title compound as a yellowish-white solid (475 mg, yield: 77%).

Reference Synthetic Example 10

1-Cyclohexyl-7-{[2-(trimethylsilyl)ethoxy]methyl}-2,3-dihydro-1H-pyrrolo[3',2':5,6]pyrido[4,3-d]pyrimidin-4(7H)-one

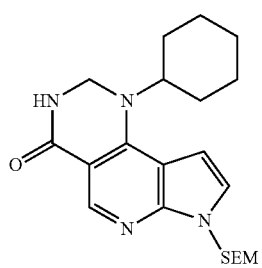 [SMILES: C[Si](C)(C)CCOCn1ccc2c3c(cnc21)C(=O)NCN3C1CCCCC1]

To a solution of 1-cyclohexyl-7-{[2-(trimethylsilyl)ethoxy]methyl}-1H-pyrrolo[3',2':5,6]pyrido[4,3-d]pyrimidin-4(7H)-one (50 mg, 0.125 mmol) in methanol (1.5 mL), sodium borohydride (4.8 mg, 0.127 mmol) was added, and the mixture was stirred at room temperature for 2 hours. The reaction mixture was mixed with saturated aqueous ammonium chloride and water and extracted with ethyl acetate. The resulting organic layer was dried over anhydrous sodium sulfate and concentrated under reduced pressure to obtain the title compound as a colorless oil (59.9 mg, quantitative yield). The resulting oil was used for the next step without further purification.

Reference Synthetic Example 11

1-Cyclohexyl-3-methyl-7-{[2-(trimethylsilyl)ethoxy]methyl}-2,3-dihydro-1H-pyrrolo[3',2':5,6]pyrido[4,3-d]pyrimidin-4(7H)-one

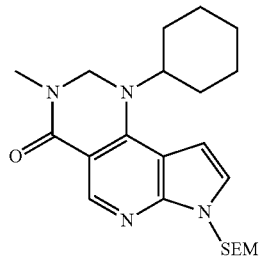 [SMILES: CN1CN(C2CCCCC2)c2c(cnc3c2ccn3COCC[Si](C)(C)C)C1=O]

To a solution of 1-cyclohexyl-7-{[2-(trimethylsilyl)ethoxy]methyl}-2,3-dihydro-1H-pyrrolo[3',2':5,6]pyrido[4,3-d]pyrimidin-4(7H)-one (30 mg, 0.075 mmol) in N,N-dimethylformamide (1 mL), sodium hydride (60 wt % dispersion in liquid paraffin, 4 mg, 0.1 mmol) was added, and the mixture was stirred at room temperature for 1 hour. To the reaction mixture, methyl iodide (5.6 μL, 0.090 mmol) was added, and the mixture was stirred at room temperature for 3 hours. To the reaction mixture, water, ethyl acetate and aqueous sodium thiosulfate were added, and the mixture was stirred at room temperature for 3 days. The organic layer was separated, washed with water and saturated aqueous sodium chloride, dried over anhydrous sodium sulfate and concentrated under reduced pressure. The residue was purified by silica gel column chromatography (hexane/ethyl

Reference Synthetic Example 12

(trans-4-Aminocyclohexyl)methanol

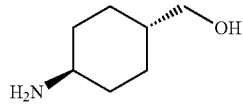

trans-4-Aminocyclohexane carboxylic acid (314 mg, 2.19 mmol) was added little by little to a solution of sodium bis(2-methoxyethoxy)aluminum hydride-toluene solution (65 wt %, 3.0 mL) in toluene (3 mL) warmed to 75° C. in advance, and the mixture was stirred for 7 hours. The reaction mixture was allowed to cool to room temperature and mixed with 1M aqueous sodium hydroxide (20 mL), followed by stirring at 80° C. for 10 minutes. The reaction mixture was allowed to cool to room temperature and separated into an aqueous layer and a toluene layer, and the aqueous layer was extracted with chloroform three times. The organic layers were combined, dried over anhydrous sodium sulfate and concentrated under reduced pressure to obtain the title compound as a white solid (170 mg, yield: 60%).

Reference Synthetic Example 13

Dimethyl trans-cyclohexane-1,4-dicarboxylate

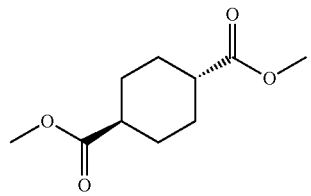

To a solution of trans-cyclohexane-1,4-dicarboxylic acid (25.9 g, 0.151 mol) in N,N-dimethylformamide (125 mL), methyl iodide (64.7 g, 0.456 mol) and potassium carbonate (63.4 g, 0.459 mol) were added, and the mixture was stirred at room temperature for 1 day. To the reaction mixture, diethyl ether (600 mL) and water (500 mL) were added. The organic layer was separated, washed with water (500 mL) and saturated aqueous sodium chloride, dried over anhydrous magnesium sulfate and concentrated under reduced pressure. Hexane was added to the residue, followed by stirring at ice bath temperature, and the residue was collected by filtration and washed with ice-cold hexane to obtain the title compound as a white solid (21.0 g, yield: 70%).

Reference Synthetic Example 14 trans-4-(Methoxycarbonyl)cyclohexane carboxylic acid

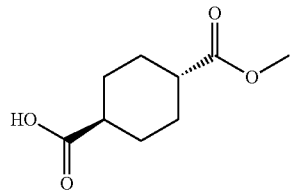

To a solution of dimethyl trans-cyclohexane-1,4-dicarboxylate (60.4 g, 0.302 mol) in methanol (500 mL), barium hydroxide (28.4 g, 0.166 mol) and water (125 mL) were added, and the mixture was stirred at room temperature for 1 day. The reaction mixture was concentrated under reduced pressure, and hexane (500 mL) and water (1,200 mL) were added to it. The aqueous layer was separated, washed with hexane (500 mL), acidified with concentrated hydrochloric acid and extracted with ethyl acetate (400 mL) three times. The organic layers were combined, dried over anhydrous magnesium sulfate and concentrated under reduced pressure. The residue was mixed with chloroform, the insolubles were filtered off, and the filtrate was concentrated under reduced pressure. The resulting solid was washed with hexane to obtain the title compound as a white solid (30.9 g, yield: 55%).

Reference Synthetic Example 15

Methyl trans-4-{[(benzyloxy)carbonyl]amino}cyclohexane carboxylate

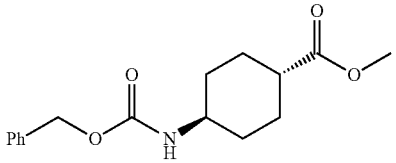 [SMILES: COC(=O)[C@H]1CC[C@H](NC(=O)OCc2ccccc2)CC1]

A solution of trans-4-(methoxycarbonyl)cyclohexane carboxylic acid (15.7 g, 84.3 mmol) and triethylamine (35.0 mL, 253 mmol) in toluene (160 mL) was heated to 110° C., and diphenylphosphoryl azide (20.0 mL, 92.7 mmol) was added dropwise to it over 30 minutes, followed by stirring at 110° C. for 3 hours. Then benzyl alcohol (11.3 mL, 110 mmol) was added dropwise over 10 minutes, followed by stirring at 110° C. for 6 hours. The reaction mixture was allowed to cool to room temperature, mixed with water, acidified with aqueous citric acid, and extracted with ethyl acetate. The organic layer was washed with saturated aqueous sodium hydrogencarbonate and saturated aqueous sodium chloride, dried over anhydrous sodium sulfate and concentrated under reduced pressure. The resulting yellow solid was washed with ethyl acetate/hexane (1/5 (v/v)) to obtain the title compound as a white solid (21.4 g, yield: 73%).

Reference Synthetic Example 16 trans-4-{[(Benzyloxy)carbonyl]amino}cyclohexane carboxylic acid

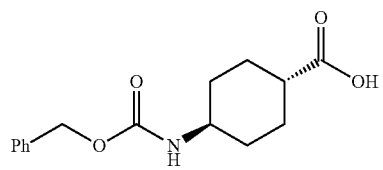 [SMILES: O=C(N[C@H]1CC[C@H](C(=O)O)CC1)OCc1ccccc1]

To a solution of methyl trans-4-{[(benzyloxy)carbonyl]amino}cyclohexane carboxylate (21.4 g, 73.5 mmol) in methanol (200 mL), 1M aqueous sodium hydroxide (200 mL, 200 mmol) was added, and the mixture was stirred at room temperature for 3 days. Concentrated hydrochloric acid was added until the reaction mixture was adjusted to pH 4, and the precipitated solid was collected by filtration and washed with ethyl acetate and water to obtain the title compound as a white solid (19.0 g, yield: 93%).

Reference Synthetic Example 17

Benzyl (trans-4-(hydroxymethyl)cyclohexyl)carbamate

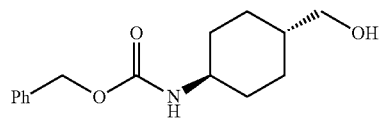 [SMILES: O=C(N[C@H]1CC[C@H](CO)CC1)OCc1ccccc1]

To a solution of trans-4-{[(benzyloxy)carbonyl]amino}cyclohexane carboxylic acid (19.0 g, 68.5 mmol) in tetrahydrofuran (100 mL), borane-tetrahydrofuran complex (1.0M tetrahydrofuran solution, 100 mL, 100 mmol) was added, and the mixture was stirred at room temperature for 1 day. To the reaction mixture, acetic acid (10 mL) was added, and the mixture was stirred for 1 hour. The reaction mixture was mixed with water and extracted with ethyl acetate. The organic layer was washed with saturated aqueous sodium hydrogencarbonate and water, dried over anhydrous sodium sulfate and concentrated under reduced pressure. The resulting solid was washed with ethyl acetate/hexane (1/9 (v/v)) to obtain the title compound as a white solid (13.0 g, yield: 72%).

Reference Synthetic Example 18

(trans-4-Aminocyclohexyl)methanol

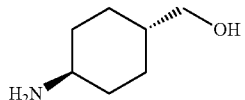

To a solution of benzyl (trans-4-(hydroxymethyl)cyclohexyl)carbamate (24.0 g, 91.1 mmol) in methanol (200 mL), 5% palladium carbon (2.4 g) was added under an argon atmosphere, and the mixture was stirred at room temperature for 1 day under a hydrogen atmosphere. The reaction mixture was filtered, and the filtrate was concentrated under reduced pressure to obtain the title compound as a white solid (11.4 g, yield: 97%) (alternative synthetic method to Reference Synthetic Example 12).

Reference Synthetic Example 19

4-{[trans-4-(Hydroxymethyl)cyclohexyl]amino}-1-{[2-(trimethylsilyl)ethoxy]methyl}-1H-pyrrolo[2,3-b]pyridine-5-carboxamide

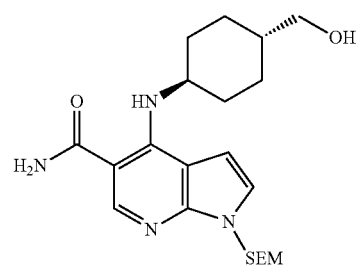 [SMILES: C[Si](C)(C)CCOCn1ccc2c(N[C@H]3CC[C@H](CO)CC3)c(C(N)=O)cnc21]

To a solution of 4-chloro-1-{[2-(trimethylsilyl)ethoxy]methyl}-1H-pyrrolo[2,3-b]pyridine-5-carboxamide (680 mg, 2.09 mol) obtained in Reference Synthetic Example 7 in N,N-dimethylacetamide (1.1 mL), N,N-diisopropylethylamine (1.1 mL) and (trans-4-aminocyclohexyl)methanol (945 mg, 7.31 mmol) obtained in Reference Synthetic Example 12 were added, and the mixture was stirred at 130° C. for 3 hours. The reaction mixture was allowed to cool to room temperature, mixed with saturated aqueous ammonium chloride and extracted with ethyl acetate. The organic layer was dried over anhydrous sodium sulfate and concentrated under reduced pressure. The residue was purified by silica gel column chromatography (ethyl acetate/hexane=5/1) (v/v)) to obtain the title compound as a white solid (781 mg, yield: 89%).

Reference Synthetic Example 20

4-[(trans-4-{[(tert-Butyldimethylsilyl)oxy]methyl}cyclohexyl)amino]-1-{[2-(trimethylsilyl)ethoxy]methyl}-1H-pyrrolo[2,3-b]pyridin-5-carboxamide

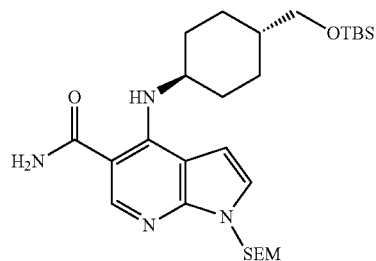

To a solution of 4-{[trans-4-(hydroxymethyl)cyclohexyl]amino}-1-{[2-(trimethylsilyl)ethoxy]methyl}-1H-pyrrolo[2,3-b]pyridine-5-carboxamide (2.8 g, 7.41 mmol) in N,N-dimethylformamide (30 mL), imidazole (1.37 g, 20.1 mmol) and t-butyldimethylchlorosilane (3.03 g, 20.1 mmol) were added, and the mixture was stirred at room temperature for 1 day. The reaction mixture was mixed with water and extracted with ethyl acetate. The organic layer was washed with water, saturated aqueous ammonium chloride, water and saturated aqueous sodium chloride, dried over anhydrous sodium sulfate and concentrated under reduced pressure. The residue was purified by silica gel column chromatography (hexane/ethyl acetate=100/0→20/80 (v/v)) to obtain the title compound as a white amorphous substance (3.34 g, yield: 85%).

Reference Synthetic Example 21

1-(trans-4-{[(tert-Butyldimethylsilyl)oxy]methyl}cyclohexyl)-7-{[2-(trimethylsilyl)ethoxy]methyl}-1H-pyrrolo[3',2':5,6]pyrido[4,3-d]pyrimidin-4(7H)-one

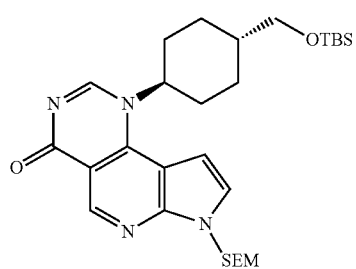 [SMILES: CC(C)(C)[Si](C)(C)OC[C@H]1CC[C@H](n2cnc(=O)c3cnc4c(ccn4COCC[Si](C)(C)C)c32)CC1]

To 4-[(trans-4-{[(tert-butyldimethylsilyl)oxy]methyl}cyclohexyl)amino]-1-{[2-(trimethylsilyl)ethoxy]methyl}-1H-pyrrolo[2,3-b]pyridin-5-carboxamide (3.34 g, 6.27 mmol), triethyl orthoformate (60 mL) and scandium (III) trifluoromethanesulfonate (308 mg, 0.627 mmol) were added, and the mixture was stirred at 50° C. for 24 hours. The reaction mixture was mixed with saturated aqueous sodium hydrogencarbonate at ice bath temperature and extracted with ethyl acetate. The organic layer was washed with water and saturated aqueous sodium chloride, dried over anhydrous sodium sulfate and concentrated under reduced pressure. The resulting yellowish-white solid was washed with hexane and dried at 50° C. under reduced pressure to obtain the title compound as a yellowish-white solid (2.76 g, yield: 81%).

Reference Synthetic Example 22

1-[trans-4-(hydroxymethyl)cyclohexyl]-7-{[2-(trimethylsilyl)ethoxy]methyl}-1H-pyrrolo[3',2':5,6]pyrido[4,3-d]pyrimidin-4(7H)-one

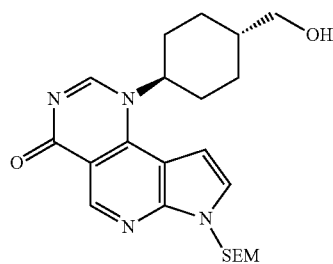 [SMILES: C[Si](C)(C)CCOCn1ccc2c1ncc1c(=O)ncn([C@H]3CC[C@H](CO)CC3)c12]

To a solution of 1-(trans-4-{[(tert-butyldimethylsilyl)oxy]methyl}cyclohexyl)-7-{[2-(trimethylsilyl)ethoxy]methyl}-1H-pyrrolo[3',2':5,6]pyrido[4,3-d]pyrimidin-4(7H)-one (5.24 g, 9.65 mmol) in 1,4-dioxane (100 mL), 1M hydrochloric acid (10.6 mL, 10.6 mmol) was added dropwise, and the mixture was stirred at room temperature for 2 hours. The reaction mixture was neutralized with 1M aqueous sodium hydroxide (10.6 mL, 10.6 mmol) at ice bath temperature and extracted with chloroform twice. The organic layers were combined and washed with saturated aqueous sodium chloride. The aqueous layer was extracted with chloroform again, and the combined organic layer was dried over anhydrous sodium sulfate and concentrated under reduced pressure. The resulting residue was mixed with ethyl acetate (100 mL), and the insoluble white solid was collected by filtration and purified by silica gel column chromatography (ethyl acetate→chloroform/methanol=1/0→5/1 (v/v)) to obtain the title compound as a white solid (3.61 g, yield: 87%).

Reference Synthetic Example 23 trans-4-(4-oxo-7-{[2-(Trimethylsilyl)ethoxy]methyl}-4,7-dihydro-1H-pyrrolo[3',2':5,6]pyrido[4,3-d]pyrimidin-1-yl)cyclohexanecarbaldehyde

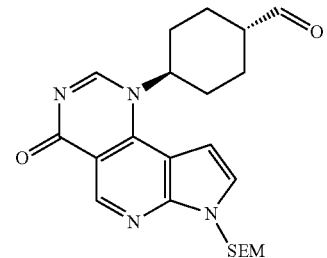

To a solution of 1-[trans-4-(hydroxymethyl)cyclohexyl]-7-{[2-(trimethylsilyl)ethoxy]methyl}-1H-pyrrolo[3',2':5,6]pyrido[4,3-d]pyrimidin-4(7H)-one (3.6 g, 8.4 mmol) in dimethylsulfoxide (130 mL), 2-iodoxybenzoic acid (2.83 g, 10.1 mmol) was added, and the mixture was stirred at room temperature for 5 hours, and additionally stirred at 25° C. for 17 hours. To the reaction mixture, aqueous sodium thiosulfate (60 mL) was added, and the mixture was stirred at room temperature for 3 hours. The reaction mixture was mixed with water and extracted with ethyl acetate twice. The organic layers were combined, washed with saturated aqueous sodium hydrogencarbonate five times, dried over anhydrous sodium sulfate and concentrated under reduced pressure. The resulting yellow solid was washed with diethyl ether and dried under reduced pressure to obtain the title compound as a white solid (3.08 g, yield: 86%).

Reference Synthetic Example 24

1-(trans-4-{[(2-Bromo-2,2-difluoroethyl)amino]methyl}cyclohexyl)-7-{[2-(trimethylsilyl)ethoxy]methyl}-2,3-dihydro-1H-pyrrolo[3',2':5,6]pyrido[4,3-d]pyrimidin-4(7H)-one

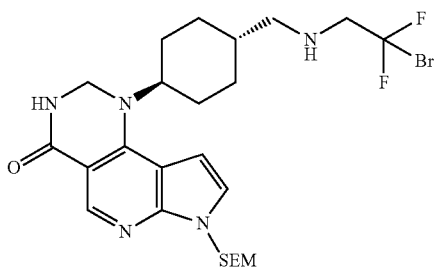 [SMILES: C[Si](C)(C)CCOCn1ccc2c3c(cnc21)C(=O)NCN3[C@H]1CC[C@H](CNCC(F)(F)Br)CC1]

To a solution of trans-4-(4-oxo-7-{[2-(trimethylsilyl)ethoxy]methyl}-4,7-dihydro-1H-pyrrolo[3',2':5,6]pyrido[4,3-d]pyrimidin-1-yl)cyclohexanecarbaldehyde (30 mg, 0.070 mmol) in chloroform (1 mL), 2-bromo-2,2-difluoroethylamine hydrochloride (14 mg, 0.071 mmol) and sodium triacetoxyborohydride (33 mg, 0.15 mmol) were added, and the mixture was stirred at room temperature for 30 minutes. Sodium triacetoxyborohydride (20 mg, 0.094 mmol) was added again, followed by stirring at room temperature for 20 minutes. The reaction mixture was mixed with saturated aqueous ammonium chloride, chloroform and water, and extracted with chloroform. The organic layer was washed with saturated aqueous sodium chloride, dried over anhydrous sodium sulfate and concentrated under reduced pressure. The residue was purified by thin-layer silica gel column chromatography (chloroform/methanol=10/1 (v/v)) to obtain the title compound as a white solid (14.4 mg, yield: 35%).

Reference Synthetic Example 25

1-(trans-4-{[(2,2,2-Trifluoroethyl)amino]methyl}cyclohexyl)-7-{[2-(trimethylsilyl)ethoxy]methyl}-2,3-dihydro-1H-pyrrolo[3',2':5,6]pyrido[4,3-d]pyrimidin-4(7H)-one

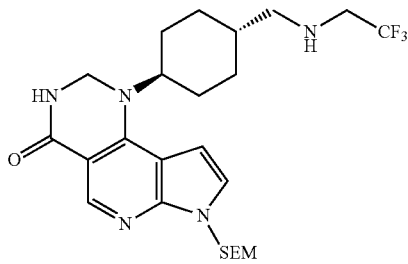 [SMILES: C[Si](C)(C)CCOCn1ccc2c3c(cnc21)C(=O)NCN3[C@H]1CC[C@H](CNCC(F)(F)F)CC1]

To a solution of trans-4-(4-oxo-7-{[2-(trimethylsilyl)ethoxy]methyl}-4,7-dihydro-1H-pyrrolo[3',2':5,6]pyrido[4,3-d]pyrimidin-1-yl)cyclohexanecarbaldehyde (3.08 g, 7.22 mmol) obtained in Reference Synthetic Example 23 in methanol (60 mL), 2,2,2-trifluoroethylamine hydrochloride (4.89 g, 36.1 mmol) and 2-picoline borane (1.54 g, 14.4 mmol) were added, and the mixture was stirred at room temperature for 3 hours. The reaction mixture was mixed with aqueous sodium hydrogencarbonate at ice bath temperature, stirred for 30 minutes, mixed with water and extracted with chloroform twice. The organic layers were combined, dried over anhydrous sodium sulfate and concentrated under reduced pressure. The residue was purified by silica gel column chromatography (ethyl acetate/methanol=1/0→5/1 (v/v)) to obtain the title compound as a white solid (2.47 g, yield: 67%).

Reference Synthetic Example 26

1-(trans-4-{[(tert-Butyldimethylsilyl)oxy]methyl}cyclohexyl)-7-{[2-(trimethylsilyl)ethoxy]methyl}-2,3-dihydro-1H-pyrrolo[3',2':5,6]pyrido[4,3-d]pyrimidin-4(7H)-one

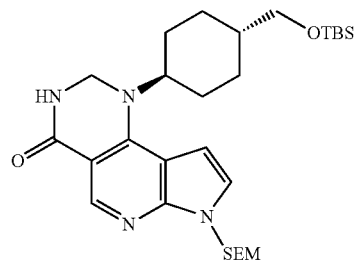 [SMILES: CC(C)(C)[Si](C)(C)OC[C@H]1CC[C@H](N2CNC(=O)c3cnc4c(ccn4COCC[Si](C)(C)C)c32)CC1]

To a solution of 1-(trans-4-{[(tert-butyldimethylsilyl)oxy]methyl}cyclohexyl)-7-{[2-(trimethylsilyl)ethoxy]methyl}-1H-pyrrolo[3',2':5,6]pyrido[4,3-d]pyrimidin-4(7H)-one (500 mg, 0.921 mmol) obtained in Reference Synthetic Example 21 in a mixed solvent of ethanol (5.0 mL) and tetrahydrofuran (5.0 mL), sodium borohydride (104 mg, 2.74 mmol) was added at ice bath temperature, and the mixture was stirred for 10 minutes. The reaction mixture was mixed with saturated aqueous ammonium chloride and water, and extracted with ethyl acetate. The organic layer was dried over anhydrous sodium sulfate and concentrated under reduced pressure to obtain the title compound as a pale yellow solid (524 mg). The resulting pale yellow solid was used for the next step without further purification.

Reference Synthetic Example 27

1-(trans-4-{[(tert-Butyldimethylsilyl)oxy]methyl}cyclohexyl)-3-methyl-7-{[2-(trimethylsilyl)ethoxy]methyl}-2,3-dihydro-1H-pyrrolo[3',2':5,6]pyrido[4,3-d]pyrimidin-4(7H)-one

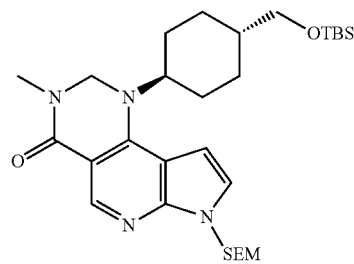 [SMILES: CN1CN([C@H]2CC[C@H](CO[Si](C)(C)C(C)(C)C)CC2)c2c(cnc3c2ccn3COCC[Si](C)(C)C)C1=O]

To a solution of 1-(trans-4-{[(tert-butyldimethylsilyl)oxy]methyl}cyclohexyl)-7-{[2-(trimethylsilyl)ethoxy]methyl}-

2,3-dihydro-1H-pyrrolo[3',2':5,6]pyrido[4,3-d]pyrimidin-4 (7H)-one (524 mg) in tetrahydrofuran (5 mL), sodium hydride (55 wt % dispersion in liquid paraffin, 48.2 mg, 1.11 mmol) was added at ice bath temperature, and methyl iodide (74 μL, 1.2 mmol) was added, and the mixture was stirred at room temperature for 30 minutes. The reaction mixture was mixed with water, and extracted with ethyl acetate. The organic layer was washed with water and saturated aqueous sodium chloride, dried over anhydrous sodium sulfate and concentrated under reduced pressure to obtain the title compound as a pale yellow oil (655 mg). The resulting pale yellow oil was used for the next step without further purification.

Reference Synthetic Example 28

1-[trans-4-(Hydroxymethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one

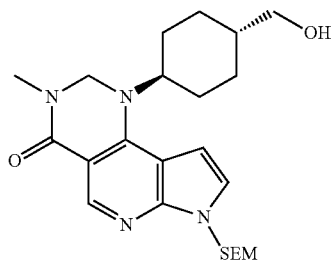 [SMILES: CN1CN([C@H]2CC[C@H](CO)CC2)c2c(cnc3c2ccn3COCC[Si](C)(C)C)C1=O]

To a solution of 1-(trans-4-{[(tert-butyldimethylsilyl)oxy]methyl}cyclohexyl)-3-methyl-7-{[2-(trimethylsilyl)ethoxy]methyl}-2,3-dihydro-1H-pyrrolo[3',2':5,6]pyrido[4,3-d]pyrimidin-4(7H)-one (655 mg) in 1,4-dioxane (10 mL), 1M hydrochloric acid (1.11 mL, 1.11 mmol) was added dropwise, and the mixture was stirred at room temperature for 30 minutes. The reaction mixture was neutralized with saturated aqueous sodium hydrogencarbonate and extracted with ethyl acetate. The organic layer was washed with saturated aqueous sodium chloride, dried over anhydrous sodium sulfate and concentrated under reduced pressure. The residue was purified by silica gel column chromatography (ethyl acetate) to obtain the title compound as a white solid (386 mg, yield: 95% (3 steps).

Reference Synthetic Example 29 trans-4-(3-Methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde

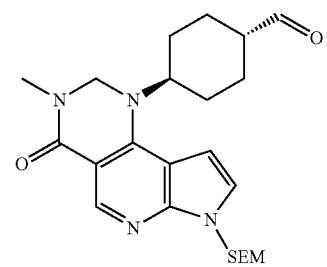

To a solution of 1-[trans-4-(hydroxymethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one (200 mg, 0.450 mmol) in dimethylsulfoxide (5 mL), 2-iodoxybenzoic acid (189 mg, 0.675 mmol) was added, and the mixture was stirred at room temperature for 28 hours. The reaction mixture was mixed with aqueous sodium thiosulfate and saturated aqueous sodium hydrogencarbonate, stirred at room temperature for 30 minutes and extracted with ethyl acetate. The organic layer was washed with aqueous sodium hydrogencarbonate, dried over anhydrous sodium sulfate and concentrated under reduced pressure. The residue was purified by silica gel column chromatography (ethyl acetate) to obtain a pale yellow oil containing the title compound (155 mg). The resulting pale yellow oil was used for the next step without further purification.

Reference Synthetic Example 30

3-Methyl-1-(trans-4-{[(2,2,2-trifluoroethyl)amino]methyl}cyclohexy)-7-{[2-(trimethylsilyl)ethoxy]methyl}-2,3-dihydro-1H-pyrrolo[3'2':5,6]pyrido[4,3-d]pyrimidin-4(7H)-one

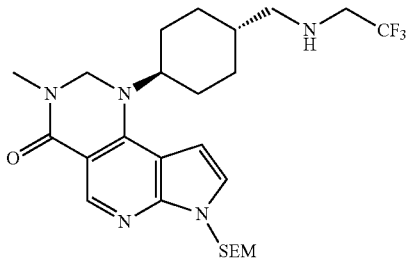 [SMILES: CN1CN([C@H]2CC[C@H](CNCC(F)(F)F)CC2)c2c(cnc3c2ccn3COCC[Si](C)(C)C)C1=O]

To a solution of trans-4-(3-methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (30.0 mg, 0.0678 mmol) in chloroform (1 mL), 2,2,2-trifluoroethylamine (27.0 μL, 0.339 mmol) and sodium triacetoxyborohydride (36.0 mg, 0.170 mmol) were added, and the mixture was stirred at room temperature for 27 hours. The reaction mixture was mixed with 1M aqueous sodium hydroxide and extracted with ethyl acetate. The organic layer was washed with saturated aqueous sodium chloride, dried over anhydrous sodium sulfate and concentrated under reduced pressure. The residue was purified by silica gel thin-layer chromatography (ethyl acetate) to obtain a colorless oil containing the title compound (21.5 mg). The resulting colorless oil was used for the next step without further purification.

Reference Synthetic Example 31

1-[trans-4-(Difluoromethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one

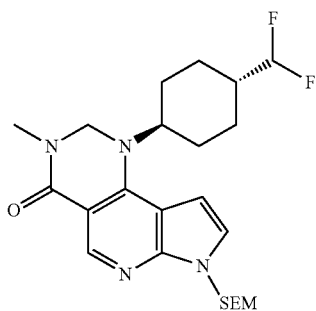 [SMILES: CN1CN([C@H]2CC[C@H](C(F)F)CC2)c2c(cnc3c2ccn3COCC[Si](C)(C)C)C1=O]

To a solution of trans-4-(3-methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (30.0 mg, 0.0678 mmol) obtained in Reference Synthetic Example 29 in dichloromethane (1 mL), N,N-diethylaminosulfur trifluoride (20.0 μL, 0.149 mmol) was added at ice bath temperature, and the mixture was stirred at room temperature for 4 hours. The reaction mixture was cooled to ice bath temperature, mixed with saturated aqueous sodium hydrogencarbonate and extracted with ethyl acetate. The organic layer was washed with saturated aqueous sodium chloride, dried over anhydrous sodium sulfate and concentrated under reduced pressure. The residue was purified by silica gel column chromatography (ethyl acetate/hexane=1/3 (v/v)) to obtain a pale yellow oil containing the title compound (22.7 mg). The resulting pale yellow oil was used for the next step without further purification.

Reference Synthetic Example 32

1-[trans-4-(Fluoromethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one

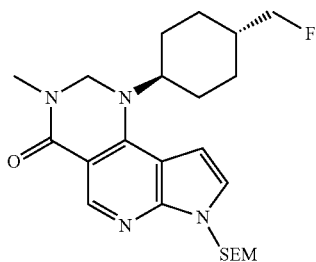 [SMILES: CN1CN([C@H]2CC[C@H](CF)CC2)c2c(cnc3c2ccn3COCC[Si](C)(C)C)C1=O]

To a solution of 1-[trans-4-(hydroxymethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one (30.0 mg, 0.0674 mmol) obtained in Reference Synthetic Example 28 in dichloromethane (1 mL), N,N-diethylaminosulfur trifluoride (10.0 μL, 0.0801 mmol) was added at ice bath temperature, and the mixture was stirred at room temperature for 4 hours. The reaction mixture was cooled to ice bath temperature, mixed with saturated aqueous sodium hydrogencarbonate and extracted with ethyl acetate. The organic layer was washed with saturated aqueous sodium chloride, dried over anhydrous sodium sulfate and concentrated under reduced pressure. The residue was purified by silica gel column chromatography (ethyl acetate/hexane=1/3→1/0 (v/v)) to obtain a pale yellow oil containing the title compound (22.6 mg). The resulting pale yellow oil was used for the next step without further purification.

Reference Synthetic Example 33

1-{trans-4-[Hydroxy(methoxy)methyl]cyclohexyl}-7-{[2-(trimethylsilyl)ethoxy]methyl}-1H-pyrrolo[3',2':5,6]pyrido[4,3-d]pyrimidin-4(7H)-one

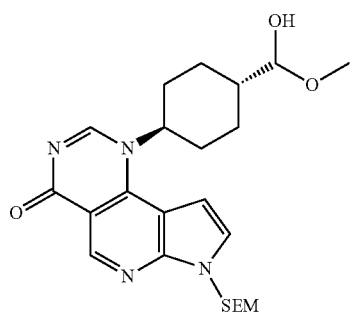 [SMILES: COC(O)[C@H]1CC[C@H](n2cnc(=O)c3cnc4c(ccn4COCC[Si](C)(C)C)c32)CC1]

trans-4-(4-oxo-7-{[2-(Trimethylsilyl)ethoxy]methyl}-4,7-dihydro-1H-pyrrolo[3',2':5,6]pyrido[4,3-d]pyrimidin-1-yl)cyclohexanecarbaldehyde (1.7 g) obtained in Reference Synthetic Example 23 was dissolved in a mixed solvent of chloroform/methanol, and purified by silica gel column chromatography (ethyl acetate→chloroform/methanol=1/0→5/1 (v/v)) to obtain a mixture of the title compound and the starting compound (3:1) as a white solid (1.4 g, yield: 74%).

LC/MS: measurement condition 2, retention time=2.27 min.

LC/MS (ESI$^+$) m/z; 427 [M+H-MeOH]$^+$ (detected as a demethanolated body)

Reference Synthetic Example 34

1-[trans-4-({[1-(Trifluoromethyl)cyclopropyl]amino}methyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one

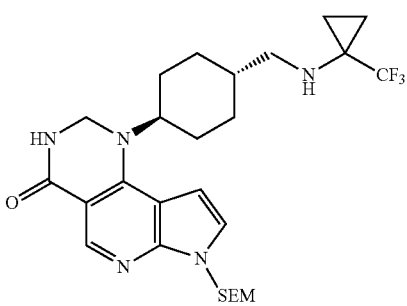 [SMILES: C[Si](C)(C)CCOCn1ccc2c3c(cnc21)C(=O)NCN3[C@H]1CC[C@H](CNC2(C(F)(F)F)CC2)CC1]

To a solution of 1-{trans-4-[hydroxy(methoxy)methyl]cyclohexyl}-7-{[2-(trimethylsilyl)ethoxy]methyl}-1H-pyrrolo[3',2':5,6]pyrido[4,3-d]pyrimidin-4(7H)-one (40.0 mg, 0.0872 mmol) in methanol (1.2 mL), 1-(trifluoromethyl)cyclopropanamine (40.3 μL, 0.436 mmol) and 2-picoline borane (18.6 mg, 0.174 mmol) were added, and the mixture was stirred at 40° C. for 3 hours. The reaction mixture was allowed to cool to room temperature, mixed with sodium borohydride (4.95 mg, 0.131 mmol) and stirred for 30 minutes. The reaction mixture was mixed with saturated aqueous ammonium chloride and extracted with chloroform. The organic layer was washed with saturated aqueous sodium chloride, dried over anhydrous sodium sulfate and concentrated under reduced pressure to obtain the title compound (46.8 mg). The resulting title compound was used for the next step without further purification.

Reference Synthetic Example 35

1-[trans-4-(Bromomethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one

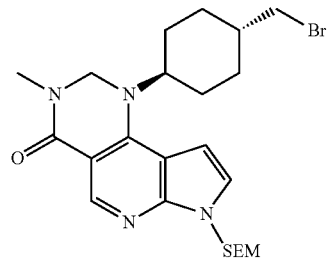 [SMILES: CN1CN([C@H]2CC[C@H](CBr)CC2)c2c(cnc3c2ccn3COCC[Si](C)(C)C)C1=O]

To a solution of 1-[trans-4-(hydroxymethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one (186 mg, 0.418 mmol) obtained in Reference Synthetic Example 28 in dichloromethane (5 mL), 2,3-dichloro-5,6-dicyano-p-benzoquinone (190 mg, 0.837 mmol), triphenylphosphine (219 mg, 0.837 mmol) and tetrabutylammonium bromide (270 mg, 0.837 mmol) were added, and the mixture was stirred at room temperature for 2 hours. The reaction mixture was mixed with saturated aqueous sodium hydrogencarbonate and extracted with ethyl acetate. The organic layer was washed with saturated aqueous ammonium chloride and saturated aqueous sodium chloride, dried over anhydrous sodium sulfate and concentrated under reduced pressure. The residue was purified by silica gel column chromatography (ethyl acetate/hexane=3/2→2/1→6/1→4/1 (v/v)) to obtain a mixture of the title compound and triphenylphosphine oxide. The resulting mixture was used for the next step without further purification.

Reference Synthetic Example 36

1-[trans-4-(Aminomethyl)cyclohexyl]-3-methy-7-{[2-(trimethylsilyl)ethoxy]methyl}-2,3-dihydro-1H-pyrrolo[3',2':5,6]pyrido[4,3-d]pyrimidin-4(7H)-one

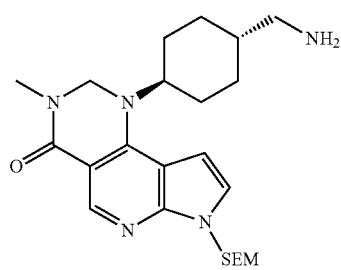 [SMILES: CN1CN([C@H]2CC[C@H](CN)CC2)c2c(cnc3c2ccn3COCC[Si](C)(C)C)C1=O]

To a solution of the mixture of 1-[trans-4-(bromomethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one and triphenylphosphine oxide obtained in Reference Synthetic Example 35 in tetrahydrofuran (5 mL), trimethylsilyl azide (115 μL, 0.837 mmol) and tetrabutylammonium fluoride (1.0M tetrahydrofuran solution, 0.84 mL, 0.84 mmol) were added, and the mixture was stirred at 50° C. for 2 hours. The reaction mixture was mixed with water and extracted with ethyl acetate. The organic layer was washed with saturated aqueous ammonium chloride and saturated aqueous sodium hydrogencarbonate, dried over anhydrous sodium sulfate and concentrated under reduced pressure. The residue was purified by silica gel column chromatography (ethyl acetate/hexane=1/1→2/1→3/1 (v/v)) to obtain a white solid. A suspension of the resulting white solid and 5% palladium-carbon (20.0 mg) in methanol (3 mL) was stirred under a hydrogen atmosphere at room temperature for 2 hours. The reaction mixture was filtered, and the filtrate was concentrated under reduced pressure. The residue was purified by silica gel column chromatography (ethyl acetate→chloroform/methanol=10/1 (v/v)) to obtain the title compound as a white solid (98.2 mg, yield: 53% (3 steps)).

Reference Synthetic Example 37

2-(1-Cyclohexyl-4-oxo-7-{[2-(trimethylsilyl)ethoxy]methyl}-1H-pyrrolo[3',2':5,6]pyrido[4,3-d]pyrimidin-3(2H,4H,7H)-yl)acetonitrile

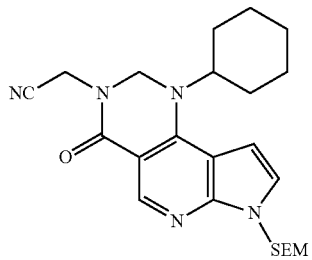 [SMILES: C[Si](C)(C)CCOCn1ccc2c3c(cnc21)C(=O)N(CC#N)CN3C1CCCCC1]

To a solution of 1-cyclohexyl-7-{[2-(trimethylsilyl)ethoxy]methyl}-2,3-dihydro-1H-pyrrolo[3',2':5,6]pyrido[4,3-d]pyrimidin-4(7H)-one (50.0 mg, 0.125 mmol) obtained in Reference Synthetic Example 10 in N,N-dimethylformamide (1 mL), sodium hydride (60 wt % dispersion in liquid paraffin, 8.0 mg, 0.18 mmol) was added at ice bath temperature, and then chloroacetonitrile (15 μL, 0.24 mmol) was added, and the mixture was stirred at room temperature for 4 hours. The reaction mixture was mixed with saturated aqueous ammonium chloride and extracted with ethyl acetate. The organic layer was washed with saturated aqueous ammonium chloride, dried over anhydrous sodium sulfate and concentrated under reduced pressure. The residue was purified by silica gel column chromatography (hexane/ethyl acetate=1/1 (v/v)) to obtain the title compound as a pale yellow oil (35.0 mg, yield: 64%).

Reference Synthetic Example 38

1-[trans-4-(Hydroxymethyl)cyclohexyl]-1H-pyrrolo[3',2':5,6]pyrido[4,3-d]pyrimidin-4(7H)-one

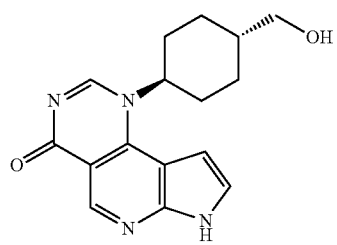 [SMILES: O=c1ncn([C@H]2CC[C@H](CO)CC2)c2c1cnc1[nH]ccc12]

To a solution of 1-(trans-4-{[(tert-butyldimethylsilyl)oxy]methyl}cyclohexyl)-7-{[2-(trimethylsilyl)ethoxy]methyl}-1H-pyrrolo[3',2':5,6]pyrido[4,3-d]pyrimidin-4(7H)-one (36.9 mg, 0.068 mmol) obtained in Reference Synthetic Example 21 in dichloromethane (1 mL), trifluoroacetic acid (0.5 mL) was added, and the mixture was stirred at room temperature for 1 hour, and the reaction mixture was concentrated under reduced pressure. The residue was mixed with toluene and concentrated under reduced pressure. To a solution of the resulting residue in a mixed solvent of water (0.05 mL) and methanol (1 mL), 1M aqueous sodium hydroxide (0.05 mL) and ethylenediamine (0.05 mL) were added, and the mixture was stirred at room temperature for 17 hours. The reaction mixture was mixed with water, and the insolubles were collected by filtration and dried under reduced pressure to obtain the title compound as a white solid (15 mg, yield: 74%).

Reference Synthetic Example 39 trans-4-(4-oxo-4,7-Dihydro-1H-pyrrolo[3',2':5,6]pyrido[4,3-d]pyrimidin-1-yl)cyclohexanecarbaldehyde

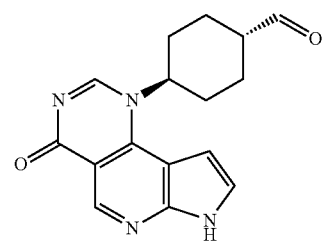 [SMILES: O=C[C@H]1CC[C@H](n2cnc(=O)c3cnc4[nH]ccc4c32)CC1]

To a solution of 1-[trans-4-(Hydroxymethyl)cyclohexyl]-1H-pyrrolo[3',2':5,6]pyrido[4,3-d]pyrimidin-4(7H)-one (10 mg, 0.034 mmol) in dimethylsulfoxide (0.5 mL), 2-iodoxybenzoic acid (11 mg, 0.041 mmol) was added, and the mixture was stirred at room temperature for 17 hours. After 2-iodoxybenzoic acid (2 mg, 0.007 mmol) was added again, the mixture was stirred at room temperature for 6 hours. After further addition of 2-iodoxybenzoic acid (4 mg, 0.014 mmol), the mixture was stirred at room temperature for 15 hours. The reaction mixture was mixed with aqueous sodium hydrogencarbonate and aqueous sodium thiosulfate, and the mixture was stirred at room temperature for 1 hour. The reaction mixture was extracted with chloroform twice, with a mixed solvent of chloroform/2-propanol (5/1 (v/v)) twice, and with a mixed solvent of chloroform/methanol (10/1 (v/v)) five times. The resulting organic layers were combined, dried over anhydrous sodium sulfate and concentrated under reduced pressure. The residue was purified by reversed-phase silica gel column chromatography (IsoluteC18, water/methanol=90/10→0/100 (v/v)) to obtain the title compound as a white solid (10.4 mg, quantitative yield).

Reference Synthetic Example 40

1-(trans-4-{[(2,2-Difluoroethyl)amino]methyl}cyclohexyl)-3-methyl-7-{[2-(trimethylsilyl)ethoxy]methyl}-2,3-dihydro-1H-pyrrolo[3',2':5,6]pyrido[4,3-d]pyrimidin-4(7H)-one

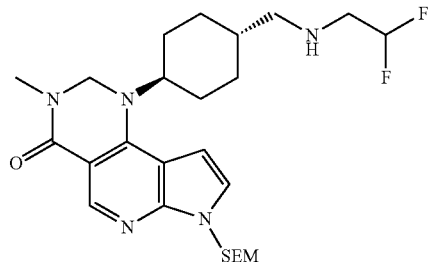 [SMILES: CN1CN([C@H]2CC[C@H](CNCC(F)F)CC2)c2c(cnc3c2ccn3COCC[Si](C)(C)C)C1=O]

To a solution of trans-4-(3-methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (24 mg, 0.053 mmol) obtained in Reference Synthetic Example 29 in methanol (0.5 mL), 2,2-difluoroethylamine (5.0 μL, 0.069 mmol) and 2-picoline borane (7.4 mg, 0.069 mmol) were added, and the mixture was stirred at room temperature for 20 hours. The reaction mixture was mixed with 1M aqueous sodium hydroxide and extracted with ethyl acetate. The organic layer was dried over anhydrous sodium sulfate and concentrated under reduced pressure. The residue was purified by silica gel thin-layer chromatography (ethyl acetate/2-propanol=9/1 (v/v)) to obtain the title compound as a pale green oil (17.4 mg, yield: 65%).

Reference Synthetic Example 41

2-(Methyl{[trans-4-(3-methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}amino)acetonitrile

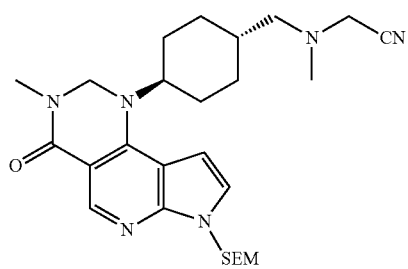 [SMILES: CN(CC#N)C[C@H]1CC[C@H](N2CN(C)C(=O)c3cnc4c(ccn4COCC[Si](C)(C)C)c32)CC1]

To a solution of trans-4-(3-methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (25 mg, 0.056 mmol) obtained in Reference Synthetic Example 29 in methanol (0.5 mL), methylaminoacetonitrile hydrochloride (7.8 mg, 0.073 mmol) and 2-picoline borane (8.1 mg, 0.073 mmol) were added, and the mixture was stirred at room temperature for 3 hours. The reaction mixture was mixed with 1M aqueous sodium hydroxide and extracted with ethyl acetate. The organic layer was dried over anhydrous sodium sulfate and concentrated under reduced pressure. The residue was purified by silica gel thin-layer chromatography (ethyl acetate/2-propanol=9/1 (v/v)) to obtain the title compound as a colorless oil (27.5 mg, yield: 99%).

Reference Synthetic Example 42

2-({[trans-4-(3-Methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}amino)acetonitrile

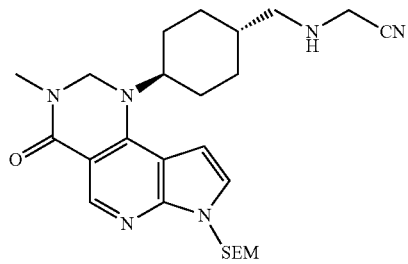 [SMILES: CN1CN([C@H]2CC[C@H](CNCC#N)CC2)c2c(cnc3c2ccn3COCC[Si](C)(C)C)C1=O]

To a solution of trans-4-(3-methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (26 mg, 0.058 mmol) obtained in Reference Synthetic Example 29 in methanol (0.5 mL), aminoacetonitrile hydrochloride (7.1 mg, 0.077 mmol) and 2-picoline borane (8.2 mg, 0.073 mmol) were added, and the mixture was stirred at room temperature for 3 hours. The reaction mixture was mixed with 1M aqueous sodium hydroxide and extracted with ethyl acetate. The organic layer was dried over anhydrous sodium sulfate and concentrated under reduced pressure. The residue was purified by silica gel thin-layer chromatography (ethyl acetate/2-propanol=9/1 (v/v)) to obtain the title compound as a colorless oil (19.5 mg, yield: 40%).

Reference Synthetic Example 43

3-Methyl-1-{trans-4-[(methylamino)methyl]cyclohexyl}-7-{[2-(trimethylsilyl)ethoxy]methyl}-2,3-dihydro-1H-pyrrolo[3',2':5,6]pyrido[4,3-d]pyrimidin-4(7H)-one

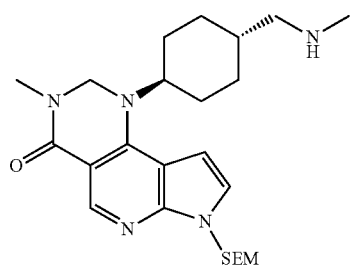

To a solution of trans-4-(3-methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (22 mg, 0.050 mmol) obtained in Reference Synthetic Example 29 in methanol (0.5 mL), methylamine (2M methanol solution, 0.1 mL) and 2-picoline borane (8.1 mg, 0.073 mmol) were added, and the mixture was stirred at room temperature for 3 hours. The reaction mixture was mixed with 1M aqueous sodium hydroxide and extracted with ethyl acetate. The organic layer was dried over anhydrous sodium sulfate and concentrated under reduced pressure to obtain a green oil containing the title compound (30.4 mg). The resulting green oil was used for the next step without further purification.

Reference Synthetic Example 44

N-Methyl-N-{[trans-4-(3-methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}methanesulfonamide

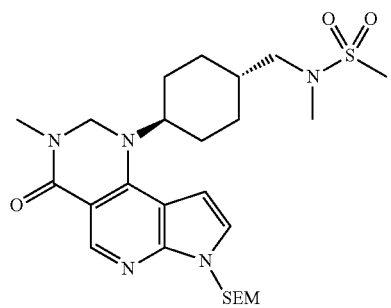

To a solution of 3-methyl-1-{trans-4-[(methylamino)methyl]cyclohexyl}-7-{[2-(trimethylsilyl)ethoxy]methyl}-2,3-dihydro-1H-pyrrolo[3',2':5,6]pyrido[4,3-d]pyrimidin-4(7H)-one (30 mg, 0.056 mmol) in dichloromethane (1.0 mL), N,N-diisopropylethylamine (0.10 mL, 0.58 mmol) and methanesulfonyl chloride (50 µL, 0.64 mmol) were added, and the mixture was stirred at room temperature for 24 hours. The reaction mixture was mixed with saturated aqueous ammonium chloride and extracted with chloroform. The organic layer was dried over anhydrous sodium sulfate and concentrated under reduced pressure. The residue was purified by silica gel thin-layer chromatography (ethyl acetate/2-propanol=20/1 (v/v)) to obtain the title compound as a colorless oil (8.6 mg, yield: 32%).

Reference Synthetic Example 45 tert-Butyl {[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate

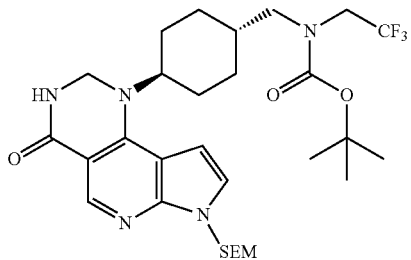 [SMILES: CC(C)(C)OC(=O)N(CC(F)(F)F)C[C@H]1CC[C@H](N2CNC(=O)c3cnc4c(ccn4COCC[Si](C)(C)C)c32)CC1]

To a solution of 1-(trans-4-{[(2,2,2-trifluoroethyl)amino]methyl}cyclohexyl)-7-{[2-(trimethylsilyl)ethoxy]methyl}-2,3-dihydro-1H-pyrrolo[3',2':5,6]pyrido[4,3-d]pyrimidin-4(7H)-one (130 mg, 0.255 mmol) obtained in Reference Synthetic Example 25 in dichloromethane (2.5 mL), di-tert-butyl dicarbonate (111 mg, 0.510 mmol) and triethylamine (88.9 µL, 0.638 mmol) were added, and the mixture was stirred at room temperature for 2 days. The reaction mixture was mixed with saturated aqueous ammonium chloride and extracted with ethyl acetate. The organic layer was washed with saturated aqueous sodium chloride, dried over anhydrous sodium sulfate and concentrated under reduced pressure. The residue was purified by silica gel column chromatography (2-propanol/ethyl acetate=1/15→1/10→1/4 (v/v)) to obtain the title compound as a pale yellow oil (121 mg, yield: 78%).

Reference Synthetic Example 46 tert-Butyl ({trans-4-[3-(2-methoxyethyl)-4-oxo-7-{[2-(trimethylsilyl)ethoxy]methyl}-2,3,4,7-tetrahydro-1H-pyrrolo[3',2':5,6]pyrido[4,3-d]pyrimidin-1-yl]cyclohexyl}methyl)(2,2,2-trifluoroethyl)carbamate

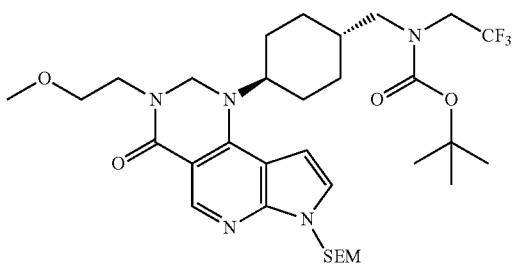 [SMILES: COCCN1CN([C@H]2CC[C@H](CN(CC(F)(F)F)C(=O)OC(C)(C)C)CC2)c2c(cnc3c2ccn3COCC[Si](C)(C)C)C1=O]

To a solution of tert-butyl {[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate (53.6 mg, 0.0876 mmol) in N,N-dimethylformamide (0.5 mL), sodium hydride (60 wt % dispersion in liquid paraffin, 5.2 mg, 0.13 mmol) was added, and the mixture was stirred at room temperature for 30 minutes, and 1-bromo-2-methoxyethane (15 µL, 0.13 mmol) was added, and the mixture was stirred at room temperature for 3 hours. The reaction mixture was mixed with water and extracted with ethyl acetate. The organic layer was dried over anhydrous sodium sulfate and concentrated under reduced pressure. The residue was purified by silica gel thin-layer chromatography (ethyl acetate/hexane=2/3 (v/v)) to obtain the title compound as a colorless oil (26.8 mg, yield: 45%).

Reference Synthetic Example 47 tert-Butyl [(trans-4-{3-[(methylthio)methyl]-4-oxo-7-{[2-(trimethylsilyl)ethoxy]methyl}-2,3,4,7-tetrahydro-1H-pyrrolo[3',2':5,6]pyrido[4,3-d]pyrimidin-1-yl}cyclohexyl)methyl](2,2,2-trifluoroethyl)carbamate

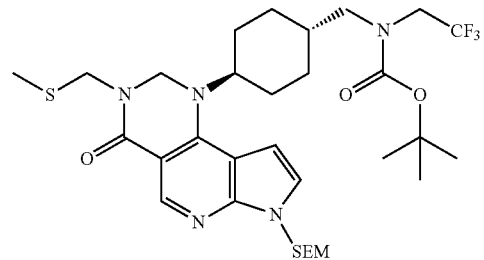 [SMILES: CSCN1CN([C@H]2CC[C@H](CN(CC(F)(F)F)C(=O)OC(C)(C)C)CC2)c2c(cnc3c2ccn3COCC[Si](C)(C)C)C1=O]

To a solution of tert-butyl {[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate (61.5 mg, 0.101 mmol) obtained in Reference Synthetic Example 45 in N,N-dimethylformamide (0.5 mL), sodium hydride (60 wt % dispersion in liquid paraffin, 6.0 mg, 0.15 mmol) was added, and the mixture was stirred at room temperature for 30 minutes, and methylchloromethyl sulfide (12.5 µL, 0.15 mmol) was added, and the mixture was stirred at room temperature for 3 hours. The reaction mixture was mixed with water and extracted with ethyl acetate. The organic layer was dried over anhydrous sodium sulfate and concentrated under reduced pressure. The residue was purified by silica gel thin-layer chromatography (ethyl acetate/hexane=2/1 (v/v)) to obtain the title compound as a colorless oil (24.1 mg, yield: 36%).

Reference Synthetic Example 48 tert-Butyl {[trans-4-(4-oxo-3-(2,2,2-trifluoroethyl)-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate

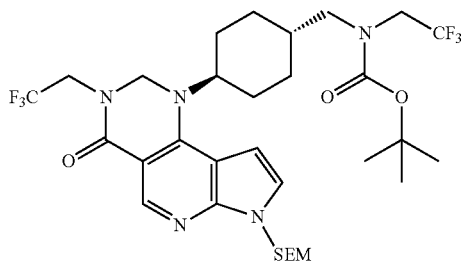 [SMILES: CC(C)(C)OC(=O)N(CC(F)(F)F)C[C@H]1CC[C@H](N2CN(CC(F)(F)F)C(=O)c3cnc4c(ccn4COCC[Si](C)(C)C)c32)CC1]

To a solution of tert-butyl {[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate (30.0 mg, 0.0490 mmol) obtained in Reference Synthetic Example 45 in N,N-dimethylformamide (1 mL), sodium hydride (55 wt % dispersion in liquid paraffin, 3.2 mg, 0.074 mmol) was added at ice bath temperature, and the mixture was stirred for 10 minutes, and 2,2,2-trifluoroethyl trifluoromethanesulfonate (10.6 μL, 0.0735 mmol) was added, and the mixture was stirred at room temperature for 2 hours. The reaction mixture was mixed with water and saturated aqueous sodium hydrogencarbonate and extracted with chloroform three times. The organic layer was dried over anhydrous sodium sulfate and concentrated under reduced pressure. The residue was purified by silica gel thin-layer chromatography (ethyl acetate/hexane=1/2 (v/v)) to obtain the title compound as a pale yellow oil (20.0 mg, yield: 59%).

Reference Synthetic Example 49 tert-Butyl {[trans-4-(3-(methoxymethyl)-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate

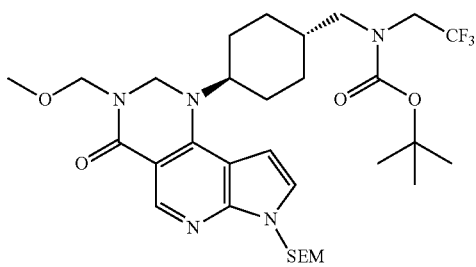 [SMILES: COCN1CN([C@H]2CC[C@H](CN(CC(F)(F)F)C(=O)OC(C)(C)C)CC2)c2c(cnc3c2ccn3COCC[Si](C)(C)C)C1=O]

To a solution of tert-Butyl {[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate (30.0 mg, 0.0490 mmol) obtained in Reference Synthetic Example 45 in N,N-dimethylformamide (1 mL), sodium hydride (55 wt % dispersion in liquid paraffin, 3.2 mg, 0.074 mmol) was added at ice bath temperature, and the mixture was stirred for 10 minutes, and chloromethyl methyl ether (10.0 μL, 0.133 mmol) was added, and the mixture was stirred at room temperature for 1 day. The reaction mixture was mixed with water and saturated aqueous sodium hydrogencarbonate and extracted with chloroform three times. The organic layers were combined, dried over anhydrous sodium sulfate and concentrated under reduced pressure. The residue was purified by silica gel thin-layer chromatography (ethyl acetate/hexane=1/2 (v/v)) to obtain the title compound as a pale yellow oil (18.0 mg, yield: 56%).

Reference Synthetic Example 50

1-(trans-4-{[(tert-Butyldimethylsilyl)oxy]methyl}cyclohexyl)-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one

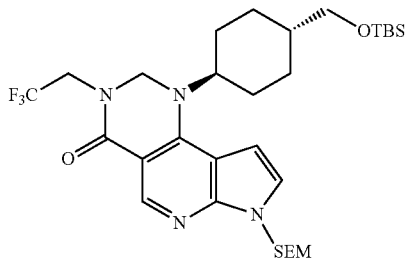 [SMILES: CC(C)(C)[Si](C)(C)OC[C@H]1CC[C@H](N2CN(CC(F)(F)F)C(=O)c3cnc4c(ccn4COCC[Si](C)(C)C)c32)CC1]

To a solution of 1-(trans-4-{[(tert-butyldimethylsilyl)oxy]methyl}cyclohexyl)-7-{[2-(trimethylsilyl)ethoxy]methyl}-2,3-dihydro-1H-pyrrolo[3',2':5,6]pyrido[4,3-d]pyrimidin-4(7H)-one (300 mg, 0.551 mmol) obtained in Reference Synthetic Example 26 in N,N-dimethylformamide (3 mL), sodium hydride (55 wt % dispersion in liquid paraffin, 31 mg, 0.72 mmol) was added, and the mixture was stirred at room temperature for 1 hour, and 2,2,2-trifluoroethyl trifluoromethanesulfonate (0.103 mL, 0.716 mmol) was added, and the mixture was stirred at room temperature for 1.5 hours. The reaction mixture was mixed with water and aqueous ammonium chloride and extracted with ethyl acetate. The organic layer was washed with water and saturated aqueous sodium chloride, dried over anhydrous sodium sulfate and concentrated under reduced pressure. The residue was purified by silica gel column chromatography to obtain the title compound as a colorless oil (176 mg, yield: 51%).

Reference Synthetic Example 51

1-[trans-4-(Hydroxymethyl)cyclohexyl]-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one

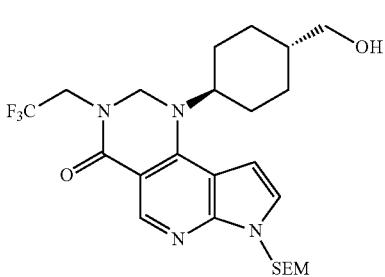 [SMILES: C[Si](C)(C)CCOCn1ccc2c3c(cnc21)C(=O)N(CC(F)(F)F)CN3[C@H]1CC[C@H](CO)CC1]

The title compound was obtained as a colorless oil (141 mg, yield: 98%) substantially in the same manner as in Reference Synthetic Example 28 except that 1-(trans-4-{[(tert-butyldimethylsilyl)oxy]methyl}cyclohexyl)-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one was used instead of 1-(trans-4-{[(tert-butyldimethylsilyl)oxy]methyl}cyclohexyl)-3-methyl-7-{[2-(trimethylsilyl)ethoxy]methyl}-2,3-dihydro-1H-pyrrolo[3',2':5,6]pyrido[4,3-d]pyrimidin-4(7H)-one.

Reference Synthetic Example 52

1-[trans-4-(Bromomethyl)cyclohexyl]-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one

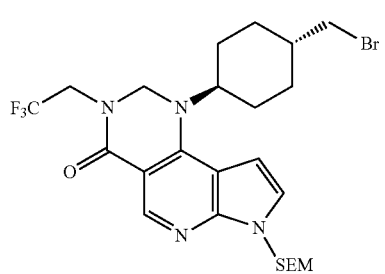 [SMILES: C[Si](C)(C)CCOCn1ccc2c3c(cnc21)C(=O)N(CC(F)(F)F)CN3[C@H]1CC[C@H](CBr)CC1]

The title compound was obtained as a colorless oil (124 mg, yield: 79%) substantially in the same manner as in Reference Synthetic Example 35 except that 1-[trans-4-(hydroxymethyl)cyclohexyl]-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one was used instead of 1-[trans-4-(hydroxymethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one.

Reference Synthetic Example 53

1-[trans-4-(Aminomethyl)cyclohexyl]-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one

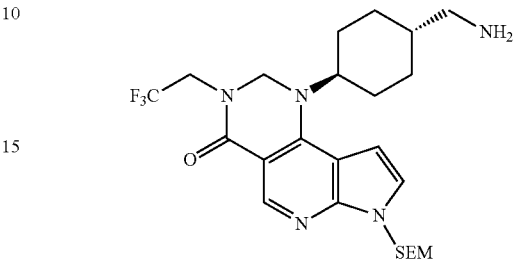

The title compound was obtained as a colorless oil (96.0 mg, yield: 87%) substantially in the same manner as in Reference Synthetic Example 36 except that 1-[trans-4-(bromomethyl)cyclohexyl]-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one was used instead of the mixture containing 1-[trans-4-(bromomethyl)cyclohexyl]-3-methy-7-{[2-(trimethylsilyl)ethoxy]methyl}-2,3-dihydro-1H-pyrrolo[3',2':5,6]pyrido[4,3-d]pyrimidin-4(7H)-one.

Reference Synthetic Example 54

N-({trans-4-[4-oxo-3-(2,2,2-Trifluoroethyl)-7-{[2-(trimethylsilyl)ethoxy]methyl}-2,3,4,7-tetrahydro-1H-pyrrolo[3',2':5,6]pyrido[4,3-d]pyrimidin-1-yl]cyclohexyl}methyl)methanesulfonamide

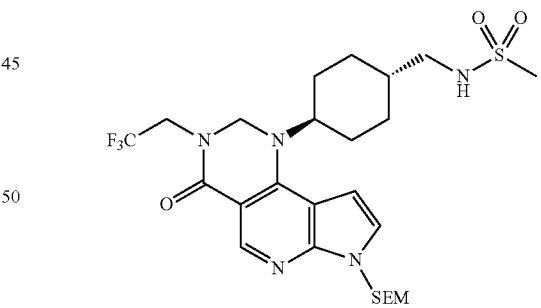

To a solution of 1-[trans-4-(aminomethyl)cyclohexyl]-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one (30 mg, 0.059 mmol) in dichloromethane (1.5 mL), triethylamine (0.025 mL, 0.18 mmol) and methanesulfonyl chloride (6.8 μL, 0.088 mmol) were added, and the mixture was stirred at room temperature for 17 hours. The reaction mixture was mixed with water and extracted with ethyl acetate. The organic layer was washed with saturated aqueous sodium chloride, dried over anhydrous sodium sulfate and concentrated under reduced pressure. The residue was purified by silica gel column chromatography (hexane/ethyl acetate/methanol=100/0/0→0/100/0→0/90/10 (v/v/v)) to obtain the title compound as a colorless oil (22.9 mg, yield: 66%).

Reference Synthetic Example 55

N-{[trans-4-(4-oxo-3-(2,2,2-Trifluoroethyl)-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}cyclopropanesulfonamide

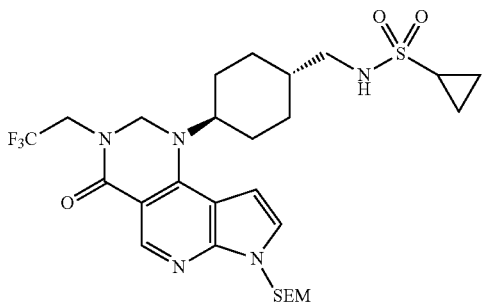 [SMILES: C[Si](C)(C)CCOCn1ccc2c3c(cnc21)C(=O)N(CC(F)(F)F)CN3[C@H]1CC[C@H](CNS(=O)(=O)C2CC2)CC1]

The title compound was obtained as a colorless oil (29.7 mg, yield: 82%) substantially in the same manner as in Reference Synthetic Example 54 except that cyclopropanesulfonyl chloride was used instead of methanesulfonyl chloride.

Reference Synthetic Example 56

1-{trans-4-[(Cyclopropylamino)methyl]cyclohexyl}-3-methyl-7-{[2-(trimethylsilyl)ethoxy]methyl}-2,3-dihydro-1H-pyrrolo[3',2':5,6]pyrido[4,3-d]pyrimidin-4(7H)-one

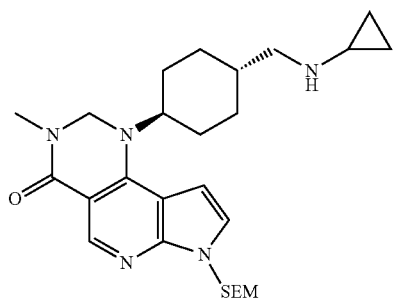 [SMILES: CN1CN([C@H]2CC[C@H](CNC3CC3)CC2)c2c(cnc3c2ccn3COCC[Si](C)(C)C)C1=O]

The title compound was obtained as a colorless amorphous substance (18.0 mg, yield: 43%) substantially in the same manner as in Reference Synthetic Example 30 except that cyclopropylamine was used instead of 2,2,2-trifluoroethylamine.

Reference Synthetic Example 57 tert-Butyl ({trans-4-[3-(cyclopropylmethyl)-4-oxo-7-{[2-(trimethylsilyl)ethoxy]methyl}-2,3,4,7-tetrahydro-1H-pyrrolo[3',2':5,6]pyrido[4,3-d]pyrimidin-1-yl]cyclohexyl}methyl)(2,2,2-trifluoroethyl)carbamate

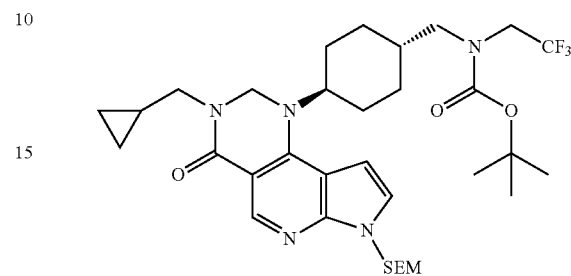

The title compound was obtained as a colorless oil (30.5 mg, yield: 93%) substantially in the same manner as in Reference Synthetic Example 46 except that (bromomethyl)cyclopropane was used instead of 1-bromo-2-methoxyethane.

Reference Synthetic Example 58 tert-Butyl [(trans-4-{4-oxo-3-[(tetrahydrofuran-2-yl)methyl]-7-{[2-(trimethylsilyl)ethoxy]methyl}-2,3,4,7-tetrahydro-1H-pyrrolo[3',2':5,6]pyrido[4,3-d]pyrimidin-1-yl}cyclohexyl)methyl](2,2,2-trifluoroethyl)carbamate

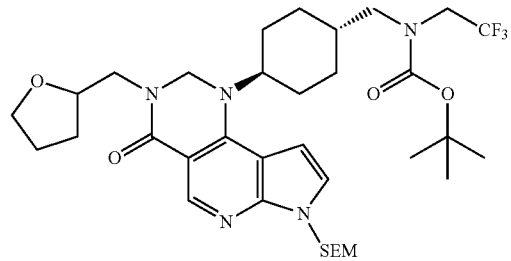 [SMILES: CC(C)(C)OC(=O)N(CC(F)(F)F)C[C@H]1CC[C@H](N2CN(CC3CCCO3)C(=O)c3cnc4c(ccn4COCC[Si](C)(C)C)c32)CC1]

The title compound was obtained as a colorless oil (20.7 mg, yield: 61%) substantially in the same manner as in Reference Synthetic Example 46 except that 2-(bromomethyl)tetrahydrofuran was used instead of 1-bromo-2-methoxyethane.

Reference Synthetic Example 59 tert-Butyl {[trans-4-(3-cyanopropyl)-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate

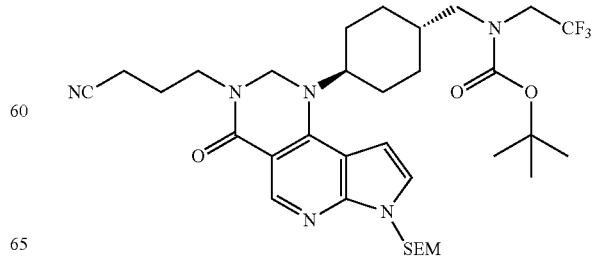

The title compound was obtained as a colorless oil (34.3 mg, yield: 78%) substantially in the same manner as in Reference Synthetic Example 46 except that 4-bromobutyronitrile was used instead of 1-bromo-2-methoxyethane.

Reference Synthetic Example 60 tert-Butyl {[trans-4-(3-cyclopropyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate

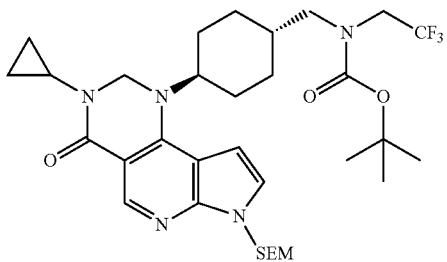 [SMILES: CC(C)(C)OC(=O)N(CC(F)(F)F)C[C@H]1CC[C@H](N2CN(C3CC3)C(=O)c3cnc4c(ccn4COCC[Si](C)(C)C)c32)CC1]

To a solution of tert-butyl {[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate (40.0 mg, 0.0654 mmol) obtained in Reference Synthetic Example 45 in 1,2-dichloroethane (1.5 mL), cyclopropylboronic acid (11.3 mg, 0.131 mmol), copper(II) acetate (13.1 mg, 0.0719 mmol), 2,2'-bipyridine (11.2 mg, 0.0791 mmol) and sodium carbonate (13.9 mg, 0.131 mmol) were added, and the mixture was stirred at 70° C. for 2 hours. To the reaction mixture, cyclopropylboronic acid (11.3 mg, 0.131 mmol), copper(II) acetate (13.1 mg, 0.0719 mmol) and 2,2'-bipyridine (11.2 mg, 0.0791 mmol) were added, and the mixture was stirred at 70° C. for 2 hours, and then cyclopropylboronic acid (11.3 mg, 0.131 mmol), copper(II) acetate (13.1 mg, 0.0719 mmol) and 2,2'-bipyridine (11.2 mg, 0.0791 mmol) were added again, and the mixture was stirred at 70° C. for 1.5 hours. The reaction mixture was mixed with saturated aqueous ammonium chloride and extracted with ethyl acetate. The organic layer was washed with saturated aqueous sodium hydrogencarbonate and saturated aqueous sodium chloride, dried over anhydrous sodium sulfate and concentrated under reduced pressure. The residue was purified by silica gel column chromatography (hexane/ethyl acetate=1/1→0/2 (v/v)→ethyl acetate) to obtain the title compound as a yellow oil (27.5 mg, yield: 65%).

LC/MS: measurement condition 1, retention time=5.00 min.

LC/MS (ESI$^+$) m/z; 652 [M+H]$^+$

LC/MS (ESI$^-$) m/z; 696 [M–H+HCO$_2$H]$^-$ (detected as a formic acid adduct)

Reference Synthetic Example 61 tert-Butyl {[trans-4-(3-ethyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate

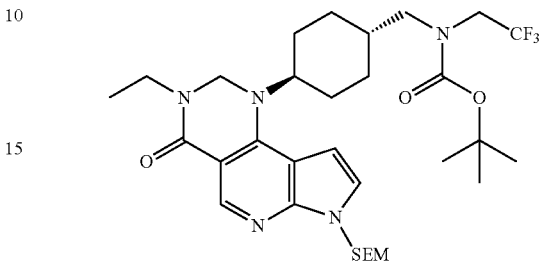

The title compound was obtained as a colorless oil (42.3 mg, yield: 81%) substantially in the same manner as in Reference Synthetic Example 46 except that ethyl iodide was used instead of 1-bromo-2-methoxyethane.

LC/MS: measurement condition 1, retention time=4.99 min.

LC/MS (ESI$^+$) m/z; 640 [M+H]$^+$

LC/MS (ESI$^-$) m/z; 684 [M–H+HCO$_2$H]$^-$ (detected as a formic acid adduct)

Reference Synthetic Example 62

1-{trans-4-[(1,1-Dioxidoisothiazolidin-2-yl)methyl]cyclohexyl]-3-(2,2,2-trifluoroethyl)-7-{[2-(trimethtylsilyl)ethoxy]methyl}-2,3-dihydro-1H-pyrrolo[3',2':5,6]pyrido[4,3-d]pyrimidin-4(7H)-one

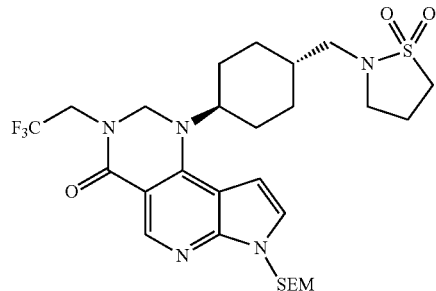 [SMILES: C[Si](C)(C)CCOCn1ccc2c3c(cnc21)C(=O)N(CC(F)(F)F)CN3[C@H]1CC[C@H](CN2CCCS2(=O)=O)CC1]

To a solution of 1-[trans-4-(aminomethyl)cyclohexyl]-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one (30 mg, 0.059 mmol) obtained in Reference Synthetic Example 53 in dichloromethane (1.5 mL), triethylamine (0.025 mL, 0.18 mmol) and 3-chloropropane-1-sulfonyl chloride (0.011 mL, 0.088 mmol) were added, and the mixture was stirred at room temperature for 17 hours. The reaction mixture was mixed with water and extracted with ethyl acetate. The organic layer was washed with saturated aqueous sodium chloride, dried over anhydrous sodium sulfate and concentrated under reduced pressure. To a solution of the resulting residue in tetrahydrofuran (1 mL), sodium hydride (55 wt % dispersion in liquid paraffin, 4.2 mg, 0.097 mmol) was added, and the mixture was stirred at room temperature for 24 hours. After further addition of sodium hydride (55 wt % dispersion in liquid paraffin, 4.2 mg, 0.097 mmol), the mixture was stirred at room temperature for 4 days. To the reaction mixture, 1,8-diazabicyclo[5.4.0]undec-7-ene (9.7 µL, 0.065 mmol) was added, and the mixture was stirred at room temperature for 24 hours. Additional amount of 1,8-diazabicyclo[5.4.0]undec-7-ene (0.019 mL, 0.13 mmol) was added, and the mixture was stirred at room temperature for 4 days. Additional amount of 1,8-diazabicyclo[5.4.0]undec-7-ene (0.095 mL, 0.65 mmol) was added again, and the mixture was stirred at room temperature for 2 days. The reaction mixture was mixed with water and aqueous ammonium chloride and extracted with ethyl acetate. The organic layer was washed with aqueous ammonium chloride twice, with water once and with saturated aqueous sodium chloride once, dried over anhydrous sodium sulfate and concentrated under reduced pressure. The residue was purified by silica gel column chromatography (hexane/ethyl acetate/methanol=100/0/0→0/100/0→0/90/10 (v/v/v)) to obtain the title compound as a colorless oil (10 mg, yield: 25%).

Reference Synthetic Example 63

2-[1-(trans-4-{[(tert-Butoxycarbonyl)(2,2,2-trifluoroethyl)amino]methyl}cyclohexyl)-4-oxo-7-{[2-(trimethylsilyl)ethoxy]methyl}-1H-pyrrolo[3',2':5,6]pyrido[4,3-d]pyrimidin-3(2H,4H,7H)-yl]acetic acid

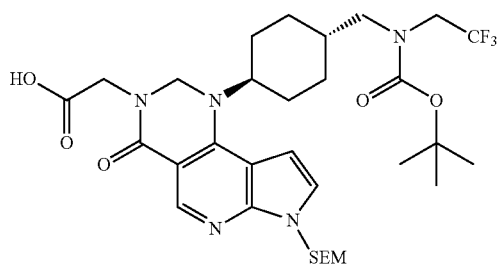 [SMILES: CC(C)(C)OC(=O)N(CC(F)(F)F)C[C@H]1CC[C@H](N2CN(CC(=O)O)C(=O)c3cnc4c(ccn4COCC[Si](C)(C)C)c32)CC1]

The title compound was obtained as a colorless oil (34.2 mg, yield: 52%) substantially in the same manner as in Reference Synthetic Example 46 except that ethyl bromoacetate was used instead of 1-bromo-2-methoxyethane.

Reference Synthetic Example 64 tert-Butyl [(trans-4-{3-[2-(dimethylamino)-2-oxoethyl]-4-oxo-7-{[2-(trimethylsilyl)ethoxy]methyl}-2,3,4,7-tetrahydro-1H-pyrrolo[3',2':5,6]pyrido[4,3-d]pyrimidin-1-yl}cyclohexyl)methyl](2,2,2-trifluoroethyl)carbamate

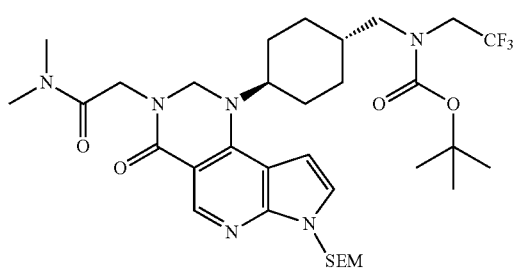 [SMILES: CN(C)C(=O)CN1CN([C@H]2CC[C@H](CN(CC(F)(F)F)C(=O)OC(C)(C)C)CC2)c2c(cnc3c2ccn3COCC[Si](C)(C)C)C1=O]

To a solution of 2-[1-(trans-4-{[(tert-butoxycarbonyl)(2,2,2-trifluoroethyl)amino]methyl}cyclohexyl)-4-oxo-7-{[2-(trimethylsilyl)ethoxy]methyl}-1H-pyrrolo[3',2':5,6]pyrido[4,3-d]pyrimidin-3(2H,4H,7H)-yl]acetic acid (21.7 mg, 0.032 mmol) in N,N-dimethylformamide (1 ml), dimethylamine (about 50% aqueous solution, 10.0 µL, 0.065 mmol), 0-(7-azabenzotriazol-1-yl)-N,N,N',N'-tetramethyluronium hexafluorophosphate (25.0 mg, 0.065 mmol) and N,N-diisopropylethylamine (11.0 µL, 0.065 mmol) were added, and the mixture was stirred at room temperature for 1 day. The reaction mixture was mixed with water and saturated aqueous ammonium chloride and extracted with chloroform. The organic layer was dried over anhydrous magnesium sulfate and concentrated under reduced pressure. The residue was purified by silica gel column chromatography (chloroform/methanol=9/1 (v/v)) to obtain the title compound as a yellow oil (17.6 mg, yield: 79%).

Reference Synthetic Example 65

2-[1-(trans-4-{[(tert-Butyldimethylsilyl)oxy]methyl}cyclohexyl)-4-oxo-7-{[2-(trimethylsilyl)ethoxy]methyl}-1H-pyrrolo[3',2':5,6]pyrido[4,3-d]pyrimidin-3(2H,4H,7H)-yl]acetonitrile

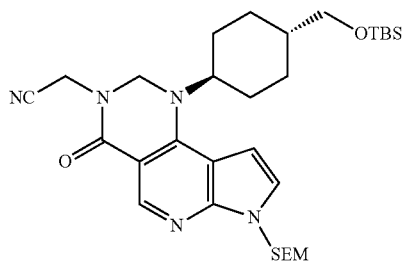 [SMILES: CC(C)(C)[Si](C)(C)OC[C@H]1CC[C@H](N2CN(CC#N)C(=O)c3cnc4c(ccn4COCC[Si](C)(C)C)c32)CC1]

The title compound was obtained as a pale brown oil (206 mg, yield: 96%) substantially in the same manner as in Reference Synthetic Example 27 except that bromoacetonitrile was used instead of methyl iodide.

Reference Synthetic Example 66

N-methyl-N-{[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}methanesulfonamide

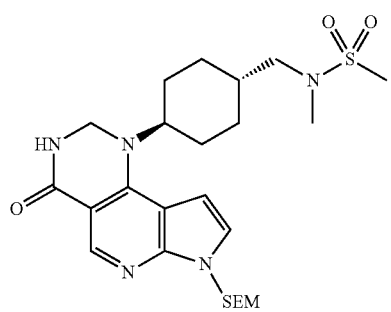 [SMILES: CN(C[C@H]1CC[C@H](N2CNC(=O)c3cnc4c(ccn4COCC[Si](C)(C)C)c32)CC1)S(C)(=O)=O]

To a solution of 1-{trans-4-[hydroxy(methoxy)methyl]cyclohexyl}-7-{[2-(trimethylsilyl)ethoxy]methyl}-1H-pyrrolo[3',2':5,6]pyrido[4,3-d]pyrimidin-4(7H)-one (124 mg, 0.270 mmol) obtained in Reference Synthetic Example 33 in methanol (1 mL), methylamine (2M methanol solution, 1.0 mL, 2.0 mmol), 2-picoline borane (58.7 mg, 0.541 mmol) and acetic acid (0.1 mL) were added, and the mixture was stirred at 40° C. for 4 hours, and sodium borohydride was added, and the mixture was stirred at room temperature for 3 hours. The reaction mixture was mixed with 1M aqueous sodium hydroxide and extracted with ethyl acetate. The organic layer was dried over anhydrous sodium sulfate and concentrated under reduced pressure to obtain a colorless oil (243 mg). To a solution of the resulting colorless oil in dichloromethane (1.0 mL), N,N-diisopropylethylamine (0.200 mL, 1.15 mmol) and methanesulfonyl chloride (0.100 mL, 1.29 mmol) were added, and the mixture was stirred at room temperature for 24 hours. The reaction mixture was mixed with saturated aqueous ammonium chloride and extracted with chloroform. The organic layer was dried over anhydrous sodium sulfate and concentrated under reduced pressure. The resulting residue was purified by silica gel thin-layer chromatography (chloroform/methanol=5/1 (v/v)) to obtain the title compound as a colorless amorphous substance (94.3 mg, yield: 67%).

Reference Synthetic Example 67

N-methyl-N-{[trans-4-(4-oxo-3-(2,2,2-trifluoroethyl)-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}methanesulfonamide

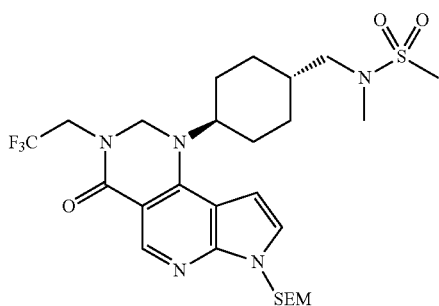 [SMILES: CN(C[C@H]1CC[C@H](N2CN(CC(F)(F)F)C(=O)c3cnc4c(ccn4COCC[Si](C)(C)C)c32)CC1)S(C)(=O)=O]

To a solution of N-methyl-N-{[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}methanesulfonamide (45.6 mg, 0.0875 mmol) in N,N-dimethylformamide (0.5 mL), sodium hydride (60 wt % dispersion in liquid paraffin, 5.2 mg, 0.13 mmol) was added, and the mixture was stirred at room temperature for 30 minutes, and 2,2,2-trifluoroethyl trifluoromethanesulfonate (19 µL, 0.13 mmol) was added, and the mixture was stirred at room temperature for 6 hours. The reaction mixture was mixed with water and extracted with ethyl acetate. The organic layer was dried over anhydrous sodium sulfate and concentrated under reduced pressure. The residue was purified by silica gel thin-layer chromatography (ethyl acetate/hexane=2/1 (v/v)) to obtain the title compound as a colorless oil (15.7 mg, yield: 30%).

Reference Synthetic Example 68

N-{[trans-4-(3-cyclopropyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}-N-methylmethanesulfonamide

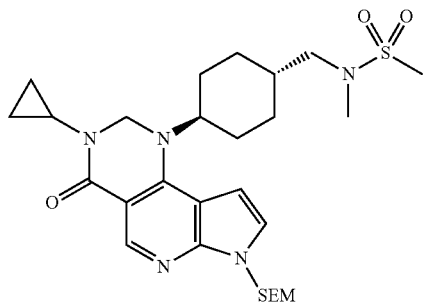 [SMILES: CN(C[C@H]1CC[C@H](N2CN(C3CC3)C(=O)c3cnc4c(ccn4COCC[Si](C)(C)C)c32)CC1)S(C)(=O)=O]

To a solution of N-methyl-N-{[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}methanesulfonamide (42 mg, 0.080 mmol) obtained in Reference Synthetic Example 66 in 1,2-dichloroethane (0.5 mL), cyclopropylboronic acid (13.8 mg, 0.161 mmol), copper(II) acetate (16.2 mg, 0.089 mmol), 2,2'-bipyridine (13.9 mg, 0.089 mmol) and sodium carbonate (17.0 mg, 0.16 mmol) were added, and the mixture was stirred at 70° C. for 3 hours. To the reaction mixture, cyclopropylboronic acid (13.8 mg, 0.16 mmol), copper(II) acetate (16.2 mg, 0.0892 mmol) and 2,2'-bipyridine (13.9 mg, 0.0890 mmol) were added, and the mixture was stirred at 70° C. for 3 hours. The reaction mixture was mixed with saturated aqueous ammonium chloride and extracted with ethyl acetate. The organic layer was dried over anhydrous sodium sulfate and concentrated under reduced pressure. The residue was purified by silica gel thin-layer chromatography (ethyl acetate/hexane=9/1 (v/v)) to obtain the title compound as a colorless amorphous substance (21.2 mg, yield: 47%).

Reference Synthetic Example 69

N-{[trans-4-(3-ethyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}-N-methylmethanesulfonamide

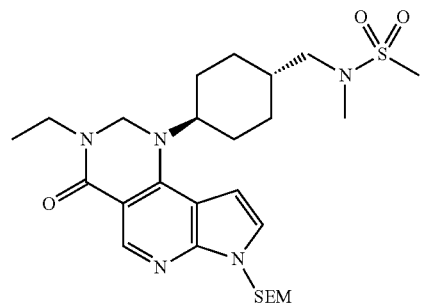 [SMILES: CCN1CN([C@H]2CC[C@H](CN(C)S(C)(=O)=O)CC2)c2c(cnc3c2ccn3COCC[Si](C)(C)C)C1=O]

To a solution of N-methyl-N-{[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}methanesulfonamide (39.7 mg, 0.0762 mmol) obtained in Reference Synthetic Example 66 in N,N-dimethylformamide (0.5 mL), sodium hydride (60 wt % dispersion in liquid paraffin, 4.6 mg, 0.11 mmol) was added, and the mixture was stirred at room temperature for 30 minutes, and ethyl iodide (9.2 μL, 0.11 mmol) was added, and the mixture was stirred at room temperature for 1.5 hours. The reaction mixture was mixed with water and extracted with ethyl acetate. The organic layer was dried over anhydrous sodium sulfate and concentrated under reduced pressure. The residue was purified by silica gel thin-layer chromatography (ethyl acetate/hexane=9/1 (v/v)) to obtain the title compound as a colorless amorphous substance (11.0 mg, yield: 27%).

Reference Synthetic Example 70 tert-Butyl {[trans-4-(3-(cyanomethyl)-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate

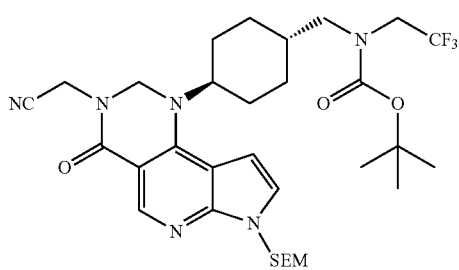 [SMILES: CC(C)(C)OC(=O)N(CC(F)(F)F)C[C@H]1CC[C@H](N2CN(CC#N)C(=O)c3cnc4c(ccn4COCC[Si](C)(C)C)c32)CC1]

To a solution of tert-butyl {[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate (80.0 mg, 0.13 mmol) obtained in Reference Synthetic Example 45 in N,N-dimethylformamide (1.0 mL), sodium hydride (55 wt % dispersion in liquid paraffin, 8.7 mg, 0.20 mmol) was added at ice bath temperature, and the mixture was stirred at room temperature for 1 hour, and bromoacetonitrile (13.0 μL, 0.20 mmol) was added, and the mixture was stirred at room temperature for 4 hours. Sodium hydride (55 wt % dispersion in liquid paraffin, 5.6 mg, 0.13 mmol) and bromoacetonitrile (8.7 μL, 0.13 mmol) were added again, and the mixture was stirred for 18 hours. The reaction mixture was mixed with water and extracted with ethyl acetate twice. The organic layers were combined, washed with saturated aqueous sodium chloride, dried over anhydrous sodium sulfate and concentrated under reduced pressure. The residue was purified by silica gel column chromatography (hexane/ethyl acetate=76/24→45/55 (v/v)) to obtain the title compound as a colorless oil (58.0 mg, yield: 68%).

Reference Synthetic Example 71

1-[trans-4-(Dimethoxymethyl)cyclohexyl]-7-{[2-(trimethylsilyl)ethoxy]methyl}-1H-pyrrolo[3',2':5,6]pyrido[4,3-d]pyrimidin-4(7H)-one

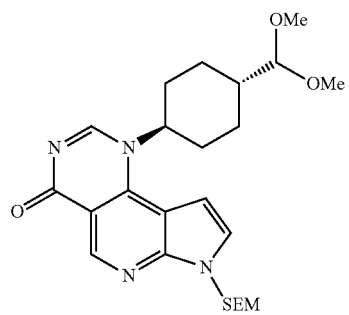 [SMILES: COC(OC)[C@H]1CC[C@H](n2cnc(=O)c3cnc4c(ccn4COCC[Si](C)(C)C)c32)CC1]

To a solution of trans-4-(4-oxo-7-{[2-(trimethylsilyl)ethoxy]methyl}-4,7-dihydro-1H-pyrrolo[3',2':5,6]pyrido[4,3-d]pyrimidin-1-yl)cyclohexanecarbaldehyde (63.8 mg, 0.150 mmol) obtained in Reference Synthetic Example 23 in a mixed solvent of methanol (0.70 mL) and trimethyl orthoformate (0.70 mL), a catalytic amount of p-toluenesulfonic acid monohydrate was added, and the mixture was stirred at reflux temperature for 3 hours. The reaction mixture was mixed with 1M aqueous sodium hydroxide and extracted with ethyl acetate. The organic layer was washed with saturated aqueous sodium chloride, dried over anhydrous sodium sulfate and concentrated under reduced pressure. The residue was purified by silica gel column chromatography (ethyl acetate→ethyl acetate/methanol=20/1→10/1 (v/v)) to obtain the title compound as a colorless amorphous substance (54.2 mg, yield: 77%).

Reference Synthetic Example 72

1-[trans-4-(Dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one

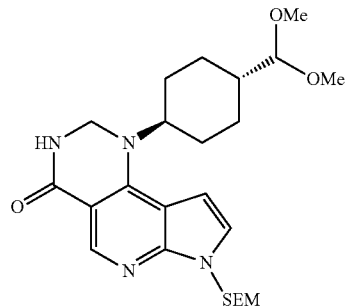 [SMILES: COC(OC)[C@H]1CC[C@H](N2CNC(=O)c3cnc4c(ccn4COCC[Si](C)(C)C)c32)CC1]

To a solution of 1-[trans-4-(dimethoxymethyl)cyclohexyl]-7-{[2-(trimethylsilyl)ethoxy]methyl}-1H-pyrrolo[3',2':5,6]pyrido[4,3-d]pyrimidin-4(7H)-one (54.2 mg, 0.115 mmol) in methanol (1.1 mL), sodium borohydride (5.20 mg, 0.138 mmol) was added at ice bath temperature, and the mixture was stirred for 30 minutes. The reaction mixture was mixed with acetone and then with water, and extracted with ethyl acetate. The organic layer was washed with

Reference Synthetic Example 73

3-Cyclopropyl-1-[trans-4-(dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one

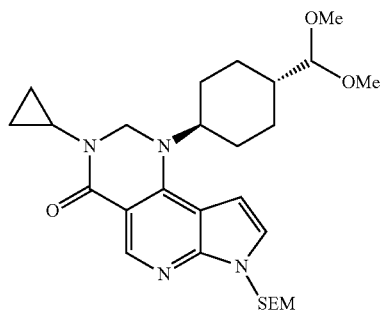 [SMILES: COC(OC)[C@H]1CC[C@H](N2CN(C3CC3)C(=O)c3cnc4c(ccn4COCC[Si](C)(C)C)c32)CC1]

The title compound was obtained as a yellow oil (50.4 mg, yield: 90%) substantially in the same manner as in Reference Synthetic Example 60 except that 1-[trans-4-(dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one was used instead of tert-butyl {[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate.

Reference Synthetic Example 74 trans-4-(3-Cyclopropyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde

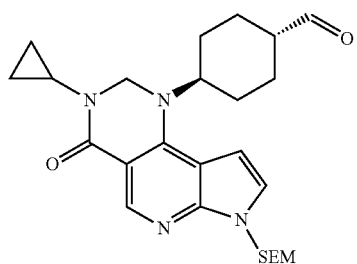 [SMILES: C[Si](C)(C)CCOCn1ccc2c3c(cnc21)C(=O)N(C1CC1)CN3[C@H]1CC[C@H](C=O)CC1]

To a solution of 3-cyclopropyl-1-[trans-4-(dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one (46.8 mg, 90.9 μmol) in a mixed solvent of acetone (1.0 mL) and water (0.15 mL), a catalytic amount of p-toluenesulfonic acid monohydrate was added, and the reaction mixture was stirred at 40° C. for 2 hours. The reaction mixture was mixed with saturated aqueous sodium hydrogencarbonate and extracted with ethyl acetate. The organic layer was washed with saturated aqueous sodium chloride, dried over anhydrous sodium sulfate and concentrated under reduced pressure. The residue was purified by silica gel column chromatography (hexane/ethyl acetate=4/1 (v/v) →ethyl acetate) to obtain the title compound as a colorless oil (24.0 mg, yield: 53%).

Reference Synthetic Example 75

1-[trans-4-(Dimethoxymethyl)cyclohexyl]-3-ethyl-7-{[2-(trimethylsilyl)ethoxy]methyl}-2,3-dihydro-1H-pyrrolo[3',2':5,6]pyrido[4,3-d]pyrimidin-4(7H)-one

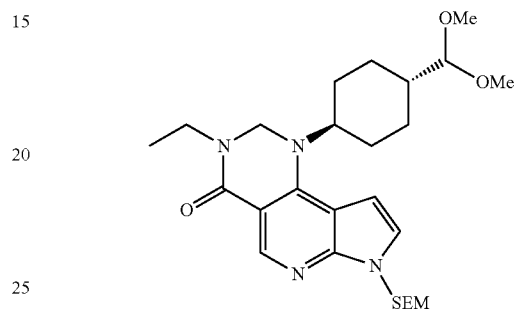

The title compound was obtained as a colorless oil (49.1 mg, yield: 84%) substantially in the same manner as in Reference Synthetic Example 69 except that 1-[trans-4-(dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one obtained in Reference Synthetic Example 72 was used instead of N-methyl-N-{[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}methanesulfonamide.

Reference Synthetic Example 76 trans-4-(3-Ethyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde

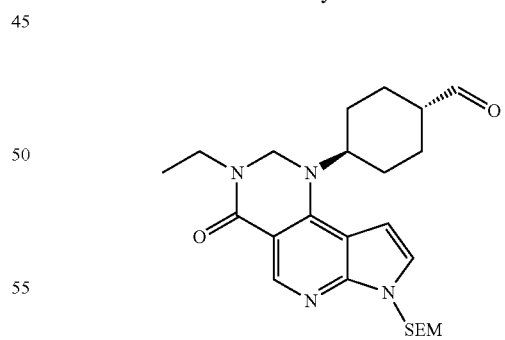

The title compound was obtained as a colorless oil (40.6 mg, yield: 91%) substantially in the same manner as in Reference Synthetic Example 74 except that 1-[trans-4-(dimethoxymethyl)cyclohexyl]-3-ethyl-7-{[2-(trimethylsilyl)ethoxy]methyl}-2,3-dihydro-1H-pyrrolo[3',2':5,6]pyrido[4,3-d]pyrimidin-4(7H)-one was used instead of 3-cyclopropyl-1-[trans-4-(dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one.

Reference Synthetic Example 77

1-[trans-4-(Dimethoxymethyl)cyclohexyl]-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one

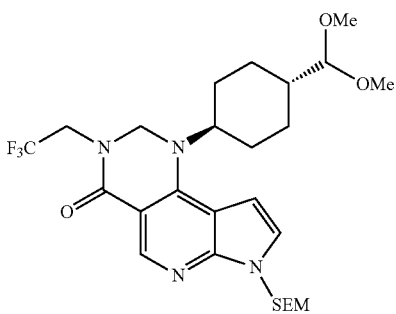 [SMILES: COC(OC)[C@H]1CC[C@H](N2CN(CC(F)(F)F)C(=O)c3cnc4c(ccn4COCC[Si](C)(C)C)c32)CC1]

The title compound was obtained as a colorless oil (36.4 mg, yield: 47%) substantially in the same manner as in Reference Synthetic Example 48 except that 1-[trans-4-(dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one obtained in Reference Synthetic Example 72 was used instead of tert-butyl {[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate.

Reference Synthetic Example 78 trans-4-(4-oxo-3-(2,2,2-Trifluoroethyl)-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde

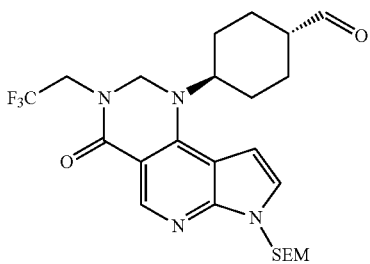

The title compound was obtained as a pale yellow amorphous substance (28.7 mg, yield: 86%) substantially in the same manner as in Reference Synthetic Example 74 except that 1-[trans-4-(dimethoxymethyl)cyclohexyl]-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one was used instead of 3-cyclopropyl-1-[trans-4-(dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one.

Reference Synthetic Example 79

3-(4-{[trans-4-(4-oxo-7-{[2-(Trimethylsilyl)ethoxy]methyl}-2,3,4,7-tetrahydro-1H-pyrrolo[3',2':5,6]pyrido[4,3-d]pyrimidin-1-yl)cyclohexyl]methyl}piperazin-1-yl)propanenitrile

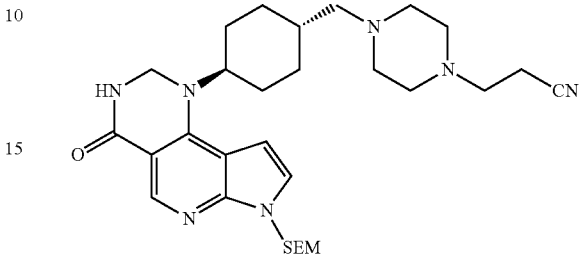

To a solution of trans-4-(4-oxo-7-{[2-(trimethylsilyl)ethoxy]methyl}-4,7-dihydro-1H-pyrrolo[3',2':5,6]pyrido[4,3-d]pyrimidin-1-yl)cyclohexanecarbaldehyde (100 mg, 0.234 mmol) obtained in Reference Synthetic Example 23 in chloroform (2.5 mL), 3-(piperazin-1-yl)propanenitrile (65.3 mg, 0.469 mmol) and sodium triacetoxyborohydride (99.4 mg, 0.469 mmol) were added at room temperature, and the mixture was stirred for 13 hours, and the reaction mixture was concentrated under reduced pressure. To the resulting residue, methanol (2.5 mL) and sodium borohydride (26.6 mg, 0.702 mmol) were added, and the mixture was stirred at room temperature for 20 hours. The reaction mixture was mixed with saturated aqueous ammonium chloride and extracted with ethyl acetate. The organic layer was washed with water and saturated aqueous sodium chloride, dried over anhydrous sodium sulfate and concentrated under reduced pressure. The residue was purified by silica gel column chromatography (ethyl acetate) to obtain the title compound as a white solid (74.0 mg, yield: 57%).

Reference Synthetic Example 80

3-(4-{[trans-4-(3-Cyclopropyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}piperazin-1-yl)propanenitrile

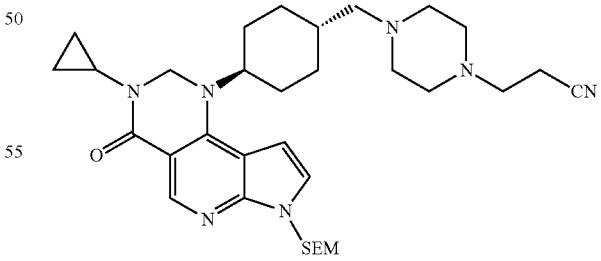

To a solution of 3-(4-{[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}piperazin-1-yl)propanenitrile (30 mg, 0.054 mmol) in 1,2-dichloroethane (1.0 mL), cyclopropylboronic acid (9.36 mg, 0.109 mmol), copper(II) acetate (10.8 mg, 0.0598 mmol), 2,2'-bipyridine (9.34 mg, 0.0598 mmol) and sodium carbonate (11.5 mg, 0.109 mmol) were added, and the mixture was stirred at 70° C. for 1 hour. To the reaction mixture, cyclopropylboronic acid (9.36 mg, 0.109 mmol), copper(II) acetate (10.8 mg, 0.0598 mmol) and 2,2'-bipyridine (9.34 mg, 0.0598 mmol) were added, and the mixture was stirred at 70° C. for 2 hours. The reaction mixture was mixed with water and extracted with ethyl acetate. The organic layer was washed with saturated aqueous sodium chloride, dried over anhydrous sodium sulfate and concentrated under reduced pressure. The residue was purified by silica gel column chromatography (ethyl acetate) to obtain the title compound as a pale yellow oil (15.0 mg, yield: 47%).

Reference Synthetic Example 81

3-(4-{[trans-4-(3-Methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}piperazin-1-yl)propanenitrile

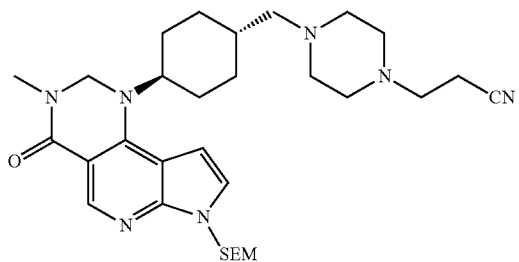 [SMILES: CN1CN([C@H]2CC[C@H](CN3CCN(CCC#N)CC3)CC2)c2c(cnc3c2ccn3COCC[Si](C)(C)C)C1=O]

To a solution of trans-4-(3-methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (33.0 mg, 0.0746 mmol) obtained in Reference Synthetic Example 29 in methanol (1 mL), acetic acid (0.1 mL), 3-(piperazin-1-yl)propanenitrile (20.8 mg, 0.149 mmol) and 2-picoline borane (15.9 mg, 0.149 mmol) were added, and the mixture was stirred for 16 hours. The reaction mixture was mixed with 1M aqueous sodium hydroxide and extracted with ethyl acetate. The organic layer was washed with saturated aqueous sodium chloride, dried over anhydrous sodium sulfate and concentrated under reduced pressure. The residue was purified by silica gel column chromatography (ethyl acetate) to obtain the title compound as a pale yellow oil (21.0 mg, yield: 50%).

Reference Synthetic Example 82

1-(trans-4-[{(tert-Butyldimethylsilyl)oxy]methyl}cyclohexyl)-3-cyclopropyl-7-{[2-(trimethylsilyl)ethoxy]methyl}-2,3-dihydro-1H-pyrrolo[3',2':5,6]pyrido[4,3-d]pyrimidin-4(7H)-one

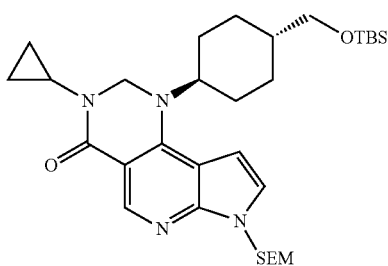 [SMILES: CC(C)(C)[Si](C)(C)OC[C@H]1CC[C@H](N2CN(C3CC3)C(=O)c3cnc4c(ccn4COCC[Si](C)(C)C)c32)CC1]

To a solution of 1-(trans-4-{[(tert-butyldimethylsilyl)oxy]methyl}cyclohexyl)-7-{[2-(trimethylsilyl)ethoxy]methyl}-2,3-dihydro-1H-pyrrolo[3',2':5,6]pyrido[4,3-d]pyrimidin-4(7H)-one (200 mg, 0.367 mmol) obtained in Reference Synthetic Example 26 in 1,2-dichloroethane (4 mL), copper (II) acetate (66.7 mg, 0.367 mmol), 2,2'-bipyridyl (57.3 mg, 0.367 mmol), cyclopropylboronic acid (63.0 mg, 0.734 mmol) and sodium carbonate (77.9 mg, 0.734 mmol) were added, and the mixture was stirred at 70° C. for 1 day. Copper acetate (66.7 mg, 0.367 mmol), 2,2'-bipyridyl (57.3 mg, 0.367 mmol) and cyclopropylboronic acid (63.0 mg, 0.734 mmol) were added again, and the mixture was stirred at 70° C. for 4 hours. The reaction mixture was mixed with saturated aqueous ammonium chloride and extracted with ethyl acetate. The organic layer was washed with saturated aqueous ammonium chloride and saturated aqueous sodium chloride, dried over anhydrous sodium sulfate and concentrated under reduced pressure. The residue was purified by silica gel column chromatography (ethyl acetate/hexane=1/1 (v/v)) to obtain the title compound as a white solid (207 mg, yield: 96%).

Reference Synthetic Example 83

3-Cyclopropyl-1-[trans-4-(hydroxymethyl)cyclohexyl]-7-[{2-(trimethylsilyl)ethoxy]methyl}-2,3-dihydro-1H-pyrrolo[3',2':5,6]pyrido[4,3-d]pyrimidin-4(7H)-one

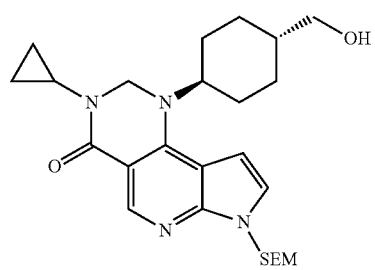 [SMILES: C[Si](C)(C)CCOCn1ccc2c3c(cnc21)C(=O)N(C1CC1)CN3[C@H]1CC[C@H](CO)CC1]

To a solution of 1-(trans-4-[{(tert-butyldimethylsilyl)oxy]methyl}cyclohexyl)-3-cyclopropyl-7-{[2-(trimethylsilyl)ethoxy]methyl}-2,3-dihydro-1H-pyrrolo[3',2':5,6]pyrido[4,3-d]pyrimidin-4(7H)-one (273 mg, 0.467 mmol) in 1,4-dioxane (4 mL), 1M hydrochloric acid (0.56 mL, 0.560 mmol) was added, and the mixture was stirred at room temperature for 1 hour. The reaction mixture was mixed with aqueous sodium hydrogencarbonate and extracted with ethyl acetate. The organic layer was washed with saturated aqueous sodium chloride, dried over anhydrous sodium sulfate and concentrated under reduced pressure. The residue was purified by silica gel column chromatography (ethyl acetate/hexane=3/1→1/0 (v/v)→ethyl acetate/methanol=40/1→20/0 (v/v)) to obtain the title compound as a pale yellow solid (198 mg, yield: 90%).

Reference Synthetic Example 84

1-[trans-4-(Bromomethyl)cyclohexyl]-3-cyclopropyl-7-{[2-(trimethylsilyl)ethoxy]methyl}-2,3-dihydro-1H-pyrrolo[3',2':5,6]pyrido[4,3-d]pyrimidin-4(7H)-one

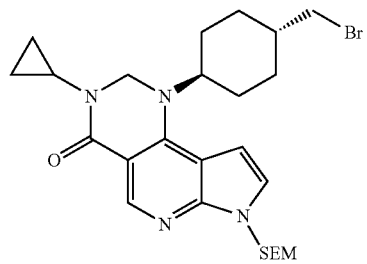 [SMILES: C[Si](C)(C)CCOCn1ccc2c3c(cnc21)C(=O)N(C1CC1)CN3[C@H]1CC[C@H](CBr)CC1]

To a solution of 3-cyclopropyl-1-[trans-4-(hydroxymethyl)cyclohexyl]-7-[{2-(trimethylsilyl)ethoxy]methyl}-2,3-dihydro-1H-pyrrolo[3',2':5,6]pyrido[4,3-d]pyrimidin-4(7H)-one (197 mg, 0.420 mmol) in dichloromethane (5 mL), 2,3-dichloro-5,6-dicyano-p-benzoquinone (191 mg, 0.840 mmol), triphenylphosphine (220 mg, 0.840 mmol) and tetrabutylammonium bromide (271 mg, 0.840 mmol) were added, and the mixture was stirred at room temperature for 2 hours. The reaction mixture was mixed with saturated aqueous sodium hydrogencarbonate and extracted with ethyl acetate. The organic layer was washed with saturated aqueous ammonium chloride and saturated aqueous sodium chloride, dried over anhydrous sodium sulfate and concentrated under reduced pressure. The residue was purified by silica gel column chromatography (ethyl acetate/hexane=1/1→3/2 (v/v)) to obtain a mixture containing the title compound (188 mg, a mixture with triphenylphosphine oxide).

Reference Synthetic Example 85

1-[trans-4-(Aminomethyl)cyclohexyl]-3-cyclopropyl-7-{[2-(trimethylsilyl)ethoxy]methyl}-2,3-dihydro-1H-pyrrolo[3',2':5,6]pyrido[4,3-d]pyrimidin-4(7H)-one

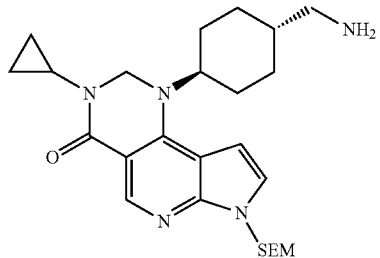 [SMILES: C[Si](C)(C)CCOCn1ccc2c3c(cnc21)C(=O)N(C1CC1)CN3[C@H]1CC[C@H](CN)CC1]

To a solution of the mixture (187 mg) containing 1-[trans-4-(bromomethyl)cyclohexyl]-3-cyclopropyl-7-{[2-(trimethylsilyl)ethoxy]methyl}-2,3-dihydro-1H-pyrrolo[3',2':5,6]pyrido[4,3-d]pyrimidin-4(7)-one obtained in Reference Synthetic Example 84 in tetrahydrofuran (3 mL), trimethylsilyl azide (73.0 μL, 0.528 mmol) and tetrabutylammonium fluoride (1.0M tetrahydrofuran solution, 0.53 mL, 0.53 mmol) were added, and the mixture was stirred at 50° C. for 2 hours. The reaction mixture was mixed with water and extracted with ethyl acetate. The organic layer was washed with saturated aqueous sodium chloride, dried over anhydrous sodium sulfate and concentrated under reduced pressure. A suspension of the resulting residue and 5% palladium-carbon (100 mg) in methanol (5 mL) was stirred at room temperature for 1 hour under a hydrogen atmosphere. The reaction mixture was filtered, and the filtrate was concentrated under reduced pressure. The residue was purified by silica gel column chromatography (ethyl acetate→chloroform/methanol=10/1 (v/v)) to obtain the title compound as a white solid (106 mg, yield: 54% (3 steps)).

Reference Synthetic Example 86

2-({[trans-4-(3-Cyclopropyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}amino)acetonitrile

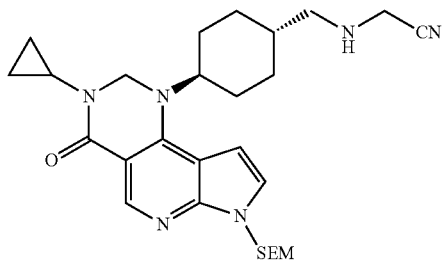 [SMILES: C[Si](C)(C)CCOCn1ccc2c3c(cnc21)C(=O)N(C1CC1)CN3[C@H]1CC[C@H](CNCC#N)CC1]

To a solution of trans-4-(3-cyclopropyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (24.0 mg, 51.2 μmol) obtained in Reference Synthetic Example 74 in a mixed solvent of methanol (1.0 mL) and acetic acid (0.10 mL), aminoacetonitrile hydrochloride (23.7 mg, 0.256 mmol) and 2-picoline borane (11.0 mg, 0.102 mmol) were added, and the mixture was stirred at room temperature for 1 day. The reaction mixture was mixed with 1M hydrochloric acid and separated with ethyl acetate. The aqueous layer was basified with 1M aqueous sodium hydroxide and extracted with ethyl acetate. The organic layer was dried over anhydrous sodium sulfate and concentrated under reduced pressure. The residue was purified by silica gel column chromatography (hexane/ethyl acetate=4/1 (v/v)→ethyl acetate→ethyl acetate/methanol=10/1 (v/v)) to obtain the title compound as a colorless oil (20.6 mg, yield: 79%).

Reference Synthetic Example 87

2-({[trans-4-(3-Ethyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}amino)acetonitrile

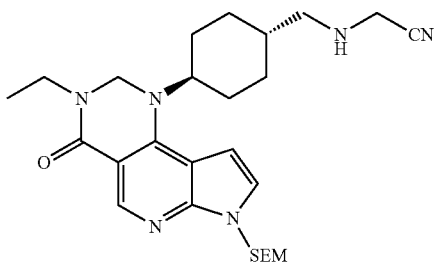 [SMILES: CCN1CN([C@H]2CC[C@H](CNCC#N)CC2)c2c(cnc3c2ccn3COCC[Si](C)(C)C)C1=O]

The title compound was obtained as a colorless amorphous substance (37.2 mg, yield: 84%) substantially in the same manner as in Reference Synthetic Example 86 except that trans-4-(3-ethyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde obtained in Reference Synthetic Example 76 was used instead of trans-4-(3-cyclopropyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde.

Reference Synthetic Example 88

2-[({trans-4-[4-oxo-3-(2,2,2-Trifluoroethyl)-7-{[2-(trimethylsilyl)ethoxy]methyl}-2,3,4,7-tetrahydro-1H-pyrrolo[3',2':5,6]pyrido[4,3-d]pyrimidin-1-yl]cyclohexyl}methyl)amino]acetonitrile

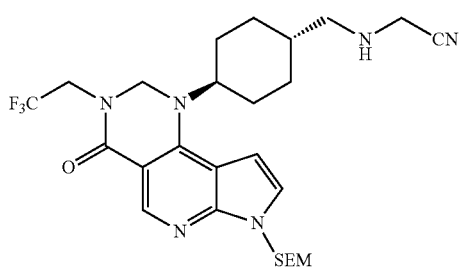 [SMILES: C[Si](C)(C)CCOCn1ccc2c3c(cnc21)C(=O)N(CC(F)(F)F)CN3[C@H]1CC[C@H](CNCC#N)CC1]

The title compound was obtained as a pale pink solid (27.5 mg, yield: 89%) substantially in the same manner as in Reference Synthetic Example 86 except that trans-4-(4-oxo-3-(2,2,2-trifluoroethyl)-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde obtained in Reference Synthetic Example 78 was used instead of trans-4-(3-cyclopropyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde.

Reference Synthetic Example 89

1-[trans-4-(Dimethoxymethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one

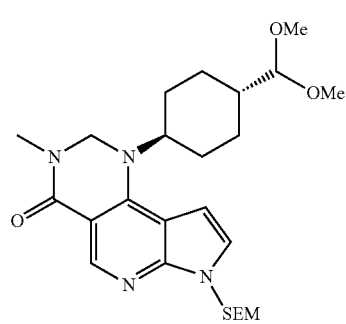 [SMILES: COC(OC)[C@H]1CC[C@H](N2CN(C)C(=O)c3cnc4c(ccn4COCC[Si](C)(C)C)c32)CC1]

The title compound was obtained as a pale yellow oil (57.4 mg, quantitative yield) substantially in the same manner as in Reference Synthetic Example 11 except that 1-[trans-4-(dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one obtained in Reference Synthetic Example 72 was used instead of 1-cyclohexyl-7-{[2-(trimethylsilyl)ethoxy]methyl}-2,3-dihydro-1H-pyrrolo[3',2':5,6]pyrido[4,3-d]pyrimidin-4(7H)-one.

Reference Synthetic Example 90 trans-4-(3-Methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde

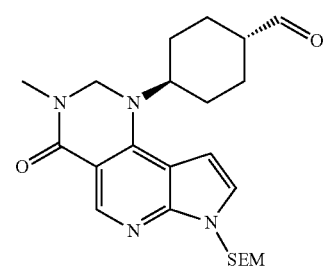 [SMILES: CN1CN([C@H]2CC[C@H](C=O)CC2)c2c(cnc3c2ccn3COCC[Si](C)(C)C)C1=O]

The title compound was obtained as a pale yellow oil (34.4 mg, yield: 68%) substantially in the same manner as in Reference Synthetic Example 74 except that 1-[trans-4-(dimethoxymethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one was used instead of 3-cyclopropyl-1-[trans-4-(dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one.

Reference Synthetic Example 91

1-[trans-4-(Hydroxymethyl)cyclohexyl]-7-[{2-(trimethylsilyl)ethoxy]methyl}-2,3-dihydro-1H-pyrrolo[3',2':5,6]pyrido[4,3-d]pyrimidin-4(7H)-one

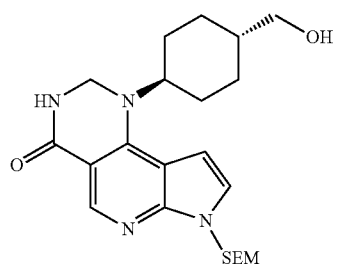 [SMILES: C[Si](C)(C)CCOCn1ccc2c3c(cnc21)C(=O)NCN3[C@H]1CC[C@H](CO)CC1]

To a solution of 1-[trans-4-(hydroxymethyl)cyclohexyl]-7-{[2-(trimethylsilyl)ethoxy]methyl}-1H-pyrrolo[3',2':5,6]pyrido[4,3-d]pyrimidin-4(7H)-one (411 mg, 0.959 mmol) obtained in Reference Synthetic Example 22 in methanol (5 mL), sodium borohydride (54.4 mg, 1.44 mmol) was added at ice bath temperature, and the mixture was stirred at room temperature for 1 hour. The reaction mixture was mixed with water and extracted with ethyl acetate. The organic layer was washed with saturated aqueous sodium chloride, dried over anhydrous sodium sulfate and concentrated under reduced pressure. The residue was purified by silica gel column chromatography (ethyl acetate/methanol=1/0→40/1→20/1 (v/v)) to obtain the title compound as a white solid (260 mg, yield: 63%).

Reference Synthetic Example 92

1-[trans-4-(Bromomethyl)cyclohexyl]-7-[{2-(trimethylsilyl)ethoxy]methyl}-2,3-dihydro-1H-pyrrolo[3',2':5,6]pyrido[4,3-d]pyrimidin-4(7H)-one

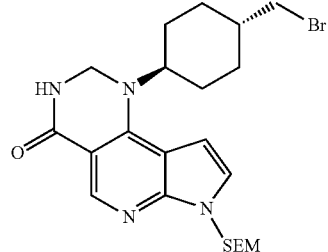

A mixture containing the title compound was obtained (246 mg, a mixture with triphenylphosphine oxide) substantially in the same manner as in Reference Synthetic Example 84 except that 1-[trans-4-(hydroxymethyl)cyclohexyl]-7-[{2-(trimethylsilyl)ethoxy]methyl}-2,3-dihydro-1H-pyrrolo[3',2':5,6]pyrido[4,3-d]pyrimidin-4(7H)-one was used instead of 3-cyclopropyl-1-[trans-4-(hydroxymethyl)cyclohexyl]-7-[{2-(trimethylsilyl)ethoxy]methyl}-2,3-dihydro-1H-pyrrolo[3',2':5,6]pyrido[4,3-d]pyrimidin-4(7H)-one.

Reference Synthetic Example 93

1-[trans-4-(Azidomethyl)cyclohexyl]-7-[{2-(trimethylsilyl)ethoxy]methyl}-2,3-dihydro-1H-pyrrolo[3',2':5,6]pyrido[4,3-d]pyrimidin-4(7H)-one

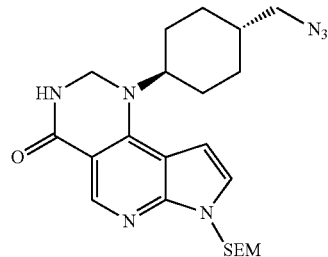 [SMILES: C[Si](C)(C)CCOCn1ccc2c3c(cnc21)C(=O)NCN3[C@H]1CC[C@H](CN=[N+]=[N-])CC1]

To a solution of the mixture (246 mg) containing 1-[trans-4-(bromomethyl)cyclohexyl]-7-[{2-(trimethylsilyl)ethoxy]methyl}-2,3-dihydro-1H-pyrrolo[3',2':5,6]pyrido[4,3-d]pyrimidin-4(7H)-one obtained in Reference Synthetic Example 92 in tetrahydrofuran (10 mL), trimethylsilyl azide (102 μL, 0.747 mmol) and tetrabutylammonium fluoride (1.0M tetrahydrofuran solution, 0.75 mL, 0.750 mmol) were added, and the mixture was stirred at 50° C. for 2 hours. The reaction mixture was mixed with water and extracted with ethyl acetate. The organic layer was washed with saturated aqueous sodium chloride, dried over anhydrous sodium sulfate and concentrated under reduced pressure to obtain a mixture containing the title compound (227 mg, a mixture with triphenylphosphine oxide).

Reference Synthetic Example 94

1-[trans-4-(Azidomethyl)cyclohexyl]-3-ethyl-7-[{2-(trimethylsilyl)ethoxy]methyl}-2,3-dihydro-1H-pyrrolo[3',2':5,6]pyrido[4,3-d]pyrimidin-4(7H)-one

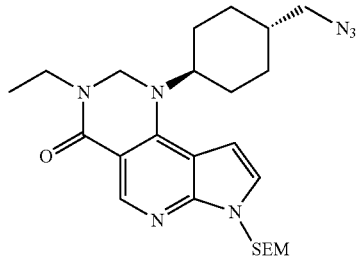 [SMILES: CCN1CN([C@H]2CC[C@H](CN=[N+]=[N-])CC2)c2c(cnc3c2ccn3COCC[Si](C)(C)C)C1=O]

To a solution of the mixture (227 mg) containing 1-[trans-4-(azidomethyl)cyclohexyl]-7-[{2-(trimethylsilyl)ethoxy]methyl}-2,3-dihydro-1H-pyrrolo[3',2':5,6]pyrido[4,3-d]pyrimidin-4(7H)-one obtained in Reference Synthetic Example 93 in N,N-dimethylformamide (5 mL), sodium hydride (55 wt % dispersion in liquid paraffin, 8.7 mg, 0.20 mmol) was added at ice bath temperature, and the mixture was stirred for 30 minutes, and ethyl iodide (60.1 μL, 0.748 mmol) was added, and the mixture was stirred at room temperature for 30 minutes. The reaction mixture was mixed with water and extracted with ethyl acetate. The organic layer was washed with saturated aqueous sodium hydrogencarbonate and saturated aqueous ammonium chloride, dried over anhydrous sodium sulfate and concentrated under reduced pressure to obtain a mixture containing the title compound (280 mg, a mixture with triphenylphosphine oxide).

Reference Synthetic Example 95

1-[trans-4-(Aminomethyl)cyclohexyl]-3-ethyl-7-[{2-(trimethylsilyl)ethoxy]methyl}-2,3-dihydro-1H-pyrrolo[3',2':5,6]pyrido[4,3-d]pyrimidin-4(7H)-one

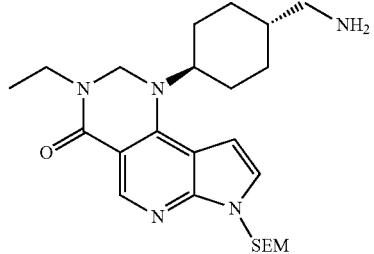 [SMILES: CCN1CN([C@H]2CC[C@H](CN)CC2)c2c(cnc3c2ccn3COCC[Si](C)(C)C)C1=O]

A suspension of the mixture (280 mg) containing 1-[trans-4-(azidomethyl)cyclohexyl]-3-ethyl-7-[{2-(trimethylsilyl)ethoxy]methyl}-2,3-dihydro-1H-pyrrolo[3',2':5,6]pyrido[4,3-d]pyrimidin-4(7H)-one obtained in Reference Synthetic Example 94 and 5% palladium-carbon (140 mg) in methanol (10 mL) was stirred at room temperature for 1 hour under a hydrogen atmosphere. The reaction mixture was filtered, and the filtrate was concentrated under reduced pressure. The residue was purified by silica gel column chromatography (ethyl acetate/methanol=20/1 (v/v)→chloroform/methanol=10/1 (v/v)) to obtain the title compound as a white solid (128 mg, yield: 46% (4 steps)).

Reference Synthetic Example 96

1-(trans-4-{[(S)-3-Fluoropyrrolidin-1-yl]methyl}cyclohexyl)-7-{[2-(trimethylsilyl)ethoxy]methyl}-2,3-dihydro-1H-pyrrolo[3',2':5,6]pyrido[4,3-d]pyrimidin-4(7H)-one

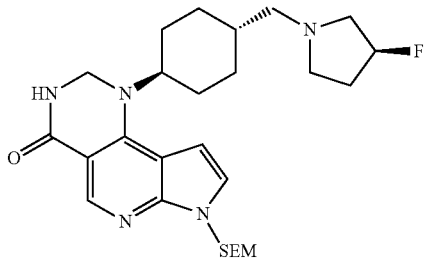 [SMILES: C[Si](C)(C)CCOCn1ccc2c3c(cnc21)C(=O)NCN3[C@H]1CC[C@H](CN2CC[C@H](F)C2)CC1]

The title compound was obtained as a colorless oil (35.0 mg, yield: 99%) substantially in the same manner as in Reference Synthetic Example 24 except that (S)-3-fluoropyrrolidine was used instead of 2-bromo-2,2-difluoroethylamine hydrochloride.

Reference Synthetic Example 97

3-{[trans-4-(3-Methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methoxy}propanenitrile

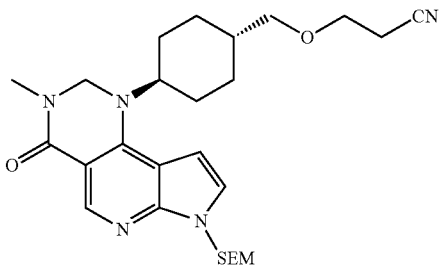 [SMILES: CN1CN([C@H]2CC[C@H](COCCC#N)CC2)c2c(cnc3c2ccn3COCC[Si](C)(C)C)C1=O]

To a solution of 1-[trans-4-(hydroxymethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one (30.0 mg, 0.0675 mmol) obtained in Reference Synthetic Example 28 in tetrahydrofuran (1 mL), sodium hydride (60 wt % dispersion in liquid paraffin, 4.42 mg, 0.101 mmol) and acrylonitrile (6.62 µL, 0.101 mmol) were added at room temperature, and the mixture was stirred for 3 hours. The reaction mixture was mixed with water and extracted with ethyl acetate. The organic layer was washed with saturated aqueous sodium chloride, dried over anhydrous sodium sulfate and concentrated under reduced pressure. The residue was purified by silica gel column chromatography (ethyl acetate) to obtain the title compound as a colorless oil (31.9 mg, yield: 95%).

Reference Synthetic Example 98 tert-Butyl(2,2-difluoroethyl){[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}carbamate

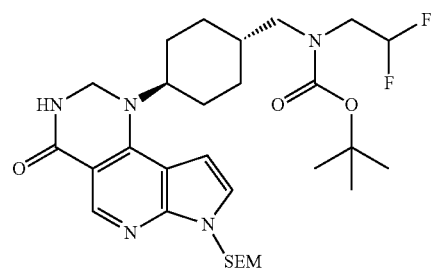 [SMILES: CC(C)(C)OC(=O)N(CC(F)F)C[C@H]1CC[C@H](N2CNC(=O)c3cnc4c(ccn4COCC[Si](C)(C)C)c32)CC1]

To a solution of trans-4-(4-oxo-7-{[2-(trimethylsilyl)ethoxy]methyl}-4,7-dihydro-1H-pyrrolo[3',2':5,6]pyrido[4,3-d]pyrimidin-1-yl)cyclohexanecarbaldehyde (338.5 mg, 0.793 mmol) obtained in Reference Synthetic Example 23 in methanol (3 mL), 2,2-difluoroethylamine (72.6 µL, 1.03 mmol), 2-picoline borane (110 mg, 1.03 mmol) and acetic acid (0.3 mL) were added, and the mixture was stirred at room temperature for 2 hours. To the reaction mixture, sodium borohydride (60 mg, 1.6 mmol) was added, the mixture was stirred at room temperature for 3 hours. The reaction mixture was mixed with 1M aqueous sodium hydroxide and extracted with ethyl acetate. The organic layer was dried over anhydrous sodium sulfate and concentrated under reduced pressure to obtain a colorless oil (516 mg). To a solution of the resulting colorless oil in dichloromethane (2.5 mL), di-tert-butyl dicarbonate (1.01 g, 4.36 mmol) and triethylamine (0.3 mL, 2.15 mmol) were added, and the mixture was stirred at room temperature for 15 hours. The reaction mixture was mixed with saturated aqueous ammonium and extracted with ethyl acetate. The organic layer was dried over anhydrous sodium sulfate and concentrated under reduced pressure. The residue was purified by silica gel column chromatography (hexane/ethyl acetate=1/1→1/9 (v/v)) to obtain the title compound as a pale yellow amorphous substance (349 mg, yield: 74%).

Reference Synthetic Example 99 tert-Butyl {[trans-4-(3-cyclopropyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2-difluoroethyl)carbamate

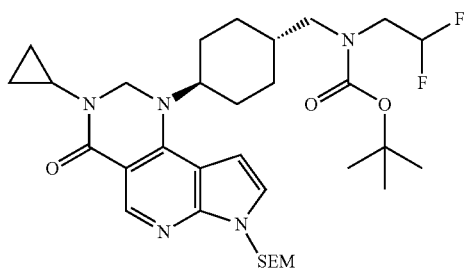 [SMILES: CC(C)(C)OC(=O)N(CC(F)F)C[C@H]1CC[C@H](N2CN(C3CC3)C(=O)c3cnc4c(ccn4COCC[Si](C)(C)C)c32)CC1]

To a solution of tert-butyl(2,2-difluoroethyl){[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}carbamate (59 mg, 0.10 mmol) in 1,2-dichloroethane (1.0 mL), cyclopropylboronic acid (17 mg, 0.20 mmol), copper(II) acetate (20 mg, 0.11 mmol), 2,2'-dipyridine (17 mg, 0.11 mmol) and sodium carbonate (21 mg, 0.20 mmol) were added, and the mixture was stirred at 70° C. for 5 hours. To the reaction mixture, cyclopropylboronic acid (17 mg, 0.20 mmol), copper(II) acetate (20 mg, 0.11 mmol) and 2,2'-bipyridine (17 mg, 0.11 mmol) were added, and the mixture was stirred at 70° C. for 3 hours. The reaction mixture was mixed with saturated aqueous ammonium chloride and extracted with ethyl acetate. The organic layer was dried over anhydrous sodium sulfate and concentrated under reduced pressure. The residue was purified by silica gel thin-layer chromatography (ethyl acetate/hexane=3/1 (v/v)) to obtain the title compound as a colorless oil (12 mg, yield: 19%).

Reference Synthetic Example 100 tert-Butyl(2,2-difluoroethyl){[trans-4-(3-ethyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}carbamate

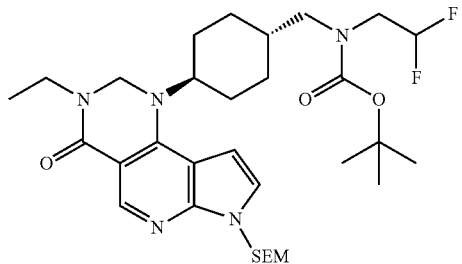 [SMILES: CCN1CN([C@H]2CC[C@H](CN(CC(F)F)C(=O)OC(C)(C)C)CC2)c2c(cnc3c2ccn3COCC[Si](C)(C)C)C1=O]

To a solution of tert-butyl(2,2-difluoroethyl){[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}carbamate (75.1 mg, 0.13 mmol) obtained in Reference Synthetic Example 98 in N,N-dimethylformamide (0.7 mL), sodium hydride (60 wt % dispersion in liquid paraffin, 9.0 mg, 0.19 mmol) was added, and the mixture was stirred at room temperature for 30 minutes, and ethyl iodide (15 μL, 0.19 mmol) was added, and the mixture was stirred at room temperature for 4 hours. The reaction mixture was mixed with water and extracted with ethyl acetate. The organic layer was dried over anhydrous sodium sulfate and concentrated under reduced pressure. The residue was purified by silica gel thin-layer chromatography (ethyl acetate/hexane=9/1 (v/v)) to obtain the title compound as a colorless oil (48.6 mg, yield: 62%).

Reference Synthetic Example 101 tert-Butyl (2,2-difluoroethyl){[trans-4-(3-(methoxymethyl)-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}carbamate

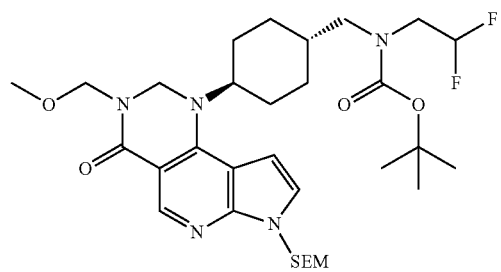 [SMILES: COCN1CN([C@H]2CC[C@H](CN(CC(F)F)C(=O)OC(C)(C)C)CC2)c2c(cnc3c2ccn3COCC[Si](C)(C)C)C1=O]

To a solution of tert-butyl(2,2-difluoroethyl){[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}carbamate (55.0 mg, 0.093 mmol) obtained in Reference Synthetic Example 98 in N,N-dimethylformamide (1.5 mL), sodium hydride (55 wt % dispersion in liquid paraffin, 6.0 mg, 0.14 mmol) was added at ice bath temperature, the mixture was stirred at room temperature for 10 minutes, and then chloromethyl methyl ether (12.0 μL, 0.139 mmol) was added, and the mixture was stirred at room temperature for 1 day. The reaction mixture was mixed with water and saturated aqueous ammonium chloride and extracted with chloroform three times. The organic layers were combined, dried over anhydrous sodium sulfate and concentrated under reduced pressure. The residue was purified by silica gel column chromatography (chloroform/2-propanol=10/1 (v/v)) to obtain the title compound as a colorless oil (55.0 mg, yield: 92%).

Reference Synthetic Example 102

2-[1-(trans-4-{[(tert-Butoxycarbonyl)(2,2-difluoroethyl)amino]methyl}cyclohexyl)-4-oxo-7-{[2-(trimethylsilyl)ethoxy]methyl}-1H-pyrrolo[3',2':5,6]pyrido[4,3-d]pyrimidin-3(2H,4H,7H)-yl]acetic acid

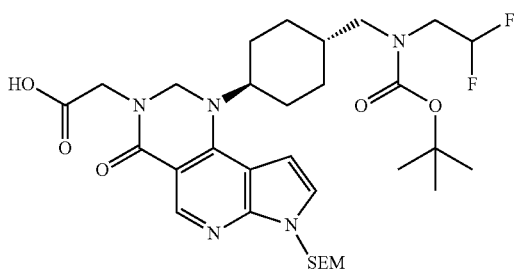 [SMILES: CC(C)(C)OC(=O)N(CC(F)F)C[C@H]1CC[C@H](N2CN(CC(=O)O)C(=O)c3cnc4c(ccn4COCC[Si](C)(C)C)c32)CC1]

To a solution of tert-butyl(2,2-difluoroethyl){[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}carbamate (50.0 mg, 0.084 mmol) obtained in Reference Synthetic Example 98 in N,N-dimethylformamide (1.5 mL), sodium hydride (55 wt % dispersion in liquid paraffin, 6.0 mg, 0.14 mmol) was added at ice bath temperature, and the mixture was stirred at room temperature for 10 minutes, and then ethyl bromoacetate (13.0 μL, 0.118 mmol) was added, and the mixture was stirred for 1 day. The reaction mixture was mixed with water and saturated aqueous ammonium chloride and extracted with chloroform three times. The organic layers were combined, dried over anhydrous sodium sulfate and concentrated under reduced pressure. The residue was purified by silica gel column chromatography (chloroform/methanol=9/1→3/1 (v/v))) to obtain the title compound as a colorless oil (44.8 mg, yield: 83%).

Reference Synthetic Example 103

2-{4-oxo-1-[trans-4-({[1-(Trifluoromethyl)cyclopropyl]amino}methyl)cyclohexyl]-7-{[2-(trimethylsilyl)ethoxy]methyl}-1H-pyrrolo[3',2':5,6]pyrido[4,3-d]pyrimidin-3(2H,4H,7H)-yl}acetonitrile

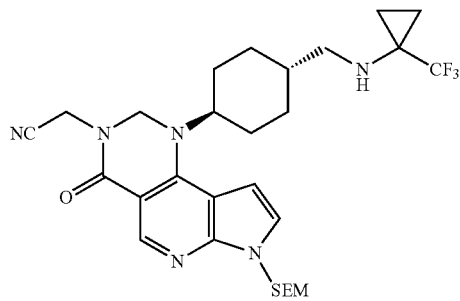 [SMILES: C[Si](C)(C)CCOCn1ccc2c3c(cnc21)C(=O)N(CC#N)CN3[C@H]1CC[C@H](CNC2(C(F)(F)F)CC2)CC1]

To a solution of 1-[trans-4-({[1-(trifluoromethyl)cyclopropyl]amino}methyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one (44 mg, 0.082 mmol) obtained in Reference Synthetic Example 34 in N,N-dimethylformamide (1.0 mL), sodium hydride (55 wt % dispersion in liquid paraffin, 7.0 mg, 0.16 mmol) was added at ice bath temperature, and the mixture was stirred at room temperature for 10 minutes, and bromoacetonitrile (11.0 μL, 0.163 mmol) was added, and the mixture was stirred for 2 hours. The reaction mixture was mixed with water and saturated aqueous ammonium chloride and extracted with chloroform three times. The organic layers were combined, dried over anhydrous sodium sulfate and concentrated under reduced pressure. The residue was purified by silica gel column chromatography (chloroform/methanol=10/1 (v/v)) to obtain the title compound as a brown oil (40.0 mg, yield: 84%).

Reference Synthetic Example 104

1-({[trans-4-(3-Methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}amino)cyclopropanecarbonitrile

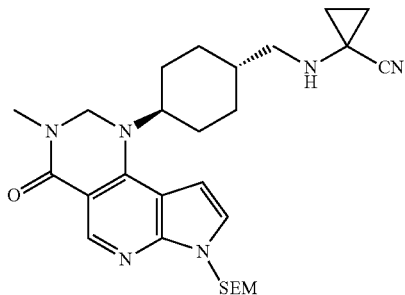 [SMILES: CN1CN([C@H]2CC[C@H](CNC3(C#N)CC3)CC2)c2c(cnc3c2ccn3COCC[Si](C)(C)C)C1=O]

The title compound was obtained as a colorless oil (36.0 mg, yield: 63%) substantially in the same manner as in Reference Synthetic Example 30 except that 1-aminocyclopropanecarbonitrile hydrochloride was used instead of 2,2,2-trifluoroethylamine.

Reference Synthetic Example 105 tert-Butyl {[trans-4-(3-(cyanomethyl)-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2-difluoroethyl)carbamate

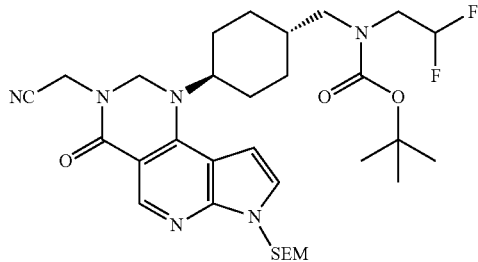 [SMILES: CC(C)(C)OC(=O)N(CC(F)F)C[C@H]1CC[C@H](N2CN(CC#N)C(=O)c3cnc4c(ccn4COCC[Si](C)(C)C)c32)CC1]

To a solution of tert-butyl (2,2-difluoroethyl){[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}carbamate (58.6 mg, 0.098 mmol) obtained in Reference Synthetic Example 98 in N,N-dimethylformamide (0.5 mL), sodium hydride (60 wt % dispersion in liquid paraffin, 7.1 mg, 0.15 mmol) was added, and the mixture was stirred at room temperature for 30 minutes, and bromoacetonitrile (10.2 μL, 0.15 mmol) was added, and the mixture was stirred at room temperature for 2 hours. The reaction mixture was mixed with water and extracted with ethyl acetate. The organic layer was dried over anhydrous sodium sulfate and concentrated under reduced pressure. The residue was purified by silica gel thin-layer chromatography (ethyl acetate/hexane=1/1 (v/v)) to obtain the title compound as a colorless oil (18.7 mg, yield: 30%).

Reference Synthetic Example 106

3-Methyl-1-[trans-4-({[1-(trifluoromethyl)cyclopropyl]amino}methyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one

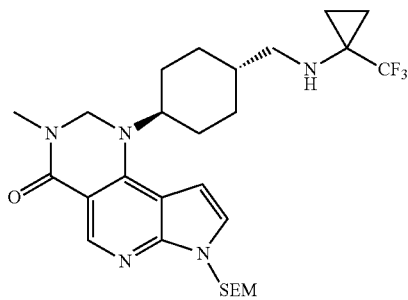 [SMILES: CN1CN([C@H]2CC[C@H](CNC3(C(F)(F)F)CC3)CC2)c2c(cnc3c2ccn3COCC[Si](C)(C)C)C1=O]

The title compound was obtained as a colorless oil (30.1 mg, yield: 70%) substantially in the same manner as in Reference Synthetic Example 30 except that 1-(trifluoromethyl)cyclopropanamine was used instead of 2,2,2-trifluoroethylamine.

LC/MS: measurement condition 1, retention time=4.72 min.

LC/MS (ESI$^+$) m/z; 552 [M+H]$^+$

LC/MS (ESI$^-$) m/z; 596 [M−H+HCO$_2$H]$^-$ (detected as a formic acid adduct)

Reference Synthetic Example 107

2-({[trans-4-(3-Cyclopropyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(methyl)amino)acetonitrile

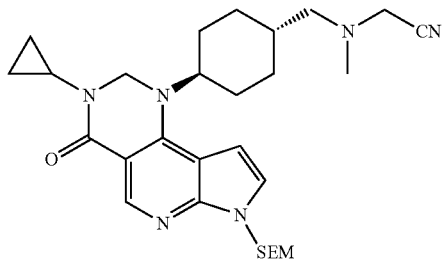 [SMILES: CN(CC#N)C[C@H]1CC[C@H](N2CN(C3CC3)C(=O)c3cnc4c(ccn4COCC[Si](C)(C)C)c32)CC1]

The title compound was obtained as a colorless oil (30.0 mg, yield: 86%) substantially in the same manner as in Reference Synthetic Example 86 except that methylaminoacetonitrile hydrochloride was used instead of aminoacetonitrile hydrochloride.

Reference Synthetic Example 108

2-({[trans-4-(3-Ethyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(methyl)amino)acetonitrile

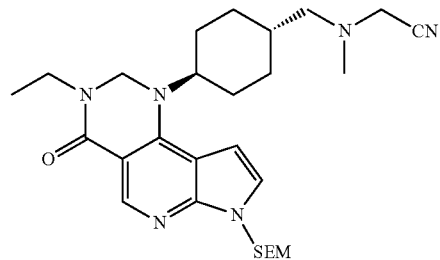 [SMILES: CCN1CN([C@H]2CC[C@H](CN(C)CC#N)CC2)c2c(cnc3c2ccn3COCC[Si](C)(C)C)C1=O]

The title compound was obtained as a colorless oil (30.0 mg, yield: 75%) substantially in the same manner as in Reference Synthetic Example 87 except that methylaminoacetonitrile hydrochloride was used instead of aminoacetonitrile hydrochloride.

Reference Synthetic Example 109

2-{1-[trans-4-(Dimethoxymethyl)cyclohexyl]-4-oxo-7-{[2-(trimethylsilyl)ethoxy]methyl}-1H-pyrrolo[3',2':5,6]pyrido[4,3-d]pyrimidin-3(2H,4H,7H)-yl)acetonitrile

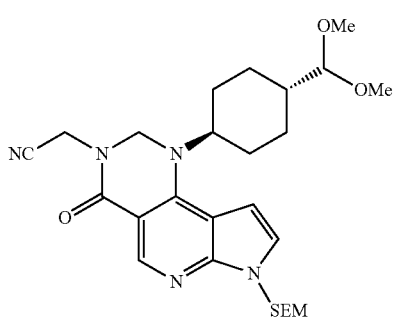 [SMILES: COC(OC)[C@H]1CC[C@H](N2CN(CC#N)C(=O)c3cnc4c(ccn4COCC[Si](C)(C)C)c32)CC1]

The title compound was obtained as a pale orange amorphous substance (36.6 mg, yield: 34%) substantially in the same manner as in Reference Synthetic Example 70 except that 1-[trans-4-(dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one obtained in Reference Synthetic Example 72 was used instead of tert-butyl {[trans-4-(4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate.

Reference Synthetic Example 110

2-(1-(trans-4-Formylcyclohexyl)-4-oxo-7-{[2-(trimethylsilyl)ethoxy]methyl}-1H-pyrrolo[3',2':5,6]pyrido[4,3-d]pyrimidin-3(2H,4H,7H)-yl)acetonitrile

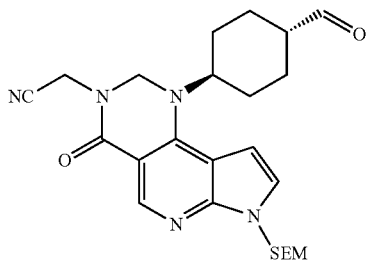

The title compound was obtained as a yellow amorphous substance (29.8 mg, yield: 89%) substantially in the same manner as in Reference Synthetic Example 74 except that 2-{1-[trans-4-(dimethoxymethyl)cyclohexyl]-4-oxo-7-{[2-(trimethylsilyl)ethoxy]methyl}-1H-pyrrolo[3',2':5,6]pyrido[4,3-d]pyrimidin-3(2H,4H,7H)-yl)acetonitrile was used instead of 3-cyclopropyl-1-[trans-4-(dimethoxymethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one.

Reference Synthetic Example 111

2-(1-{trans-4-[(Cyclopropylamino)methyl]cyclohexyl}-4-oxo-7-{[2-(trimethylsilyl)ethoxy]methyl}-1H-pyrrolo[3',2':5,6]pyrido[4,3-d]pyrimidin-3(2H,4H,7H)-yl)acetonitrile

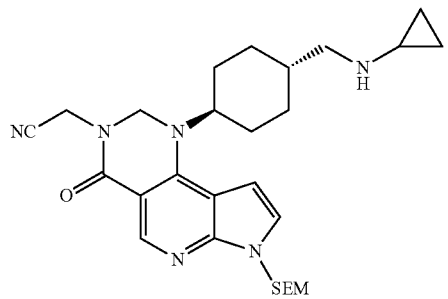 [SMILES: C[Si](C)(C)CCOCn1ccc2c3c(cnc21)C(=O)N(CC#N)CN3[C@H]1CC[C@H](CNC2CC2)CC1]

To a solution of 2-(1-(trans-4-formylcyclohexyl)-4-oxo-7-{[2-(trimethylsilyl)ethoxy]methyl}-1H-pyrrolo[3',2':5,6]pyrido[4,3-d]pyrimidin-3(2H,4H,7H)-yl)acetonitrile (29.8 mg, 0.0637 mmol) in methanol (1.2 mL), cyclopropylamine (0.0128 mL, 0.319 mmol) and 2-picoline borane (13.6 mg, 0.127 mmol) were added, and the mixture was stirred at room temperature for 1 day. The reaction mixture was mixed with acetic acid (0.1 mL) and stirred at room temperature for 1.5 hours. The reaction mixture was mixed with 1M hydrochloric acid and separated with ethyl acetate. The aqueous layer was basified with 1M aqueous sodium hydroxide and extracted with ethyl acetate. The organic layer was dried over anhydrous sodium sulfate and concentrated under reduced pressure to obtain the title compound as a yellow oil (24.7 mg, yield: 76%).

Reference Synthetic Example 112

3-Cyclopropyl-1-[trans-4-(fluoromethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one

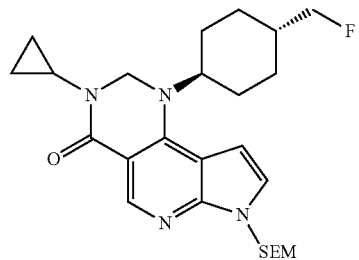 [SMILES: C[Si](C)(C)CCOCn1ccc2c3c(cnc21)C(=O)N(C1CC1)CN3[C@H]1CC[C@H](CF)CC1]

To a solution of 3-cyclopropyl-1-[trans-4-(hydroxymethyl)cyclohexyl]-7-[{2-(trimethylsilyl)ethoxy]methyl}-2,3-dihydro-1H-pyrrolo[3',2':5,6]pyrido[4,3-d]pyrimidin-4(7H)-one (80.2 mg, 0.170 mmol) obtained in Reference Synthetic Example 83 in dichloromethane (15 mL), N,N-diethylaminosulfur trifluoride (100 µL, 0.757 mmol) was added at ice bath temperature, and the mixture was stirred for 1 hour. The reaction mixture was mixed with saturated aqueous sodium hydrogencarbonate and extracted with ethyl acetate. The organic layer was washed with saturated aqueous sodium chloride, dried over anhydrous magnesium sulfate and concentrated under reduced pressure. The residue was purified by silica gel column chromatography (hexane/ethyl acetate=1/3 (v/v)) to obtain the yellow oil containing the title compound (41.3 mg). The resulting yellow oil was used for the next step without further purification.

Reference Synthetic Example 113

1-{trans-4-[(3-hydroxyazetidin-1-yl)methyl]cyclohexyl}-3-methyl-7-{[2-(trimethylsilyl)ethoxy]methyl}-2,3-dihydro-1H-pyrrolo[3',2':5,6]pyrido[4,3-d]pyrimidin-4(7H)-one

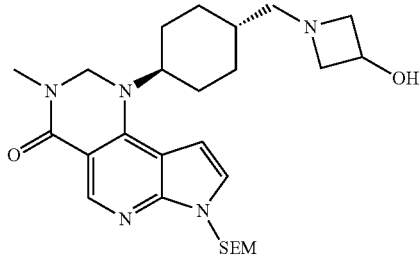 [SMILES: CN1CN([C@H]2CC[C@H](CN3CC(O)C3)CC2)c2c(cnc3c2ccn3COCC[Si](C)(C)C)C1=O]

To a solution of trans-4-(3-methyl-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (40.1 mg, 0.0906 mmol) obtained in Reference Synthetic Example 90 in methanol (2.7 mL), acetic acid (0.3 mL), 3-hydroxyazetidine hydrochloride (50.2 mg, 0.458 mmol) and 2-picoline borane (51.1 mg, 0.478 mmol) were added, and the mixture was stirred at room temperature for 2.5 hours. The reaction mixture was mixed with water and 1M hydrochloric acid and separated with ethyl acetate. The resulting aqueous layer was basified with 1M aqueous sodium hydroxide and extracted with ethyl acetate. The organic layer was washed with saturated aqueous sodium chloride, dried over anhydrous magnesium sulfate and concentrated under reduced pressure. The resulting residue containing the title compound was used for the next step without further purification.

Reference Synthetic Example 114

(trans-4-{[(Benzyloxy)carbonyl]amino}cyclohexyl)methyl 4-methylbenzenesulfonate

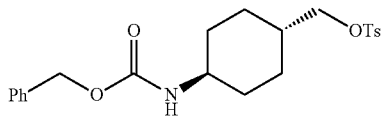 [SMILES: Cc1ccc(S(=O)(=O)OC[C@H]2CC[C@H](NC(=O)OCc3ccccc3)CC2)cc1]

To a solution of benzyl (trans-4-(hydroxymethyl)cyclohexyl carbamate (5.02 g, 19.1 mmol) obtained in Reference Synthetic Example 17 in dichloromethane (100 mL), triethylamine (6.97 mL, 49.6 mmol) was added at room temperature, and the mixture was stirred for 10 minutes, and a solution of p-toluenesulfonyl chloride (9.53 g, 49.6 mmol) in dichloromethane (25 mL) was added dropwise, and the mixture was stirred for 1 day. The reaction mixture was mixed with water and saturated aqueous ammonium chloride and extracted with ethyl acetate three times. The organic layers were combined, dried over anhydrous sodium sulfate and concentrated under reduced pressure. The resulting brown solid was purified by silica gel column chromatography (hexane/ethyl acetate=10/1→1/1 (v/v)) to obtain the title compound as a white solid (7.20 g, yield: 90%).

Reference Synthetic Example 115

Benzyl [trans-4-(fluoromethyl)cyclohexyl]carbamate

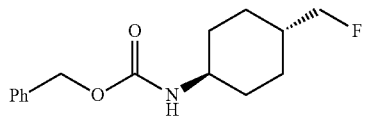 [SMILES: O=C(N[C@H]1CC[C@H](CF)CC1)OCc1ccccc1]

To a solution of (trans-4-{[(benzyloxy)carbonyl]amino}cyclohexyl)methyl 4-methylbenzenesulfonate (1.58 g, 3.78 mmol) in acetonitrile (16 mL), tetra-n-butylammonium fluoride trihydrate (7.76 g, 24.6 mmol) was added at room temperature, and the mixture was stirred for 1 day. The reaction mixture was mixed with water and saturated aqueous ammonium chloride and extracted with chloroform. The organic layer was dried over anhydrous sodium sulfate and concentrated under reduced pressure. The resulting pale yellow oil was purified by silica gel column chromatography (hexane/ethyl acetate=10/1 (v/v)) to obtain the title compound as a white solid (600 mg, yield: 60%).

Reference Synthetic Example 116 trans-4-(Fluoromethyl)cyclohexanamine

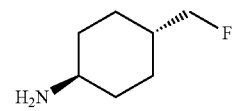

To a solution of benzyl [trans-4-(fluoromethyl)cyclohexyl]carbamate (2.3 g, 8.7 mmol) in methanol (25 mL), 5% palladium-carbon (230 mg) was added, and the mixture was stirred at room temperature for 1 day under a hydrogen atmosphere. The reaction mixture was filtered, and the filtrate was concentrated under reduced pressure to obtain the title compound as a gray solid (1.12 g, yield: 99%).

Reference Synthetic Example 117

4-{[trans-4-(Fluoromethyl)cyclohexyl]amino}-1-{[2-(trimethylsilyl)ethoxy]methyl}-1H-pyrrolo[2,3-b]pyridine-5-carboxamide

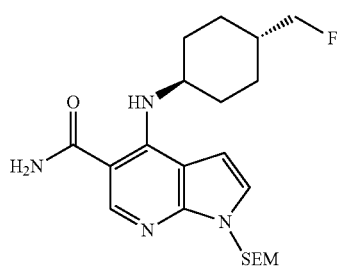 [SMILES: C[Si](C)(C)CCOCn1ccc2c(N[C@H]3CC[C@H](CF)CC3)c(C(N)=O)cnc21]

To a solution of trans-4-(fluoromethyl)cyclohexanamine (1.04 g, 7.91 mmol) and 4-chloro-1-{[2-(trimethylsilyl)ethoxy]methyl}-1H-pyrrolo[2,3-b]pyridine-5-carboxamide (736 mg, 2.26 mmol) obtained in Reference Synthetic Example 7 in N,N-dimethylacetamide (0.55 mL), N,N-diisopropylethylamine (0.55 mL, 7.5 mmol) was added, and the mixture was stirred at 150° C. for 3 hours. The reaction mixture was allowed to cool to room temperature, mixed with water and extracted with ethyl acetate. The organic layer was dried over anhydrous sodium sulfate and concentrated under reduced pressure. The residue was purified by silica gel column chromatography (ethyl acetate/hexane=1/3→1/1 (v/v)) to obtain the title compound as a colorless amorphous substance (917 mg, yield: 96%).

Reference Synthetic Example 118

1-[trans-4-(Fluoromethyl)cyclohexyl]-7-{[2-(trimethylsilyl)ethoxy]methyl}-1H-pyrrolo[3',2':5,6]pyrido[4,3-d]pyrimidin-4(7H)-one

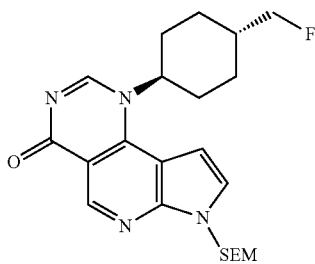 [SMILES: C[Si](C)(C)CCOCn1ccc2c1ncc1c(=O)ncn([C@H]3CC[C@H](CF)CC3)c12]

To a solution of 4-{[trans-4-(fluoromethyl)cyclohexyl]amino}-1-{[2-(trimethylsilyl)ethoxy]methyl}-1H-pyrrolo[2,3-b]pyridine-5-carboxamide (917 mg, 2.18 mmol) in triethyl orthoformate (18 mL), scandium(III) trifluoromethanesulfonate (107 mg, 0.218 mmol) was added, and the mixture was stirred at 55° C. for 15 hours. The reaction mixture was allowed to cool to room temperature, mixed with saturated aqueous sodium hydrogencarbonate and extracted with ethyl acetate. The organic layer was dried over anhydrous sodium sulfate and concentrated under reduced pressure. The resulting solid was washed with hexane to obtain the title compound as a pale yellow solid (810 mg, yield: 86%).

Reference Synthetic Example 119

1-[trans-4-(Fluoromethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one

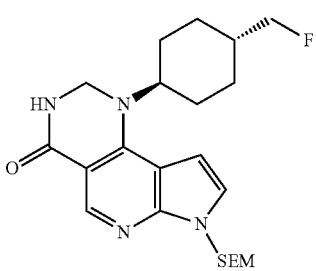 [SMILES: C[Si](C)(C)CCOCn1ccc2c3c(cnc21)C(=O)NCN3[C@H]1CC[C@H](CF)CC1]

The title compound was obtained as a white solid (773 mg, yield: 95%) substantially in the same manner as in Reference Synthetic Example 26 except that 1-[trans-4-(fluoromethyl)cyclohexyl]-7-{[(2-(trimethylsilyl)ethoxy]methyl}-1H-pyrrolo[3',2':5,6]pyrido[4,3-d]pyrimidin-4(7H)-one was used instead of 1-(trans-4-{[(tert-butyldimethylsilyl)oxy]methyl}cyclohexyl)-7-{[2-(trimethylsilyl)ethoxy]methyl}-1H-pyrrolo[3',2':5,6]pyrido[4,3-d]pyrimidin-4(7H)-one.

Reference Synthetic Example 120

1-[trans-4-(Fluoromethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one

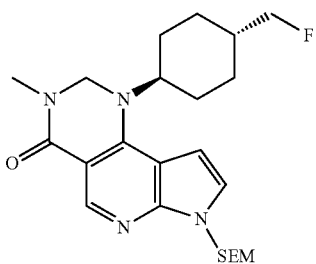 [SMILES: CN1CN([C@H]2CC[C@H](CF)CC2)c2c(cnc3c2ccn3COCC[Si](C)(C)C)C1=O]

To a solution of 1-[trans-4-(fluoromethyl)cyclohexyl]-7-{[2-(trimethylsilyl)ethoxy]methyl}-2,3-dihydro-1H-pyrrolo[3',2':5,6]pyrido[4,3-d]pyrimidin-4(7H)-one (39.6 mg, 0.092 mmol) in N,N-dimethylformamide (1.0 mL), sodium hydride (55 wt % dispersion in liquid paraffin, 8.0 mg, 0.18 mmol) was added at ice bath temperature, and the mixture was stirred for 30 minutes, and methyl iodide (17.2 μL, 0.28 mmol) was added, and the mixture was stirred at room temperature for 70 minutes. The reaction mixture was mixed with saturated aqueous ammonium chloride and extracted with ethyl acetate twice. The organic layers were combined, washed with saturated aqueous sodium chloride, dried over anhydrous sodium sulfate and concentrated under reduced pressure. The residue was purified by silica gel column chromatography (hexane/ethyl acetate=32/681/99 (v/v)) to obtain the title compound as a yellow solid (32.8 mg, yield: 79%) (alternative synthetic method to Reference Synthetic Example 32).

NMR spectral data of the compounds obtained in the above Reference Synthetic Examples are shown in Tables 1 to 9.

TABLE 1

| Rf | Data |
|---|---|
| 1 | $^{1}$H-NMR (CDCl$_3$) δ: 6.55 (d, J = 3.3 Hz, 1H), 7.06 (dd, J = 8.0, 6.3 Hz, 1H), 7.43 (d, J = 3.3 Hz, 1H), 7.70 (d, J = 8.0 Hz, 1H), 8.26 (d, J = 6.3 Hz, 1H). |
| 2 | $^{1}$H-NMR (CDCl$_3$) δ: 6.63 (d, J = 3.6 Hz, 1H), 7.14 (d, J = 5.2 Hz, 1H), 7.39 (d, J = 3.6 Hz, 1H), 8.22 (d, J = 5.2 Hz, 1H), 10.4 (br s, 1H). |
| 3 | $^{1}$H-NMR (CDCl$_3$) δ: 1.11 (d, J = 7.5 Hz, 18H), 1.84 (septet, J = 7.5 Hz, 3H), 6.65 (d, J = 3.6 Hz, 1H), 7.06 (d, J = 5.2 Hz, 1H), 7.33 (d, J = 3.6 Hz, 1H), 7.75 (d, J = 5.2 Hz, 1H). |
| 4 | $^{1}$H-NMR (DMSO-d$_6$) δ: 6.73 (dd, J = 3.6, 2.1 Hz, 1H), 7.75 (br t, J = 3.0 Hz, 1H), 8.68 (s, 1H), 10.4 (s, 1H), 12.5 (br s, 1H). |
| 7 | $^{1}$H-NMR (CDCl$_3$) δ: −0.06 (s, 9H), 0.91 (t, J = 8.4 Hz, 2H), 3.53 (t, J = 8.4 Hz, 2H), 5.68 (s, 2H), 6.71 (d, J = 3.6 Hz, 1H), 7.45 (d, J = 3.9 Hz, 1H), 8.81 (s, 1H). |
| 8 | $^{1}$H-NMR (CDCl$_3$) δ: −0.05 (s, 9H), 0.90 (t, J = 8.3 Hz, 2H), 1.26-1.49 (m, 6H), 1.75-1.90 (m, 2H), 2.05-2.15 (m, 2H), 3.53 (t, J = 8.3 Hz, 2H), 3.85-4.05 (m, 1H), 5.58 (br s, 2H), 5.58 (s, 2H), 6.59 (d, J = 3.6 Hz, 1H), 7.07 (d, J = 3.8 Hz, 1H), 8.29 (s, 1H), 9.32 (d, J = 6.6 Hz, 1H). |
| 9 | $^{1}$H-NMR (CDCl$_3$) δ: −0.06 (s, 9H), 0.92 (t, J = 8.3 Hz, 2H), 1.34-1.64 (m, 3H), 1.74-1.94 (m, 3H), 1.99-2.19 (m, 2H), 2.31-2.39 (m, 2H), 3.56 (t, J = 8.3 Hz, 2H), 4.69-4.84 (m, 1H), 5.79 (s, 2H), 6.89 (d, J = 3.8 Hz, 1H), 7.56 (d, J = 3.8 Hz, 1H), 8.49 (s, 1H), 9.32 (s, 1H). |
| 10 | $^{1}$H-NMR (CDCl$_3$) δ: −0.05 (s, 9H), 0.92 (t, J = 8.2 Hz, 2H), 1.10-1.30 (m, 1H), 1.35-1.80 (m, 5H), 1.92-2.00 (m, 2H), 2.05-2.15 (m, 2H), 3.56 (t, J = 8.3 Hz, 2H), 4.10-4.25 (m, 1H), 4.68 (d, J = 1.9 Hz, 2H), 5.65 (s, 2H), 6.58 (d, J = 3.8 Hz, 1H), 6.84 (br s, 1H), 7.21 (d, J = 3.8 Hz, 1H), 8.82 (s, 1H). |
| 11 | $^{1}$H-NMR (CDCl$_3$) δ: −0.06 (s, 9H), 0.86-0.96 (m, 2H), 1.10-1.29 (m, 1H), 1.33-1.59 (m, 4H), 1.71-1.81 (m, 1H), 1.87-1.99 (m, 2H), 2.00-2.12 (m, 2H), 3.08 (s, 3H), 3.51-3.61 (m, 2H), 4.05-4.19 (m, 1H), 4.57 (s, 2H), 5.65 (s, 2H), 6.50 (d, J = 3.7 Hz, 1H), 7.21 (d, J = 3.7 Hz, 1H), 8.85 (s, 1H). |
| 12 | $^{1}$H-NMR (CDCl$_3$) δ: 0.92-1.19 (m, 4H), 1.41-1.51 (m, 1H), 1.74-1.96 (m, 4H), 2.55-2.68 (m, 1H), 3.45 (d, J = 6.3 Hz, 2H). |
| 13 | $^{1}$H-NMR (CDCl$_3$) δ: 1.37-1.56 (m, 4H), 1.97-2.13 (m, 4H), 2.20-2.36 (m, 2H), 3.67 (s, 6H). |
| 14 | $^{1}$H-NMR (CDCl$_3$) δ: 1.37-1.59 (m, 4H), 1.98-2.18 (m, 4H), 2.20-2.42 (m, 2H), 3.67 (s, 3H). |
| 19 | $^{1}$H-NMR (CDCl$_3$) δ: −0.05 (s, 9H), 0.95 (t, J = 8.4 Hz, 2H), 1.23 (m, 2H), 1.47 (m, 3H), 2.00 (d, J = 8.7 Hz, 2H), 2.33 (d, J = 8.7 Hz, 2H), 3.58 (m, 4H), 5.63 (br s, 4H), 6.62 (d, J = 4.0 Hz, 1H), 7.13 (d, J = 4.0 Hz, 1H), 8.33 (s, 1H), 9.29 (d, J = 7.8 Hz, 1H). |
| 20 | $^{1}$H-NMR (CDCl$_3$) δ: −0.05 (s, 9H), 0.06 (s, 6H), 0.91 (t, J = 8.4 Hz, 2H), 0.91 (s, 9H), 1.07-1.52 (m, 5H), 1.85-1.97 (m, 2H), 2.19-2.31 (m, 2H), 3.47 (d, J = 6.1 Hz, 2H), 3.53 (t, J = 8.4 Hz, 2H), 3.78-3.91 (m, 1H), 5.49-5.62 (m, 2H), 5.58 (s, 2H), 6.58 (d, J = 3.7 Hz, 1H), 7.08 (d, J = 3.7 Hz, 1H), 8.28 (s, 1H), 9.23 (d, J = 8.2 Hz, 1H). |

TABLE 2

| Rf | Data |
|---|---|
| 21 | $^{1}$H-NMR (CDCl$_3$) δ: −0.06 (s, 9H), 0.09 (s, 6H), 0.87-0.97 (m, 2H), 0.93 (s, 9H), 1.27-1.44 (m, 2H), 1.63-1.75 (m, 1H), 1.82-1.99 (m, 2H), 2.08-2.19 (m, 2H), 2.31-2.41 (m, 2H), 3.51-3.60 (m, 4H), 4.69-4.82 (m, 1H), 5.79 (s, 2H), 6.74 (d, J = 3.7 Hz, 1H), 7.50 (d, J = 3.7 Hz, 1H), 8.49 (s, 1H), 9.32 (s, 1H). |
| 22 | $^{1}$H-NMR (CDCl$_3$) δ: −0.06 (s, 9H), 0.93 (t, J = 8.4 Hz, 2H), 1.35-1.54 (m, 2H), 1.65-1.77 (m, 1H), 1.85-2.01 (m, 2H), 2.13-2.23 (m, 2H), 2.35-2.45 (m, 2H), 3.56 (t, J = 8.4 Hz, 2H), 3.61-3.67 (m, 2H), 4.72-4.84 (m, 1H), 5.79 (s, 2H), 6.75 (d, J = 3.7 Hz, 1H), 7.51 (d, J = 3.7 Hz, 1H), 8.50 (s, 1H), 9.32 (s, 1H). |
| 23 | $^{1}$H-NMR (CDCl$_3$) δ: −0.06 (s, 9H), 0.93 (t, J = 8.2 Hz, 2H), 1.60-1.76 (m, 2H), 1.89-2.07 (m, 2H), 2.37-2.57 (m, 5H), 3.56 (t, J = 8.2 Hz, 2H), 4.71-4.86 (m, 1H), 5.79 (s, 2H), 6.71 (d, J = 3.7 Hz, 1H), 7.52 (d, J = 3.7 Hz, 1H), 8.48 (s, 1H), 9.32 (s, 1H), 9.79 (s, 1H). |
| 24 | $^{1}$H-NMR (CDCl$_3$) δ: −0.05 (s, 9H), 0.92 (t, J = 8.3 Hz, 2H). 1.10-1.30 (m, 2H), 1.35-1.55 (m, 2H), 1.55-1.75 (m, 2H), 1.95-2.10 (m, 4H), 2.72 (d, J = 6.6 Hz, 2H), 3.37 (t, J = 9.6 Hz, 2H), 3.55 (t, J = 8.3 Hz, |

TABLE 2-continued

| Rf | Data |
|---|---|
| | 2H), 4.11-4.24 (m, 1H), 4.72 (d, J = 1.8 Hz, 2H), 5.66 (s, 2H), 6.17 (s, 1H), 6.50 (d, J = 3.7 Hz, 1H), 7.22 (d, J = 3.7 Hz, 1H), 8.83 (s, 1H). |
| 25 | $^1$H-NMR (CDCl$_3$) δ: −0.05 (s, 9H), 0.86-0.97 (m, 2H), 1.07-1.28 (m, 3H), 1.38-1.53 (m, 1H), 1.60-1.71 (m, 2H), 1.94-2.17 (m, 4H), 2.58-2.69 (m, 2H), 3.12-3.26 (m, 2H), 3.50-3.60 (m, 2H), 4.11-4.24 (m, 1H), 4.66 (d, J = 2.5 Hz, 2H), 5.65 (s, 2H), 6.24 (s, 1H), 6.50 (d, J = 3.4 Hz, 1H), 7.22 (d, J = 3.4 Hz, 1H), 8.83 (s, 1H). |
| 26 | $^1$H-NMR (CDCl$_3$) δ: −0.05 (s, 9H), 0.06 (s, 6H), 0.91 (s, 9H), 0.81-0.92 (m, 2H), 1.08-1.20 (m, 2H), 1.50-1.69 (m, 3H), 1.95-2.12 (m, 4H), 3.45 (d, J = 6.0 Hz, 2H), 3.55 (t, J = 8.1 Hz, 2H), 4.13-4.21 (m, 1H), 4.66 (d, J = 3.0 Hz, 2H), 5.65 (s, 2H), 6.50 (d, J = 3.6 Hz, 1H), 7.21 (d, J = 3.7 Hz, 1H), 8.81 (s, 1H). |
| 27 | $^1$H-NMR (CDCl$_3$) δ: −0.06 (s, 9H), 0.06 (s, 6H), 0.91 (s, 9H), 0.83-0.94 (m, 2H), 1.07-1.19 (m, 2H), 1.45-1.66 (m, 3H), 1.95-2.09 (m, 4H), 3.08 (s, 3H), 3.45 (d, J = 6.3 Hz, 2H), 3.55 (t, J = 7.5 Hz, 2H), 4.11 (tt, J = 6.9, 3.9 Hz, 1H), 4.57 (s, 2H), 5.65 (s, 2H), 6.48 (d, J = 3.6 Hz, 1H), 7.21 (d, J = 3.6 Hz, 1H), 8.85 (s, 1H). |
| 28 | $^1$H-NMR (CDCl$_3$) δ: −0.06 (s, 9H), 0.92 (t, J = 8.1 Hz, 2H), 1.13-1.26 (m, 2H), 1.53-1.71 (m, 3H), 1.98-2.13 (m, 4H), 3.08 (s, 3H), 3.52-3.57 (m, 4H), 4.12 (tt, J = 12.3, 3.6 Hz, 1H), 4.57 (s, 2H), 5.64 (s, 2H), 6.48 (d, J = 3.6 Hz, 1H), 7.21 (d, J = 3.6 Hz, 1H), 8.84 (s, 1H). |
| 29 | $^1$H-NMR (CDCl$_3$) δ: −0.06 (s, 9H), 0.86-0.96 (m, 2H), 1.31-1.76 (m, 5H), 2.01-2.33 (m, 4H), 3.08 (s, 3H), 3.50-3.59 (m, 2H), 4.05-4.17 (m, 1H), 4.57 (s, 2H), 5.65 (s, 2H), 6.43-6.46 (m, 1H), 7.2 3 (d, J = 3.6 Hz, 1H), 8.86 (s, 1H), 9.68 (d, J = 0.8 Hz, 1H). |
| 30 | $^1$H-NMR (CDCl$_3$) δ: −0.06 (s, 9H), 0.91 (t, J = 8.1 Hz, 2H), 1.08-1.65 (m, 5H), 1.98-2.11 (m, 4H), 2.62 (d, J = 6.6 Hz, 2H), 3.07 (s, 3H), 3.14-3.23 (m, 2H), 3.52-3.57 (m, 2H), 4.11 (tt, J = 12, 3.6 Hz 1H), 4.56 (s, 2H), 5.64 (s, 2H), 6.47 (d, J = 3.6 Hz, 1H), 7.21 (d, J = 3.6 Hz, 1H), 8.84 (s, 1H). |

TABLE 3

| Rf | Data |
|---|---|
| 31 | $^1$H-NMR (CDCl$_3$) δ: −0.05 (s, 9H), 0.89-0.94 (m, 2H), 1.37-1.45 (m, 2H), 1.55-1.64 (m, 2H), 1.77-1.86 (m, 1H), 2.04-2.18 (m, 4H), 3.08 (s, 3H), 3.52-3.58 (m, 2H), 4.08-4.16 (m, 1H), 4.57 (s, 2 H), 5.51-5.82 (m, 3H), 6.45-6.47 (m, 1H), 7.23-7.25 (m, 1H), 8.86 (s, 1H). |
| 32 | $^1$H-NMR (CDCl$_3$) δ: −0.06 (s, 9H), 0.89-0.94 (m, 2H), 1.21-1.33 (m, 2H), 1.55-1.69 (m, 3H), 1.97-2.09 (m, 4H), 3.08 (s, 3H), 3.52-3.58 (m, 2H), 4.12 (tt, J = 12.3, 3.6 Hz, 1H), 4.21-4.38 (m, 2H), 4.57 (s, 2H), 5.65 (s, 2H), 6.47 (d, J = 3.6 Hz, 1H), 7.23 (d, J = 3.6 Hz, 1H), 8.86 (s, 1H). |
| 33 | $^1$H-NMR (CDCl$_3$) δ: −0.06(s, 9H), 0.93 (t, d = 8.1 Hz, 2H), 1.44-1.64 (m, 2H), 1.64-2.04 (m, 2H), 2.14-2.54 (m, 5H), 3.48 (s, 3H), 3.52 (t, J = 8.1 Hz, 2H), 4.39-4.49 (m, 1H), 4.69-4.84 (m, 1H), 5.79 (s, 2H), 6.76 (d, J = 3.8 Hz, 1H), 7.51 (d, J = 3.8 Hz, 1H), 8.48 (s, 1H), 9.31 (s, 1H). |
| 36 | $^1$H-NMR (DMSO-d$_6$) δ: −0.06 (s, 9H), 0.91 (t, J = 8.2 Hz, 1H), 1.06-1.22 (m, 2H), 1.28-143 (m, 1H), 1.47-1.69 (m, 4H), 1.91-2.16 (m, 4H), 2.61 (d, J = 6.1 Hz, 2H), 3.07 (s, 3H), 3.54(t, J = 8.2 Hz, 2H), 4.04-4.18 (m, 1H), 3.97-4.22 (m, 1H), 4.57 (s, 2H), 5.64 (s, 2H), 6.48 (d, J = 3.7 Hz, 1H), 7.20 (d, J = 3.7 Hz, 1H), 8.85 (s, 1H). |
| 37 | $^1$H-NMR (CDCl$_3$) δ: −0.05 (s, 9H), 0.92 (t, J = 8.4 Ha, 2H), 1.16-1.31 (m, 1H), 1.31-1.71 (m, 4H), 1.71-1.82 (m, 1H), 1.90-2.01 (m, 2H), 2.01-2.13 (m, 2H), 3.55 (t, J = 8.7 Hz, 2H), 4.10-4.27 (m, 1H), 4.52 (s, 2H), 4.74 (s, 2H), 5.65 (s, 2H), 6.53 (d, J = 3.6 Hz, 1H), 7.24 (d, J = 3.6 Hz, 1H), 8.83 (s, 1H). |
| 38 | $^1$H-NMR (DMSO-d$_6$) δ: 1.21-1.41 (m, 2H), 1.45-1.64 (m, 1H), 1.88-2.23 (m, 6H), 3.17 (s, 2H), 4.01-4.14 (m, 1H), 4.44-4.57 (m, 1H), 4.67-4.84 (m, 1H), 6.79 (d, J = 3.7 Hz, 1H), 7.69 (d, J = 3.7 Hz, 1H), 8.75 (s, 1H), 8.93 (s, 1H). |
| 40 | $^1$H-NMR (CDCl$_3$) δ: −0.06 (s, 9H), 0.91 (t, J = 8.1 Hz, 2H), 1.16 (ddd, J = 25.2, 12.6, 3.3 Hz, 2H), 1.46 (br s, 1H), 1.59 (ddd, J = 25.2, 12.6, 3.3 Hz, 2H), 1.97-2.11 (m, 4H), 2.58 (d, J = 6.6 Hz, 2H), 2.98 (td, J = 8.4, 3.9 Hz, 2H), 3.07 (s, 3H), 3.55 (t, J = 8.1 Hz, 2H), 4.11 (m, 1H), 4.56 (s, 2H), 5.64 (br s, 2H), 5.84 (tt, 62.4 Hz, 4.5 Hz, 1H), 6.47(d, J = 4.0 Hz, 1H), 7.21 (d, J = 4.0 Hz, 1H), 8.85 (s, 1H). |
| 41 | $^1$H-NMR (CDCl$_3$) δ: −0.04 (s, 9H), 0.90 (t, J = 8.1 Hz, 2H), 1.12 (ddd, J = 25.2, 12.5, 3.3 Hz, 2H), 1.44-1.51(m, 1H), 1.60 (ddd, J = 25.2, 12.5, 3.3 Hz, 2H), 1.99-2.12 (m, 4H), 2.33 (d, J = 7.5 Hz, |

TABLE 3-continued

| Rf | Data |
|---|---|
| | 2H), 2.36 (s, 3H), 3.08 (s, 3H), 3.52 (s, 2H), 3.55 (t, J = 8.1 Hz, 2H), 4.08-4.16 (m, 1H), 4.58 (s, 2H), 5.65 (br s, 2H), 6.47 (d, J = 4.0 Hz, 1H), 7.22 (d, J = 4.0 Hz, 1H), 8.86 (s, 1H). |
| 42 | $^1$H-NMR (CDCl$_3$) δ: −0.04 (s, 9H), 0.90 (t, J = 8.1 Hz, 2H), 1.06-1.20 (m, 2H), 1.45-1.73 (m, 3H), 1.98-2.18 (m, 4H), 2.64 (d, J = 6.6 Hz, 2H), 3.07 (s, 3H), 3.54 (t, J = 8.1 Hz, 2H), 3.60 (s, 2H), 4.08-4.15 (m, 1H), 4.55 (s, 2H), 5.64 (br s, 2H), 6.46 (d, J = 4.0 Hz, 1H), 7.21 (d, J = 4.0 Hz, 1H), 8.84 (s, 1H). |
| 44 | $^1$H-NMR (CDCl$_3$) δ: −0.05 (s, 9H), 0.91 (t, J = 8.1 Hz, 2H), 1.11-1.23 (m, 2H), 1.54-1.66 (m, 3H), 1.99-2.13 (m, 4H), 2.46 (d, J = 5.7 Hz, 1H), 2.80 (s, 3H), 2.88 (s, 3H), 2.98 (d, J = 7.5 Hz, 1H), 3.07 (s, 3H), 3.54 (t, J = 8.1 Hz, 2H), 4.08-4.16 (m, 1H), 4.56 (s, 2H), 5.65 (br s, 2H), 6.46 (d, J = 4.0 Hz, 1H), 7.23 (d, J = 4.0 Hz, 1H), 8.86 (s, 1H). |

TABLE 4

| Rf | Data |
|---|---|
| 45 | $^1$H-NMR (CDCl$_3$) δ: −0.05 (s, 9H), 0.87-0.96 (m, 2H), 1.10-1.29 (m, 2H), 1.48 (s, 9H), 1.70-1.55 (m, 3H), 1.84-1.93 (m, 2H), 2.07-2.16 (m, 2H), 3.24 (d, J = 7.0 Hz, 2H), 3.51-3.59 (m, 2H), 3.76-3.93 (m, 2H), 4.11-4.24 (m, 1H), 4.63-4.68 (m, 2H), 5.65 (s, 2H), 6.29 (br s, 1H), 6.48 (d, J = 3.5 Hz, 1H), 7.22 (d, J = 3.5 Hz, 1H), 8.82 (s, 1H). |
| 46 | $^1$H-NMR (CDCl$_3$) δ: −0.06 (s, 9H), 0.91 (t, J = 8.1 Hz, 2H), 1.13-1.25 (m, 2H), 1.48 (br s, 10H), 1.51-1.69 (m, 2H), 1.85-1.89 (m, 2H), 2.04-2.08 (m, 2H), 3.24 (d, J = 6.6 Hz, 2H), 3.36 (s, 3H), 3.54 (t, J = 8.1 Hz, 2H), 3.60-3.63 (m, 2H), 3.66-3.69 (m, 2H), 3.81-3.85 (m, 2H), 4.10-4.15 (m, 1H), 4.69 (s, 2H), 5.65 (br s, 2H), 6.48 (d, J = 4.0 Hz, 1H), 7.21 (d, J = 4.0 Hz, 1H), 8.83 (s, 1H). |
| 47 | $^1$H-NMR (CDCl$_3$) δ: −0.06 (s, 9H), 0.91 (t, J = 8.1 Hz, 2H), 1.16-1.28 (m, 2H), 1.48 (br s, 10H), 1.61-1.79 (m, 2H), 1.88-1.92 (m, 2H), 2.09-2.12 (m, 2H), 2.15 (s, 3H), 3.26 (d, J = 6.6 Hz, 2H), 3.55 (t, J = 8.1 Hz, 2H), 3.82-3.86 (m, 2H), 4.18-4.24 (m, 1H), 4.67 (s, 2H), 4.75 (s, 2H), 5.65 (br s, 2H), 6.49 (d, J = 4.0 Hz, 1 H), 7.23 (d, J = 4.0 Hz, 1H), 8.83 (s, 1H). |
| 50 | $^1$H-NMR (CDCl$_3$) δ: −0.05 (s, 9H), 0.06 (s, 6H), 0.87-0.95 (m, 2H), 0.91 (s, 9H), 1.09-1.25 (m, 2H), 1.46-1.61 (m, 3H), 1.93-2.14 (m, 4H), 3.46 (d, J = 6.5 Hz, 2H), 3.54 (t, J = 8.4 Hz, 2H), 4.08-4.20 (m, 1H), 4.14 (q, J = 9.2 Hz, 2H), 4.70 (s, 2H), 5.65 (s, 2H), 6.51 (d, J = 3.7 Hz, 1H), 7.23 (d, J = 3.7 Hz, 1H), 8.86 (s, 1H). |
| 52 | $^1$H-NMR (CDCl$_3$) δ: −0.05 (s, 9H), 0.91 (t, J = 8.3 Hz, 2H), 1.21-1.39 (m, 2H), 1.49-1.75 (m, 1H), 1.59-1.74 (m, 2H), 2.05-2.17 (m, 4H), 3.35 (d, J = 6.1 Hz, 2H), 3.54 (t, J = 8.3 Hz, 2H), 4.08-4.23 (m, 1H), 4.14 (q, J = 9.2 Hz, 2H), 4.70 (s, 2H), 5.66 (s, 2H), 6.49 (d, J = 3.6 Hz, 1H), 7.25 (d, J = 3.6 Hz, 1H), 8.86 (s, 1H). |
| 53 | $^1$H-NMR (CDCl$_3$) δ: −0.05 (s, 9H), 0.91 (t, J = 8.4 Hz, 2H), 1.05-1.34 (m, 3H), 1.51-1.71 (m, 2H), 1.94-2.16 (m, 4H), 2.62 (d, J = 6.1 Hz, 2H), 3.55 (t, J = 8.2 Hz, 2H), 4.06-4.24 (m, 1H), 4.14 (q, J = 9.1 Hz, 2H), 4.71 (s, 2H), 5.65 (s, 2H), 6.51 (d, J = 3.7 Hz, 1H), 7.23 (d, J = 3.7 Hz, 1H), 8.86 (s, 1H). |
| 54 | $^1$H-NMR (CDCl$_3$) δ: −0.05 (s, 9H), 0.91 (t, J = 8.2 Hz, 2H), 1.11-1.30 (m, 3H), 1.53-1.71 (m, 2H), 1.98-2.17 (m, 4H), 2.98 (s, 3H), 3.06 (t, J = 6.6 Hz, 2H), 3.55 (t, J = 8.2 Hz, 2H), 4.05-4.21 (m, 1H), 4.14 (q, J = 9.0 Hz, 2H), 4.30-4.42 (m, 1H), 4.70 (s, 2H), 5.65 (s, 2H), 6.48 (d, J = 3.7 Hz, 1H), 7.24 (d, J = 3.7 Hz, 1H), 8.86 (s, 1H). |
| 55 | $^1$H-NMR (CDCl$_3$) δ: −0.05 (s, 9H), 0.92 (t, J = 8.2 Hz, 2H), 0.98-1.06 (m, 2H), 1.12-1.29 (m, 5H), 1.52-1.69 (m, 2H), 1.99-2.17 (m, 4H), 2.36-2.48 (m, 1H), 3.09 (t, J = 6.5 Hz, 2H), 3.55 (t, J = 8.2 Hz, 2H), 4.08-4.20 (m, 1H), 4.14 (q, J = 9.0 Hz, 2H), 4.22-4.32 (m, 1H), 4.70 (s, 2H), 5.65 (s, 2H), 6.48 (d, J = 3.7 Hz, 1H), 7.24 (d, J = 3.7 Hz, 1H), 8.86 (s, 1H). |
| 57 | $^1$H-NMR (CDCl$_3$) δ: −0.06 (s, 9H), 0.31-0.32 (m, 2H), 0.58-0.60 (m, 2H), 0.88-0.94 (m, 2H), 1.05-1.26 (m, 3H), 1.48 (s, 9H), 1.60-1.68 (m, 3H), 1.87-1.91 (m, 2H), 2.08-2.12 (m, 2H), 3.24 (d, J = 7.5 Hz, 2H), 3.40 (d, J = 6.9 Hz, 2H), 3.54 (t, J = 8.1 Hz, 2H), 3.81-3.84 (m, 2H), 4.12-4.18 (m, 1H), 4.67 (s, 2H), 5.64 (s, 2H), 6.47 (d, J = 3.6 Hz, 1H), 7.20 (d, J = 3.6 Hz, 1H), 8.85 (s, 1H). |

TABLE 5

| Rf | Data |
|---|---|
| 58 | $^1$H-NMR (CDCl$_3$) δ: −0.05 (s, 9H), 0.88-0.94 (m, 2H), 1.20-1.31 (m, 2H), 1.45-1.55 (m, 10H), 1.60-1.75 (m, 3H), 1.82-2.11 (m, 7H), 3.23-3.40 (m, 3H), 3.51-3.57 (m, 2H), 3.73-3.93 (m, 4H), 4.04-4.18 (m, 3H), 4.65 (d, J = 11.1 Hz, 1H), 4.79 (d, J = 11.1 Hz, 1H), 5.64 (s, 2H), 6.48 (d, J = 3.6 Hz, 1H), 7.20 (d, J = 3.6 Hz, 1H), 8.83 (s, 1H). |
| 59 | $^1$H-NMR (CDCl$_3$) δ: −0.05 (s, 9H), 0.91 (t, J = 8.2 Hz, 2H), 1.19-1.28 (m, 2H), 1.48 (br s, 9H), 1.56-1.68 (m, 3H), 1.91 (d, J = 12.8 Hz, 2H), 1.99-2.12 (m, 4H), 2.47 (t, J = 7.2 Hz, 2H), 3.26 (d, J = 7.4 Hz, 2H), 3.51-3.63 (m, 4H), 3.81-3.84 (m, 2H), 4.15-4.23 (m, 1H), 4.61 (s, 2H), 5.64 (s, 2H), 6.48 (d, J = 3.7 Hz, 1H), 7.22 (d, J = 3.7 Hz, 1H), 8.81 (s, 1H). |
| 61 | $^1$H-NMR (CDCl$_3$) δ: −0.06 (s, 9H), 0.87-0.95 (m, 2H), 1.12-1.33 (m, 5H), 1.48 (s, 9H), 1.53-1.76 (m, 3H), 1.84-1.94 (m, 2H), 2.05-2.15 (m, 2H), 3.25 (d, J = 7.6 Hz, 2H), 3.50-3.62 (m, 4H), 3.77-3.95 (m, 2H), 4.09-4.22 (m, 1H), 4.58 (s, 2H), 5.65 (s, 2H), 6.47 (d, J = 4.0 Hz, 1H), 7.21 (d, J = 3.3 Hz, 1H), 8.85 (s, 1H). |
| 62 | $^1$H-NMR (CDCl$_3$) δ: −0.05 (s, 9H), 0.91 (t, J = 8.3 Hz, 2H), 1.08-1.27 (m, 2H), 1.51-1.72 (m, 3H), 2.00-2.16 (m, 4H), 2.37 (tt, J = 7.7, 6.7 Hz, 2H), 2.92 (d, J = 6.9 Hz, 2H), 3.16 (t, J = 7.7 Hz, 2H), 3.28 (t, J = 6.7 Hz, 2H), 3.55 (t, J = 8.3 Hz, 2H), 4.07-4.25 (m, 1H), 4.14 (q, J = 9.2 Hz, 2H), 4.69 (s, 2H), 5.65 (s, 2H), 6.49 (d, J = 3.9 Hz, 1H), 7.24 (d, J = 3.9 Hz, 1H), 8.86 (s, 1H). |
| 66 | $^1$H-NMR (CDCl$_3$) δ: −0.05 (s, 9H), 0.91 (t, J = 8.1 Hz, 2H), 1.11-1.24 (m, 2H), 1.58-1.75 (m, 3H), 1.96-2.13 (m, 4H), 2.80 (s, 3H), 2.86 (s, 3H), 2.98 (d, J = 7.5 Hz, 2H), 3.54 (t, J = 8.1 Hz, 2H), 4.11-4.23 (m, 1H), 4.66 (s, 2H), 5.64 (br s, 2H), 6.47 (d, J = 4.0 Hz, 1H), 7.13 (br s, 1H), 7.21 (d, J = 4.0 Hz, 1H), 8.80 (s, 1H). |
| 67 | $^1$H-NMR (CDCl$_3$) δ: −0.05 (s, 9H), 0.92 (t, J = 8.1 Hz, 2H), 1.13-1.26 (m, 2H), 1.55-1.68 (m, 3H), 2.01-2.14 (m, 4H), 2.81 (s, 3H), 2.88 (s, 3H), 2.99 (d, J = 7.5 Hz, 2H), 3.54 (t, J = 8.1 Hz, 2H), 4.08-4.23 (m, 3H), 4.70 (s, 2H), 5.65 (br s, 2H), 6.49 (d, J = 4.0 Hz, 1H), 7.24 (d, J = 4.0 Hz, 1H), 8.86 (s, 1H). |
| 68 | $^1$H-NMR (CDCl$_3$) δ: −0.05 (s, 9H), 0.72-0.78 (m, 2H), 0.86-0.92 (m, 2H), 0.91 (t, J = 8.1 Hz, 2H), 1.14-1.25 (m, 2H), 1.60-1.69 (m, 3H), 2.04-2.08 (m, 4H), 2.66-2.75 (m, 1H), 2.80 (s, 3H), 2.89 (s, 3H), 3.00 (d, J = 7.5 Hz, 2H), 3.54 (t, J = 8.1 Hz, 2H), 4.14-4.22 (m, 1H), 4.59 (s, 2H), 5.64 (br s, 2H), 6.47 (d, J = 4.0 Hz, 1H), 7.19 (d, J = 4.0 Hz, 1H), 8.86 (s, 1H). |
| 69 | $^1$H-NMR (CDCl$_3$) δ: −0.05 (s, 9H), 0.91 (t, J = 8.1 Hz, 2H), 1.12-1.28 (m, 2H), 1.25 (t, J = 7.2 Hz, 3H), 1.58-1.69 (m, 3H), 2.00-2.11 (m, 4H), 2.46 (d, J = 5.7 Hz, 1H), 2.81 (s, 3H), 2.88 (s, 3H), 2.99 (d, J = 7.5 Hz, 1H), 3.51-3.62 (m, 4H), 4.13-4.22 (m, 1H), 4.59 (s, 2H), 5.65 (br s, 2H), 6.47 (d, J = 4.0 Hz, 1H), 7.21 (d, J = 4.0 Hz, 1H), 8.85 (s, 1H). |
| 70 | $^1$H-NMR (CDCl$_3$) δ: −0.05 (s, 9H), 0.92 (t, J = 8.2 Hz, 2H), 1.18-1.28 (m, 2H), 1.48 (br s, 9H), 1.60-1.72 (m, 3H), 1.90 (d, J = 11.9 Hz, 2H), 2.12 (d, J = 11.6 Hz, 2H), 3.25 (d, J = 7.0 Hz, 2H), 3.55 (t, J = 8.3 Hz, 2H), 3.81-3.84 (m, 2H), 4.18-4.22 (m, 1H), 4.51 (s, 2H), 4.72 (s, 2H). 5.65 (s, 2H), 6.48 (d, J = 3.7 Hz, 1H), 7.24 (s, 1H), 8.82 (s, 1H). |

TABLE 6

| Rf | Data |
|---|---|
| 71 | $^1$H-NMR (CDCl$_3$) δ: −0.06 (s, 9H), 0.89-0.96 (m, 2H), 1.45 (qd, J = 12.7, 2.9 Hz, 2H), 1.76-1.86 (m, 1H), 1.88 (qd, J = 12.7, 2.9 Hz, 2H), 2.12-2.22 (m, 2H), 2.34-2.43 (m, 2H), 3.42 (s, 6H), 3.52-3.59 (m, 2H), 4.15 (d, J = 6.1 Hz, 1H), 4.75 (tt, J = 11.9, 2.9 Hz, 1H), 5.79 (s, 2H), 6.75 (d, J = 3.7 Hz, 1H), 7.50 (d, J = 3.7 Hz, 1H), 8.48 (s, 1H), 9.31 (s, 1H). |
| 72 | $^1$H-NMR (CDCl$_3$) δ: −0.05 (s, 9H), 0.85-0.96 (m, 3H), 1.18-1.33 (m, 2H), 1.47-1.68 (m, 2H), 1.97-2.05 (m, 2H), 2.07-2.16 (m, 2H), 3.38 (s, 6H), 3.51-3.58 (m, 2H), 4.05 (d, J = 6.5 Hz, 1H), 4.16 (tt, J = 12.3, 3.3 Hz, 1H), 4.65 (d, J = 3.3 Hz, 2H), 5.65 (s, 2H), 5.73-5.79 (m, 1H), 6.50 (d, J = 4.1 Hz, 1H), 7.28 (d, J = 4.1 Hz, 1H), 8.82 (s, 1H). |
| 73 | $^1$H-NMR (CDCl$_3$) δ: −0.06 (s, 9H), 0.73-0.78 (m, 2H), 0.87-0.94 (m, 2H), 1.19-1.34 (m, 4H), 1.51-1.69 (m, 3H), 1.97-2.13 (m, 4H), 2.64-2.72 (m, 1H), 3.39 (s, 6H), 3.50-3.57 (m, 2H), 4.14 (d, J = 6.5 Hz, 1H), 4.15-4.26 (m, 1H), 4.59 (s, 2H), 5.63 (s, 2H), 6.48 (d, J = 3.7 Hz, 1H), 7.18 (d, J = 3.7 Hz, 1H), 8.85 (s, 1H). |
| 74 | $^1$H-NMR (CDCl$_3$) δ: −0.06 (s, 9H), 0.72-0.78 (m, 2H), 0.89-0.95 (m, 4H), 1.41-1.58 (m, 2H), 1.60-1.76 (m, 3H), 2.14-2.36 (m, 4H), 2.65-2.73 (m, 1H), 3.50-3.57 (m, 2H), 4.10-4.23 (m, 1H), 4.60 (s, |

TABLE 6-continued

| Rf | Data |
|---|---|
| | 2H), 5.64 (s, 2H), 6.45 (d, J = 3.6 Hz, 1H), 7.21 (d, J = 3.6 Hz, 1H), 8.87 (s, 1H), 9.70 (s, 1 H). |
| 75 | $^1$H-NMR (CDCl$_3$) δ: −0.06 (s, 9H), 0.87-0.95 (m, 2H), 1.18-1.29 (m, 5H), 1.57-1.80 (m, 3H), 1.97-2.05 (m, 2H), 2.06-2.14 (m, 2H), 3.38 (s, 6H), 3.50-3.57 (m, 2H), 3.58 (q, J = 7.4 Hz, 2H), 4.05 (d, J = 6.5 Hz, 1H), 4.07-4.19 (m, 1H), 4.58 (s, 2H), 5.64 (s, 2H), 6.48 (d, J = 3.7 Hz, 1H), 7.20 (d, J = 3.7 Hz, 1H), 8.84 (s, 1H). |
| 76 | $^1$H-NMR (CDCl$_3$) δ: −0.06 (s, 9H), 0.88-0.95 (m, 2H), 1.22-1.29 (m, 1H), 1.26 (t, J = 6.9 Hz, 3H), 1.45-1.59 (m, 2H), 1.68 (qd, J = 12.6, 2.6 Hz, 2H), 2.17-2.35 (m, 4H), 3.51-3.58 (m, 2H), 3.59 (q, J = 7.6 Hz, 2H), 4.15 (tt, J = 11.9, 3.3 Hz, 1H), 4.60 (s, 2H), 5.65 (s, 2H), 6.45 (d, J = 3.6 Hz, 1H), 7.23 (d, J = 3.6 Hz, 1H), 8.87 (s, 1H), 9.69 (s, 1H). |
| 77 | $^1$H-NMR (CDCl$_3$) δ: −0.05 (s, 9H), 0.88-0.95 (m, 2H), 1.19-1.34 (m, 2H), 1.49-1.72 (m, 3H), 1.98-2.05 (m, 2H), 2.07-2.14 (m, 2H), 3.38 (s, 6H), 3.51-3.58 (m, 2H), 4.06 (d, J = 6.5 Hz, 1H), 4.08-4.20 (m, 3H), 4.69 (s, 2H), 5.65 (s, 2H), 6.50 (d, J = 3.7 Hz, 1 H), 7.22 (d, J = 3.7 Hz, 1H), 8.85 (s, 1H). |
| 78 | $^1$H-NMR (CDCl$_3$) δ: −0.05 (s, 9H), 0.87-0.96 (m, 2H), 1.45-1.60 (m, 3H), 1.65 (qd, J = 12.7, 2.9 Hz, 2H), 2.17-2.31 (m, 4H), 3.51-3.58 (m, 2H), 4.09-4.23 (m, 3H), 4.70 (s, 2H), 5.65 (s, 2H), 6.47 (d, J = 3.7 Hz, 1H), 7.24 (d, J = 3.7 Hz, 1H), 8.87 (s, 1H), 9.69 (s, 1H). |
| 79 | $^1$H-NMR (CDCl$_3$) δ: −0.05 (s, 9H), 0.89-0.94 (m, 2H), 1.02-1.14 (m, 2H). 1.52-1.70 (m, 3H), 1.99-2.10 (m, 4H), 2.19 (d, J = 6.9 Hz, 2H), 2.45-2.53 (m, 10H), 2.70 (t, J = 6.6 Hz, 2H), 3.53-3.58 (m, 2H), 4.14-4.22 (m, 1H), 4.67 (d, J = 2.7 Hz, 2H), 5.65 (s, 2H), 6.50 (d, J = 3.6 Hz, 1H), 7.20 (d, J = 3.6 Hz, 1H), 7.49 (br s, 1H), 8.81 (s, 1H). |
| 80 | $^1$H-NMR (CDCl$_3$) δ: −0.06 (s, 9H), 0.72-0.77(m, 2H), 0.88-0.93 (m, 4H), 1.04-1.16 (m, 2H), 1.54-1.68 (m, 3H), 2.02-2.07 (m, 4H), 2.19 (d, J = 6.9 Hz, 2H), 2.46-2.53 (m, 10H), 2.66-2.73(m, 3H), 3.51-3.56 (m, 2H), 4.13-4.21 (m, 1H), 4.60 (s, 2H), 5.64 (s, 2H), 6.48 (d, J = 3.6 Hz, 1H), 7.18 (d, J = 3.6 Hz, 1H), 8.86 (s, 1H). |

TABLE 7

| Rf | Data |
|---|---|
| 81 | $^1$H-NMR (CDCl$_3$) δ: −0.06 (s, 9H), 0.88-0.94 (m, 2H), 1.02-1.14 (m, 2H), 1.52-1.68 (m, 3H), 1.98-2.09 (m, 4H), 2.18 (d, J = 7.2 Hz, 2H), 2.45-2.54 (m, 10H), 2.67-2.72 (m, 2H), 3.06 (s, 3H), 3.52-3.58 (m, 2H), 4.08-4.15 (m, 1H), 4.56 (s, 2H), 5.64 (s, 2H), 6.47 (d, J = 3.6 Hz, 1H), 7.20 (d, J = 3.6 Hz, 1H), 8.84 (s, 1H). |
| 82 | $^1$H-NMR (CDCl$_3$) δ: −0.06 (s, 9H), 0.06 (s, 6H), 0.72-0.78 (m, 2H), 0.83-0.96 (m, 4H), 0.91 (s, 9H), 1.09-1.31 (m, 3H), 1.55-1.67 (m, 2H), 1.92-2.10 (m, 4H), 2.64-2.74 (m, 1H), 3.46 (d, J = 6.1 Hz, 2H), 3.53 (d, J = 8.2 Hz, 2H), 4.19-4.25 (m, 1H), 4.60 (s, 2H), 5.63 (s, 2H), 6.48 (d, J = 3.7 Hz, 1H), 7.18 (d, J = 3.3 Hz, 1H), 8.85 (s, 1H). |
| 83 | $^1$H-NMR (CDCl$_3$) δ: −0.06 (s, 9H), 0.71-0.79 (m, 2H), 0.85-0.96 (m, 4H), 1.13-1.30 (m, 2H), 1.39 (t, J = 5.1 Hz, 1H), 1.55-1.72 (m, 2H), 1.96-2.14 (m, 4H), 2.65-2.72 (m, 1H), 3.49-3.57 (m, 4H), 4.09-4.23 (m, 1H), 4.60 (s, 2H), 5.63 (s, 2H), 6.48 (d, J = 3.7 Hz, 1H), 7.19 (d, J = 3.7 Hz, 1H), 8.85 (s, 1H). |
| 85 | $^1$H-NMR (CDCl$_3$) δ: −0.06 (s, 9H), 0.71-0.80 (m, 2H), 0.86-0.96 (m, 4H), 1.05-1.24 (m, 2H), 1.24-1.74 (m, 5H), 1.94-2.14 (m, 4H), 2.62 (d, J = 6.3 Hz, 2H), 2.64-2.73 (m, 1H), 3.54 (t, J = 8.3 Hz, 2H), 4.05-4.31 (m, 1H), 4.60 (s, 2H), 5.64 (s. 2H), 6.48 (d, J = 3.6 Hz, 1H), 7.19 (d, J = 3.6 Hz, 1H), 8.85 (s, 1H). |
| 86 | $^1$H-NMR (CDCl$_3$) δ: −0.06 (s, 9H), 0.72-0.78 (m, 2H), 0.87-0.95 (m, 4H), 1.20 (qd, J = 12.6, 2.6 Hz, 2H), 1.47-1.60 (m, 1H), 1.63 (qd, J = 12.6, 2.6 Hz, 2H), 1.98-2.06 (m, 2H), 2.05-2.12 (m, 2H), 2.66-2.73 (m, 1H), 2.66 (d, J = 6.6 Hz, 2H), 3.51-3.57 (m, 2H), 3.62 (s, 2H), 4.18 (tt, J = 11.6, 3.0 Hz, 1H), 4.60 (s, 2H), 5.64 (s, 2H), 6.47 (d, J = 3.6 Hz, 1H), 7.20 (d, J = 3.6 Hz, 1H), 8.86 (s, 1H). |
| 87 | $^1$H-NMR (CDCl$_3$) δ: −0.05 (s, 9H), 0.87-0.95 (m, 2H), 1.16-1.29 (m, 5H), 1.48-1.60 (m, 1H), 1.64 (qd, J = 12.3, 2.5 Hz, 2H), 1.98-2.06 (m, 2H), 2.07-2.15 (m, 2H), 2.65 (d, J = 7.0 Hz, 2H), 3.50-3.60 (m, 4H), 3.61 (s, 2H), 4.16 (tt, J = 12.3, 3.7 Hz, 1H), 4.59 (s, 2H), 5.64 (s, 2H), 6.47 (d, J = 3.7 Hz, 1H), 7.21 (d, J = 3.7 Hz, 1H), 8.85 (s, 1H). |
| 88 | $^1$H-NMR (CDCl$_3$) δ: −0.05 (s, 9H), 0.88-0.95 (m, 2H), 1.20 (qd, J = 12.7, 2.9 Hz, 2H), 1.47-1.56 (m, 1H), 1.61 (qd, J = 12.7, 2.9 Hz, 2H), 1.99-2.06 (m, 2H), 2.07-2.14 (m, 2H), 2.65 (d, J = 6.5 Hz, 2H), 3.51-3.58 (m, 2H), 3.61 (s, 2H), 4.09-4.23 (m, 3H), 4.70 (s, 2H), 5.65 |

TABLE 7-continued

| Rf | Data |
|---|---|
|  | (s, 2H), 6.49 (d, J = 3.7 Hz, 1H), 7.24 (d, J = 3.7 Hz, 1H), 8.86 (s, 1H). |
| 91 | $^1$H-NMR (DMSO-d$_6$) δ: −0.08 (s, 9H), 0.82 (t, J = 8.0 Hz, 2H), 1.04-1.22 (m, 2H), 1.32-1.50 (m, 1H), 1.57-1.78 (m, 2H), 1.80-1.94 (m, 4H), 3.25 (t, J = 5.7 Hz, 2H), 3.51 (t, J = 8.0 Hz, 2H), 4.00-4.20 (m, 1H), 4.42 (t, J = 5.1 Hz, 1H), 4.53 (d, J = 2.9 Hz, 2H), 5.56 (s, 2H), 6.54 (d, J = 3.7 Hz, 1H), 7.47 (d, J = 3.7 Hz, 1H), 7.89 (s, 1H), 8.48 (s, 1H). |
| 95 | $^1$H-NMR (CDCl$_3$) δ: −0.06 (s, 9H), 0.91 (t, J = 8.3 Hz, 2H), 1.06-1.72 (m, 10H), 1.93-2.17 (m, 4H), 2.62 (d, J = 6.6 Hz, 2H), 3.49-3.64 (m, 4H), 4.08-4.23 (m, 1H), 4.59 (s, 2H), 5.65 (s, 2H), 6.49 (d, J = 3.6 Hz, 1H), 7.21 (d, J = 3.6 Hz, 1H), 8.85 (s, 1H). |

TABLE 8

| Rf | Data |
|---|---|
| 96 | $^1$H-NMR (CDCl$_3$) δ: −0.05 (s, 9H), 0.89-0.94 (m, 2H), 1.06-1.19 (m, 2H), 1.45-1.55 (m, 1H), 1.59-1.70 (m, 2H), 2.04-2.11 (m, 6H), 2.36-2.47 (m, 3H), 2.76-2.91 (m, 3H), 3.52-3.58 (m, 2H), 4.13-4.22 (m, 1H), 4.68 (s, 2H), 5.07-5.28 (m, 1H), 5.64 (s, 2H), 6.50-6.51 (m, 1H), 7.20-7.21 (m, 1H), 7.61 (s, 1H), 8.80 (s, 1H). |
| 97 | $^1$H-NMR (CDCl$_3$) δ: −0.06 (s, 9H), 0.88-0.94 (m, 2H), 1.14-1.28 (m, 2H), 1.55-1.66 (m, 3H), 1.98-2.11 (m, 4H), 2.61(t, J = 6.0 Hz, 2H), 3.07 (s, 3H), 3.35 (d, J = 6.0 Hz, 2H), 3.52-3.57 (m, 2H), 3.65 (t, J = 6.0 Hz, 2H), 4.08-4.15 (m, 1H), 4.57 (s, 2H), 5.64 (s, 2H), 6.47-6.48 (m, 1H), 7.20-7.21 (m, 1H), 8.84 (s, 1H). |
| 98 | $^1$H-NMR (CDCl$_3$) δ: −0.05 (s, 9H), 0.92 (t, J = 8.1 Hz, 2H), 1.10-1.26 (m, 2H), 1.48 (s, 9H), 1.58-1.68 (m, 3H), 1.85-1.90 (m, 2H), 2.09-2.13 (m, 2H), 3.19 (br s, 2H), 3.49-3.57 (m, 4H), 4.11-4.22 (m, 1H), 4.66 (s, 2H), 5.65 (br s, 2H), 5.87-6.17 (m, 1H), 6.49 (d, J = 4.0 Hz, 1H), 7.22 (d, J = 4.0 Hz, 1H), 8.82 (s, 1H). |
| 99 | $^1$H-NMR (CDCl$_3$) δ: −0.05 (s, 9H), 0.73-0.75 (m, 2H), 0.82-0.93 (m, 4H), 1.13-1.26 (m, 2H), 1.48 (s, 9H), 1.55-1.66 (m, 3H), 1.87-1.91 (m, 2H), 2.04-2.07 (m, 2H), 2.65-2.70 (m, 1H), 3.20-3.23 (m, 2H), 3.47-3.56 (m, 4H), 4.12-4.23 (m, 1H), 4.58 (s, 2H), 5.63 (br s, 2H), 5.68-6.20 (m, 1H), 6.46 (d, J = 4.0 Hz, 1H), 7.20 (d, J = 4.0 Hz, 1H), 8.85 (s, 1H). |
| 100 | $^1$H-NMR (CDCl$_3$) δ: −0.05 (s, 9H), 0.90 (t, J = 8.1 Hz, 2H), 1.12-1.26 (m, 5H), 1.48 (s, 9H), 1.54-1.66 (m, 3H), 1.86-1.90 (m, 2H), 2.07-2.10 (m, 2H), 3.19-3.21 (m, 2H), 3.45-3.61 (m, 6H), 4.11-4.18 (m, 1H), 4.58 (s, 2H), 5.64 (br s, 2H), 5.68-6.20 (m, 1H), 6.47 (d, J = 4.0 Hz, 1H), 7.21 (d, J = 4.0 Hz, 1H), 8.84 (s, 1H). |
| 105 | $^1$H-NMR (CDCl$_3$) δ: −0.05 (s, 9H), 0.92 (t, J = 8.1 Hz, 2H), 1.13-1.26 (m, 2H), 1.48 (s, 9H), 1.60-1.71 (m, 3H), 1.88-1.92 (m, 2H), 2.10-2.14 (m, 2H), 3.18-3.22 (m, 2H), 3.46-3.57 (m, 4H), 4.12-4.25 (m, 1H), 4.51 (s, 2H), 4.72 (s, 2H), 5.65 (br s, 2H), 5.79-6.17 (m, 1H), 6.49 (d, J = 4.0 Hz, 1H), 7.23-7.25 (d, J = 4.0 Hz, 1H), 8.83 (s, 1H). |

TABLE 9

| Rf | Data |
|---|---|
| 114 | $^1$H-NMR (CDCl$_3$) δ: 0.91-1.16 (m, 4H), 1.56-1.67 (m, 1H), 1.71-1.80 (m, 2H), 1.97-2.07 (m, 2H), 2.45 (s, 3H), 3.30-3.48 (m, 1H), 3.81 (d, J = 6.5 Hz, 2H), 4.50-4.62 (m, 1H), 5.07 (s, 2H), 7.29-7.38 (m, 7H), 7.77 (d, J = 8.2 Hz, 2H). |
| 115 | $^1$H-NMR (CDCl$_3$) δ: 1.04-1.22 (m, 4H), 1.59-1.73 (m, 1H), 1.76-1.92 (m, 2H), 2.01-2.14 (m, 2H), 3.35-3.56 (m, 1H), 4.14 (d, J = 6.1 Hz, 1H), 4.30 (d, J = 6.1 Hz, 1H), 4.59 (br s, 1H), 5.08 (s, 2H), 7.29-7.38 (m, 5H). |
| 116 | $^1$H-NMR (CDCl$_3$) δ: 0.95-1.22 (m, 4H), 1.47-2.02 (m, 5H), 2.28 (br s, 2H), 2.53-2.75 (m, 1H), 4.15 (d, J = 6.1 Hz, 1H), 4.31 (d, J = 5.7 Hz, 1H). |
| 117 | $^1$H-NMR (CDCl$_3$) δ: −0.04 (s, 9H), 0.90 (t, J = 8.1 Hz, 2H), 1.21-1.33 (m, 2H), 1.36-1.49 (m, 2H), 1.74-1.80 (m, 1H), 1.90-1.95 (m, 2H), 2.27-2.31 (m, 2H), 3.53 (t, J = 8.1 Hz, 2H), 3.81-4.94 (m, 1H), 4.30 (dd, J = 47.8, 5.7 Hz, 2H), 5.58 (s, 2H), 5.64 (br s, 2H), 6.57 (d, J = 4.0 Hz, 1H), 7.09 (d, J = 4.0 Hz, 1H), 8.30 (s, 1H), 9.26 (d, J = 7.8 Hz, 1H). |
| 118 | $^1$H-NMR (CDCl$_3$) δ: −0.04 (s, 9H), 1.00 (t, J = 8.1 Hz, 2H), 1.52-1.69 (m, 2H), 1.91-2.19 (m, 3H), 2.21-2.25 (m, 2H), 2.47-2.51 (m, 2H), 3.63 (t, J = 8.1 Hz, 2H), 4.42 (dd, J = 47.8, 5.4 Hz, 2H), 4.85 (tt, J = 12.0, 3.3 Hz, 1H), 5.86 (br s, 2H), 6.80 (d, J = 4.0 Hz, 1H), 7.59 (d, J = 4.0 Hz, 1H), 8.56 (s, 1H), 9.38 (s, 1H). |
| 119 | $^1$H-NMR (CDCl$_3$) δ: −0.04 (s, 9H), 0.90 (t, J = 8.1 Hz, 2H), 1.21-1.34 (m, 2H), 1.59-1.73 (m, 3H), 1.96-2.05 (m, 2H), 2.12-2.17 (m, 2H), 3.55 (t, J = 8.1 Hz, 2H), 4.13-4.23 (m, 1H), 4.58 (dd, J = 47.8, 5.4 Hz, 2H), 4.67 (d, J = 3.0 Hz, 2H), |

TABLE 9-continued

| Rf | Data |
|---|---|
|  | 5.65 (s, 2H), 6.21 (br s, 1H), 6.50 (d, J = 4.0 Hz, 1H), 7.23 (d, J = 4.0 Hz, 1H), 8.83 (s, 1H). |
| 120 | $^1$H-NMR (CDCl$_3$) δ: −0.06 (s, 9H), 0.88-0.94 (m, 2H), 1.21-1.34 (m, 2H), 1.56-1.77 (m, 3H), 1.98 (d, J = 12.8 Hz, 2H), 2.12 (d, J = 11.1 Hz, 2H), 3.08 (s, 3H), 3.52-3.57 (m, 2H), 4.08-4.16 (m, 1H), 4.29 (dd, J = 47.8, 5.8 Hz, 2H), 4.57 (s, 2H), 5.65 (s, 2H), 6.47 (d, J = 3.7 Hz, 1H), 7.22 (d, J = 3.7 Hz, 1H), 8.85 (s, 1H). |

LC/MS spectral data of the compounds obtained in the above Reference Synthetic Examples are shown in Tables 10 to 13.

TABLE 10

| Rf | condition | R. time (min) | ESI+ | ESI− |
|---|---|---|---|---|
| 1 | 1 | 0.64 | 135 | — |
| 2 | 1 | 3.16 | 153, 155 | — |
| 3 | 1 | 6.91 | 309, 311 | — |
| 4 | 1 | 3.19 | 181, 183 | 179, 181 |
| 5 | 1 | 4.79 | 311, 313 | — |
| 6 | 2 | 2.66 | 327, 329 | 325, 327 |
| 7 | 2 | 2.40 | 326, 328 | — |
| 8 | 2 | 2.57 | 389 | — |
| 9 | 2 | 2.56 | 399 | — |
| 10 | 2 | 2.60 | 401 | — |
| 11 | 2 | 2.78 | 415 | — |
| 12 | 2 | 0.29 | 130 | — |
| 13 | 1 | 3.36 | 201 | — |
| 14 | 1 | 1.95 | 187 | — |
| 15 | 2 | 2.22 | 292 | — |
| 16 | 2 | 1.89 | 278 | — |
| 17 | 2 | 1.89 | 264 | — |
| 18 | 2 | 0.33 | 130 | — |
| 19 | 2 | 1.99 | 419 | — |
| 22 | 1 | 3.77 | 429 | — |
| 23 | 1 | 3.90 | 427 | — |
| 24 | 2 | 2.42 | 572 | — |
| 25 | 2 | 2.21 | 512 | — |
| 27 | 1 | 5.65 | 559 | — |
| 28 | 1 | 3.67 | 445 | — |
| 29 | 1 | 3.98 | 443 | — |
| 30 | 1 | 3.62 | 526 | — |
| 31 | 1 | 4.30 | 465 | — |
| 32 | 1 | 4.30 | 447 | — |
| 33 | 2 | 2.27 | 427 (−MeOH) | — |
| 34 | 2 | 2.91 | 538 | — |
| 35 | 2 | 2.87 | 507 | — |
| 36 | 2 | 1.89 | 444 | — |
| 37 | 2 | 2.87 | 440 | — |
| 38 | 1 | 0.94 | 299 | — |
| 39 | 1 | 0.92 | 297 | — |
| 40 | 2 | 2.05 | 508 | — |

TABLE 11

| Rf | condition | R. time (min) | ESI+ | ESI− |
|---|---|---|---|---|
| 41 | 2 | 2.47 | 497 | — |
| 42 | 2 | 2.06 | 483 | — |
| 43 | 2 | 1.90 | 458 | — |
| 44 | 2 | 2.35 | 536 | — |
| 45 | 1 | 4.75 | 612 | — |
| 46 | 2 | 3.17 | 670 | — |
| 47 | 2 | 3.30 | 672 | — |
| 48 | 1 | 5.27 | 694 | — |
| 49 | 1 | 5.07 | 656 | — |
| 50 | 4 | 5.03 | 627 | — |
| 51 | 2 | 2.53 | 513 | — |
| 52 | 2 | 3.16 | 575 | — |
| 53 | 2 | 2.20 | 512 | — |
| 54 | 2 | 2.55 | 590 | — |
| 55 | 2 | 2.68 | 616 | — |
| 56 | 1 | 3.04 | 484 | — |
| 57 | 1 | 5.14 | 666 | — |
| 58 | 1 | 5.12 | 696 | — |
| 59 | 2 | 3.12 | 679 | — |
| 60 | 1 | 5.00 | 652 | 696 (+HCO$_2$H) |
| 61 | 1 | 4.99 | 640 | 684 (+HCO$_2$H) |
| 62 | 2 | 2.67 | 616 | — |
| 63 | 1 | 4.78 | 670 | 668 |
| 64 | 2 | 3.02 | 697 | — |
| 65 | 1 | 5.82 | 584 | — |
| 66 | 2 | 2.25 | 522 | — |
| 67 | 2 | 2.68 | 604 | — |
| 68 | 2 | 2.48 | 562 | — |
| 69 | 2 | 2.43 | 550 | — |
| 70 | 2 | 3.19 | 651 | — |
| 71 | 1 | 4.12 | 473 | — |
| 73 | 1 | 4.39 | 515 | — |
| 74 | 1 | 4.15 | 469 | — |
| 75 | 1 | 4.30 | 503 | — |
| 76 | 1 | 4.07 | 457 | — |
| 78 | 1 | 4.50 | 511 | — |
| 79 | 1 | 3.04 | 552 | — |
| 80 | 1 | 3.17 | 592 | — |

TABLE 12

| Rf | condition | R. time (min) | ESI+ | ESI− |
|---|---|---|---|---|
| 81 | 1 | 3.04 | 566 | — |
| 82 | 2 | 3.82 | 585 | — |
| 83 | 2 | 2.23 | 471 | — |
| 84 | 2 | 2.99 | 533 | — |
| 85 | 2 | 1.95 | 470 | — |
| 86 | 1 | 3.40 | 509 | — |
| 87 | 1 | 3.37 | 497 | — |
| 88 | 1 | 3.79 | 551 | — |
| 89 | 1 | 4.18 | 489 | — |
| 90 | 1 | 3.98 | 443 | — |
| 91 | 2 | 2.03 | 431 | — |
| 92 | 2 | 2.71 | 493 | — |
| 93 | 2 | 2.63 | 456 | — |
| 94 | 2 | 2.86 | 484 | — |
| 95 | 2 | 1.94 | 458 | — |
| 96 | 1 | 3.00 | 502 | — |
| 97 | 1 | 4.10 | 498 | — |
| 98 | 2 | 2.89 | 594 | — |
| 99 | 2 | 3.10 | 634 | — |
| 100 | 2 | 3.07 | 622 | — |
| 101 | 2 | 3.10 | 638 | — |
| 102 | 2 | 2.87 | 652 | 650 |
| 103 | 1 | 4.92 | 577 | — |
| 104 | 2 | 2.52 | 509 | — |
| 105 | 2 | 3.09 | 633 | — |
| 106 | 1 | 4.72 | 552 | 596 (+HCO$_2$H) |
| 107 | 1 | 4.22 | 523 | — |
| 108 | 1 | 4.18 | 511 | — |
| 109 | 2 | 2.72 | 514 | — |
| 110 | 1 | 4.24 | 468 | — |
| 111 | 2 | 2.17 | 509 | — |
| 112 | 1 | 4.42 | 473 | — |
| 113 | 1 | 2.99 | 500 | — |

TABLE 13

| Rf | condition | R. time (min) | ESI+ | ESI− |
|---|---|---|---|---|
| 114 | 1 | 4.50 | 418 | — |
| 115 | 1 | 4.09 | 266 | — |
| 116 | 1 | 0.32 | 132 | — |

TABLE 13-continued

| Rf | condition | R. time (min) | ESI+ | ESI− |
|---|---|---|---|---|
| 117 | 2 | 2.54 | 421 | — |
| 118 | 2 | 2.48 | 431 | — |
| 119 | 2 | 2.50 | 433 | — |
| 120 | 2 | 2.63 | 447 | — |

Synthetic Example 1

1-Cyclohexyl-2,3-dihydro-1H-pyrrolo[3',2':5,6]pyrido[4,3-d]pyrimidin-4(7H)-one

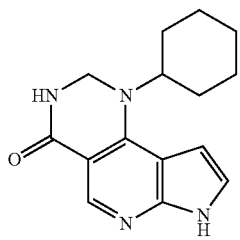 [SMILES: O=C1NCN(C2CCCCC2)c2c1cnc1[nH]ccc21]

To a solution of 1-cyclohexyl-7-{[2-(trimethylsilyl)ethoxy]methyl}-2,3-dihydro-1H-pyrrolo[3',2':5,6]pyrido[4,3-d]pyrimidin-4(7H)-one (30 mg, 0.075 mmol) obtained in Reference Synthetic Example 10 in dichloromethane (0.5 mL), trifluoroacetic acid (0.5 mL) was added, and the mixture was stirred at room temperature for 3 hours, and the reaction mixture was concentrated under reduced pressure. To a solution of the resulting residue in a mixed solvent of water (0.2 mL) and methanol (0.8 mL), 1M aqueous sodium hydroxide (0.04 mL) and ethylenediamine (0.04 mL) were added, and the mixture was stirred at room temperature for 1 day. The resulting reaction mixture was mixed with water and chloroform, the organic layer was separated, and the aqueous layer was extracted with chloroform twice. The organic layers were combined, washed with saturated aqueous sodium chloride and concentrated under reduced pressure. The resulting residue was mixed with ethyl acetate, and the precipitated solid was collected by filtration and dried under reduced pressure to obtain the title compound as a white solid (15.2 mg, yield: 75%).

$^1$H-NMR (DMSO-$d_6$) δ: 1.08-1.26 (m, 1H), 1.32-1.50 (m, 2H), 1.54-1.71 (m, 3H), 1.75-1.92 (m, 4H), 4.13 (t, J=11.7 Hz, 1H), 4.51 (d, J=3.0 Hz, 2H), 6.47 (d, J=2.3 Hz, 1H), 7.29 (t, J=2.8 Hz, 1H), 7.81 (s, 1H), 8.44 (s, 1H), 11.71 (s, 1H).

LC/MS: measurement condition 2, retention time=1.44 min.

LC/MS (ESI$^+$) m/z; 271 [M+H]$^+$

Synthetic Example 2

1-(trans-4-{[(2-Bromo-2,2-difluoroethyl)amino]methyl}cyclohexyl)-2,3-dihydro-1H-pyrrolo[3',2':5,6]pyrido[4,3-d]pyrimidin-4(7H)-one

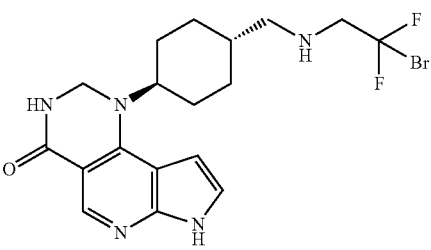 [SMILES: O=C1NCN([C@H]2CC[C@H](CNCC(F)(F)Br)CC2)c2c1cnc1[nH]ccc21]

To a solution of 1-(trans-4-{[(2-bromo-2,2-difluoroethyl)amino]methyl}cyclohexyl)-7-{[2-(trimethylsilyl)ethoxy]methyl}-2,3-dihydro-1H-pyrrolo[3',2':5,6]pyrido[4,3-d]pyrimidin-4(7H)-one (14 mg, 0.024 mmol) obtained in Reference Synthetic Example 24 in dichloromethane (1 mL), trifluoroacetic acid (0.5 mL) was added, and the mixture was stirred at room temperature for 2 hours, and the reaction mixture was concentrated under reduced pressure. To a solution of the resulting residue in a mixed solvent of water (0.2 mL) and methanol (0.8 mL), 1M aqueous sodium hydroxide (0.04 mL) and ethylenediamine (0.04 mL) were added, and the mixture was stirred at room temperature for 1 day. The reaction mixture was mixed with water and extracted with chloroform. The organic layer was dried over anhydrous sodium sulfate and concentrated under reduced pressure. The residue was purified by silica gel thin-layer column chromatography (NH-PLC, manufactured by FUJI SILYSIA CHEMICAL LTD., chloroform/methanol=15/1 (v/v)), washed with diethyl ether and dried under reduced pressure to obtain the title compound as a white solid (8.7 mg, yield: 92%).

$^1$H-NMR (DMSO-$d_6$) δ: 1.02-1.18 (m, 3H), 1.33-1.50 (m, 1H), 1.58-1.75 (m, 2H), 1.82-1.96 (m, 4H), 2.42-2.60 (m, 2H), 3.25-3.45 (m, 2H), 4.04-4.19 (m, 1H), 4.51 (d, J=2.5 Hz, 2H), 6.46 (s, 1H), 7.28 (s, 1H), 7.80 (s, 1H), 8.44 (s, 1H), 11.70 (s, 1H).

LC/MS: measurement condition 2, retention time=1.20 min.

LC/MS (ESI$^+$) m/z; 442 [M+H]$^+$

Synthetic Examples 3 to 11

Compounds in Synthetic Examples 3 to 11 were synthesized substantially in the same manner as in Synthetic Example 1 except that the compound obtained in Reference Synthetic Example 11, 25, 37, 54, 55, 65, 86, 87 or 88 was used instead of 1-cyclohexy-7-{[2-(trimethylsilyl)ethoxy]methyl}-2,3-dihydro-1H-pyrrolo[3',2':5,6]pyrido[4,3-d]pyrimidin-4(7H)-one. Of the synthesized compounds, the chemical structural formulae are shown below, the compound names, the morphologies and the yields are shown in Table 14, and the physical data are shown in Table 15.

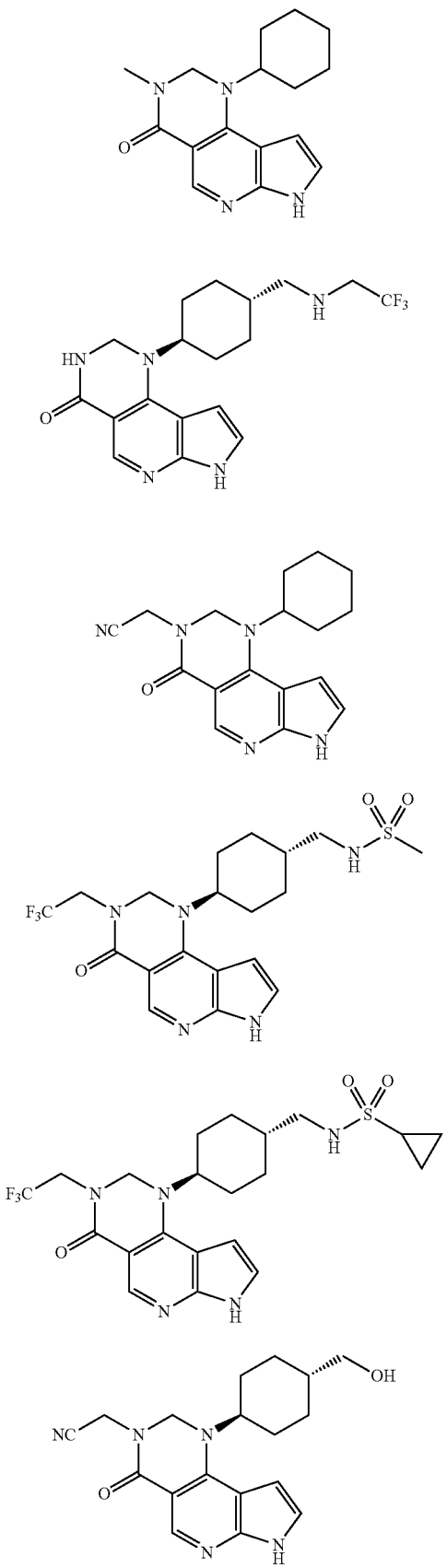
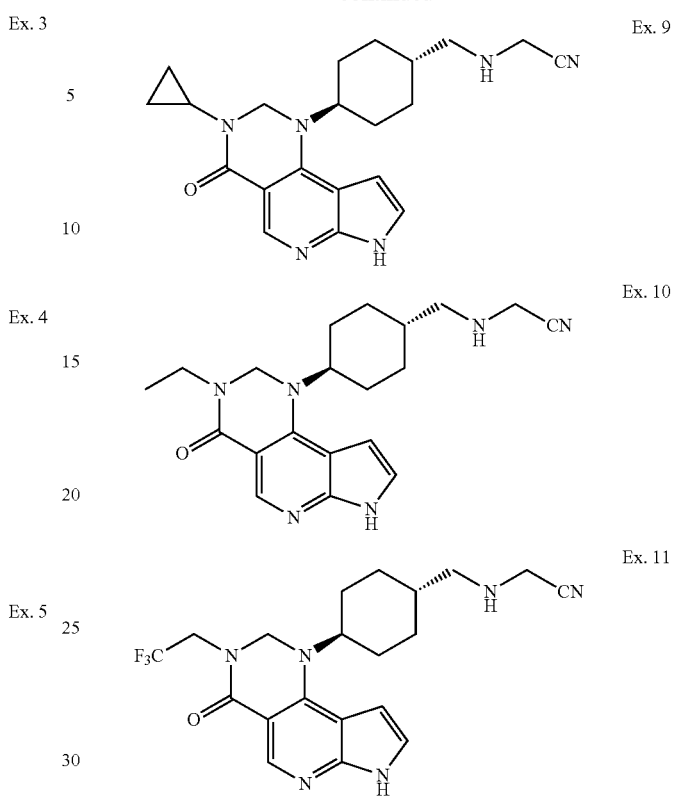

TABLE 14

| Ex | Compound Name | Morphology | Yield |
|----|---------------|------------|-------|
| 3 | 1-cyclohexyl-3-methyl-2,3-dihydro-1H-pyrrolo[3',2': 5,6]pyrido[4,3-d]pyrimidin-4(7H)-one | white solid | 50% |
| 4 | 1-(trans-4-{[(2,2,2-trifluoroethyl)amino]methyl}cyclohexyl)-2,3-dihydro-1H-pyrrolo[3',2': 5,6]pyrido[4,3-d]pyrimidin-4(7H)-one | white solid | 31% |
| 5 | 2-(1-cyclohexyl-4-oxo-1H-pyrrolo[3',2': 5,6]pyrido[4,3-d]pyrimidin-3(2H,4H,7H)-yl)acetonitrile | white solid | 44% |
| 6 | N-({trans-4-[4-oxo-3-(2,2,2-trifluoroethyl)-2,3,4,7-tetrahydro-1H-pyrrolo[3',2': 5,6]pyrido[4,3-d]pyrimidin-1-yl]cyclohexyl}methyl)methanesulfonamide | white solid | 70% |
| 7 | N-({trans-4-[4-oxo-3-(2,2,2-trifluoroethyl)-2,3,4,7-tetrahydro-1H-pyrrolo[3',2': 5,6]pyrido[4,3-d]pyrimidin-1-yl]cyclohexyl}methyl)cyclopropanesulfonamide | pale yellow solid | 67% |
| 8 | 2-{1-[trans-4-(hydroxymethyl)cyclohexyl]-4-oxo-1H-pyrrolo[3',2': 5,6]pyrido[4,3-d]pyrimidin-3(2H,4H,7H)-yl}acetonitrile | white solid | 70% |
| 9 | 2-({[trans-4-(3-cyclopropyl-4-oxo-2,3,4,7-tetrahydro-1H-pyrrolo[3',2': 5,6]pyrido[4,3-d]pyrimidin-1-yl)cyclohexyl]methyl}amino)acetonitrile | white solid | 44% |
| 10 | 2-({[trans-4-(3-ethyl-4-oxo-2,3,4,7-tetrahydro-1H-pyrrolo[3',2': 5,6]pyrido[4,3-d]pyrimidin-1-yl)cyclohexyl]methyl}amino)acetonitrile | white solid | 69% |
| 11 | 2-[({trans-4-[4-oxo-3-(2,2,2-trifluoroethyl)-2,3,4,7-tetrahydro-1H-pyrrolo[3',2': 5,6]pyrido[4,3-d]pyrimidin-1-yl]cyclohexyl}methyl)amino]acetonitrile | white solid | 49% |

TABLE 15

| Ex | Data |
|---|---|
| 3 | $^1$H-NMR (DMSO-$d_6$) δ: 1.13-1.27 (m, 1H), 1.32-1.50 (m, 2H), 1.59-1.75 (m, 3H), 1.77-1.90 (m, 4H), 2.94 (s, 3H), 4.02-4.16 (m, 1H), 4.64 (s, 2H), 6.46 (d, J = 2.1 Hz, 1H), 7.30 (t, J = 2.8 Hz, 1H), 8.46 (s, 1H), 11.73 (s, 1H). LC/MS: condition 2, retention time = 1.60 min LC/MS(ESI$^+$) m/z; 285 [M + H]$^+$ |
| 4 | $^1$H-NMR (DMSO-$d_6$) δ: 1.00-1.19 (m, 2H), 1.33-1.47 (m, 1H), 1.58-1.75 (m, 2H), 1.82-1.94 (m, 4H), 2.28 (br s, 1H), 3.20 (q, J = 10.2 Hz, 2H), 3.31 (s, 2H), 4.05-4.21 (m, 1H), 4.51 (d, J = 2.5 Hz, 2H), 6.46 (d, J = 3.7 Hz, 1H), 7.28 (t, J = 2.7 Hz, 1H), 7.81 (s, 1H), 8.44 (s, 1H), 11.71 (s, 1H). LC/MS: condition 3, retention time = 1.32 min LC/MS(ESI$^+$) m/z; 382 [M + H]$^+$ |
| 5 | $^1$H-NMR(DMSO-$d_6$) δ: 1.11-1.27 (m, 1H), 1.31-1.53 (m, 2H), 1.58-1.96 (m, 7H), 4.05-4.20 (m, 1H), 4.55 (s, 2H), 4.81 (s, 2H), 6.59 (d, J = 3.6 Hz, 1H), 7.34 (d, J = 3.6 Hz, 1H), 8.51 (s, 1H), 11.85 (br s, 1H). LC/MS: condition 2, retention time = 1.64 min LC/MS(ESI$^+$) m/z; 310 [M + H]$^+$ |
| 6 | $^1$H-NMR (DMSO-$d_6$) δ: 1.09-1.27 (m, 2H), 1.41-1.55 (m, 1H), 1.60-1.78 (m, 2H), 1.83-1.93 (m, 4H), 2.78-2.87 (m, 2H), 2.89 (s, 3H), 4.04-4.26 (m, 1H), 4.28 (q, J = 9.7 Hz, 2H), 4.78 (s, 2H), 6.51 (d, J = 3.3 Hz, 1H), 7.03 (t, J = 5.9 Hz, 1H), 7.34 (d, J = 3.3 Hz, 1H), 8.50 (s, 1H), 11.84 (s, 1H). LC/MS: condition 2, retention time = 1.56 min LC/MS(ESI$^+$) m/z; 460 [M + H]$^+$ |
| 7 | $^1$H-NMR (DMSO-$d_6$) δ: 0.87-0.97 (m, 4H), 1.09-1.26 (m, 2H), 1.41-1.55 (m, 1H), 1.58-1.79 (m, 2H), 1.79-1.97 (m, 4H), 2.52-2.59 (m, 1H), 2.83-2.91 (m, 2H), 4.07-4.23 (m, 1H), 4.28 (q, J = 9.7 Hz, 2H), 4.78 (s, 2H), 6.51 (d, J = 3.3 Hz, 1H), 7.04-7.12 (m, 1H), 7.34 (d, J = 3.3 Hz, 1H), 8.50 (s, 1H), 11.84 (s, 1H). LC/MS: condition 2, retention time = 1.72 min LC/MS(ESI$^+$) m/z; 486 [M + H]$^+$ |
| 8 | LC/MS: condition 1, retention time = 0.57 min LC/MS(ESI$^+$) m/z; 340 [M + H]$^+$ LC/MS(ESI$^-$) m/z; 338 [M − H]$^-$ |
| 9 | $^1$H-NMR (DMSO-$d_6$) δ: 0.61-0.68 (m, 2H), 0.76-0.84 (m, 2H), 1.07-1.23 (m, 2H), 1.40-1.55 (m, 1H), 1.63-1.78 (m, 2H), 1.82-1.93 (m, 4H), 2.42-2.47 (m, 2H), 2.63-2.71 (m, 1H), 3.57-3.62 (m, 2H), 4.06-4.19 (m, 1H), 4.57 (s, 2H), 6.46 (d, J = 3.0 Hz, 1H), 7.28 (d, J = 3.0 Hz, 1H), 8.47 (s, 1H), 11.72 (br s, 1H). LC/MS: condition 1, retention time = 0.34 min LC/MS(ESI$^+$) m/z; 379 [M + H]$^+$ |
| 10 | $^1$H-NMR (DMSO-$d_6$) δ: 1.10-1.17 (m, 2H), 1.13 (t, J = 7.3 Hz, 3H), 1.40-1.52 (m, 1H), 1.67-1.82 (m, 2H), 1.83-1.94 (m, 4H), 2.42-2.47 (m, 2H), 3.46 (q, J = 7.3 Hz, 2H), 3.57-3.62 (m, 2H), 4.06-4.18 (m, 1H), 4.65 (s, 2H), 6.45-6.48 (m, 1H), 7.27-7.30 (m, 1H), 8.46 (s, 1H), 11.70 (br s, 1H). LC/MS: condition 1, retention time = 0.32 min LC/MS(ESI$^+$) m/z; 367 [M + H]$^+$ |
| 11 | LC/MS: condition 1, retention time = 0.40 min LC/MS(ESI$^+$) m/z; 421 [M + H]$^+$ |

Synthetic Examples 12 to 35

Compounds in Synthetic Examples 12 to 35 were synthesized substantially in the same manner as in Synthetic Example 2 except that the compound obtained in Reference Synthetic Example 30, 31, 32, 34, 40, 41, 42, 44, 46, 47, 48, 49, 56, 57, 58, 59, 60, 61, 64, 67, 68, 69, 80 or 81 was used instead of 1-(trans-4-{[(2-bromo-2,2-difluoroethyl)amino]methyl}cyclohexyl)-7-{[2-(trimethylsilyl)ethoxy]methyl}-2,3-dihydro-1H-pyrrolo[3',2':5,6]pyrido[4,3-d]pyrimidin-4(7H)-one. Of the synthesized compounds, the chemical structural formulae are shown below, the compound names, the morphologies and the yields are shown in Tables 16 and 17, and the physical data are shown in Tables 18 to 21.

Ex. 12

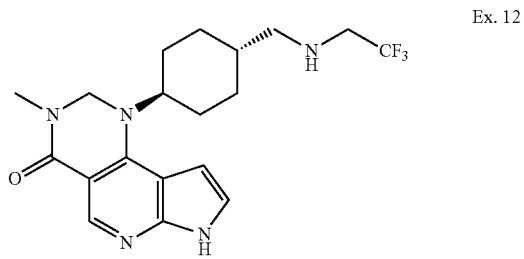

| | |
|---|---|
| Ex. 13 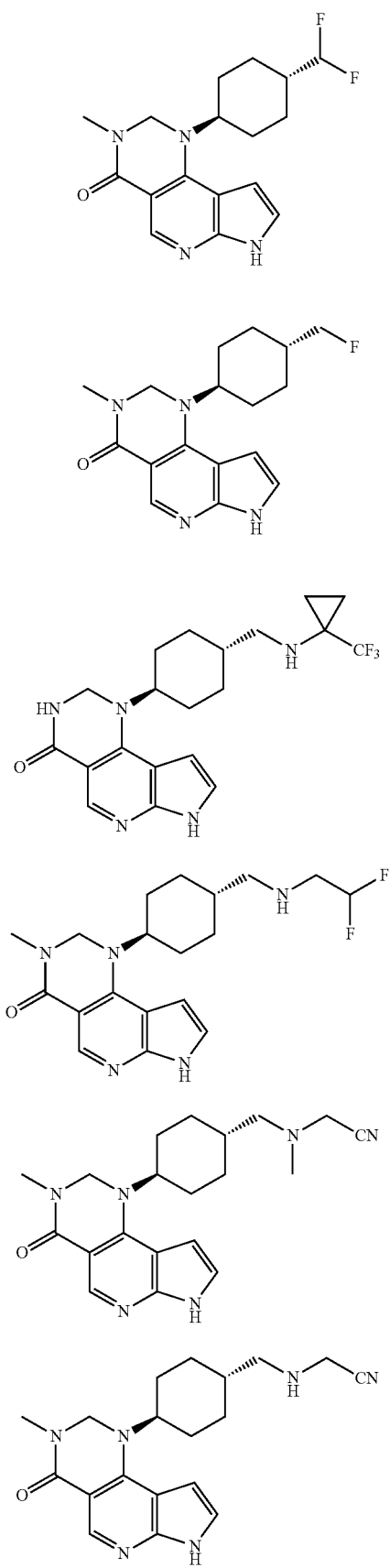 | Ex. 19 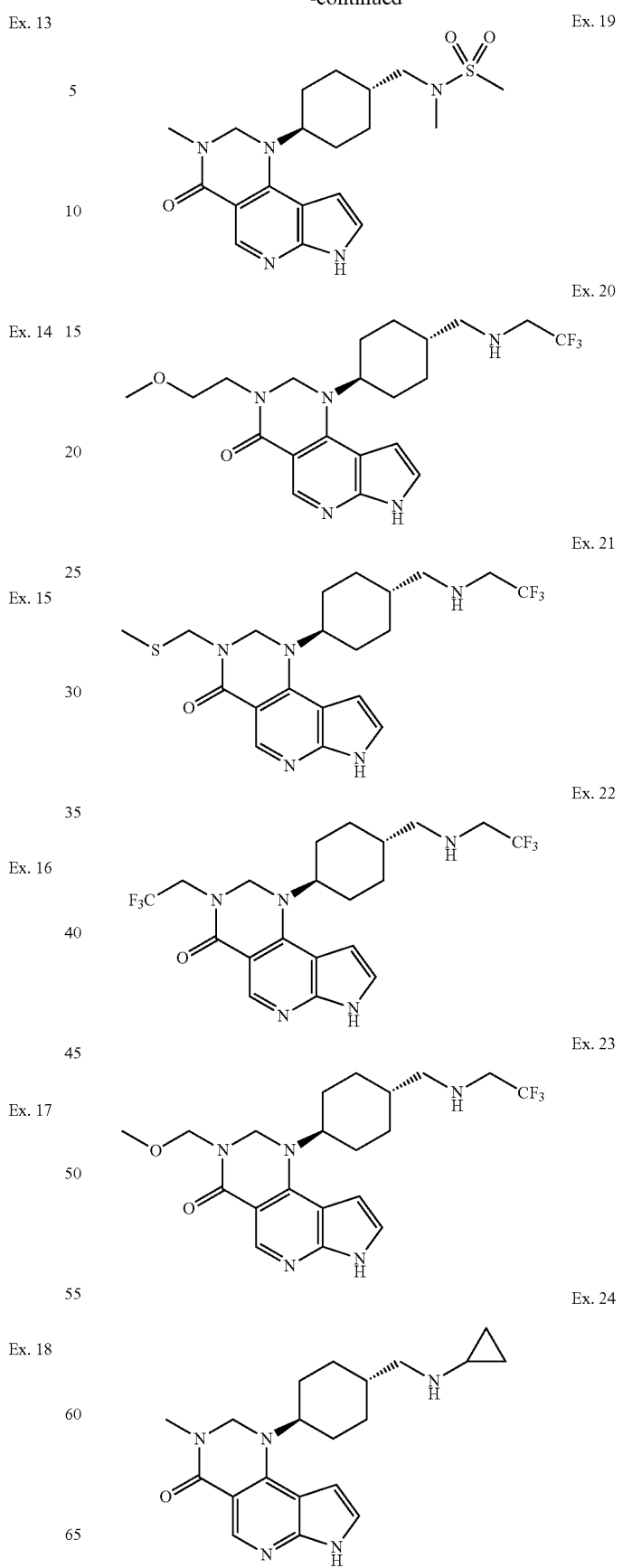 |
| Ex. 14 | Ex. 20 |
| Ex. 15 | Ex. 21 |
| Ex. 16 | Ex. 22 |
| Ex. 17 | Ex. 23 |
| Ex. 18 | Ex. 24 |

Ex. 25 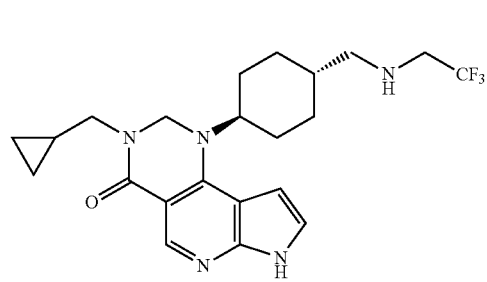
Ex. 26 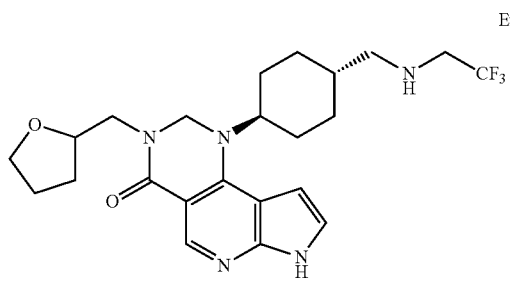
Ex. 27 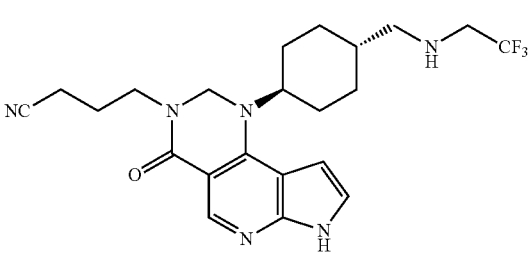
Ex. 28 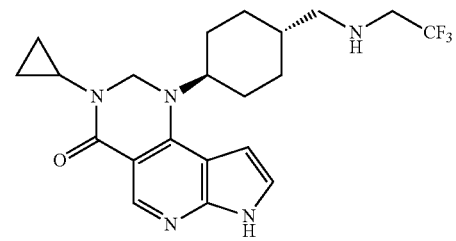
Ex. 29 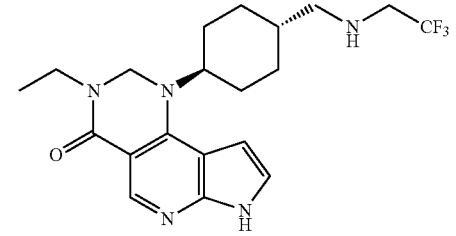
Ex. 30 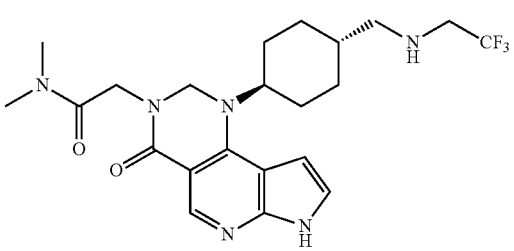
Ex. 31 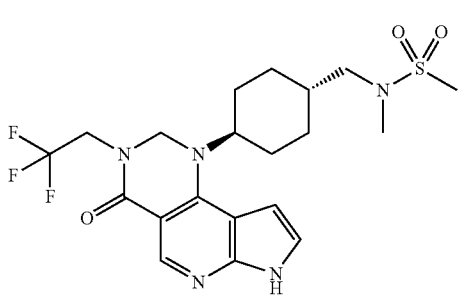
Ex. 32 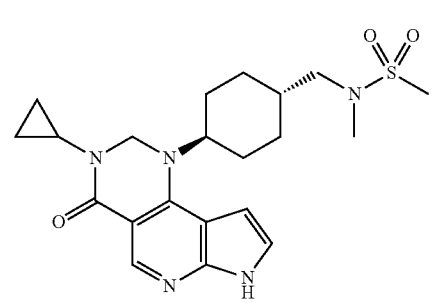
Ex. 33 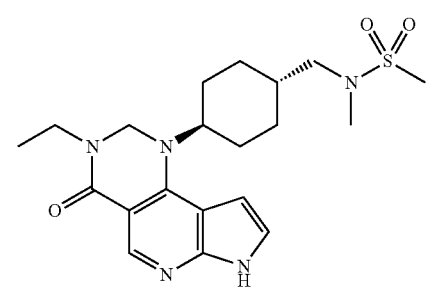
Ex. 34 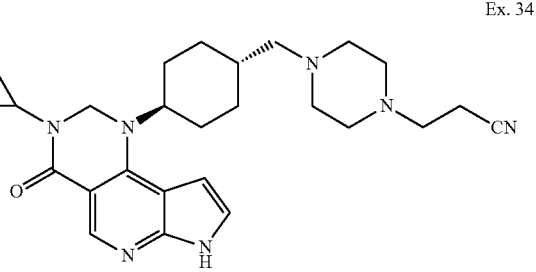
Ex. 35 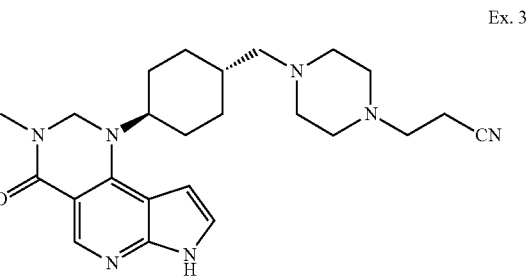
TABLE 16
| Ex | Compound Name | Morphology | Yield |
|---|---|---|---|
| 12 | 3-methyl-1-(trans-4-{[(2,2,2-trifluoroethyl}amino]methyl}cyclohexyl)- | white solid | 76% |

TABLE 16-continued

| Ex | Compound Name | Morphology | Yield |
|---|---|---|---|
| | 2,3-dihydro-1H-pyrrolo[3',2': 5,6]pyrido[4,3-d]pyrimidin-4(7H)-one | | |
| 13 | 1-[trans-4-(difluoromethyl)cyclohexyl]-3-methyl-2,3-dihydro-1H-pyrrolo[3',2': 5,6]pyrido[4,3-d]pyrimidin-4(7H)-one | white solid | 48% (2 steps) |
| 14 | 1-[trans-4-(fluoromethyl)cyclohexyl]-3-methyl-2,3-dihydro-1H-pyrrolo[3',2': 5,6]pyrido[4,3-d]pyrimidin-4(7H)-one | white solid | 5.5% (2 steps) |
| 15 | 1-(trans-4-({[1-(trifluoromethyl)cyclopropyl]amino}methyl)cyclohexyl]-2,3-dihydro-1H-pyrrolo[3',2': 5,6]pyrido[4,3-d]pyrimidin-4(7H)-one | white solid | 58% (2 steps) |
| 16 | 1-(trans-4-{[(2,2-difluoroethyl)amino]methyl}cyclohexyl)-3-methyl-2,3-dihydro-1H-pyrrolo[3',2': 5,6]pyrido[4,3-d]pyrimidin-4(7H)-one | white solid | 50% |
| 17 | 2-(methyl{[trans-4-(3-methyl-4-oxo-2,3,4,7-tetrahydro-1H-pyrrolo[3',2': 5,6]pyrido[4,3-d]pyrimidin-1-yl)cyclohexyl]methyl}amino)acetonitrile | white solid | 41% |
| 18 | 2-({[trans-4-(3-methyl-4-oxo-2,3,4,7-tetrahydro-1H-pyrrolo[3',2': 5,6]pyrido[4,3-d]pyrimidin-1-yl)cyclohexyl]methyl}amino)acetonitrile | white solid | 78% |
| 19 | N-methyl-N-{[trans-4-(3-methyl-4-oxo-2,3,4,7-tetrahydro-1H-pyrrolo[3',2': 5,6]pyrido[4,3-d]pyrimidin-1-yl)cyclohexyl]methyl}methanesulfonamide | white solid | 99% |
| 20 | 3-(2-methoxyethyl)-1-(trans-4-{[(2,2,2-trifluoroethyl)amino]methyl}cyclohexyl)-2,3-dihydro-1H-pyrrolo[3',2': 5,6]pyrido[4,3-d]pyrimidin-4(7H)-one | white solid | 90% |
| 21 | 3-[(methylthio)methyl]-1-(trans-4-{[(2,2,2-trifluoroethyl)amino]methyl}cyclohexyl)-2,3-dihydro-1H-pyrrolo[3',2': 5,6]pyrido[4,3-d]pyrimidin-4(7H)-one | white solid | 57% |
| 22 | 3-(2,2,2-trifluoroethyl)-1-(trans-4-{[(2,2,2-trifluoroethyl)amino]methyl}cyclohexyl)-2,3-dihydro-1H-pyrrolo[3',2': 5,6]pyrido[4,3-d]pyrimidin-4(7H)-one | white solid | 11% |
| 23 | 3-(methoxymethyl)-1-(trans-4-{[(2,2,2-trifluoroethyl)amino]methyl}cyclohexyl)-2,3-dihydro-1H-pyrrolo[3',2': 5,6]pyrido[4,3-d]pyrimidin-4(7H)-one | white solid | 15% |
| 24 | 1-{trans-4-[(cyclopropylamino)methyl]cyclohexyl}-3-methyl-2,3-dihydro-1H-pyrrolo[3',2': 5,6]pyrido[4,3-d]pyrimidin-4(7H)-one | white solid | 86% |

TABLE 17

| Ex | Compound Name | Morphology | Yield |
|---|---|---|---|
| 25 | 3-(cyclopropylmethyl)-1-(trans-4-{[(2,2,2-trifluoroethyl)amino]methyl}cyclohexyl)-2,3-dihydro-1H-pyrrolo[3',2': 5,6]pyrido[4,3-d]pyrimidin-4(7H)-one | white solid | 58% |
| 26 | 3-[(tetrahydrofuran-2-yl)methyl]-1-(trans-4-{[(2,2,2-trifluoroethyl)amino]methyl}cyclohexyl)-2,3-dihydro-1H-pyrrolo[3',2': 5,6]pyrido[4,3-d]pyrimidin-4(7H)-one | white solid | 89% |
| 27 | 4-[4-oxo-1-(trans-4-{[(2,2,2-trifluoroethyl)amino]methyl}cyclohexyl)-1H-pyrrolo[3',2': 5,6]pyrido[4,3-d]pyrimidin-3(2H,4H,7H)-yl)butanenitrile | white solid | 65% |
| 28 | 3-cyclopropyl-1-(trans-4-{[(2,2,2-trifluoroethyl)amino]methyl}cyclohexyl)-2,3-dihydro-1H-pyrrolo[3',2': 5,6]pyrido[4,3-d]pyrimidin-4(7H)-one | white solid | 79% |
| 29 | 3-ethyl-1-(trans-4-{[(2,2,2-trifluoroethyl)amino]methyl}cyclohexyl)-2,3-dihydro-1H-pyrrolo[3',2': 5,6]pyrido[4,3-d]pyrimidin-4(7H)-one | white solid | 77% |
| 30 | N,N-dimethyl-2-[4-oxo-1-(trans-4-{[(2,2,2-trifluoroethyl)amino]methyl}cyclohexyl)-1H-pyrrolo[3',2': 5,6]pyrido[4,3-d]pyrimidin-3(2H,4H,7H)-yl)acetamide | white solid | 72% |
| 31 | N-methyl-N-({trans-4-[4-oxo-3-(2,2,2-trifluoroethyl)-2,3,4,7-tetrahydro-1H-pyrrolo[3',2': 5,6]pyrido[4,3-d]pyrimidin-1-yl]cyclohexyl}methyl)methanesulfonamide | white solid | 74% |
| 32 | N-{[trans-4-(3-cyclopropyl-4-oxo-2,3,4,7-tetrahydro-1H-pyrrolo[3',2': 5,6]pyrido[4,3-d]pyrimidin-1-yl)cyclohexyl]methyl}-N-methylmethanesulfonamide | white solid | 44% |
| 33 | N-{[trans-4-(3-ethyl-4-oxo-2,3,4,7-tetrahydro-1H-pyrrolo[3',2': 5,6]pyrido[4,3-d]pyrimidin-1-yl)cyclohexyl]methyl}-N-methylmethanesulfonamide | white solid | 57% |
| 34 | 3-(4-{[trans-4-(3-cyclopropyl-4-oxo-2,3,4,7-tetrahydro-1H-pyrrolo[3',2': 5,6]pyrido[4,3-d]pyrimidin-1-yl)cyclohexyl]methyl}piperazin-1-yl)propanenitrile | white solid | 83% |
| 35 | 3-(4-{[trans-4-(3-methyl-4-oxo-2,3,4,7-tetrahydro-1H-pyrrolo[3',2': 5,6]pyrido[4,3-d]pyrimidin-1-yl)cyclohexyl]methyl}piperazin-1-yl)propanenitrile | white solid | 77% |

TABLE 18

| Ex | Data |
|---|---|
| 12 | $^1$H-NMR (CDCl$_3$) δ: 1.08-1.35 (m, 2H), 1.52-1.72 (m, 3H), 1.97-2.16 (m, 4H), 2.63 (d, J = 6.6 Hz, 2H), 3.08 (s, 3H), 3.14-3.24 (m, 2H), 4.12-4.20 (m, 1H), 4.58 (s, 2H), 6.47 (d, J = 3.3 Hz, 1H), 7.18 (d, J = 3.3 Hz, 1H), 8.83 (s, 1H), 9.83 (br s, 1H). LC/MS: condition 2, retention time = 1.08 min LC/MS(ESI$^+$) m/z; 396 [M + H]$^+$ |
| 13 | $^1$H-NMR (CDCl$_3$) δ: 1.32-1.48 (m, 2H), 1.56-1.70 (m, 2H), 1.76-1.88 (m, 1H), 2.00-2.23 (m, 4H), 3.09 (s, 3H), 4.16 (tt, J = 12, 3.6, 1H), 4.58 (s, 2H), 5.43-5.82 (m, 1H), 6.45-6.46 (m, 1H), 7.22-7.23 (m, 1H), 8.86 (s, 1H), 10.15 (br s, 1H). LC/MS: condition 1, retention time = 2.60 min LC/MS(ESI$^+$) m/z; 335 [M + H]$^+$ |
| 14 | $^1$H-NMR (CDCl$_3$) δ: 1.20-1.36 (m, 2H), 1.59-1.81 (m, 3H), 1.94-2.19 (m, 4H), 3.09 (s, 3H), 4.17 (tt, J = 12, 3.6, 1H), 4.21-4.39 (m, 2H), 4.59 (s, 2H), 6.46-6.47 (m, 1H), 7.19-7.20 (m, 1H), 8.84 (s, 1H), 9.93 (br s, 1H). LC/MS: condition 1, retention time = 2.37 min LC/MS(ESI$^+$) m/z; 317 [M + H]$^+$ |

TABLE 18-continued

| Ex | Data |
|---|---|
| 15 | $^1$H-NMR (DMSO-d$_6$) δ: 0.81-0.97 (m, 4H), 1.01-1.17 (m, 2H), 1.21-1.34 (m, 1H), 1.55-1.71 (m, 2H), 1.81-1.92 (m, 4H), 2.47-2.57 (m, 2H), 2.67 (t, J = 6.5 Hz, 1H), 4.05-4.17 (m, 1H), 4.48-4.52 (m, 2H), 6.45 (d, J = 3.7 Hz, 1H), 7.27 (d, J = 3.7 Hz, 1H), 7.80 (s, 1H), 8.43 (s, 1H), 11.70 (s, 1H).<br>LC/MS: condition 2, retention time = 3.39 min<br>LC/MS(ESI$^+$) m/z; 408 [M + H]$^+$ |
| 16 | LC/MS: condition 2, retention time = 0.59 min<br>LC/MS(ESI$^+$) m/z; 378 [M + H]$^+$ |
| 17 | $^1$H-NMR (CD$_3$OD) δ: 1.07-1.21 (m, 2H), 1.54-1.62 (m, 1H), 1.72-1.84 (m, 2H), 1.98-2.03 (m, 4H), 2.32 (d, J = 7.5 Hz, 2H), 2.34 (s, 3H), 3.07 (s, 3H), 3.65 (s, 2H), 4.25 (tt, J = 12.0 Hz, 3.3H, z 1H), 4.71 (s, 2H), 6.55 (d, J = 4.0 Hz, 1H), 7.25 (d, J = 4.0 Hz, 1H), 8.56 (s, 1H).<br>LC/MS: condition 2, retention time = 1.36 min<br>LC/MS(ESI$^+$) m/z; 367 [M + H]$^+$ |
| 18 | $^1$H-NMR (CD$_3$OD) δ: 1.15-1.28 (m, 2H), 1.53-1.60 (m, 1H), 1.72-1.84 (m, 2H), 1.98-2.08 (m, 4H), 2.58 (d, J = 6.6 Hz, 2H), 3.07 (s, 3H), 3.63 (s, 2H), 4.26 (tt, J = 12.0 Hz, 4.2 Hz, 1H), 4.71 (s, 2H), 6.55 (d, J = 4.0 Hz, 1H), 7.25 (d, J = 4.0 Hz, 1H), 8.56 (s, 1H).<br>LC/MS: condition 2, retention time = 0.67 min<br>LC/MS(ESI$^+$) m/z; 353 [M + H]$^+$ |
| 19 | $^1$H-NMR (CDCl$_3$) δ: 1.19-1.30 (m, 2H), 1.61-1.74 (m, 3H), 2.07-2.22 (m, 4H), 2.86 (s, 3H), 2.95 (s, 3H), 3.05 d, (J = 4.5 Hz, 2H), 3.15 (s, 3H), 4.27 (tt, J = 12.6 Hz, 3.7H, z 1H), 4.65 (s, 2H), 6.53 (d, J = 4.0 Hz, 1H), 7.31 (d, J = 4.0 Hz, 1H), 8.91 (s, 1H), 11.36 (br s, 1H).<br>LC/MS: condition 2, retention time = 1.37 min<br>LC/MS(ESI$^+$) m/z; 406 [M + H]$^+$ |

TABLE 19

| Ex | Data |
|---|---|
| 20 | $^1$H-NMR (CDCl$_3$) δ: 1.11-1.25 (m, 2H), 1.44-1.50 (m, 1H), 1.59-1.71 (m, 2H), 1.98-2.13 (m, 4H), 2.63 (d, J = 6.6 Hz, 2H), 3.19 (q, J = 9.4 Hz, 2H), 3.37 (s, 3H), 3,61-3.65 (m, 2H), 3.69-3.72 (m, 2H), 4.17-4.25 (m, 1H), 4.72 (s, 2H), 6.47 (d, J = 4.0 Hz, 1H), 7.23 (d, J = 4.0 Hz, 1H), 8.85 (s, 1H), 11.96 (br s, 1H).<br>LC/MS: condition 2, retention time = 1.16 min<br>LC/MS(ESI$^+$) m/z; 440 [M + H]$^+$ |
| 21 | $^1$H-NMR (CDCl$_3$) δ: 1.12-1.25 (m, 2H), 1.45-1.51 (m, 1H), 1.69-1.81 (m, 2H), 2.00-2.08 (m, 4H), 2.14 (s, 3H), 2.64 (d, J = 6.6 Hz, 2H), 3.20 (q, J = 9.4 Hz, 2H), 4.24-4.32 (m, 1H), 4.69 (s, 2H), 4.75 (s, 2H), 6.50 (d, J = 4.0 Hz, 1H), 7.23 (d, J = 4.0 Hz, 1H), 8.84 (s, 1H), 11.63 (br s, 1H).<br>LC/MS: condition 2, retention time = 1.34 min<br>LC/MS(ESI$^+$) m/z; 442 [M + H]$^+$ |
| 22 | $^1$H-NMR (CDCl$_3$) δ: 1.08-1.30 (m, 2H), 1.47-1.73 (m, 3H), 1.92-2.18 (m, 4H), 2.64 (d, J = 6.6 Hz, 2H), 3.19 (q, J = 9.6 Hz, 2H), 4.05-4.32 (m, 3H), 4.72 (s, 2H), 6.49 (d, J = 3.6 Hz, 1H), 7.26 (d, J = 3.9 Hz, 1H), 8.86 (s, 1H), 11.21 (br s, 1H).<br>LC/MS: condition 2, retention time = 1.53 min<br>LC/MS(ESI$^+$) m/z; 464 [M + H]$^+$ |
| 23 | $^1$H-NMR (CDCl$_3$) δ: 1.10-1.30 (m, 2H), 1.41-1.76 (m, 3H), 1.95-2.15 (m, 4H), 2.64 (d, J = 6.6 Hz, 2H), 3.19 (q, J = 9.6 Hz, 2H), 3.38 (s, 3H), 4.17-4.31 (m, 1H), 4.68 (s, 2H), 4.96 (s, 2H), 6.49 (d, J = 3.6 Hz, 1H), 7.19 (d, J = 3.6 Hz, 1H), 8.85 (s, 1H), 10.01 (br s, 1H).<br>LC/MS: condition 2, retention time = 1.16 min<br>LC/MS(ESI$^+$) m/z; 426 [M + H]$^+$ |
| 24 | $^1$H-NMR (DMSO-d$_6$) δ: 0.10-0.25 (m, 2H), 0.28-0.43 (m, 2H), 0.75-1.30 (m, 3H), 1.32-1.54 (m, 1H), 1.55-1.96 (m, 6H), 1.98-2.13 (m, 1H), 2.94 (s, 3H), 3.95-4.20 (m, 1H), 4.63 (s, 2H), 6.35-6.55 (m, 1H), 7.20-7.35 (m, 1H), 8.45 (s, 1H), 11.71 (s, 1H).<br>LC/MS: condition 1, retention time = 0.32 min<br>LC/MS(ESI$^+$) m/z; 354 [M + H]$^+$ |
| 25 | $^1$H-NMR (CDCl$_3$) δ: 0.31-0.35 (m, 2H), 0.59-0.61 (m, 2H), 1.03-1.25 (m, 3H), 1.40-1.55 (m, 1H), 1.59-1.70 (m, 2H), 1.99-2.03 (m, 2H), 2.10-2.14 (m, 2H), 2.63 (d, J = 6.0 Hz, 2H), 3.18-3.24 (m, 2H), 3.43 (d, J = 7.2 Hz, 2H), 4.19-4.27 (m, 1H), 4.70 (s, 2H), 6.47 (d, J = 3.3 Hz, 1H), 7.24 (d, J = 3.3 Hz, 1H), 8.86 (s, 1H).<br>LC/MS: condition 1, retention time = 1.03 min<br>LC/MS(ESI$^+$) m/z; 436 [M + H]$^+$ |
| 26 | 1H-NMR (CDCl3) δ: 1.11-1.25 (m, 2H), 1.45-1.50 (m, 1H), 1.61-1.70 (m, 3H), 1.88-2.09 (m, 7H), 2.63 (d, J = 6.3 Hz, 2H), 3.15-3.24 (m, 2H), 3.36-3.43 (m, 1H), 3.71-3.79 (m, 1H), 3.88-3.95 (m, 2H), |

TABLE 19-continued

| Ex | Data |
|---|---|
| | 4.08-4.11 (m, 1H), 4.18-4.26 (m, 1H), 4.69 (d, J = 11.1 Hz, 1H), 4.81 (d, J = 11.1 Hz, 1H), 6.47 (d, J = 3.6 Hz, 1H), 7.25 (d, J = 3.6 Hz, 1H), 8.83 (s, 1H) 11.83 (br s, 1H).<br>LC/MS: condition 1, retention time = 0.34 min<br>LC/MS(ESI$^+$) m/z; 466 [M + H]$^+$ |

TABLE 20

| Ex | Data |
|---|---|
| 27 | $^1$H-NMR (CDCl$_3$) δ: 1.17-1.25 (m, 2H), 1.58-1.66 (m, 4H), 2.02-2.13 (m, 5H), 2.48 (t, J = 7.2 Hz, 2H), 2.65 (d, J = 6.6 Hz, 2H), 3.20 (q, J = 9.5 Hz, 2H), 3.63 (t, J = 6.8 Hz, 2H), 4.20-4.28 (m, 1H), 4.63 (s, 2H), 6.48 (d, J = 3.7 Hz, 1H), 7.21 (d, J = 3.3 Hz, 1H), 8.81 (s, 1H), 10.5 (br s, 1H).<br>LC/MS: condition 2, retention time = 1.18 min<br>LC/MS(ESI$^+$) m/z; 449 [M + H]$^+$<br>LC/MS(ESI$^-$) m/z; 447 [M − H]$^-$ |
| 28 | $^1$H-NMR (CDCl$_3$) δ: 0.72-0.79 (m, 2H), 0.89-0.96 (m, 2H), 1.18 (qd, J = 12.7, 2.9 Hz, 2H), 1.42-1.54 (m, 1H), 1.63 (qd, J = 12.7, 2.9 Hz, 2H), 1.97-2.13 (m, 4H), 2.64 (d, J = 6.5 Hz, 2H), 2.66-2.74 (m, 1H), 3.20 (q, J = 9.4 Hz, 2H), 4.21 (tt, J = 11.9, 3.3 Hz, 1H), 4.61 (s, 2H), 6.46 (d, J = 3.7 Hz, 1H), 7.17 (d, J = 3.7 Hz, 1H), 8.84 (s, 1H), 9.96 (br s, 1H).<br>LC/MS: condition 1, retention time = 0.35 min<br>LC/MS(ESI+) m/z; 422 [M + H]+ |
| 29 | $^1$H-NMR (CDCl$_3$) δ: 1.18 (qd, J = 12.5, 2.8 Hz, 2H), 1.26 (t, J = 7.0 Hz, 3H), 1.40-1.55 (m, 1H), 1.63 (qd, J = 12.5, 2.8 Hz, 2H), 1.96-2.16 (m, 4H), 2.64 (d, J = 6.1 Hz, 2H), 3.19 (q, J = 9.4 Hz, 2H), 3.59 (q, J = 7.0 Hz, 2H), 4.22 (tt, J = 11.4, 2.9 Hz, 1H), 4.60 (s, 2H), 6.46 (d, J = 3.7 Hz, 1H), 7.21 (d, J = 3.7 Hz, 1H), 8.85 (s, 1H), 11.15 (br s, 1H).<br>LC/MS: condition 1, retention time = 0.36 min<br>LC/MS(ESI+) m/z; 410 [M + H]+ |
| 30 | $^1$H-NMR (CDCl$_3$) δ: 1.06-1.30 (m, 2H), 1.52-1.73 (m, 3H), 1.94-2.15 (m, 4H), 2.63 (d, J = 3.6 Hz, 2H), 2.98 (s, 3H), 3.11 (s, 3H), 3.20 (q, J = 9.6 Hz, 2H), 4.11-4.29 (m, 1H), 4.38 (s, 2H), 4.79 (s, 2H), 6.48 (d, J = 3.9 Hz, 1H), 7.20 (d, J = 3.9 Hz, 1H), 8.83 (s, 1H), 10.90 (br s, 1H).<br>LC/MS: condition 2, retention time = 1.06 min<br>LC/MS(ESI$^+$) m/z; 467 [M + H]$^+$ |
| 31 | $^1$H-NMR (DMSO-d$_6$) δ: 1.12-1.25 (m, 2H), 1.66-1.75 (m, 3H), 1.85-1.94 (m, 4H), 2.77 (s, 3H), 2.87 (s, 3H), 2.91 (d, J = 4.5 Hz, 2H), 4.19-4.35 (m, 3H), 4.79 (s, 2H), 6.53 (d, J = 4.0 Hz, 1H), 7.34 (d, J = 4.0 Hz, 1H), 8.51 (s, 1H), 11.82 (br s, 1H).<br>LC/MS: condition 2, retention time = 1.72 min<br>LC/MS(ESI$^+$) m/z; 474 [M + H]$^+$ |
| 32 | $^1$H-NMR (DMSO-d$_6$) δ: 0.65-0.68 (m, 2H), 0.78-0.84 (m, 2H), 1.09-1.21 (m, 2H), 1.68-1.80 (m, 3H), 1.88-1.92 (m, 4H), 2.68-2.73 (m, 1H), 2.77 (s, 3H), 2.86 (s, 3H), 2.90 (d J = 7.5 Hz, 2H), 4.13-4.19 (m, 1H), 4.58 (s, 2H), 6.49 (d, J = 4.0 Hz, 1H), 7.30 (d, J = 4.0 Hz, 1H), 8.48 (s, 1H), 11.72 (br s, 1H).<br>LC/MS: condition 2, retention time = 1.72 min<br>LC/MS(ESI$^+$) m/z; 432 [M + H]$^+$ |
| 33 | $^1$H-NMR (CD$_3$OD) δ: 1.20-1.29 (m, 5H), 1.72-1.91 (m, 3H), 1.99-2.09 (m, 4H), 2.85 (s, 3H), 2.87 (s, 3H), 3.01 (d, J = 7.5 Hz, 2H), 3.01 (q, J = 7.2 Hz, 2H), 4.23-4.32 (m, 1H), 4.75 (s, 2H), 6.57 (d, J = 4.0 Hz, 1H), 7.25 (d, J = 4.0 Hz, 1H), 8.57 (s, 1H).<br>LC/MS: condition 2, retention time = 1.72 min<br>LC/MS(ESI$^+$) m/z; 420 [M + H]$^+$ |

TABLE 21

| Ex | Data |
|---|---|
| 34 | $^1$H-NMR (CDCl$_3$) δ: 0.73-0.78 (m, 2H), 0.89-0.96 (m, 2H), 1.06-1.17 (m, 2H), 1.56-1.68 (m, 3H), 2.01-2.09 (m, 4H), 2.20 (d, J = 7.5 Hz, 2H), 2.47-2.53 (m, 10H), 2.68-2.73 (m, 3H), 4.19-4.28 (m, 1H), (4.61 s, 2H), 6.46-6.47 (m, 1H), 7.19-7.20 (m, 1H), 8.85 (s, 1H).<br>LC/MS: condition 1, retention time = 0.32 min<br>LC/MS(ESI$^+$) m/z; 462 [M + H]$^+$ |
| 35 | $^1$H-NMR (CDCl$_3$) δ: 1.05-1.17 (m, 2H), 1.53-1.65 (m, 3H), 2.00-2.11 (m, 4H), 2.19 (d, J = 6.9 Hz, 2H), 2.46-2.53 (m, 10H), 2.70 (t, J = 6.9 Hz, 2H), 3.09 (s, 3H), 4.16-4.24 (m, 1H), 4.58 (s, 2H), 6.46-6.47 (m, 1H), 7.23-7.24 (m, 1H), 8.85 (s, 1H), 11.8 (br s, 1H).<br>LC/MS: condition 1, retention time = 0.32 min<br>LC/MS(ESI$^+$) m/z: 436 [M + H]$^+$ |

Synthetic Example 36

2,2,2-Trifluoro-N-{[trans-4-(3-methyl-4-oxo-2,3,4,7-tetrahydro-1H-pyrrolo[3',2':5,6]pyrido[4,3-d]pyrimidin-1-yl)cyclohexyl]methyl}ethanesulfonamide

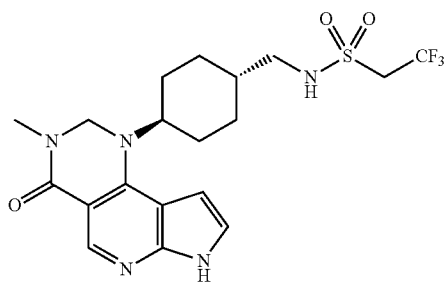 [SMILES: CN1CN([C@H]2CC[C@H](CNS(=O)(=O)CC(F)(F)F)CC2)c2c(cnc3[nH]ccc23)C1=O]

To a solution of 1-[trans-4-(aminomethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one (20.0 mg, 0.0740 mmol) obtained in Reference Synthetic Example 36 in dichloromethane (2 mL), triethylamine (38.0 μL, 0.270 mmol) and 2,2,2-trifluoroethanesulfonyl chloride (16.0 μL, 0.135 mmol) were added, and the mixture was stirred at room temperature for 1 day. The reaction mixture was mixed with saturated aqueous ammonium chloride and extracted with ethyl acetate. The organic layer was washed with saturated aqueous sodium chloride, dried over anhydrous sodium sulfate and concentrated under reduced pressure. The residue was purified by silica gel column chromatography (ethyl acetate→ethyl acetate/methanol=40/1 (v/v)) to obtain a crude product (45.6 mg). To a solution of the resulting crude product in dichloromethane (2 mL), trifluoroacetic acid (2 mL) was added, and the mixture was stirred at room temperature for 2 hours, and the reaction mixture was concentrated under reduced pressure. To a solution of the resulting residue in a mixed solvent of water (0.6 mL) and methanol (2.4 mL), 1M aqueous sodium hydroxide (0.12 mL) and ethylenediamine (0.18 mL) were added, and the mixture was stirred at room temperature for 1 day. The reaction mixture was mixed with water and extracted with ethyl acetate. The organic layer was washed with saturated aqueous ammonium chloride and saturated aqueous sodium hydrogencarbonate, dried over anhydrous sodium sulfate and concentrated under reduced pressure. The resulting solid was washed with hexane/ethyl acetate and dried under reduced pressure to obtain the title compound as a white solid (7.50 mg, yield: 18% (2 steps)).

$^1$H-NMR (DMSO-d$_6$) δ: 1.09-1.24 (m, 2H), 1.41-1.59 (m, 1H), 1.62-1.79 (m, 2H), 1.81-1.93 (m, 4H), 2.85-2.92 (m, 2H), 2.94 (s, 3H), 4.03-4.15 (m, 1H), 3.97-4.22 (m, 1H), 4.37 (q, J=10.2 Hz, 2H), 4.63 (s, 2H), 6.46 (d, J=3.3 Hz, 1H), 7.30 (d, J=3.7 Hz, 1H), 8.46 (s, 1H), 11.72 (br s, 1H).

LC/MS: measurement condition 2, retention time=1.60 min.
LC/MS (ESI$^+$) m/z; 460 [M+H]$^+$
LC/MS (ESI$^-$) m/z; 458 [M−H]$^-$

Synthetic Example 37

N-{[trans-4-(3-Methyl-4-oxo-2,3,4,7-tetrahydro-1H-pyrrolo[3',2':5,6]pyrido[4,3-d]pyrimidin-1-yl)cyclohexyl]methyl}methanesulfonamide

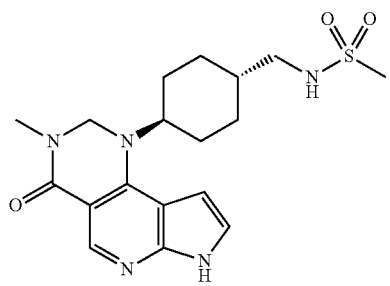 [SMILES: CN1CN([C@H]2CC[C@H](CNS(C)(=O)=O)CC2)c2c(cnc3[nH]ccc23)C1=O]

The title compound was obtained as a white solid (3.1 mg, yield: 23% (2 stages)) substantially in the same manner as in Synthetic Example 36 except that methanesulfonyl chloride was used instead of 2,2,2-trifluoroethanesulfonyl chloride.

$^1$H-NMR (DMSO-d$_6$) δ: 1.05-1.26 (m, 2H), 1.39-1.58 (m, 1H), 1.62-1.80 (m, 2H), 1.81-1.95 (m, 4H), 2.79-2.86 (m, 2H), 2.88 (s, 3H), 2.94 (s, 3H), 3.97-4.20 (m, 1H), 4.63 (s, 2H), 6.46 (d, J=3.3 Hz, 1H), 6.93-7.16 (m, 1H), 7.30 (d, J=3.7 Hz, 1H), 8.46 (s, 1H), 11.72 (br s, 1H).

LC/MS: measurement condition 2, retention time=1.23 min.
LC/MS (ESI$^+$) m/z; 392 [M+H]$^+$
LC/MS (ESI$^-$) m/z; 390 [M−H]$^-$

Synthetic Example 38

1-(trans-4-{[1,1-Dioxidoisothiazolidin-2-yl)methyl}cyclohexyl]-3-methyl-2,3-dihydro-1H-pyrrolo[3',2':5,6]pyrido[4,3-d]pyrimidin-4(7H)-one

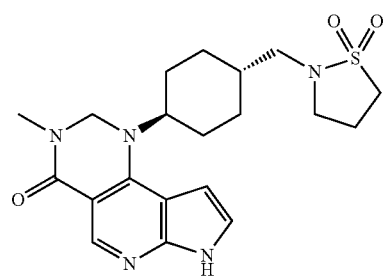 [SMILES: CN1CN([C@H]2CC[C@H](CN3CCCS3(=O)=O)CC2)c2c(cnc3[nH]ccc23)C1=O]

To a solution of 1-[trans-4-(aminomethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one (40.0 mg, 0.0901 mmol) obtained in Reference Synthetic Example 36 in dichloromethane (2 mL), triethylamine (38.0 μL, 0.270 mmol) and 3-chloropropanesulfonyl chloride (16.0 μL, 0.135 mmol) were added, and the mixture was stirred at room temperature for 1 day. The reaction mixture was mixed with saturated aqueous ammonium chloride and extracted with ethyl acetate. The organic layer was washed with saturated aqueous sodium chloride, dried over anhydrous sodium sulfate and concentrated under reduced pressure. To a solution of the resulting residue in tetrahydrofuran (3 mL), sodium hydride (55 wt % dispersion in liquid paraffin, 5.8 mg, 0.135 mol) was added, and the mixture was stirred at room temperature for 3 days. The reaction mixture was mixed with water and extracted with ethyl acetate. The organic layer was washed with saturated aqueous sodium chloride, dried over anhydrous sodium sulfate and concentrated under reduced pressure. The residue was purified by silica gel column chromatography (ethyl acetate/methanol=20/1 (v/v)) to obtain a crude product. To a solution of the resulting crude product in dichloromethane (2 mL), trifluoroacetic acid (2 mL) was added, and the mixture was stirred at room temperature for 2 hours, and the reaction mixture was concentrated under reduced pressure. To a solution of the resulting residue in a mixed solvent of water (0.6 mL) and methanol (2.4 mL), 1M aqueous sodium hydroxide (0.12 mL) and ethylenediamine (0.18 mL) were added, and the mixture was stirred at room temperature for 1 day. The reaction mixture was mixed with water, and the precipitated solid was collected by filtration, washed with water and dried under reduced pressure to obtain the title compound as a white solid (19.5 mg, yield: 52% (2 steps)).

$^1$H-NMR (DMSO-d$_6$) δ: 1.05-1.23 (m, 2H), 1.51-1.64 (m, 1H), 1.64-1.81 (m, 2H), 1.83-1.94 (m, 4H), 2.17-2.29 (m, 2H), 2.76 (d, J=7.0 Hz, 2H), 2.94 (s, 3H), 3.13-3.23 (m, 4H), 3.97-4.22 (m, 1H), 4.63 (s, 2H), 6.47 (d, J=3.7 Hz, 1H), 7.30 (d, J=3.3 Hz, 1H), 8.46 (s, 1H), 11.72 (br s, 1H).

LC/MS: measurement condition 2, retention time=1.37 min.

LC/MS (ESI$^+$) m/z; 418 [M+H]$^+$

Synthetic Example 39

1-{trans-4-[(Dimethylamino)methyl]cyclohexyl}-2,3-dihydro-1H-pyrrolo[3',2':5,6]pyrido[4,3-d]pyrimidin-4(7H)-one

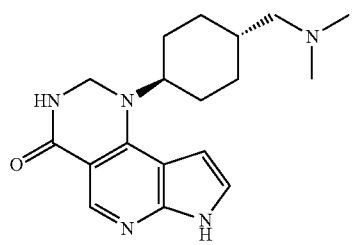 [SMILES: CN(C)C[C@H]1CC[C@H](N2CNC(=O)c3cnc4[nH]ccc4c32)CC1]

To a solution of trans-4-(4-oxo-4,7-dihydro-1H-pyrrolo[3',2':5,6]pyrido[4,3-d]pyrimidin-1-yl)cyclohexanecarbaldehyde (10.4 mg, 0.034 mmol) obtained in Reference Synthetic Example 39 in methanol (1 mL), dimethylamine hydrochloride (3.4 mg, 0.046 mmol), 2-picoline borane (5.0 mg, 0.046 mmol) and acetic acid (0.1 mL) were added, and the mixture was stirred at room temperature for 1 hour. The reaction mixture was mixed with aqueous sodium hydroxide and chloroform until the aqueous layer was adjusted to pH 5, and the mixture was extracted with chloroform. The aqueous layer was adjusted to pH 9 to 10 with additional amount of aqueous sodium hydroxide and the mixture was extracted with chloroform. The organic layer was dried over anhydrous sodium sulfate and concentrated under reduced pressure to obtain a mixture (6.3 mg) containing the title compound. Of the resulting mixture, 4.6 mg was purified by thin-layer silica gel column chromatography (NH-PLC manufactured by FUJI SILYSIA CHEMICAL LTD., chloroform/methanol=10/1 (v/v)) to obtain the title compound as a white solid (3.0 mg, yield: 27%).

$^1$H-NMR (CD$_3$OD) δ: 1.08-1.27 (m, 2H), 1.50-1.65 (m, 1H), 1.68-1.86 (m, 2H), 1.93-2.10 (m, 4H), 2.24 (s, 6H), 2.18-2.29 (m, 2H), 4.22-4.35 (m, 1H), 4.66 (s, 2H), 6.57 (d, J=3.7 Hz, 1H), 7.24 (d, J=3.7 Hz, 1H), 8.56 (s, 1H).

LC/MS: measurement condition 1, retention time=0.30 min.

LC/MS (ESI$^+$) m/z; 328 [M+H]$^+$

Synthetic Example 40

3-Methyl-1-(trans-4-{[methyl(2,2,2-trifluoroethyl)amino]methyl}cyclohexyl)-2,3-dihydro-1H-pyrrolo[3',2':5,6]pyrido[4,3-d]pyrimidin-4(7H)-one

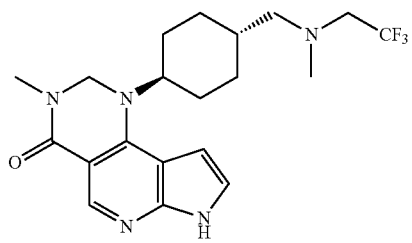 [SMILES: CN(CC(F)(F)F)C[C@H]1CC[C@H](N2CN(C)C(=O)c3cnc4[nH]ccc4c32)CC1]

To a solution of 3-methyl-1-(trans-4-{[(2,2,2-trifluoroethyl)amino]methyl}cyclohexyl)-2,3-dihydro-1H-pyrrolo[3',2':5,6]pyrido[4,3-d]pyrimidin-4(7H)-one (22.7 mg, 57.4 μmol) obtained in Synthetic Example 12 in methanol (1.5 mL), 37% aqueous formaldehyde (11.6 μL, 115 μmol) and 2-picoline borane (12.3 mg, 115 μmol) were added, and the mixture was stirred at room temperature for 1 day. The precipitated solid was collected by filtration and washed with water and ethyl acetate to obtain the title compound as a white solid (14.9 mg, yield: 63%).

$^1$H-NMR (CDCl$_3$) δ: 1.07 (qd, J=11.9, 2.9 Hz, 2H), 1.40-1.50 (m, 1H), 1.60 (qd, J=11.9, 2.9 Hz, 2H), 2.00-2.14 (m, 4H), 2.40 (d, J=7.0 Hz, 2H), 2.43 (s, 3H), 2.99 (q, J=9.8 Hz, 2H), 3.09 (s, 3H), 4.17 (tt, J=11.9, 3.7 Hz, 1H), 4.58 (s, 2H), 6.45-6.49 (m, 1H), 7.18-7.21 (m, 1H), 8.84 (s, 1H), 10.29 (br s, 1H).

LC/MS: measurement condition 1, retention time=2.75 min.

LC/MS (ESI$^+$) m/z; 410 [M+H]$^+$

Synthetic Example 41

3-(Methoxymethyl)-1-(trans-4-{[methyl(2,2,2-trifluoroethyl)amino]methyl}cyclohexyl)-2,3-dihydro-1H-pyrrolo[3',2':5,6]pyrido[4,3-d]pyrimidin-4(7H)-one

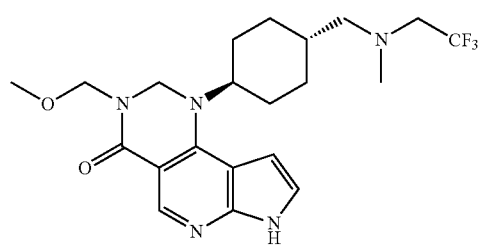 [SMILES: COCN1CN([C@H]2CC[C@H](CN(C)CC(F)(F)F)CC2)c2c(cnc3[nH]ccc23)C1=O]

To a solution of 3-(methoxymethyl)-1-(trans-4-{[(2,2,2-trifluoroethyl)amino]methyl}cyclohexyl)-2,3-dihydro-1H-pyrrolo[3',2':5,6]pyrido[4,3-d]pyrimidin-4(7H)-one (18.2 mg, 0.019 mmol) obtained in Synthetic Example 23 in methanol (1.0 mL), 37% aqueous formaldehyde (10.0 μL, 100 μmol) and 2-picoline borane (10 mg, 0.093 mmol) were added, and the mixture was stirred at room temperature for 1 day. The reaction mixture was purified by silica gel thin-layer chromatography (chloroform/methanol=9/1 (v/v)) to obtain the title compound as a white solid (10.46 mg, yield: 55%).

$^1$H-NMR (CDCl3) δ: 1.00-1.18 (m, 2H), 1.56-1.73 (m, 3H), 2.00-2.16 (m, 4H), 2.40 (d, J=6.9 Hz, 2H), 2.43 (s, 3H), 3.00 (q, J=9.6 Hz, 2H), 3.38 (s, 3H), 4.15-4.32 (m, 1H), 4.68 (s, 2H), 4.96 (s, 2H), 6.50 (d, J=3.6 Hz, 1H), 7.18 (d, J=3.6 Hz, 1H), 8.85 (s, 1H), 9.87 (br s, 1H).

LC/MS: measurement condition 2, retention time=1.92 min.

LC/MS (ESI$^+$) m/z; 440 [M+H]$^+$

Synthetic Example 42

2-[4-oxo-1-(trans-4-{[(2,2,2-Trifluoroethyl)amino]methyl}cyclohexyl)-1H-pyrrolo[3',2':5,6]pyrido[4,3-d]pyrimidin-3(2H,4H,7H)-yl]acetonitrile

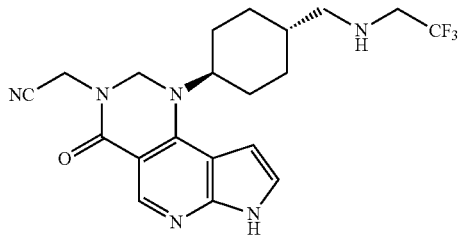 [SMILES: N#CCN1CN([C@H]2CC[C@H](CNCC(F)(F)F)CC2)c2c(cnc3[nH]ccc23)C1=O]

To a solution of tert-butyl {[trans-4-(3-(cyanomethyl)-4-oxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}(2,2,2-trifluoroethyl)carbamate (52.3 mg, 0.0804 mmol) obtained in Reference Synthetic Example 70 in dichloromethane (1.0 mL), trifluoroacetic acid (0.5 mL) was added, and the mixture was stirred at room temperature for 4 hours. The reaction mixture was azeotropically distilled with toluene and mixed with methanol (1.0 mL) and ethylenediamine (50 μL), followed by stirring at room temperature for 1.5 hours. The mixture was mixed with additional amount of ethylenediamine (150 μL), and the mixture was stirred at room temperature for 1.5 hours. The reaction mixture was concentrated under reduced pressure, and the resulting residue was purified by silica gel column chromatography (chloroform/methanol=1/0→93/7 (v/v)) to obtain the title compound as a white solid (27.1 mg, yield: 80%).

$^1$H-NMR (CDCl$_3$) δ: 1.12-1.23 (m, 2H), 1.49-1.74 (m, 3H), 2.02-2.15 (m, 4H), 2.64 (d, J=6.2 Hz, 2H), 3.19 (q, J=9.3 Hz, 2H), 4.20-4.28 (m, 1H), 4.72 (s, 2H), 4.75 (s, 2H), 6.50 (d, J=2.3 Hz, 1H), 7.24 (dd, J=3.6, 2.0 Hz, 1H), 8.84 (s, 1H), 10.5 (br s, 1H).

LC/MS: measurement condition 2, retention time=1.13 min.

LC/MS (ESI$^+$) m/z; 421 [M+H]$^+$

Synthetic Example 43

N-{[trans-4-(3-Cyclopropyl-4-oxo-2,3,4,7-tetrahydro-1H-pyrrolo[3',2':5,6]pyrido[4,3-d]pyrimidin-1-yl)cyclohexyl]methyl}methanesulfonamide

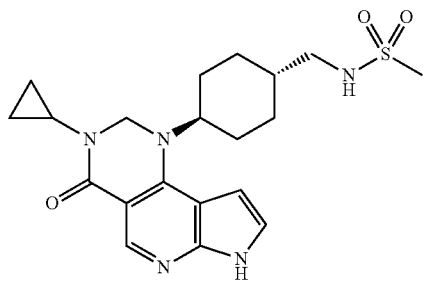 [SMILES: CS(=O)(=O)NC[C@H]1CC[C@H](N2CN(C3CC3)C(=O)c3cnc4[nH]ccc4c32)CC1]

To a solution of 1-[trans-4-(aminomethyl)cyclohexyl]-3-cyclopropyl-7-{[2-(trimethylsilyl)ethoxy]methyl}-2,3-dihydro-1H-pyrrolo[3',2':5,6]pyrido[4,3-d]pyrimidin-4(7H)-one (30.0 mg, 0.0639 mmol) obtained in Reference Synthetic Example 85 in dichloromethane (1 mL), triethylamine (26.8 μL, 0.192 mmol) and methanesulfonyl chloride (7.4 μL, 0.0959 mmol) were added, and the mixture was stirred at room temperature for 2 hours. The reaction mixture was mixed with water and extracted with ethyl acetate. The organic layer was washed with saturated aqueous ammonium chloride and saturated aqueous sodium hydrogencarbonate, dried over anhydrous sodium sulfate and concentrated under reduced pressure. The residue was purified by silica gel column chromatography (ethyl acetate/hexane=2/1→1/0 (v/v)→ethyl acetate/methanol=20/1 (v/v)) to obtain a crude product. To a solution of the resulting crude product in dichloromethane (2 mL), trifluoroacetic acid (2 mL) was added, and the mixture was stirred at room temperature for 2 hours, and the reaction mixture was concentrated under reduced pressure. To a solution of the resulting residue in a mixed solvent of water (0.6 mL) and methanol (2.4 mL), 1M aqueous sodium hydroxide (0.12 mL) and ethylenediamine (0.18 mL) were added, and the mixture was stirred at room temperature for 5 hours. The resulting reaction mixture was mixed with water and extracted with ethyl acetate. The organic layer was washed with saturated aqueous ammonium chloride and saturated aqueous sodium hydrogencarbonate, dried over anhydrous sodium sulfate and concentrated under reduced pressure. The residue was washed with a mixed solvent of hexane and ethyl acetate and dried under reduced pressure to obtain the title compound as a white solid (6.9 mg, yield: 26% (2 steps)).

$^1$H-NMR (DMSO-d$_6$) δ: 0.58-0.71 (m, 2H), 0.73-0.85 (m, 2H), 1.01-1.25 (m, 2H), 1.41-1.59 (m, 1H), 1.61-1.95 (m, 6H), 2.63-2.70 (m, 1H), 2.79-2.88 (m, 2H), 2.89 (s, 3H), 4.05-4.20 (m, 1H), 4.57 (s, 2H), 6.43-6.49 (m, 1H), 6.97-7.05 (m, 1H), 7.25-7.31 (m, 1H), 8.46 (s, 1H), 11.72 (br s, 1H).

LC/MS: measurement condition 2, retention time=1.37 min.

LC/MS (ESI$^+$) m/z; 418 [M+H]$^+$
LC/MS (ESI$^-$) m/z; 416 [M-H]$^-$

Synthetic Example 44

3-Cyclopropyl-1-{trans-4-[(1,1-dioxidoisothiazolidin-2-yl)methyl]cyclohexyl}-2,3-dihydro-1H-pyrrolo[3',2':5,6]pyrido[4,3-d]pyrimidin-4(7H)-one

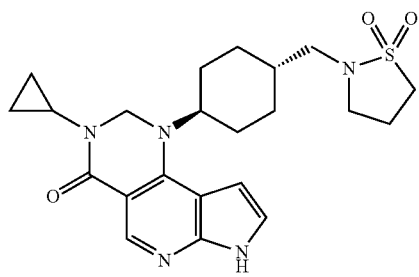 [SMILES: O=C1c2cnc3[nH]ccc3c2N([C@H]2CC[C@H](CN3CCCS3(=O)=O)CC2)CN1C1CC1]

To a solution of 1-[trans-4-(aminomethyl)cyclohexyl]-3-cyclopropyl-7-{[2-(trimethylsilyl)ethoxy]methyl}-2,3-dihydro-1H-pyrrolo[3',2':5,6]pyrido[4,3-d]pyrimidin-4(7H)-one (40.0 mg, 0.0852 mmol) obtained in Reference Synthetic Example 85 in dichloromethane (2 mL), triethylamine (38.0 µL, 0.270 mmol) and 3-chloropropanesulfonyl chloride (16.0 µL, 0.135 mmol) were added, and the mixture was stirred at room temperature for 2 hours. The reaction mixture was mixed with water and extracted with ethyl acetate. The organic layer was washed with saturated aqueous ammonium chloride and saturated aqueous sodium hydrogencarbonate, dried over anhydrous sodium sulfate and concentrated under reduced pressure. To a solution of the resulting residue in tetrahydrofuran (5 mL), sodium hydride (55 wt % dispersion in liquid paraffin, 5.6 mg, 0.13 mmol) was added, and the mixture was stirred at room temperature for 1 day. The reaction mixture was mixed with water and extracted with ethyl acetate. The organic layer was washed with saturated aqueous sodium chloride, dried over anhydrous sodium sulfate and concentrated under reduced pressure. The residue was purified by silica gel column chromatography (ethyl acetate/hexane=2/1→1/0 (v/v) →ethyl acetate/methanol=40/1 (v/v)) to obtain a crude product. To a solution of the resulting crude product in dichloromethane (2 mL), trifluoroacetic acid (2 mL) was added, and the mixture was stirred at room temperature for 2 hours. The reaction mixture was concentrated under reduced pressure. To a solution of the resulting residue in a mixed solvent of water (0.3 mL) and methanol (1.2 mL), 1M aqueous sodium hydroxide (0.06 mL) and ethylenediamine (0.09 mL) were added, and the mixture was stirred at room temperature for 1 day. The resulting reaction mixture was mixed with water and extracted with ethyl acetate. The organic layer was washed with saturated aqueous ammonium chloride and saturated aqueous sodium hydrogencarbonate, dried over anhydrous sodium sulfate and concentrated under reduced pressure. The residue was purified by silica gel column chromatography (ethyl acetate/methanol=1/0→20/1→10/1 (v/v)) and dried under reduced pressure to obtain the title compound as a white solid (2.3 mg, yield: 6% (3 steps)).

LC/MS: measurement condition 2, retention time=1.51 min.

LC/MS (ESI$^+$) m/z; 444 [M+H]$^+$

Synthetic Example 45

2-({[trans-4-(4-oxo-2,3,4,7-Tetrahydro-1H-pyrrolo[3',2':5,6]pyrido[4,3-d]pyrimidin-1-yl)cyclohexyl]methyl}amino)acetonitrile

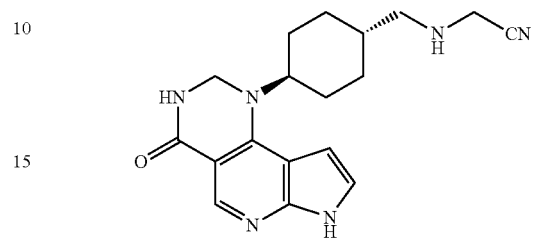

To a solution of 1-{trans-4-[hydroxy(methoxy)methyl]cyclohexyl}-7-{[2-(trimethylsilyl)ethoxy]methyl}-1H-pyrrolo[3',2':5,6]pyrido[4,3-d]pyrimidin-4(7H)-one (50.0 mg, 0.109 mmol) obtained in Reference Synthetic Example 33 in methanol (3 mL), aminoacetonitrile hydrochloride (51.0 mg, 0.546 mmol) and 2-picoline borane (23.0 mg, 0.218 mmol) were added, and the mixture was stirred at room temperature for 1 day. The reaction mixture was mixed with saturated aqueous sodium hydrogencarbonate and extracted with ethyl acetate. The organic layer was washed with saturated aqueous sodium chloride, dried over anhydrous sodium sulfate and concentrated under reduced pressure. The residue was purified by silica gel column chromatography (ethyl acetate/methanol=1/0→20/1→10/1→8/1 (v/v)) to obtain a white solid (39.2 mg). To a solution of the resulting white solid in dichloromethane (2 mL), trifluoroacetic acid (2 mL) was added, and the mixture was stirred at room temperature for 2 hours, and the reaction mixture was concentrated under reduced pressure. To a solution of the resulting residue in a mixed solvent of water (0.6 mL) and methanol (2.4 mL), 1M aqueous sodium hydroxide (0.12 mL) and ethylenediamine (0.18 mL) were added, and the mixture was stirred at room temperature for 1 day. The resulting reaction mixture was mixed with water and extracted with ethyl acetate. The organic layer was washed with saturated aqueous ammonium chloride and saturated aqueous sodium hydrogencarbonate, dried over anhydrous sodium sulfate and concentrated under reduced pressure. The resulting residue was washed with hexane/chloroform and dried under reduced pressure to obtain the title compound as a white solid (12.5 mg, yield: 34% (2 steps)).

$^1$H-NMR (DMSO-d$_6$) δ: 1.03-1.30 (m, 2H), 1.37-1.52 (m, 1H), 1.58-1.76 (m, 2H), 1.82-1.93 (m, 4H), 2.43-2.48 (m, 2H), 3.63 (s, 2H), 3.95-4.24 (m, 1H), 4.51 (s, 2H), 6.47 (d, J=3.3 Hz, 1H), 7.28 (d, J=3.3 Hz, 1H), 7.81 (s, 1H), 8.43 (s, 1H), 11.71 (s, 1H).

LC/MS: measurement condition 2, retention time=0.46 min.

LC/MS (ESI$^+$) m/z; 339 [M+H]$^+$

Synthetic Example 46

N-{[trans-4-(3-Ethyl-4-oxo-2,3,4,7-tetrahydro-1H-pyrrolo[3',2':5,6]pyrido[4,3-d]pyrimidin-1-yl)cyclohexyl]methyl}-2,2,2-trifluoroethanesulfonamide

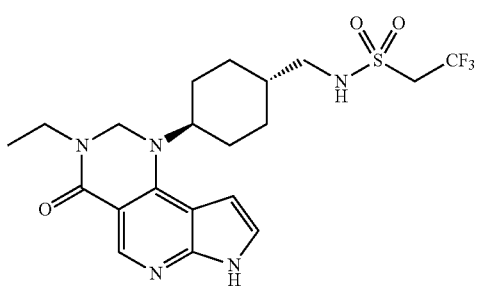 [SMILES: CCN1CN([C@H]2CC[C@H](CNS(=O)(=O)CC(F)(F)F)CC2)c2c(cnc3[nH]ccc23)C1=O]

To a solution of 1-[trans-4-(aminomethyl)cyclohexyl]-3-ethyl-7-[{2-(trimethylsilyl)ethoxy]methyl}-2,3-dihydro-1H-pyrrolo[3',2':5,6]pyrido[4,3-d]pyrimidin-4(7H)-one (40.0 mg, 0.0874 mmol) obtained in Reference Synthetic Example 95 in dichloromethane (2 mL), triethylamine (36.5 μL, 0.262 mmol) and 2,2,2-trifluoroethanesulfonyl chloride (14.9 μL, 0.135 mmol) were added, and the mixture was stirred at room temperature for 1 day. The reaction mixture was mixed with water and extracted with ethyl acetate. The organic layer was washed with saturated aqueous ammonium chloride and saturated aqueous sodium hydrogencarbonate, dried over anhydrous sodium sulfate and concentrated under reduced pressure. The residue was purified by silica gel column chromatography (ethyl acetate/hexane=3/2→3/1→5/1 (v/v)) to obtain a crude product. To a solution of the resulting crude product in dichloromethane (2 mL), trifluoroacetic acid (2 mL) was added, and the mixture was stirred at room temperature for 2 hours, and the reaction mixture was concentrated under reduced pressure. To a solution of the resulting residue in a mixed solvent of water (0.6 mL) and methanol (2.4 mL), 1M aqueous sodium hydroxide (0.12 mL) and ethylenediamine (0.18 mL) were added, and the mixture was stirred at room temperature for 1 day. The reaction mixture was mixed with water and extracted with ethyl acetate. The organic layer was washed with saturated aqueous ammonium chloride and saturated aqueous sodium hydrogencarbonate, dried over anhydrous sodium sulfate and concentrated under reduced pressure to obtain the title compound as a white solid (19.1 mg, yield: 46% (2 steps)).

$^1$H-NMR (DMSO-$d_6$) δ: 1.01-1.23 (m, 5H), 1.39-1.61 (m, 1H), 1.65-1.95 (m, 6H), 2.81-2.95 (m, 2H), 3.38-3.52 (m, 2H), 4.05-4.20 (m, 1H), 4.27-4.44 (m, 2H), 4.66 (s, 2H), 6.42-6.50 (m, 1H), 7.25-7.31 (m, 1H), 7.75-7.85 (m, 1H), 8.45 (s, 1H), 11.72 (br s, 1H).

LC/MS: measurement condition 2, retention time=1.71 min.

LC/MS (ESI$^+$) m/z; 474 [M+H]$^+$

Synthetic Example 47

N-{[trans-4-(3-Ethyl-4-oxo-2,3,4,7-tetrahydro-1H-pyrrolo[3',2':5,6]pyrido[4,3-d]pyrimidin-1-yl)cyclohexyl]methyl}cyclopropanesulfonamide

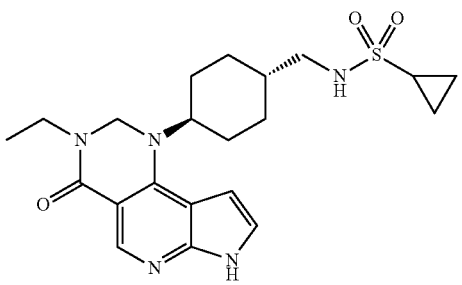 [SMILES: CCN1CN([C@H]2CC[C@H](CNS(=O)(=O)C3CC3)CC2)c2c(cnc3[nH]ccc23)C1=O]

The title compound was obtained as a white solid (8.1 mg, yield: 49% (2 steps)) substantially in the same manner as in Reference Synthetic Example 46 except that cyclopropanesulfonyl chloride was used instead of 2,2,2-trifluoroethanesulfonyl chloride.

$^1$H-NMR (DMSO-$d_6$) δ: 0.87-0.97 (m, 4H), 1.07-1.25 (m, 2H), 1.13 (t, J=7.0 Hz, 3H), 1.42-1.57 (m, 1H), 1.66-1.95 (m, 6H), 2.50-2.60 (m, 1H), 2.87 (t, J=6.3 Hz, 2H), 3.46 (q, J=7.1 Hz, 2H), 4.05-4.21 (m, 1H), 4.66 (s, 2H), 6.44-6.49 (m, 1H), 7.09 (t, J=5.9 Hz, 1H), 7.29 (t, J=3.1 Hz, 1H), 8.45 (s, 1H), 11.72 (br s, 1H).

LC/MS: measurement condition 2, retention time=1.51 min.

LC/MS (ESI$^+$) m/z; 432 [M+H]$^+$

Synthetic Example 48

2-{1-[trans-4-(Fluoromethyl)cyclohexyl]-4-oxo-1H-pyrrolo[3',2':5,6]pyrido[4,3-d]pyrimidin-3(2H,4H,7H)-yl}acetonitrile

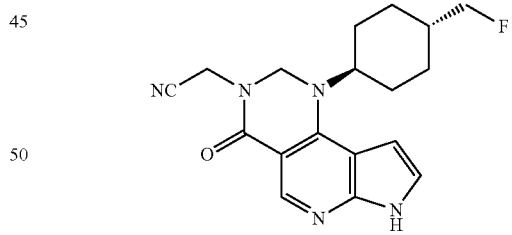

The title compound was obtained as a white solid (2.54 mg, yield: 3.6%) substantially in the same manner as in Reference Synthetic Example 32 except that 2-{1-[trans-4-(hydroxymethyl)cyclohexyl]-4-oxo-1H-pyrrolo[3',2':5,6]pyrido[4,3-d]pyrimidin-3(2H,4H,7H)-yl}acetonitrile obtained in Synthetic Example 8 was used instead of 1-[trans-4-(hydroxymethyl)cyclohexyl]-3-methyl-7-{[2-(trimethylsilyl)ethoxy]methyl}-2,3-dihydro-1H-pyrrolo[3',2':5,6]pyrido[4,3-d]pyrimidin-4(7H)-one.

LC/MS: measurement condition 1, retention time=3.80 min.

LC/MS (ESI$^+$) m/z; 342 [M+H]$^+$
LC/MS (ESI$^-$) m/z; 340 [M–H]$^-$

Synthetic Example 49

N-{[trans-4-(3-Ethyl-4-oxo-2,3,4,7-tetrahydro-1H-pyrrolo[3',2':5,6]pyrido[4,3-d]pyrimidin-1-yl)cyclohexyl]methyl}methanesulfonamide

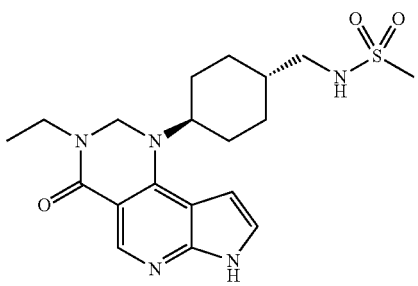 [SMILES: CCN1CN([C@H]2CC[C@H](CNS(C)(=O)=O)CC2)c2c(cnc3[nH]ccc23)C1=O]

The title compound was obtained as a white solid (12.0 mg, yield: 45%) substantially in the same manner as in Synthetic Example 46 except that methanesulfonyl chloride was used instead of 2,2,2-trifluoroethanesulfonyl chloride.

$^1$H-NMR (CD$_3$OD) δ: 1.22-1.27 (m, 5H), 1.55-1.65 (m, 1H), 1.75-1.87 (m, 2H), 2.00-2.05 (m, 4H), 2.92-2.98 (m, 5H), 3.54-3.61 (m, 2H), 4.24-4.32 (m, 1H), 4.73 (s, 2H), 6.55-6.56 (m, 1H), 7.23-7.24 (m, 1H), 8.55 (s, 1H).

LC/MS: measurement condition 2, retention time=1.34 min.
LC/MS (ESI$^+$) m/z; 406 [M+H]$^+$

Synthetic Example 50

2-[Methyl({trans-4-[4-oxo-3-(2,2,2-trifluoroethyl)-2,3,4,7-tetrahydro-1H-pyrrolo[3',2':5,6]pyrido[4,3-d]pyrimidin-1-yl]cyclohexyl}methyl)amino]acetonitrile

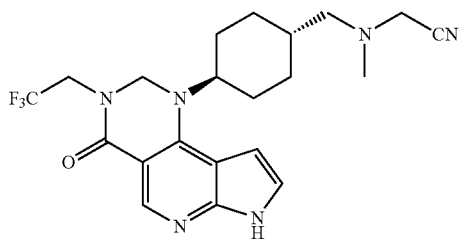 [SMILES: CN(CC#N)C[C@H]1CC[C@H](N2CN(CC(F)(F)F)C(=O)c3cnc4[nH]ccc4c32)CC1]

To a solution of 2-[({trans-4-[4-oxo-3-(2,2,2-trifluoroethyl)-2,3,4,7-tetrahydro-1H-pyrrolo[3',2':5,6]pyrido[4,3-d]pyrimidin-1-yl]cyclohexyl}methyl)amino]acetonitrile (6.2 mg, 0.015 mmol) obtained in Synthetic Example 11 in methanol (1.0 mL), 37% aqueous formaldehyde (2.3 μL, 0.030 mmol) and 2-picoline borane (3.2 mg, 0.030 mmol) were added, and the mixture was stirred at room temperature for 64 hours. Water was added to the reaction mixture, and the precipitated solid was collected by filtration and washed with water and diethyl ether to obtain the title compound as a white solid (3.09 mg, yield: 47%).

$^1$H-NMR (CDCl$_3$) δ: 1.07-1.19 (m, 2H), 1.63-1.77 (m, 3H), 2.01-2.13 (m, 4H), 2.34 (d, J=7.0 Hz, 2H), 2.37 (s, 3H), 3.52 (s, 2H), 4.11-4.27 (m, 3H), 4.72 (s, 2H), 6.49 (d, J=2.5 Hz, 1H), 7.23 (d, J=2.9 Hz, 1H), 8.86 (s, 1H), 10.6 (br s, 1H).

LC/MS: measurement condition 2, retention time=1.76 min.
LC/MS (ESI$^+$) m/z; 435 [M+H]$^+$

Synthetic Example 51

2-[1-(trans-4-{[Methyl(2,2,2-trifluoroethyl)amino]methyl}cyclohexyl)-4-oxo-1H-pyrrolo[3',2':5,6]pyrido[4,3-d]pyrimidin-3(2H,4H,7H)-yl]acetonitrile

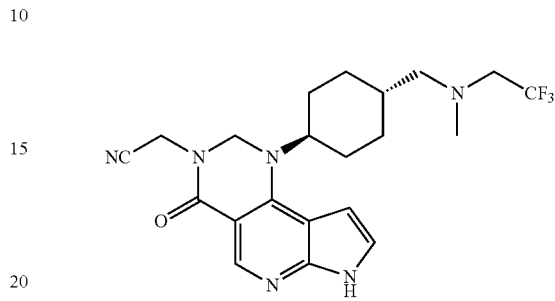

To a solution of 2-[4-oxo-1-(trans-4-{[(2,2,2-trifluoroethyl)amino]methyl}cyclohexyl)-1H-pyrrolo[3',2':5,6]pyrido[4,3-d]pyrimidin-3(2H,4H,7H)-yl]acetonitrile (21.4 mg, 0.0509 mmol) obtained in Synthetic Example 42 in methanol (2.5 mL), 37% aqueous formaldehyde (7.5 μL, 0.10 mmol) and 2-picoline borane (10.7 mg, 0.100 mmol) were added, and the mixture was stirred at room temperature for 14 hours. The reaction mixture was mixed with water, and the precipitated solid was collected by filtration and washed with water and diethyl ether to obtain the title compound as a white solid (15.8 mg, yield: 71%).

$^1$H-NMR (CDCl$_3$) δ: 1.03-1.15 (m, 2H), 1.65-1.74 (m, 3H), 2.06-2.15 (m, 4H), 2.41 (d, J=6.9 Hz, 2H), 2.43 (s, 3H), 3.00 (q, J=9.5 Hz, 2H), 4.21-4.29 (m, 1H), 4.53 (s, 2H), 4.75 (s, 2H), 6.51 (dd, J=3.5, 1.8 Hz, 1H), 7.24 (d, J=3.0 Hz, 1H), 8.84 (s, 1H), 10.7 (br s, 1H).

LC/MS: measurement condition 2, retention time=1.89 min.
LC/MS (ESI$^+$) m/z; 435 [M+H]$^+$
LC/MS (ESI$^-$) m/z; 433 [M–H]$^-$

Synthetic Examples 52 to 55

Compounds in Synthetic Examples 52 to 55 were synthesized substantially in the same manner as in Synthetic Example 1 except that the compound obtained in Reference Synthetic Example 96, 97, 104 or 106 was used instead of 1-cyclohexyl-7-{[2-(trimethylsilyl)ethoxy]methyl}-2,3-dihydro-1H-pyrrolo[3',2':5,6]pyrido[4,3-d]pyrimidin-4(7H)-one. Of the synthesized compounds, the chemical structural formulae are shown below, the compound names, the morphologies and the yields are shown in Table 22, and the physical data are shown in Table 23.

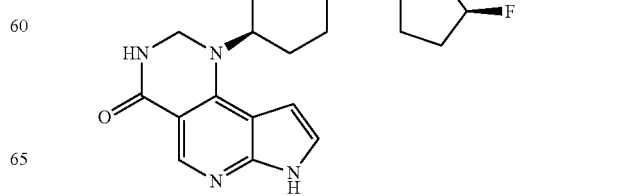

Ex. 52

-continued

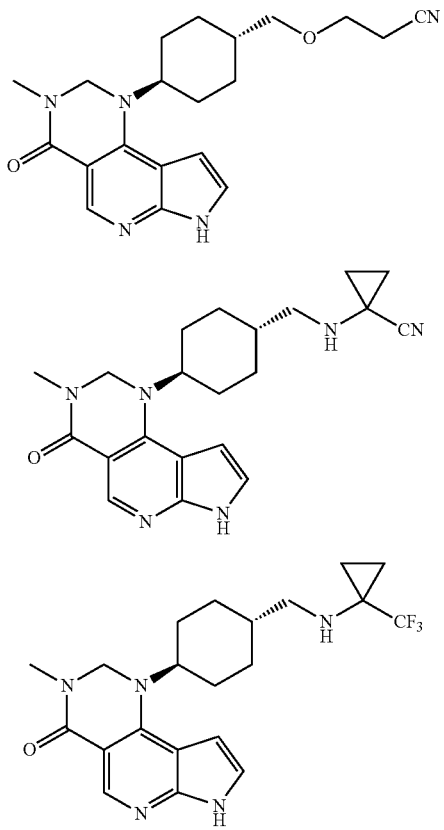

Ex. 53

Ex 54

Ex. 55

TABLE 22

| Ex | Compound Name | Morphology | Yield |
|---|---|---|---|
| 52 | 1-(trans-4-{[(S)-3-fluoropyrrolidin-1-yl]methyl}cyclohexyl)-2,3-dihydro-1H-pyrrolo[3',2':5,6]pyrido[4,3-d]pyrimidin-4(7H)-one | white solid | 82% |
| 53 | 3-{[trans-4-(3-methyl-4-oxo-2,3,4,7-tetrahydro-1H-pyrrolo[3',2': 5,6]pyrido[4,3-d]pyrimidin-1-yl)cyclohexyl]methoxy}propanenitrile | white solid | 91% |
| 54 | 1-({[trans-4-(3-methyl-4-oxo-2,3,4,7-tetrahydro-1H-pyrrolo[3',2': 5,6]pyrido[4,3-d]pyrimidin-1-yl)cyclohexyl]methyl}amino)cyclopropanecarbonitrile | white solid | 84% |
| 55 | 3-methyl-1-[trans-4-({[1-(trifluoromethyl)cyclopropyl]amino}methyl)cyclohexyl]-2,3-dihydro-1H-pyrrolo[3',2': 5,6]pyrido[4,3-d]pyrimidin-4(7H)-one | white solid | 63% |

TABLE 23

| Ex | Data |
|---|---|
| 52 | $^1$H-NMR (CDCl$_3$) δ: 1.07-1.19 (m, 2H), 1.45-1.53 (m, 1H), 1.58-1.71 (m, 4H), 2.05-2.14 (m, 4H), 2.35-2.43 (m, 4H), 2.76-2.87 (m, 2H), 4.20-4.28 (m, 1H), 4.69 (d, J = 2.7 Hz, 2H), 5.07-5.27 (m, 1H), 6.34 (s, 1H), 6.50-6.51 (m, 1H), 7.19-7.20 (m, 1H), 8.81 (s, 1H).<br>LC/MS: condition 1, retention time = 0.30 min<br>LC/MS(ESI$^+$) m/z; 372 [M + H]$^+$ |
| 53 | $^1$H-NMR (CDCl$_3$) δ: 1.16-1.28 (m, 2H), 1.56-1.67 (m, 3H), 1.99-2.13 (m, 4H), 2.61 (t, J = 6.3 Hz, 2H), 3.09 (s, 3H), 3.36 (d, J = 6.6 Hz, 2H), 3.66 (t, J = 6.3 Hz, 2H), 4.15-4.23 (m, 1H), 4.59 (s, 2H), 6.47-6.48 (m, 1H), 7.22-7.23 (m, 1H), 8.84 (s, 1H), 11.10 (br s, 1H). |

TABLE 23-continued

| Ex | Data |
|---|---|
|  | LC/MS: condition 1, retention time = 0.37 min<br>LC/MS(ESI$^+$) m/z; 368 [M + H]$^+$ |
| 54 | $^1$H-NMR (CDCl$_3$) δ: 0.98-1.08 (m, 2H), 1.08-1.28 (m, 4H), 1.39-1.61 (m, 2H), 1.79-1.88 (m, 1H), 1.98 (d, J = 11.1 Hz, 2H), 2.10 (d, J = 11.1 Hz, 2H), 2.72 (t, J = 6.9 Hz, 2H), 3.09 (s, 3H), 4.10-4.23 (m, 1H), 4.58 (s, 2H), 6.47 (d, J = 3.3 Hz, 1H), 7.21 (d, J = 3.3 Hz, 1H), 8.85 (s, 1H), 10.26 (br s, 1H).<br>LC/MS: condition 2, retention time = 1.49 min<br>LC/MS(ESI$^+$) m/z; 379 [M + H]$^+$ |
| 55 | $^1$H-NMR (CDCl$_3$) δ: 0.76-0.83 (m, 2H), 0.98-1.04 (m, 2H), 1.04-1.20 (m, 2H), 1.24-1.36 (m, 1H), 1.50-1.65 (m, 2H), 1.91-2.00 (m, 2H), 2.03-2.12 (m, 2H), 2.71 (t, J = 6.5 Hz, 2H), 3.08 (s, 3H), 4.15 (tt, J = 11.9, 3.7 Hz, 1H), 4.57 (s, 2H), 6.45-6.48 (m, 1H), 7.17-7.20 (m, 1H), 8.84 (s, 1H), 9.92 (br s, 1H).<br>LC/MS: condition 1, retention time = 3.04 min<br>LC/MS(ESI$^+$) m/z; 422 [M + H]$^+$ |

Synthetic Examples 56 to 65

Compounds in Synthetic Examples 56 to 65 were synthesized substantially in the same manner as in Synthetic Example 2 except that the compound obtained in Reference Synthetic Example 99, 100, 101, 103, 105, 107, 108, 111, 112 or 113 was used instead of 1-(trans-4-{[(2-bromo-2,2-difluoroethyl)amino]methyl}cyclohexyl)-7-{[2-(trimethylsilyl)ethoxy]methyl}-2,3-dihydro-1H-pyrrolo[3',2':5,6]pyrido[4,3-d]pyrimidin-4(7H)-one. Of the synthesized compounds, the chemical structural formulae are shown below, the compound names, the morphologies and the yields are shown in Table 24, and the physical data are shown in Tables 25 and 26.

Ex. 56

Ex. 57

Ex. 58

Ex. 59
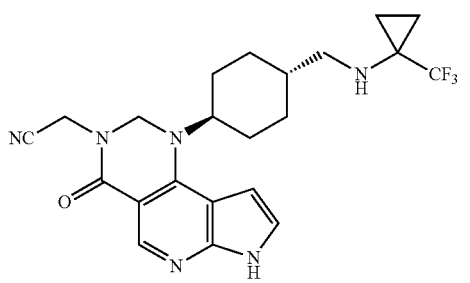

Ex. 60
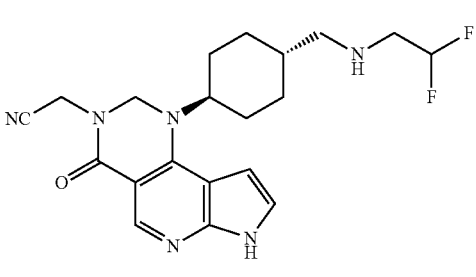

Ex. 61
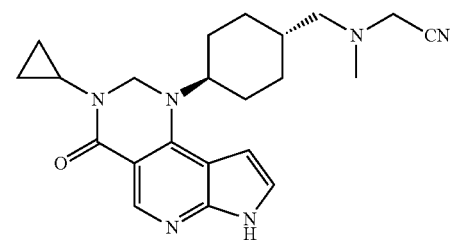

Ex. 62
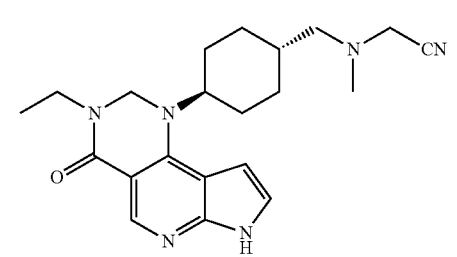

Ex. 63
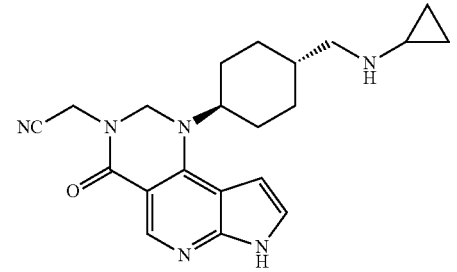

Ex. 64
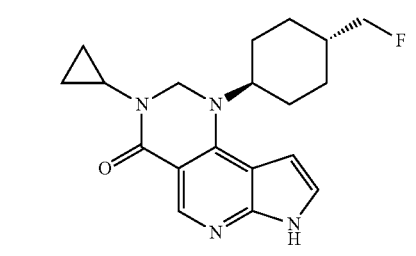

Ex. 65
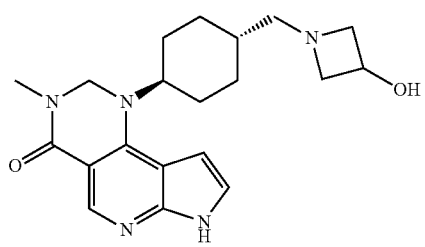

TABLE 24

| Ex | Compound Name | Morphology | Yield |
|---|---|---|---|
| 56 | 3-cyclopropyl-1-(trans-4-{[(2,2-difluoroethyl)amino]methyl}cyclohexyl)-2,3-dihydro-1H-pyrrolo[3',2': 5,6]pyrido[4,3-d]pyrimidin-4(7H)-one | white solid | 66% |
| 57 | 1-(trans-4-{[(2,2-difluoroethyl)amino]methyl}cyclohexyl)-3-ethyl-2,3-dihydro-1H-pyrrolo[3',2': 5,6]pyrido[4,3-d]pyrimidin-4(7H)-one | white solid | 75% |
| 58 | 1-(trans-4-{[(2,2-difluoroethyl)amino]methyl}cyclohexyl)-3-(methoxymethyl)-2,3-dihydro-1H-pyrrolo[3',2': 5,6]pyrido[4,3-d]pyrimidin-4(7H)-one | white solid | 30% |
| 59 | 2-{4-oxo-1-[trans-4-({[1-(trifluoromethyl)cyclopropyl]amino}methyl)cyclohexyl]-1H-pyrrolo[3',2': 5,6]pyrido[4,3-d]pyrimidin-3(2H,4H,7H)-yl}acetonitrile | white solid | 28% |
| 60 | 2-[1-(trans-4-{[(2,2-difluoroethyl)amino]methyl}cyclohexyl)-4-oxo-1H-pyrrolo[3',2': 5,6]pyrido[4,3-d]pyrimidin-3 (2H,4H,7H)-yl]acetonitrile | white solid | 30% |
| 61 | 2-({[trans-4-(3-cyclopropyl-4-oxo-2,3,4,7-tetrahydro-1H-pyrrolo[3',2': 5,6]pyrido[4,3-d]pyrimidin-1-yl)cyclohexyl]methyl}(methyl)amino)acetonitrile | white solid | 25% |
| 62 | 2-({[trans-4-(3-ethyl-4-oxo-2,3,4,7-tetrahydro-1H-pyrrolo[3',2': 5,6]pyrido[4,3-d]pyrimidin-1-yl)cyclohexyl]methyl}(methyl)amino)acetonitrile | white solid | 25% |
| 63 | 2-(1-{trans-4-[(cyclopropylamino)methyl]cyclohexyl}-4-oxo-1H-pyrrolo[3',2': 5,6]pyrido[4,3-d]pyrimidin-3(2H,4H,7H)-yl)acetonitrile | pale yellow solid | 68% |
| 64 | 3-cyclopropyl-1-[trans-4-(fluoromethyl)cyclohexyl]-2,3-dihydro-1H-pyrrolo[3',2': 5,6]pyrido[4,3-d]pyrimidin-4(7H)-one | white solid | 35% |
| 65 | 1-{trans-4-[(3-hydroxyazetidin-1-yl)methyl]cyclohexyl}-3-methyl-2,3-dihydro-1H-pyrrolo[3',2': 5,6]pyrido[4,3-d]pyrimidin-4(7H)-one | white solid | 25% |

TABLE 25

| Ex | Data |
|---|---|
| 56 | $^1$H-NMR (CDCl$_3$) δ: 0.74-0.80 (m, 2H), 0.90-0.98 (m, 2H), 1.13-1.27 (m, 2H), 1.50-1.56 (m, 1H), 1.60-1.71 (m, 2H), 2.01-2.14 (m, 4H), 2.61 (d, J = 6.6 Hz, 2H), 2.68-2.75 (m, 1H), 2.99 (td, J = 15.0, 4.2 Hz, 2H), 4.20-4.29 (m, 1H), 4.63 (s, 2H), 5.86 (tt, J = 56.7, 4.2 Hz, 1H), 6.48 (d, J = 4.0 Hz, 1H), 7.22 (d, J = 4.0 Hz, 1H), 8.87 (s, 1H), 11.28 (br s, 1H).<br>LC/MS: condition 2, retention time = 1.00 min<br>LC/MS(ESI$^+$) m/z; 404 [M + H]$^+$ |
| 57 | $^1$H-NMR (CDCl$_3$) δ: 1.18-1.25 (m, 2H), 1.25 (t, J = 7.0 Hz, 3H), 1.45-1.69 (m, 3H), 1.98-2.13 (m, 4H), 2.59 (d, J = 6.6 Hz, 2H), 2.97 (td, J = 15.3, 4.2 Hz, 2H), 3.60 (q, J = 7.0 Hz, 2H), 4.23 (tt, J = |

TABLE 25-continued

| Ex | Data |
|---|---|
|  | 12.0, 3.3 Hz, 1H), 4.61 (s, 2H), 5.85 (tt, J = 56.7, 4.2 Hz, 1H), 6.47 (d, J = 4.0 Hz, 1H), 7.24 (d, J = 4.0 Hz, 1H), 8.86 (s, 1H), 12.06 (br s, 1H).<br>LC/MS: condition 2, retention time = 0.80 min<br>LC/MS(ESI$^+$) m/z; 392 [M + H]$^+$ |
| 58 | $^1$H-NMR (CDCl$_3$) δ: 1.05-1.29 (m, 2H), 1.45-1.75 (m, 3H), 1.93-2.15 (m, 4H), 2.59 (d, J = 6.6 Hz, 2H), 2.88-3.05 (m, 2H), 3.38 (s, 3H), 4.16-4.30 (m, 1H), 4.68 (s, 2H), 4.96 (s, 2H), 5.85 (tt, J = 56.7, 4.2 Hz, 1H), 6.49 (d, J = 3.0 Hz, 1H), 7.21 (d, J = 3.0 Hz, 1H), 8.85 (s, 1H), 10.52 (br s, 1H).<br>LC/MS: condition 2, retention time = 0.70 min<br>LC/MS(ESI$^+$) m/z; 408 [M + H]$^+$ |
| 59 | $^1$H-NMR (CDCl$_3$) δ: 0.72-0.85 (m, 2H), 0.97-1.03 (m, 2H), 1.03-1.20 (m, 2H), 1.21-1.39 (m, 1H), 1.51-1.74 (m, 2H), 1.98 (d, J = 13.8 Hz, 2H), 2.10 (d, J = 13.8 Hz, 2H), 2.71 (d, J = 5.7 Hz, 2H), 4.11-4.28 (m, 1H), 4.52 (s, 2H), 4.73 (s, 2H), 6.49 (d, J = 3.0 Hz, 1H), 7.22 (d, J = 3.0 Hz, 1H), 8.82 (s, 1H), 9.93 (br s, 1H).<br>LC/MS: condition 2, retention time = 2.09 min<br>LC/MS(ESI$^+$) m/z; 447 [M + H]$^+$<br>LC/MS(ESI$^-$) m/z; 445 [M − H]$^-$ |
| 60 | $^1$H-NMR (CDCl$_3$) δ: 1.14-1.29 (m, 2H), 1.52-1.76 (m, 3H), 2.02-2.17 (m, 4H), 2.61 (d, J = 6.6 Hz, 2H), 2.99 (td, J = 15.3, 4.2 Hz, 2H), 4.25 (tt, J = 12.0, 3.3 Hz, 1H), 4.54 (s, 2H), 4.76 (s, 2H), 5.86 (tt, J = 56.7, 4.2 Hz, 1H), 6.50 (d, J = 4.0 Hz, 1H), 7.27 (d, J = 4.0 Hz, 1H), 8.85 (s, 1H), 10.98 (br s, 1H).<br>LC/MS: condition 2, retention time = 0.66 min<br>LC/MS(ESI$^+$) m/z; 403 [M + H]$^+$ |
| 61 | LC/MS: condition 2, retention time = 1.53 min<br>LC/MS(ESI$^+$) m/z; 393 [M + H]$^+$ |
| 62 | LC/MS: condition 2, retention time = 1.49 min<br>LC/MS(ESI$^+$) m/z; 381 [M + H]$^+$ |

TABLE 26

| Ex | Data |
|---|---|
| 63 | $^1$H-NMR (DMSO-d$_6$) δ: 0.16-0.21 (m, 2H), 0.31-0.38 (m, 2H), 1.01-1.15 (m, 2H), 1.38-1.49 (m, 1H), 1.64-1.79 (m, 2H), 1.83-1.93 (m, 4H), 2.00-2.06 (m, 1H), 2.45 (d, J = 6.5 Hz, 2H), 4.06-4.17 (m, 1H), 4.54 (s, 2H), 4.80 (s, 2H), 6.46-6.50 (m, 1H), 7.32-7.35 (m, 1H), 8.49 (s, 1H), 11.85 (br s, 1H).<br>LC/MS: condition 2, retention time = 0.92 min<br>LC/MS(ESI$^+$) m/z; 379 [M + H]$^+$ |
| 64 | $^1$H-NMR (CDCl$_3$) δ: 0.73-0.81 (m, 2H), 0.88-0.98 (m, 2H), 1.20-1.41 (m, 2H), 1.53-1.91 (m, 3H), 2.01 (brd, J = 10.0 Hz, 2H), 2.12 (brd, J = 10.0 Hz, 2H), 2.66-2.76 (m, 1H), 4.24 (dd, J = 14.9, 8.9 Hz, 2H), 4.40 (d, J = 5.6 Hz, 1H), 4.64 (s, 2H), 6.47 (brd, J = 3.6 Hz, 1H), 7.20 (brd, J = 3.6 Hz, 1H), 8.86 (s, 1H), 10.53 (s, 1H).<br>LC/MS: condition 1, retention time = 2.81 min<br>LC/MS(ESI$^+$) m/z; 343 [M + H]$^+$<br>LC/MS(ESI$^-$) m/z; 341 [M − H]$^-$ |
| 65 | $^1$H-NMR (DMSO-d$_6$) δ: 0.97-1.13 (m, 2H), 1.18-1.36 (m, 1H), 1.59-1.77 (m, 2H), 1.77-1.92 (m, 4H), 2.22 (d, J = 6.7 Hz, 2H), 2.63 (d, J = 6.7 Hz, 2H), 2.93 (s, 3H), 3.49 (t, J = 6.7 Hz, 2H), 4.00-4.09 (m, 1H), 4.09-4.20 (m, 1H), 4.63 (s, 2H), 5.23 (d., J = 6.3 Hz, 1H), 6.44 (brs, 1H), 7.29 (brs, 1H), 8.46 (d, J = 0.7 Hz, 1H), 11.73 (s, 1H).<br>LC/MS: condition 1, retention time = 0.30 min<br>LC/MS(ESI$^+$) m/z; 370 [M + H]$^+$<br>LC/MS(ESI$^-$) m/z; 368 [M − H]$^-$ |

Synthetic Example 66

1-(trans-4-{[Methyl(2,2,2-trifluoroethyl)amino]methyl}cyclohexyl)-2,3-dihydro-1H-pyrrolo[3',2':5,6]pyrido[4,3-d]pyrimidin-4(7H)-one

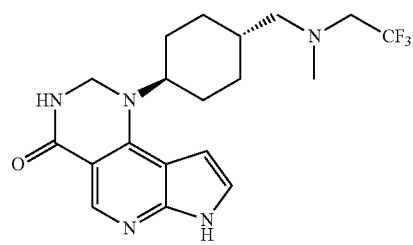 [SMILES: CN(CC(F)(F)F)C[C@H]1CC[C@H](N2CNC(=O)c3cnc4[nH]ccc4c32)CC1]

To a solution of 1-(trans-4-{[(2,2,2-trifluoroethyl)amino]methyl}cyclohexyl)-2,3-dihydro-1H-pyrrolo[3',2':5,6]pyrido[4,3-d]pyrimidin-4(7H)-one (35.8 mg, 93.9 μmol) obtained in Synthetic Example 4 in methanol (1.5 mL), 37% aqueous formaldehyde (19.1 μL, 188 μmol) and 2-picoline borane (20.1 mg, 188 μmol) were added, and the mixture was stirred at room temperature for 2 hours. The reaction mixture was mixed with water and extracted with ethyl acetate. The organic layer was washed with saturated aqueous sodium chloride, dried over anhydrous sodium sulfate and concentrated under reduced pressure. The residue was purified by silica gel column chromatography (silica gel NH type manufactured by FUJI SILYSIA CHEMICAL LTD., chloroform→chloroform/methanol=15/1 (v/v)) to obtain the title compound as a white solid (29.8 mg, yield: 80%).

$^1$H-NMR (DMSO-d$_6$) δ: 0.98-1.13 (m, 2H), 1.42-1.56 (m, 1H), 1.60-1.75 (m, 2H), 1.84-1.93 (m, 4H), 2.33-2.38 (m, 5H), 3.15 (q, J=10.2 Hz, 2H), 4.07-4.19 (m, 1H), 4.51 (d, J=2.9 Hz, 2H), 6.44-6.47 (m, 1H), 7.28 (t, J=3.3 Hz, 1H), 7.81 (s, 1H), 8.43 (s, 1H), 11.70 (br s, 1H).

LC/MS: measurement condition 2, retention time=1.63 min.

LC/MS (ESI$^+$) m/z; 396 [M+H]$^+$

Synthetic Example 67

1-{trans-4-[(1,1-Dioxidoisothiazolidin-2-yl)methyl]cyclohexyl}-3-(2,2,2-trifluoroethyl)-2,3-dihydro-1H-pyrrolo[3',2':5,6]pyrido[4,3-d]pyrimidin-4(7H)-one

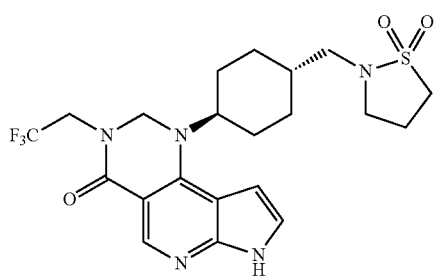 [SMILES: O=C1c2cnc3[nH]ccc3c2N([C@H]2CC[C@H](CN3CCCS3(=O)=O)CC2)CN1CC(F)(F)F]

To a solution of 1-{trans-4-[(1,1-dioxidoisothiazolidin-2-yl)methyl]cyclohexyl}-3-(2,2,2-trifluoroethyl)-7-{[2-(trimethylsilyl)ethoxy]methyl}-2,3-dihydro-1H-pyrrolo[3',2':5,6]pyrido[4,3-d]pyrimidin-4(7H)-one (10 mg, 0.016 mmol) obtained in Reference Synthetic Example 62 in dichloromethane (0.5 mL), trifluoroacetic acid (1 mL) was added, and the mixture was stirred at room temperature for 2.5 hours. The mixture was mixed with additional amount of trifluoroacetic acid (0.5 mL), the mixture was stirred at room temperature for 2 hours, and the reaction mixture was concentrated under reduced pressure. To a solution of the resulting residue in a mixed solvent of water (0.2 mL) and methanol (0.8 mL), 1M aqueous sodium hydroxide (0.04 mL) and ethylenediamine (0.04 mL) were added, and the mixture was stirred at room temperature for 1 day. The reaction mixture was mixed with water and extracted with a mixed solvent of chloroform/2-propanol (5/1 (v/v)) three times. The organic layers were combined, dried over anhydrous sodium sulfate and concentrated under reduced pressure. The residue was purified by thin-layer silica gel column chromatography (chloroform/methanol=10/1 (v/v)) to obtain the title compound as a white solid (6.3 mg, yield: 81%).

LC/MS: measurement condition 2, retention time=1.69 min.

LC/MS (ESI$^+$) m/z; 486 [M+H]$^+$

Pharmacological Assay

Now, a pharmacological assay of the compounds of the present invention will be described.

1. Enzyme Assay

The inhibitory activity of the compounds of the present invention against JAK was measured.

The respective enzymes (JAK1, JAK2, JAK3 and Tyk2) were purchased from Carna Biosciences, Inc.

As a substrate of the enzymes (hereinafter referred to as substrate), LANCE Ultra ULight-JAK-1 (Tyr1023) Peptide (manufactured by PerkinElmer Inc.) was used.

As an antibody for detecting phosphorylation of the substrate, LANCE Ultra Europium-anti-phospho tyrosine antibody (PT66) (manufactured by PerkinElmer Inc.) was used.

The other reagents were purchased from the following.

Adenosine triphosphate (ATP): Sigma-Aldrich 4-(2-Hydroxyethyl)-1-piperazineethanesulfonic acid (HEPES): DOJINDO LABORATORIES Glycol ether diamine tetraacetic acid (EGTA): DOJINDO LABORATORIES Magnesium chloride ($MgCl_2$): Wako Pure Chemical Industries, Ltd.

Dithiothreitol (DTT): Wako Pure Chemical Industries, Ltd.

Tween 20: Sigma-Aldrich

Ethylenediaminetetraacetic acid (EDTA): DOJINDO LABORATORIES

The compounds of the present invention, the enzymes (JAK1, JAK2, JAK3 and Tyk2), the substrate and ATP were used for assay as diluted with assay buffer.

As the assay buffer, one having the following composition was used.

HEPES (pH7.5): 50 mM
EGTA: 1 mM
$MgCl_2$: 10 mM
DTT: 2 mM
Tween 20: 0.01% (wt/wt)

The dilute concentration and the addition amount on a well plate as described hereinafter were adjusted so that the following final concentrations were achieved on the well plate.

The concentrations of each compound were 6 concentrations of 1 μM, 0.1 μM, 0.01 μM, 0.001 μM, 0.0001 μM and 0.00001 μM.

The enzyme concentration and the ATP concentration in the respective enzyme (JAK1, JAK2, JAK3 and Tyk2) tests were as follows.

In JAK1 enzyme assay, the enzyme concentration was 0.5 μg/mL and the ATP concentration was 70 μM; in JAK2 enzyme assay, the enzyme concentration was 0.013 μg/mL and the ATP concentration was 10 μM; in JAK3 enzyme assay, the enzyme concentration was 0.025 μg/mL and the ATP concentration was 3 μM; and in Tyk2 enzyme assay, the enzyme concentration was 0.25 μg/mL and the ATP concentration was 20 μM.

The concentration of the substrate of the enzyme was 6 nM.

The concentration of EDTA was 11 mM.

The concentration of PT66 was from 2 to 3 nM.

A dilute solution of the compound and a dilute solution of the enzyme were dispensed into wells of a 384-well black plate (manufactured by Greiner bio-one), followed by pre-incubation at room temperature for 5 minutes.

Then, a dilute solution of the substrate and then a dilute solution of ATP were added, followed by incubation at room temperature for 30 minutes.

Then, a dilute solution of EDTA and then a dilute solution of PT66 were added, followed by incubation at room temperature for 1 hour.

The fluorescences were measured with ARVO-HTS. From the plot of the logarithm of a compound concentration and inhibitory activity, the $IC_{50}$ was calculated. The results of JAK1, JAK2, JAK3 and Tyk2 enzyme assays of the compounds in Synthetic Examples are shown in Tables 27 and 28. "*" in the Tables indicates $IC_{50}$>1 μM.

TABLE 27

| Ex | Jak1 $IC_{50}$(μM) | Jak2 $IC_{50}$(μM) | Jak3 $IC_{50}$(μM) | Tyk2 $IC_{50}$(μM) |
|---|---|---|---|---|
| 1 | 0.010 | 0.014 | 0.018 | 0.026 |
| 2 | 0.00088 | 0.0021 | 0.0063 | 0.037 |
| 3 | 0.0054 | 0.016 | 0.014 | 0.046 |
| 4 | 0.0024 | 0.0046 | 0.024 | 0.022 |
| 5 | 0.0035 | 0.024 | 0.017 | 0.048 |
| 6 | 0.00088 | 0.012 | 0.037 | 0.11 |
| 7 | 0.0014 | 0.032 | 0.073 | 0.42 |
| 8 | 0.0035 | 0.030 | 0.057 | 0.052 |
| 9 | 0.0034 | 0.017 | 0.033 | 0.11 |
| 10 | 0.0050 | 0.021 | 0.037 | 0.15 |
| 11 | 0.0032 | 0.044 | 0.12 | 0.16 |
| 12 | 0.0022 | 0.016 | 0.022 | 0.062 |
| 13 | 0.0050 | 0.012 | 0.032 | 0.044 |
| 14 | 0.0030 | 0.0081 | 0.024 | 0.038 |
| 15 | 0.0014 | 0.0064 | 0.019 | 0.019 |
| 16 | 0.0020 | 0.0082 | 0.028 | 0.084 |
| 17 | 0.0055 | 0.021 | 0.16 | 0.24 |
| 18 | 0.0020 | 0.018 | 0.043 | 0.042 |
| 19 | 0.0026 | 0.0076 | 0.015 | 0.11 |
| 20 | 0.0050 | 0.016 | 0.043 | 0.060 |
| 21 | 0.0060 | 0.034 | 0.054 | 0.16 |
| 22 | 0.0032 | 0.035 | 0.067 | 0.23 |
| 23 | 0.0038 | 0.010 | 0.037 | 0.074 |
| 24 | 0.013 | 0.071 | 0.29 | 0.15 |
| 25 | 0.0052 | 0.027 | 0.043 | 0.29 |
| 26 | 0.012 | 0.0058 | 0.013 | 0.10 |
| 27 | 0.0034 | 0.036 | 0.063 | 0.20 |
| 28 | 0.0024 | 0.011 | 0.030 | 0.19 |
| 29 | 0.0033 | 0.023 | 0.042 | 0.26 |
| 30 | 0.0075 | 0.011 | 0.0049 | 0.080 |
| 31 | 0.0050 | 0.029 | 0.023 | 0.43 |
| 32 | 0.0041 | 0.0067 | 0.0095 | 0.26 |
| 33 | 0.0070 | 0.023 | 0.018 | 0.37 |
| 34 | 0.11 | 0.79 | * | * |
| 35 | 0.072 | 0.49 | * | 0.91 |
| 36 | 0.00042 | 0.0018 | 0.0054 | 0.026 |
| 37 | 0.00065 | 0.0027 | 0.0089 | 0.032 |

TABLE 27-continued

| Ex | Jak1 IC$_{50}$(μM) | Jak2 IC$_{50}$(μM) | Jak3 IC$_{50}$(μM) | Tyk2 IC$_{50}$(μM) |
|---|---|---|---|---|
| 38 | 0.00038 | 0.00062 | 0.014 | 0.094 |
| 39 | 0.011 | 0.069 | 0.49 | 0.20 |
| 40 | 0.0015 | 0.0031 | 0.0090 | 0.052 |
| 41 | 0.0032 | 0.0065 | 0.022 | 0.072 |
| 42 | 0.0022 | 0.016 | 0.016 | 0.057 |
| 43 | 0.0018 | 0.0049 | 0.018 | 0.091 |
| 44 | 0.0014 | 0.0076 | 0.018 | 0.20 |
| 45 | 0.0021 | 0.0070 | 0.028 | 0.019 |

TABLE 28

| Ex | Jak1 IC$_{50}$(μM) | Jak2 IC$_{50}$(μM) | Jak3 IC$_{50}$(μM) | Tyk2 IC$_{50}$(μM) |
|---|---|---|---|---|
| 46 | 0.0019 | 0.0064 | 0.016 | 0.17 |
| 47 | 0.0042 | 0.018 | 0.045 | 0.37 |
| 48 | 0.0044 | 0.024 | 0.039 | 0.049 |
| 49 | 0.0034 | 0.015 | 0.038 | 0.17 |
| 50 | 0.011 | 0.074 | 0.35 | 0.44 |
| 51 | 0.00090 | 0.0068 | 0.011 | 0.061 |
| 52 | 0.019 | 0.067 | 0.41 | 0.33 |
| 53 | 0.00085 | 0.0019 | 0.0049 | 0.024 |
| 54 | 0.0036 | 0.018 | 0.059 | 0.065 |
| 55 | 0.0016 | 0.0060 | 0.022 | 0.034 |
| 56 | 0.0071 | 0.019 | 0.050 | 0.29 |
| 57 | 0.0094 | 0.027 | 0.073 | 0.33 |
| 58 | 0.018 | 0.018 | 0.056 | 0.23 |
| 59 | 0.0019 | 0.015 | 0.034 | 0.045 |
| 60 | 0.0027 | 0.029 | 0.041 | 0.054 |
| 61 | 0.012 | 0.10 | 0.36 | 0.48 |
| 62 | 0.014 | 0.26 | 0.54 | 0.70 |
| 63 | 0.0065 | 0.15 | 0.24 | 0.13 |
| 64 | 0.0063 | 0.033 | 0.041 | 0.11 |
| 65 | 0.0020 | 0.043 | 0.19 | 0.061 |
| 66 | 0.0014 | 0.0046 | 0.0085 | 0.029 |
| 67 | 0.0026 | 0.028 | 0.033 | 0.35 |

As shown above, the compounds of the present invention showed favorable enzyme inhibitory effects against JAK.

2. Whole Blood Signal Assay

The inhibitory activity of the compounds in Synthetic Examples 1 to 67 which are the compounds of the present invention against cytokine signaling via JAK was measured by means of STAT phosphorylation assay using rat whole blood.

Lewis female rats were purchased from CHARLES RIVER LABORATORIES JAPAN, INC.

IL-6 was purchased from PeproTech.

FITC (fluorescein isothiocyanate)-labeled anti-CD3 antibody (FITC-CD3) was purchased from eBioscience.

BD Phosflow Lyse/Fix Buffer, BD Phosflow Perm Buffer III, BD Pharmingen Stain Buffer and BD Phosflow STAT-1 (pY701) PE (R-Phycoerythrin) fluorescently labeled antibody (hereinafter referred to as BD Phosflow STAT-1) were purchased from BD (Becton, Dickison and Company).

The dilute concentration and the addition amount in a tube as described hereinafter were adjusted so that the following final concentrations were achieved in the tube.

The concentrations of each compound were three concentrations of 1 μM, 0.1 μM and 0.01 μM or three concentrations of 10 μM, 1 μM and 0.1 μM.

The concentration of IL-6 was 100 ng/mL.

The concentration of FITC-CD3 was 1 μg/mL.

Blood was collected through the inferior of vena cava of a Lewis female rat. The blood and the compound were added to a Costar assay block tube, followed by incubation at 37° C. for 15 minutes. Then, FITC-CD3 was added, followed by incubation at 37° C. for 15 minutes. Then, IL-6 was added, followed by incubation at 37° C. for 15 minutes. Then, BD Phosflow Lyse/Fix Buffer was added in an amount of 10 times the blood, followed by incubation at 37° C. for 12 minutes. Centrifugal separation was carried out at 5,884 m/s$^2$ for 6 minutes by a centrifugal separator to precipitate the cells, and the supernatant was removed. The cell sediment was washed with 1 mL of phosphate buffered saline (PBS), and 0.6 mL of BD Phosflow Perm Buffer III was added to the cell sediment, followed by incubation on an ice bath. Centrifugal separation was carried out at 5,884 m/s$^2$ for 6 minutes by a centrifugal separator to precipitate the cells, and the supernatant was removed. The cell sediment was washed with 0.3 mL of BD Pharmingen Stain Buffer, and to the cell sediment, 0.1 mL of BD Pharmingen Stain Buffer was added and then 10 μL of BD Phosflow STAT-1 was added, followed by incubation at room temperature for 30 minutes. Then, 0.1 mL of BD Pharmingen Stain Buffer was added, and centrifugal separation was carried out at 5,884 m/s$^2$ for 6 minutes by a centrifugal separator to precipitate the cells, and the supernatant was removed. The cell sediment was washed with 0.3 mL of BD Pharmingen Stain Buffer, and 0.12 mL of BD Pharmingen Stain Buffer was added to the cell sediment. The cytokine signaling inhibition was measured by detecting FITC-labeled CD3 positive T cells and detecting the amount of phosphated STAT-1 protein in the cells as the PE fluorescence using FACSCANTO II (manufactured by BD). From the plot of the logarithm of a compound concentration and inhibitory activity, the IC$_{50}$ value was calculated. The results of rat whole blood signal assays of the compounds in Synthetic Examples are shown in Table 29.

TABLE 29

| Ex | IC$_{50}$(μM) |
|---|---|
| 1 | 0.63 |
| 2 | 0.16 |
| 3 | 0.29 |
| 4 | 0.066 |
| 5 | 0.32 |
| 6 | 0.27 |
| 7 | 0.31 |
| 8 | 0.39 |
| 9 | 0.18 |
| 10 | 0.20 |
| 11 | 0.24 |
| 12 | 0.12 |
| 13 | 0.27 |
| 14 | 0.16 |
| 15 | 0.27 |
| 16 | 0.084 |
| 17 | 0.18 |
| 18 | 0.12 |
| 19 | 0.17 |
| 20 | 0.21 |
| 21 | 0.30 |
| 22 | 0.27 |
| 23 | 0.15 |
| 24 | 0.095 |
| 25 | 0.41 |
| 26 | 0.54 |
| 27 | 0.15 |
| 28 | 0.17 |
| 29 | 0.25 |
| 30 | 0.38 |
| 31 | 0.63 |
| 32 | 0.43 |
| 33 | 0.37 |
| 34 | 0.54 |
| 35 | 0.63 |
| 36 | 0.37 |
| 37 | 0.42 |

TABLE 29-continued

| Ex | IC$_{50}$(μM) |
|---|---|
| 38 | 0.34 |
| 39 | 0.17 |
| 40 | 0.19 |
| 41 | 0.36 |
| 42 | 0.063 |
| 43 | 0.32 |
| 44 | 0.24 |
| 45 | 0.73 |
| 46 | 0.31 |
| 47 | 0.67 |
| 48 | 0.22 |
| 49 | 0.70 |
| 50 | 0.22 |
| 51 | 0.16 |
| 52 | 0.19 |
| 53 | 0.087 |
| 54 | 0.090 |
| 55 | 0.12 |
| 56 | 0.27 |
| 57 | 0.28 |
| 58 | 0.24 |
| 59 | 0.082 |
| 60 | 0.14 |
| 61 | 0.30 |
| 62 | 0.25 |
| 63 | 0.081 |
| 64 | 0.29 |
| 65 | 0.23 |
| 66 | 0.13 |
| 67 | 0.30 |

In order that a compound is highly useful against rheumatoid arthritis among diseases against which the JAK inhibitory effect is effective, the compound more preferably has a favorable inhibitory effect in the whole blood signal assay. The compounds of the present invention showed excellent inhibitory activity against JAK signaling by cytokine stimulation in the whole blood by means of the JAK inhibitory activity.

Further, the results of the rat whole blood signal assay of compound A (Example$^b$ 53), compound B (Example$^b$ 138), compound C (Example$^b$ 137), compound D (Example$^b$ 122) and compound E (Example$^b$ 127) disclosed in WO2013/024895 published after filing of the application on the basis of which the priority of the present application is claimed, are shown below.

Compound A
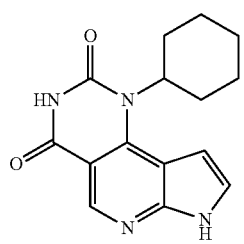

Compound B
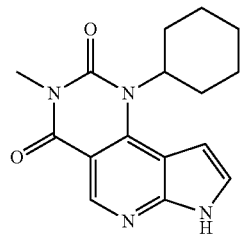

Compound C
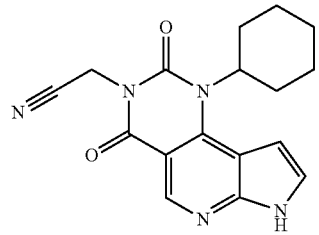

Compound D
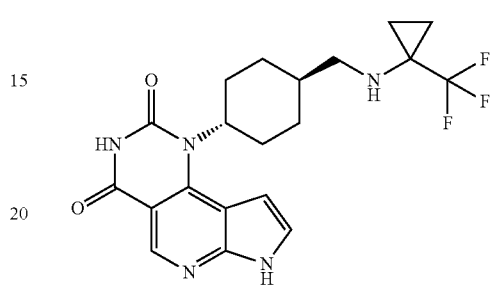

Compound E
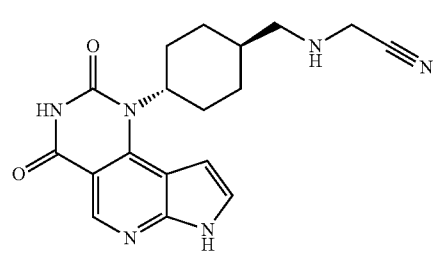

TABLE 30

| Compound | IC$_{50}$(μM) |
|---|---|
| A | >10 |
| B | 6.2 |
| C | 4.6 |
| D | 1.1 |
| E | 2.7 |

As shown above, the compounds of the present invention have higher inhibitory effect in the rat whole blood signal assay as compared with the five compounds disclosed in WO2013/024895.

3. Erythroleukemia Cell Line Proliferation Inhibitory Effect

The inhibitory activity of the compounds of the present invention against cell proliferation via the JAK signaling can be measured by human erythroleukemia cell line TF-1.

The TF-1 cells (ATCC (American Type Culture Collection)) are proliferated and maintained in a RPMI1640 culture medium containing 5% fetal bovine serum (FBS) and 1 ng/mL GM-CSF (granulocyte macrophage colony-stimulating factor) in a CO$_2$ incubator (5 vol % CO$_2$, 37° C.). The TF-1 cells washed with PBS at the time of the test are suspended in a RPMI1640 culture medium containing 5% FBS, and seeded on a 96-well culture plate at a density of 1×10$^4$ cells/well. Then, the compound is added to each well of the culture plate, followed by incubation at 37° C. for 30 minutes, and cytokine such as IL-4 or IL-6 is added. Then, the culture plate is subjected to incubation in a CO$_2$ incubator (5 vol % CO$_2$, 37° C.) for 3 days.

The degree of cell proliferation can be measured with WST-8 reagent (manufactured by Kishida Chemical Co., Ltd.) in accordance with its instructions. WST-8 reagent is added to each well of the culture plate, followed by incubation in a $CO_2$ incubator (5 vol % $CO_2$, 37° C.) for 4 hours. The color-forming formazan dye can be detected by measuring the absorbance at 450 nm using a microplate reader. The $IC_{50}$ value can be calculated from the plot of the logarithm of a compound concentration and inhibitory activity.

4. Oral Absorption Property

A compound having oral absorption property is preferred for treatment of diseases against which the JAK inhibitor effect is effective, and the oral absorption property of the compounds of the present invention may be measured using rats.

The compound is suspended in 0.5% methyl cellulose at a concentration of 0.6 mg/mL. The suspension is forcibly administered orally by a feeding needle to a Lewis female rat (CHARLES RIVER LABORATORIES JAPAN INC.) at a dose of 3 mg/kg/5 mL. Then, using heparin as an anticoagulant, after administration of the compound (after 0.5 to 8 hours), the blood is collected through the jugular vein with time. The obtained blood is subjected to centrifugal separation at 17,652 m/s$^2$ for 10 minutes by a centrifugal separator to obtain the blood plasma. The obtained blood plasma is analyzed by liquid chromatography tandem mass spectrometry (LC/MS/MS, manufactured by Waters) to calculate the transition of the concentration of the compound in the blood plasma after the oral administration (after 0.5 to 8 hours).

5. Effect in Collagen-Induced Rat Arthritis Model

To confirm the therapeutic effect of particularly rheumatoid arthritis among diseases against which the JAK inhibitory effect is effective by an experimental animal model, a collagen-induced rat arthritis model may be used (Prostaglandin & other Lipid Mediators, 2001, 66, pp. 317-327).

Bovine II types collagen solution (Chondrex, Inc.) and incomplete Freund's adjuvant (Difco) are mixed in equal amount and emulsified to prepare an immune solution. Then, the immune solution is intracutaneously administered to a Lewis female rat (CHARLES RIVER LABORATORIES JAPAN INC.) at 4 portions on the back and one portion on the tail root portion at a dose of 100 μL/portion using a Hamilton syringe. 7 Days after administration of the immune solution, the immune solution is intracutaneously administered similarly again.

The compound to be administered is suspended in 0.5% methyl cellulose at a concentration optionally determined by the $IC_{50}$ value of the cytokine signaling inhibition obtained by the above 2. whole blood signal assay and the concentration of the compound in the blood plasma obtained by the above 4. oral absorption property. The compound suspension thus obtained is orally administered daily after the second administration of the immune solution.

The thickness of the hind-paw swelling in 2 to 3 weeks after the second administration of the immune solution is measured by a caliper to calculate the degree of inhibition of arthritis by the compound.

Now, Formulation Examples for the tricyclic pyrrolopyridine compounds represented by the formula (I) of the present invention will be described.

Formulation Example 1

A granule preparation containing the following ingredients is prepared.

Ingredients

| | |
|---|---|
| Compound represented by the formula (1) | 10 mg |
| Lactose | 700 mg |
| Corn Starch | 274 mg |
| HPC-L | 16 mg |
| Total | 1,000 mg |

A compound represented by the formula (1) and lactose are sifted through a 60-mesh sieve. Corn starch is sifted through a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

Ingredients

| | |
|---|---|
| Compound represented by the formula (1) | 10 mg |
| Lactose | 79 mg |
| Corn Starch | 10 mg |
| Magnesium Stearate | 1 mg |
| Total | 100 mg |

A compound represented by the formula (1) and lactose are sifted through a 60-mesh sieve. Corn starch is sifted through a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

Ingredients

| | |
|---|---|
| Compound represented by the formula (1) | 15 mg |
| Lactose | 90 mg |
| Corn Starch | 42 mg |
| HPC-L | 3 mg |
| Total | 150 mg |

A compound represented by the formula (1) and lactose are sifted through a 60-mesh sieve. Corn starch is sifted through a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

Formulation Example 4

A tablet preparation containing the following ingredients is prepared.

Ingredients

| | |
|---|---|
| Compound represented by the formula (1) | 10 mg |
| Lactose | 90 mg |

| | |
|---|---|
| Microcrystalline cellulose | 30 mg |
| Magnesium Stearate | 5 mg |
| CMC-Na | 15 mg |
| Total | 150 mg |

A compound represented by the formula (1), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| | |
|---|---|
| Compound represented by the formula (1) | 100 mg |
| Saturated Fatty Acid Glyceride | 1,000 ml |

Solutions having the above-mentioned composition are usually administered to a patient intravenously at a rate of 1 ml per 1 minute.

INDUSTRIAL APPLICABILITY

The compounds of the present invention have excellent JAK inhibitory activity and are particularly useful for prevention or treatment of autoimmune diseases, inflammatory diseases and allergic diseases.

The entire disclosures of Japanese Patent Application No. 2013-023650 filed on Feb. 8, 2013 and Japanese Patent Application No. 2013-066124 filed on Mar. 27, 2013 including specifications, claims and summaries are incorporated herein by reference in their entireties.

The invention claimed is:
1. A compound which is represented by formula (III):

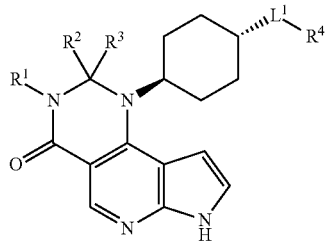

a tautomer thereof, a pharmaceutically acceptable salt thereof or a solvate thereof, wherein
$R^1$ is a hydrogen atom, a $C_{3-6}$ cycloalkyl group, a 4 to 7-membered non-aromatic heterocyclic group, a $C_{1-6}$ haloalkyl group, or a $C_{1-6}$ alkyl group, wherein the $C_{1-6}$ alkyl group is optionally substituted with a hydroxy group, a cyano group, a $C_{1-6}$ alkoxy group, a $C_{1-6}$ alkylthio group, a $C_{1-6}$ alkylsulfonyl group, a carboxy group, a carbamoyl group, a mono-$C_{1-6}$ alkylaminocarbonyl group, a di-$C_{1-6}$ alkylaminocarbonyl group, a $C_{3-6}$ cycloalkyl group or a 4 to 7-membered non-aromatic heterocyclic group,
each of $R^2$ and $R^3$ is independently a hydrogen atom, or a $C_{1-6}$ alkyl group, L is a single bond, a $C_{1-3}$ alkylene group, or a $C_{1-3}$ haloalkylene group, and
$R^4$ is a hydrogen atom, $NR^aR^b$, $NR^cS(=O)_2R^d$, $OR^e$, formula (II)-1, or formula (II)-2:

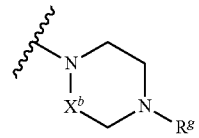

wherein $R^a$ is a $C_{1-3}$ alkyl group, a cyano-substituted $C_{1-3}$ alkyl group, a $C_{1-3}$ haloalkyl group, a $C_{1-6}$ cycloalkyl group, a cyano-substituted $C_{3-6}$ cycloalkyl group, or a $C_{1-3}$ haloalkyl-substituted $C_{3-6}$ cycloalkyl group,
each of $R^b$ and $R^c$ is independently a hydrogen atom, or a C1-3 alkyl group,
$R^d$ is a $C_{1-3}$ alkyl group, a $C_{1-3}$ haloalkyl group, or a $C_{3-6}$ cycloalkyl group,
$R^e$ is a hydrogen atom, or a cyano-substituted $C_{1-3}$ alkyl group,
$R^f$ is a halogen atom, or a hydroxy group,
$R^g$ is a cyano-substituted $C_{1-3}$ alkyl group,
$X^a$ is $S(=O)_2$, or $CH_2$,
$X^b$ is $CH_2$,
n is 0 or 1, and
m is 0 or 1.
2. The compound according to claim 1, a tautomer thereof, a pharmaceutically acceptable salt thereof or a solvate thereof, wherein $R^2$ and $R^3$ are each a hydrogen atom.
3. The compound according to claim 1, a tautomer thereof, a pharmaceutically acceptable salt thereof or a solvate thereof,
wherein $R^1$ is a hydrogen atom, a $C_{1-3}$ haloalkyl group, a $C_{3-6}$ cycloalkyl group, or a $C_{1-3}$ alkyl group,
wherein the $C_{1-3}$ alkyl group is optionally substituted with one cyano group, $C_{1-3}$ alkoxy group, $C_{1-3}$ alkylthio group, di-$C_{1-3}$ alkylaminocarbonyl group, $C_{3-6}$ cycloalkyl group or 4 to 7-membered non-aromatic heterocyclic group.
4. The compound according to claim 3, a tautomer thereof, a pharmaceutically acceptable salt thereof or a solvate thereof,
wherein $R^1$ is a $C_{1-3}$ haloalkyl group, a $C_{3-6}$ cycloalkyl group, or a $C_{1-3}$ alkyl group,
wherein the $C_{1-3}$ alkyl group is optionally substituted with a cyano group, a $C_{1-3}$ alkoxy group, a $C_{1-3}$ alkylthio group, a di-$C_{1-3}$ alkylaminocarbonyl group, a $C_{3-6}$ cycloalkyl group or a tetrahydrofuranyl group.
5. The compound according to claim 1, a tautomer thereof, a pharmaceutically acceptable salt thereof or a solvate thereof, wherein $L^1$ is a single bond or a $C_{1-3}$ haloalkylene group, and $R^4$ is a hydrogen atom.
6. The compound according to claim 1, or a tautomer thereof, a pharmaceutically acceptable salt thereof or a solvate thereof, wherein:

$L^1$ is a methylene group, $R^4$ is $NR^aR^b$, $NR^cS(=O)_2R^d$, $OR^e$, or any one of formulae (IV)-1 to (IV)-4:

(IV)-1
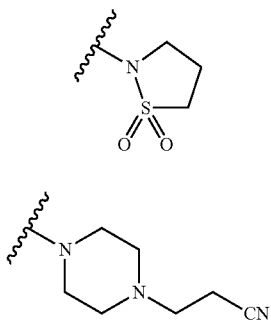

(IV)-2
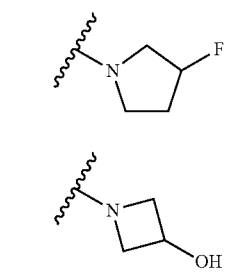

(IV)-3
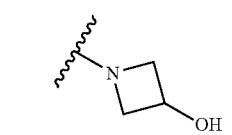

(IV)-4
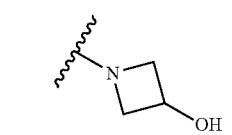

$R^a$ is a methyl group, a cyanomethyl group, a 2,2,2-trifluoroethyl group, a 2,2-difluoroethyl group, a 2-bromo-2,2-difluoroethyl group, a cyclopropyl group, a 1-cyanocycloproyl group or a 1-trifluoromethylcyclopropyl group, each of $R^b$ and $R^c$ is independently a hydrogen atom or a methyl group, $R^d$ is a methyl group, a 2,2,2-trifluoroethyl group or a cyclopropyl group, and $R^e$ is a hydrogen atom or a 2-cyanoethyl group.

7. A compound represented by any one of the following chemical structural formulae:

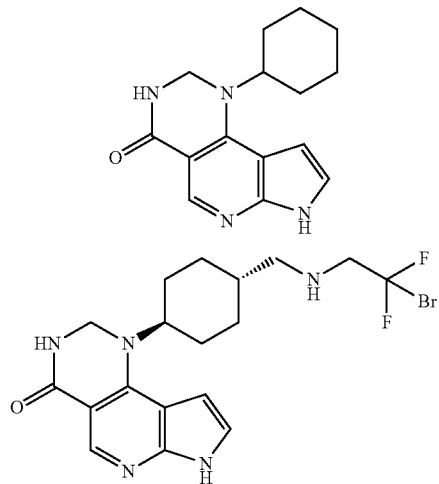

-continued

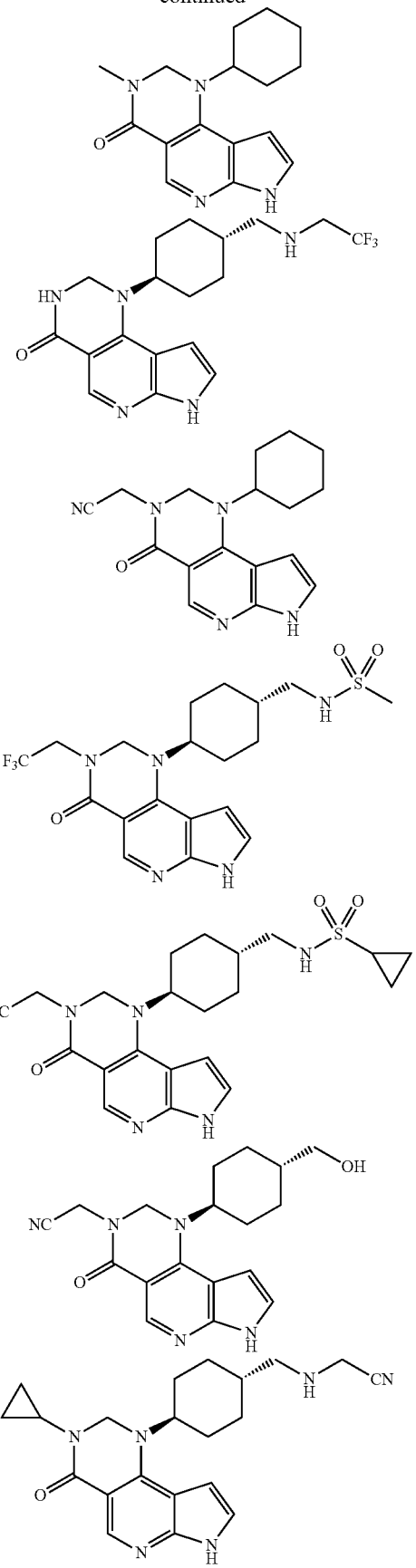

-continued
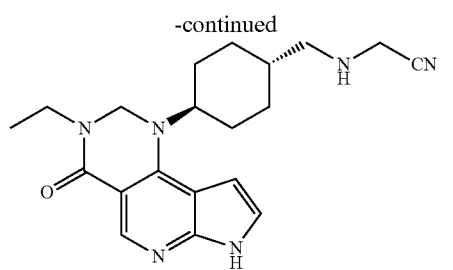
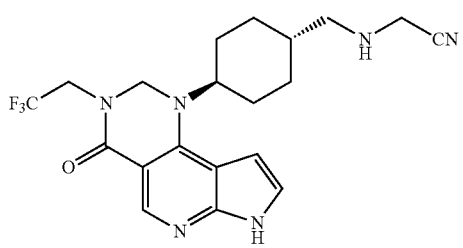
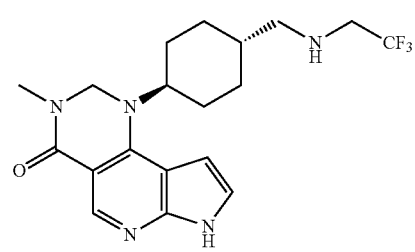
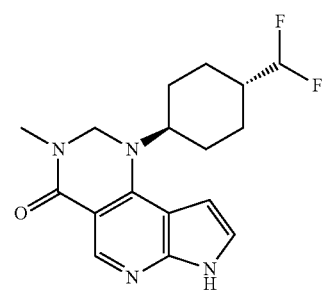
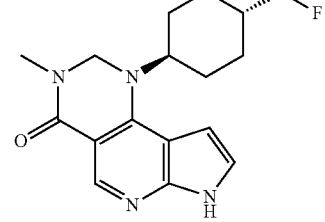
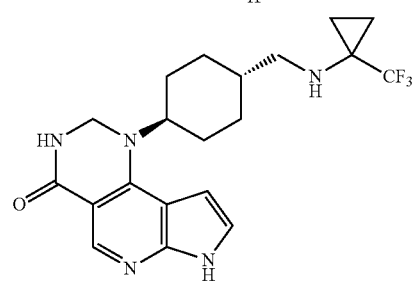
-continued
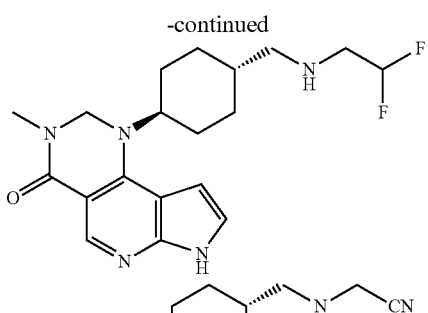
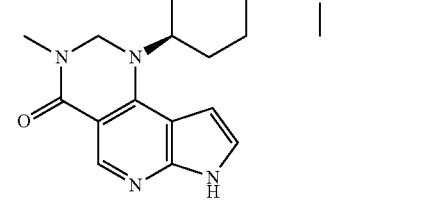
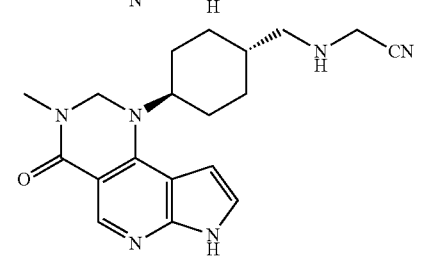
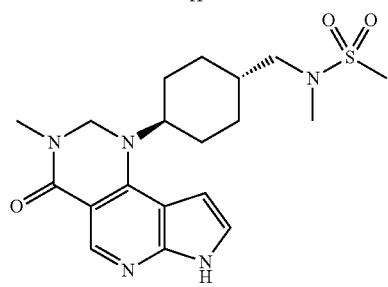
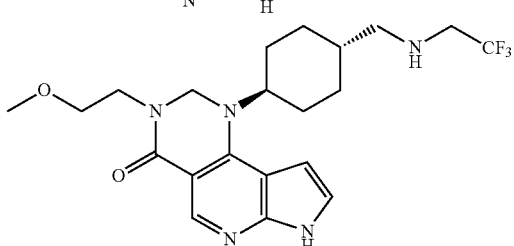
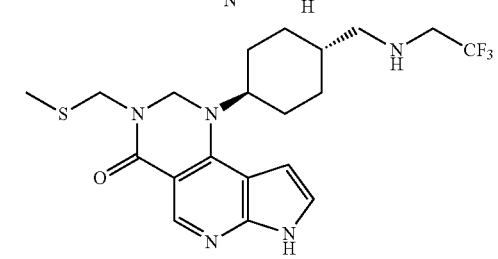
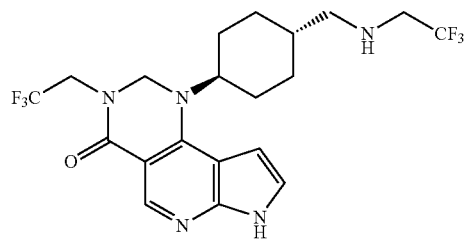

167
-continued
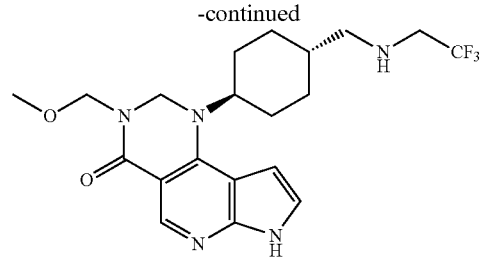
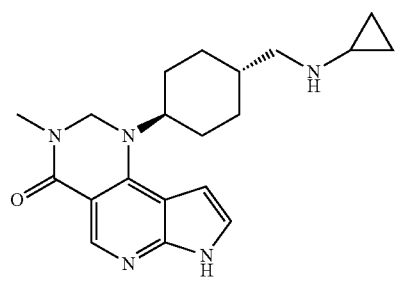
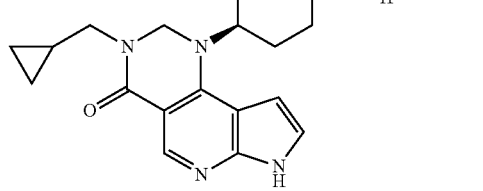
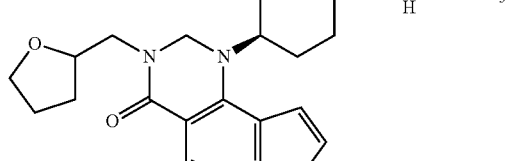
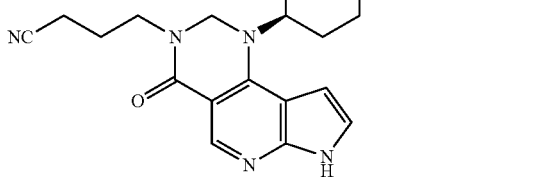
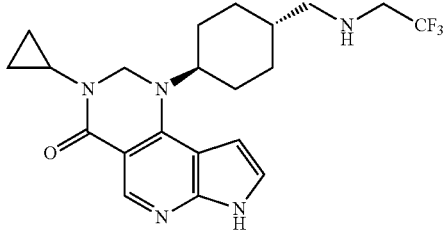
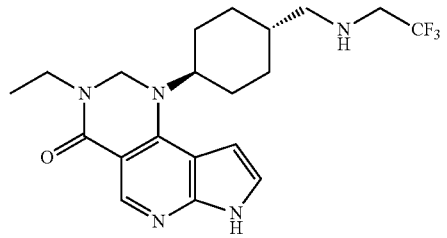
168
-continued
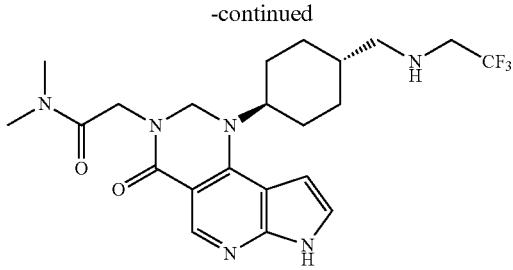
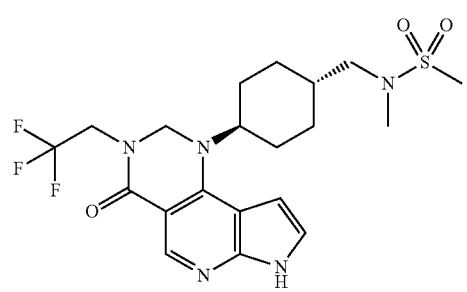
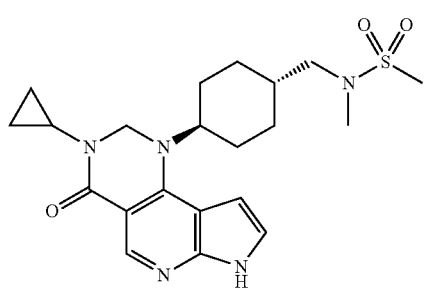
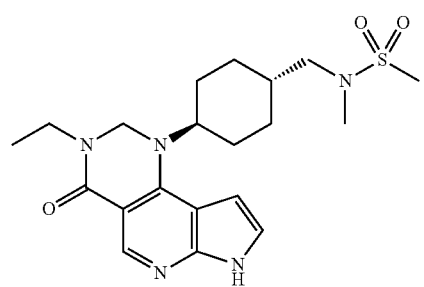
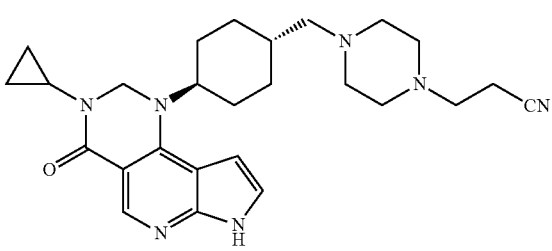
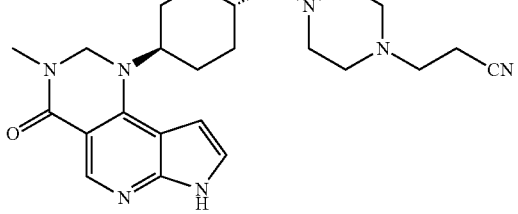

169
-continued
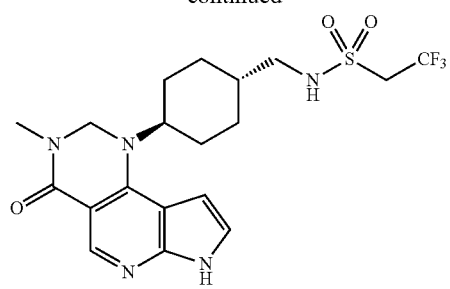
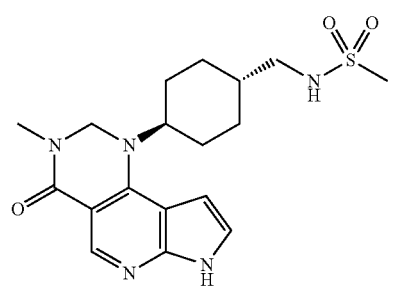
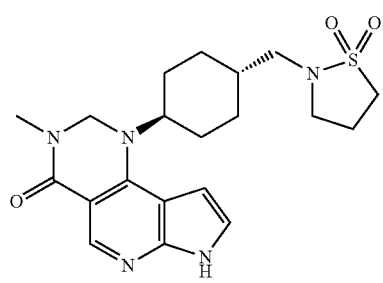
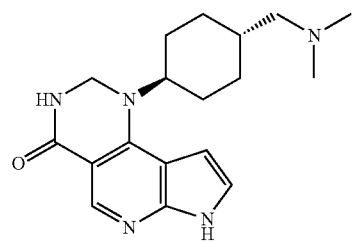
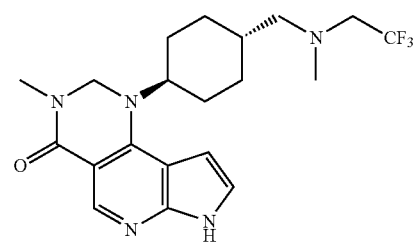
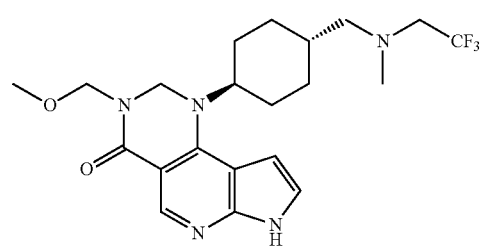
170
-continued
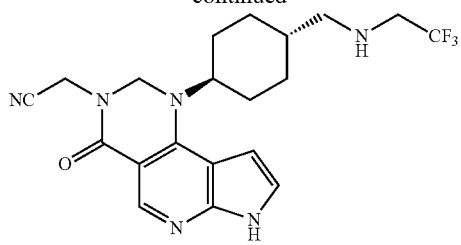
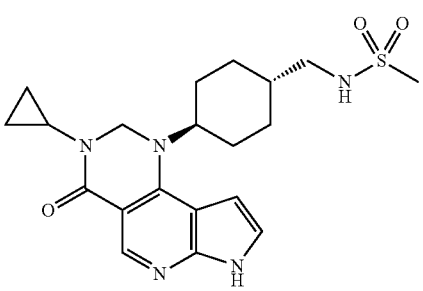
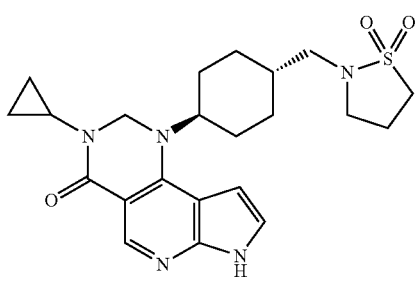
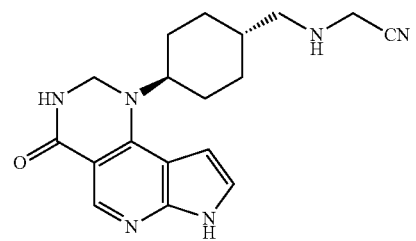
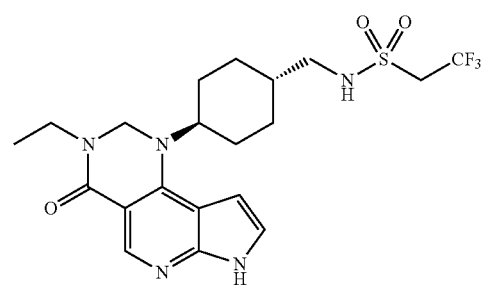
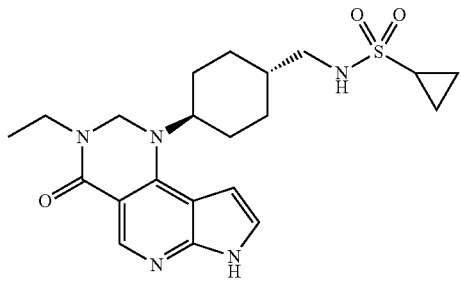

171
-continued
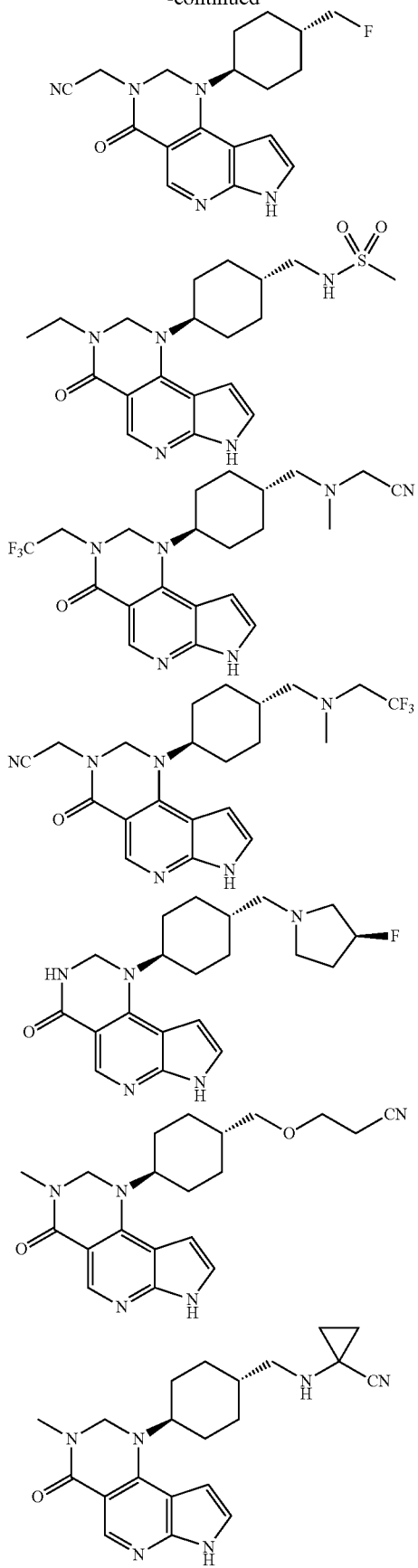
172
-continued
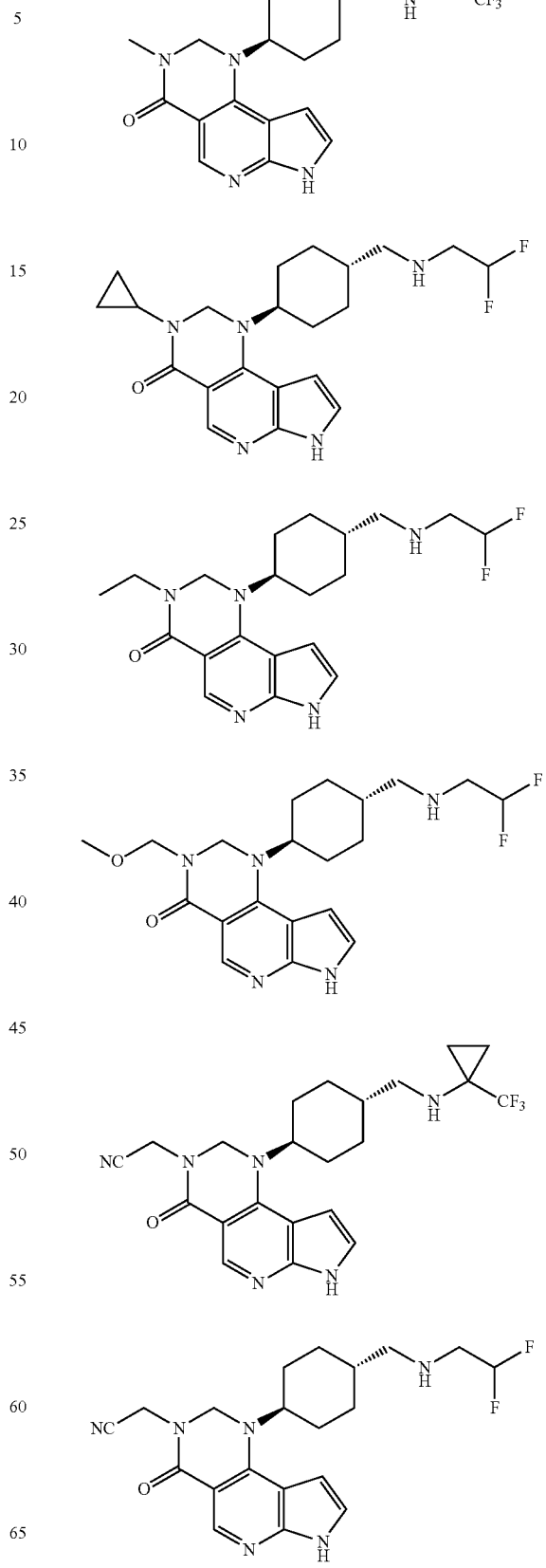

a tautomer thereof, a pharmaceutically acceptable salt thereof or a solvate thereof.

* * * * *

UNITED STATES PATENT AND TRADEMARK OFFICE
CERTIFICATE OF CORRECTION

PATENT NO. : 9,475,813 B2  
APPLICATION NO. : 14/764652  
DATED : October 25, 2016  
INVENTOR(S) : Keiji Takahashi et al.

Page 1 of 1

It is certified that error appears in the above-identified patent and that said Letters Patent is hereby corrected as shown below:

In the Claims

Column 162, Line 1, "L is a single bond,", should read --$L^1$ is a single bond,--; and
Line 21, "a $C_{1-6}$", should read --a $C_{3-6}$--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*